United States Patent [19]
DeGrado et al.

[11] Patent Number: 5,879,657
[45] Date of Patent: Mar. 9, 1999

[54] RADIOLABELED PLATELET GPIIB/IIIA RECEPTOR ANTAGONISTS AS IMAGING AGENTS FOR THE DIAGNOSIS OF THROMBOEMBOLIC DISORDERS

[75] Inventors: William Frank DeGrado, Moylan; Shaker Ahmed Mousa, Lincoln University, both of Pa.; Michael Sworin, Newark, Del.; John Andrew Barrett, West Groton; Scott David Edwards, Burlington, both of Mass.; Thomas David Harris, Salem, N.H.; Milind Rajopadhye, Westford; Shuang Liu, Chelmsford, both of Mass.

[73] Assignee: The Dupont Merck Pharmaceutical Company, Wilmington, Del.

[21] Appl. No.: 218,861

[22] Filed: Mar. 28, 1994

Related U.S. Application Data

[63] Continuation-in-part of Ser. No. 40,336, Mar. 30, 1993, abandoned.

[51] Int. Cl.⁶ ............................ A61K 51/00; A61M 36/14
[52] U.S. Cl. ................. 424/1.69; 424/1.65; 424/1.11; 424/9.1
[58] Field of Search ................... 424/1.69, 1.11, 424/1.65, 9.1, 9.3, 9.4, 9.5; 530/317, 300, 324–330; 206/569, 223, 570; 534/7, 10–16

[56] References Cited

U.S. PATENT DOCUMENTS

| | | |
|---|---|---|
| 4,444,690 | 4/1984 | Fritzberg et al. . |
| 4,517,686 | 5/1985 | Ruoslahti et al. .............................. 3/1 |
| 4,578,079 | 3/1986 | Ruoslahti et al. ........................ 623/11 |
| 4,589,881 | 5/1986 | Pierschbacher et al. ................. 623/11 |
| 4,614,517 | 9/1986 | Ruoslahti et al. ........................ 623/11 |
| 4,661,111 | 4/1987 | Ruoslahti et al. ........................ 623/11 |
| 4,670,545 | 6/1987 | Fritzberg et al. ......................... 534/14 |
| 4,673,562 | 6/1987 | Davison et al. .......................... 424/1.1 |
| 4,746,505 | 5/1988 | Jones et al. ............................... 424/1.1 |
| 4,792,525 | 12/1988 | Ruoslahti et al. ............... 435/240.243 |
| 4,861,869 | 8/1989 | Nicolotti et al. ......................... 530/402 |
| 4,879,237 | 11/1989 | Ruoslahti et al. .................. 435/240.2 |
| 4,883,862 | 11/1989 | Chervu et al. ........................... 530/331 |
| 4,897,255 | 1/1990 | Fritzberg et al. ........................ 424/1.1 |
| 4,925,650 | 5/1990 | Nosco et al. ............................. 424/1.1 |
| 4,952,562 | 8/1990 | Klein et al. ............................... 514/18 |
| 4,963,688 | 10/1990 | Bodor ....................................... 546/316 |
| 4,965,392 | 10/1990 | Fritzberg et al. ........................ 558/254 |
| 4,988,621 | 1/1991 | Ruoslahti et al. .................... 435/240.2 |
| 5,023,233 | 6/1991 | Nutt et al. ................................ 530/329 |
| 5,026,913 | 6/1991 | McBride et al. ......................... 564/440 |
| 5,037,631 | 8/1991 | Nosco ....................................... 424/1.1 |
| 5,041,380 | 8/1991 | Ruoslahti et al. .................... 435/240.2 |
| 5,053,503 | 10/1991 | Dean et al. ............................... 540/474 |
| 5,080,884 | 1/1992 | McBride et al. ......................... 424/1.1 |
| 5,082,930 | 1/1992 | Nicolotti et al. ......................... 530/402 |
| 5,095,111 | 3/1992 | Lever et al. .............................. 540/544 |
| 5,120,829 | 6/1992 | Pierschbacher et al. ............... 530/326 |
| 5,144,043 | 9/1992 | Dean et al. ............................... 548/548 |
| 5,175,256 | 12/1992 | Kasina et al. ......................... 530/391.5 |
| 5,175,343 | 12/1992 | Fritzberg et al. ........................ 560/145 |
| 5,180,816 | 1/1993 | Dean ....................................... 530/404 |
| 5,192,380 | 3/1993 | Hanada et al. ........................... 152/454 |
| 5,192,745 | 3/1993 | Krstenansky et al. .................. 530/327 |
| 5,192,746 | 3/1993 | Lobl et al. ............................... 530/329 |
| 5,218,128 | 6/1993 | Dean et al. ............................... 548/546 |
| 5,225,180 | 7/1993 | Dean et al. ............................... 424/1.1 |
| 5,236,898 | 8/1993 | Krstenansky et al. .................. 530/327 |
| 5,250,666 | 10/1993 | Gustavson et al. ................... 530/391.5 |
| 5,276,147 | 1/1994 | Thornback et al. ....................... 534/14 |
| 5,279,811 | 1/1994 | Bergstein et al. ........................ 424/1.1 |
| 5,279,812 | 1/1994 | Krstenansky et al. ................. 424/1.69 |

FOREIGN PATENT DOCUMENTS

| | | | |
|---|---|---|---|
| 0163119A2 | 4/1985 | European Pat. Off. | ...... C07C 149/24 |
| 0188256A2 | 1/1986 | European Pat. Off. | .... C07C 153/023 |
| 0247866A1 | 5/1987 | European Pat. Off. | ........ A61K 43/00 |
| 0284071A2 | 3/1988 | European Pat. Off. | ........ C07K 15/00 |
| 0332912A2 | 3/1988 | European Pat. Off. | .......... C07K 7/06 |
| 030478A1 | 8/1988 | European Pat. Off. | ........ A61K 49/02 |
| 0329481A2 | 2/1989 | European Pat. Off. | ........ A61K 43/00 |
| 0341915A2 | 5/1989 | European Pat. Off. | .......... C07F 5/00 |
| 0344724A1 | 5/1989 | European Pat. Off. | ........ A61K 49/02 |
| 0386873A1 | 1/1990 | European Pat. Off. | ........ A61K 49/02 |
| 0394126A1 | 4/1990 | European Pat. Off. | .... C07D 207/335 |
| 0412012A1 | 8/1990 | European Pat. Off. | ........ A61K 49/02 |
| 0432988A1 | 12/1990 | European Pat. Off. | ...... C07C 323/25 |
| 0425212A2 | 5/1991 | European Pat. Off. | .......... C07K 7/02 |
| 0569132A1 | 4/1993 | European Pat. Off. | ........ C07F 13/00 |

(List continued on next page.)

OTHER PUBLICATIONS

Fuster et al., *JACC*, vol. 5, No. 6, pp. 175B–183B (1985).
Rubenstein et al., *American Heart Journal*, pp. 363–367 (1981).
Hamm et al., *JACC*, vol. 10, No. 5, pp. 998–1004 (1987).
Davies et al., *Circulation*, vol. 73, No. 3, pp. 418–427 (1986).
Cerqueira et al., *Circulation*, vol. 85, No. 1, pp. 298–304 (1992).
Ord et al., *Circulation*, vol. 85, No. 1, pp. 288–297 (1992).
Wu Guo-xin et al., *Chinese Medical Journal*, vol. 105(7), pp. 553–559 (1992).
D'Amico, *Emergency Medicine Clinics of North America, Focus on Radiology: Part II*, vol. 10, No. 1, pp. 121–132 (1992).
Haddad et al., *Gastrointestinal Radiology*, vol. 17, pp 34–40 (1992).
Phillps et al., *Cell*, vol. 65, pp. 359–362 (1991).

(List continued on next page.)

*Primary Examiner*—John Kight
*Assistant Examiner*—Dameron Jones
*Attorney, Agent, or Firm*—Gerald J. Boudreaux; David H. Vance

[57] ABSTRACT

This invention provides novel radiopharmaceuticals that are radiolabeled cyclic compounds containing carbocyclic or heterocyclic ring systems which act as antagonists of the platelet glycoprotein IIb/IIIa complex; to methods of using said radiopharmaceuticals as imaging agents for the diagnosis of arterial and venous thrombi; to novel reagents for the preparation of said radiopharmaceuticals; and to kits comprising said reagents.

70 Claims, 1 Drawing Sheet

FOREIGN PATENT DOCUMENTS

| | | | |
|---|---|---|---|
| 2225579 | 6/1990 | United Kingdom | C07K 7/26 |
| WO8905150 | 12/1988 | WIPO | A61K 37/02 |
| WO8900051 | 1/1989 | WIPO | A61K 43/00 |
| WO8902752 | 4/1989 | WIPO | A61K 49/00 |
| WO8907456 | 8/1989 | WIPO | A61K 49/02 |
| WO 89/11538 | 11/1989 | WIPO . | |
| WO8910759 | 11/1989 | WIPO | A61K 49/02 |
| WO8912625 | 12/1989 | WIPO | C07C 153/07 |
| WO8912680 | 12/1989 | WIPO | C12N 9/48 |
| WO9006767 | 12/1989 | WIPO | A61K 37/02 |
| WO9005733 | 5/1990 | WIPO | C07F 13/00 |
| WO9015808 | 12/1990 | WIPO | C07F 13/00 |
| WO9015818 | 12/1990 | WIPO | C07K 5/08 |
| WO9102547 | 3/1991 | WIPO | A61K 49/02 |
| WO9102750 | 3/1991 | WIPO | C07K 7/10 |
| WO9103262 | 3/1991 | WIPO | A61K 49/02 |
| WO9115515 | 4/1991 | WIPO | C07K 15/00 |
| WO9107991 | 6/1991 | WIPO | A61K 49/02 |
| WO9116931 | 11/1991 | WIPO | A61K 49/02 |
| WO9117765 | 11/1991 | WIPO | A61K 37/10 |
| WO92/05154 | 4/1992 | WIPO | C07D 213/40 |
| WO9207860 | 5/1992 | WIPO | C07F 13/00 |
| WO9213572 | 8/1992 | WIPO | A61K 49/02 |
| WO9216520 | 10/1992 | WIPO | C07D 341/00 |
| WO9219274 | 11/1992 | WIPO | A61K 49/02 |
| WO9321151 | 1/1993 | WIPO | C07C 337/06 |
| 9307170 | 4/1993 | WIPO . | |
| WO9307170 | 4/1993 | WIPO | C07K 7/56 |
| WO9310747 | 6/1993 | WIPO . | |
| WO9312819 | 7/1993 | WIPO | A61K 49/02 |
| WO9315770 | 8/1993 | WIPO | A61K 49/02 |
| WO9315771 | 8/1993 | WIPO | A61K 49/02 |
| WO9317719 | 9/1993 | WIPO | A61K 49/02 |
| WO9321962 | 11/1993 | WIPO | A61K 49/02 |
| WO9323085 | 11/1993 | WIPO | A61K 49/02 |
| 9411398 | 5/1994 | WIPO . | |
| 9422910 | 10/1994 | WIPO . | |
| 9500544 | 1/1995 | WIPO . | |

OTHER PUBLICATIONS

Koblik et al., *Seminars in Nuclear Medicine*, vol. 19, No. 3, pp. 221–237 (1989).

Macovski, A., *Medical Imaging Systems*, Information and Systems Science Series, pp. 145–172, Kailath, T., ed., Prentice–Hall, Inc., Englewood Cliffs, NJ (1983).

Pak et al., *J. Nucl. Med.*, vol. 30, No. 5, p. 793, 36th Ann. Meet. Soc. Nucl. Med. (1989).

Epps et al., *J. Nucl. Med.*, vol. 30, No. 5, p. 794, 36th Ann. Meet. Soc. Nucl. Med. (1989).

Pak et al., *J. Nucl. Med.*, vol. 30, No. 5, p. 934, 36th Ann. Meet. Soc. Nucl. Med. (1989).

Dean et al., *J. Nucl. Med.*, vol. 30, No. 5, p. 934, 36th Ann. Meet. Soc. Nucl. Med. (1989).

Chumpradit et al., *J. Med. Chem.*, vol. 34, pp. 877–883 (1991).

Seevers et al., *Chem. Rev.*, vol. 82, pp. 575–590 (1982).

Wilson et al., *J. Org. Chem*, vol. 51, pp. 4833–4836 (1986).

D'Souza et al., *Journal of Biological Chemistry*, vol. 265, No. 6, pp. 3440–3446 (1990).

Arora et al., *J. Med. Chem*, vol. 30, pp. 918–924 (1987).

Chumpradit et al., *J. Med. Chem*, vol. 32, pp. 1431–1435 (1989).

Eckelman et al., *Journal of Nuclear Medicine*, vol. 20, pp. 350–357 (1979).

Sekiya et al., *Chemical & Pharmaceutical Bulletin*, vol. 11, pp. 551–553 (1963).

Felder et al., *Helv. Chim. Acta*, vol. 48, No. 25, pp. 259–274 (1965).

Kulin et al., *Can. J. Chem.*, vol. 51, pp. 687–693 (1973).

Merkushev, *Synthesis*, pp. 923–937 (Dec. 1988).

Ellis et al., *Aust. J. Chem*, vol. 26, pp. 907–911 (1973).

Koch et al., *Chem. Ber.*, vol. 124, pp. 2091–2100 (1991).

Hartwell, *Organic Syntheses Collective*, vol. 3, pp. 185–189 (1955).

Lucas et al., *Organic Syntheses*, vol. 2, pp. 351–357 (1943).

Schiemann et al., *Organic Syntheses*, vol. 2, pp. 299–301 (1943).

Buck et al., *Organic Syntheses*, vol. 2, pp. 130–138 (1943).

Wolf et al., "Synthesis of Radiopharmaceuticals and Labeled Compounds Using Short–Lived Isotopes", in *Radiopharmaceuticals and Labeled Compounds*, vol. 1, pp. 345–381 (1973).

Wityak et al (1995). Bioorganic & Medicinal Chemistry, Letters, vol. 5, No. 18, pp. 2097–2100, Synthesis and Antiplatelet Activity of DMP 757 Analogs.

Mihara et al (1995). Tetrahedron Letters, vol. 36, No. 27, pp. 4837–4840. Efficient Preparation of Cyclic Peptide Mixtures by Solid Phase Synthesis and Cyclization Cleavage with Oxime Resin.

Jackson et al (1994). J. Am. Chem. Soc, vol. 116, pp. 3220–3230. "Template–Constrained Cyclic Peptides: Design of High–Affinity Ligands for GPIIIb/III9".

Bach et al (1994), vol. 116, pp. 3207–3219. "Structural Studies of a Family of High Affinity Ligands for GPIIb/IIIa".

RADIOLABELED PLATELET GPIIB/IIIA RECEPTOR ANTAGONISTS AS IMAGING AGENTS FOR THE DIAGNOSIS OF THROMBOEMBOLIC DISORDERS

CROSS-REFERENCE TO RELATED APPLICATIONS

The present application is a continuation-in-part of our application U.S. Ser. No. 08/040,336 filed Mar. 30, 1993, now abandoned the disclosure of which is hereby incorporated herein by reference.

FIELD OF THE INVENTION

This invention relates to novel radiopharmaceuticals that are radiolabeled cyclic compounds containing carbocyclic or heterocyclic ring systems; to methods of using said radiopharmaceuticals as imaging agents for the diagnosis of arterial and venous thrombi; to novel reagents for the preparation of said radiopharmaceuticals; and to kits comprising said reagents.

BACKGROUND OF THE INVENTION

The clinical recognition of venous and arterial thromboembolic disorders is unreliable, lacking in both sensitivity and specificity. In light of the potentially life threatening situation, the need to rapidly diagnose thromboembolic disorders using a non invasive method is an unmet clinical need. Platelet activation and resulting aggregation has been shown to be associated with various pathophysiological conditions including cardiovascular and cerebrovascular thromboembolic disorders such as unstable angina, myocardial infarction, transient ischemic attack, stroke, atherosclerosis and diabetes. The contribution of platelets to these disease processes stems from their ability to form aggregates, or platelet thrombi, especially in the arterial wall following injury. See generally, Fuster et al., JACC, Vol. 5, No. 6, pp. 175B–183B (1985); Rubenstein et al., Am. Heart J., Vol. 102, pp. 363–367 (1981); Hamm et al., J. Am. Coll. Cardiol., Vol. 10, pp. 998–1006 (1987); and Davies et al., Circulation, Vol. 73, pp. 418–427 (1986). Recently, the platelet glycoprotein IIb/IIIa complex (GPIIb/IIIa), has been identified as the membrane protein which mediates platelet aggregation by providing a common pathway for the known platelet agonists. See Philips et al., Cell, Vol. 65, pp. 359–362 (1991).

Platelet activation and aggregation is also thought to play a significant role in venous thromboembolic disorders such as venous thrombophlebitis and subsequent pulmonary emboli. It is also known that patients whose blood flows over artificial surfaces, such as prosthetic synthetic cardiac valves, are at risk for the development of platelet plugs, thrombi and emboli. See generally Fuster et al., JACC, Vol. 5, No. 6, pp. 175B–183B (1985); Rubenstein et al., Am. Heart J., Vol. 102, pp. 363–367 (1981); Hamm et al., J. Am. Coll. Cardiol., Vol. 10, pp. 998–1006 (1987); and Davies et al., Circulation, Vol. 73, pp. 418–427 (1986).

A suitable means for the non-invasive diagnosis and monitoring of patients with such potential thromboembolic disorders would be highly useful, and several attempts have been made to develop radiolabeled agents targeted to platelets for non-invasive radionuclide imaging. For example, experimental studies have been carried out with 99mTc monoclonal antifibrin antibody for diagnostic imaging of arterial thrombus. See Cerqueira et al., Circulation, Vol., 85, pp. 298–304 (1992). The authors report the potential utility of such agents in the imaging of freshly formed arterial thrombus. Monoclonal antibodies labeled with 131I and specific for activated human platelets have also been reported to have potential application in the diagnosis of arterial and venous thrombi. However, a reasonable ratio of thrombus to blood (target/background) was only attainable at 4 hours after the administration of the radiolabeled antibody. See Wu et al., Clin. Med. J., Vol. 105, pp. 533–559 (1992). The use of 125I, 131I, 99mTc, and 111In radiolabeled 7E3 monoclonal antiplatelet antibody in imaging thrombi has also been recently discussed. Coller et al., PCT Application Publication No. WO 89/11538 (1989). The radiolabeled 7E3 antibody has the disadvantage, however, of being a very large molecular weight molecule. Other researchers have employed enzymatically inactivated t-PA radioiodinated with 123I, 125I and 131I for the detection and the localization of thrombi. See Ordm et al., Circulation, Vol. 85, pp. 288–297 (1992). Still other approaches in the radiologic detection of thromoboembolisms are described, for example, in Koblik et al., Semin. Nucl. Med., Vol. 19, pp. 221–237 (1989).

Arterial and venous thrombus detection and localization is of critical importance in accurately diagnosing thromboembolic disorders and determining proper therapy. New and better radiolabeled agents for non-invasive radionuclide imaging to detect thrombi are needed. The present invention is directed to this important end.

SUMMARY OF THE INVENTION

This invention provides novel radiopharmaceuticals that are radiolabeled cyclic compounds containing carbocyclic or heterocyclic ring systems which act as antagonists of the platelet glycoprotein IIb/IIIa complex. It also provides methods of using said radiopharmaceuticals as imaging agents for the diagnosis of arterial and venous thrombi. It further provides novel reagents for the preparation of said radiopharmaceuticals. It further provides kits comprising said reagents.

DETAILED DESCRIPTION OF THE INVENTION

Figure 1A:
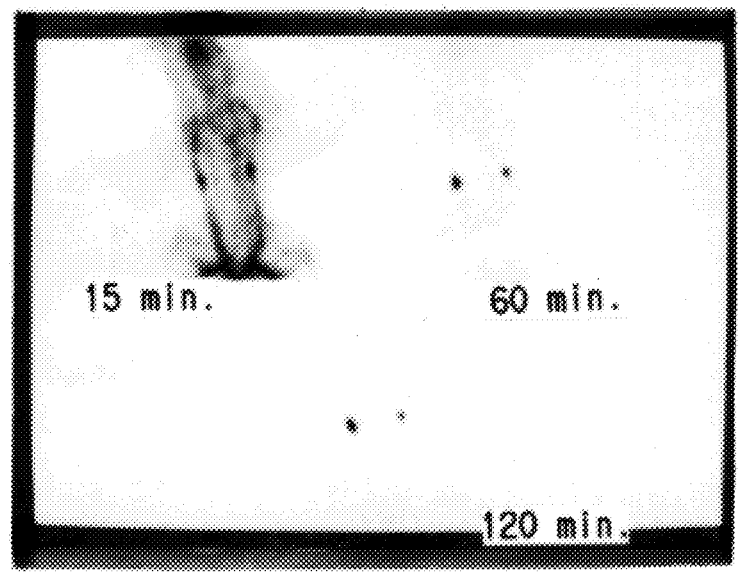
FIG 1a. Illustrated are typical images of the radiopharmaceutical compound of Example 12 administered at 1 mCi/Kg,i.v. in a canine deep venous thrombosis model. In this model thrombi were formed in the jugular veins during a period of stasis which was followed by reflow. The compounds were administered beginning at reflow. Depicted is the uptake in a rapidly growing venous thrombus at 15, 60 and 120 min post-administration.

[1] The present invention is directed to novel reagents for preparing a radiopharmaceutical of formulae:

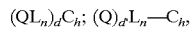

wherein, d is 1–3, d' is 2–20, $L_n$ is a linking group, $C_h$ is a metal chelator, and Q is a compound of formula (I):

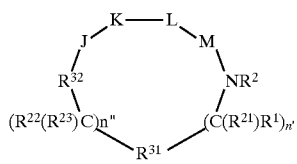

(I)

or a pharmaceutically acceptable salt or prodrug form thereof, wherein:

$R^{31}$ is a $C_6$–$C_{14}$ saturated, partially saturated, or aromatic carbocyclic ring system, substituted with 0–4 $R^{10}$ or $R^{10a}$, and optionally bearing a bond to $L_n$; a heterocyclic ring system, optionally substituted with 0–4 $R^{10}$ or $R^{10a}$, and optionally bearing a bond to $L_n$;

$R^{32}$ is selected from:
—C(=O)—;
—C(=S)—
—S(=O)$_2$—;
—S(=O)—;
—P(=Z)(ZR$^{13}$)—;

Z is S or O;

n" and n' are independently 0–2;

$R^1$ and $R^{22}$ are independently selected from the following groups:
hydrogen,
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
a bond to $L_n$;
aryl substituted with 0–2 $R^{12}$;
a 5–10-membered heterocyclic ring system containing 1–4 heteroatoms independently selected from N, S, and O, said heterocyclic ring being substituted with 0–2 $R^{12}$;
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy;

$R^1$ and $R^{21}$ can alternatively join to form a 3–7 membered carbocyclic ring substituted with 0–2 $R^{12}$;
when n' is 2, $R^1$ or $R^{21}$ can alternatively be taken together with $R^1$ or $R^{21}$ on an adjacent carbon atom to form a direct bond, thereby to form a double or triple bond between said carbon atoms;

$R^{21}$ and $R^{23}$ are independently selected from:
hydrogen;
$C_1$–$C_4$ alkyl, optionally substituted with 1–6 halogen;
benzyl;
$R^{22}$ and $R^{23}$ can alternatively join to form a 3–7 membered carbocyclic ring substituted with 0–2 $R^{12}$;
when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;
$R^1$ and $R^2$, where $R^{21}$ is H, can alternatively join to form a 5–8 membered carbocyclic ring substituted with 0–2 $R^{12}$;

$R^{11}$ is selected from one or more of the following:
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy,
$C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, $C_3$–$C_6$ cycloalkoxy, $C_1$–$C_4$ alkyl (alkyl being substituted with 1–5 groups selected independently from: —NR$^{13}$R$^{14}$, —CF$_3$, NO$_2$, —SO$_2$R$^{13a}$, or —S(=O)R$^{13a}$),
aryl substituted with 0–2 $R^{12}$,
a 5–10-membered heterocyclic ring system containing 1–4 heteroatoms independently selected from N, S, and O, said heterocyclic ring being substituted with 0–2 $R^{12}$;

$R^{12}$ is selected from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S(=O)R$^{13a}$);

$R^{13}$ is selected independently from: H, $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;

$R^{13a}$ is $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;
when two $R^{13}$ groups are bonded to a single N, said $R^{13}$ groups may alternatively be taken together to form —(CH$_2$)$_{2-5}$— or —(CH$_2$)O(CH$_2$)—;

$R^{14}$ is OH, H, $C_1$–$C_4$ alkyl, or benzyl;

$R^2$ is H or $C_1$–$C_8$ alkyl;

$R^{10}$ and $R^{10a}$ are selected independently from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)N(R$^{13}$)$^2$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl (including —C$_v$F$_w$ where v=1 to 3 and w=1 to (2v+1)), $C_1$–$C_4$ haloalkoxy, $C_1$–$C_4$ alkylcarbonyloxy, —OCH$_2$CO$_2$H, 2-(1-morpholino)

ethoxy, $C_1$–$C_4$ alkyl (alkyl being substituted with —N($R^{13}$)$_2$, —$CF_3$, $NO_2$, or —S(=O)$R^{13a}$);

J is β-Ala or an L-isomer or D-isomer amino acid of structure —N($R^3$)C($R^4$)($R^5$)C(=O)—, wherein:
$R^3$ is H or $C_1$–$C_8$ alkyl;
$R^4$ is H or $C_1$–$C_3$ alkyl;
$R^5$ is selected from:
hydrogen;
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
a bond to $L_n$;
aryl substituted with 0–2 $R^{12}$;
a 5–10-membered heterocyclic ring system containing 1–4 heteroatoms independently selected from N, S, or O, said heterocyclic ring being substituted with 0–2 $R^{12}$;
=O, F, Cl, Br, I, —$CF_3$, —CN, —$CO_2R^{13}$, —C(=O)$R^{13}$, —C(=O)N($R^{13}$)$_2$, —CHO, —$CH_2OR^{13}$, —OC(=O)$R^{13}$, —OC(=O)$OR^{13a}$, —$OR^{13}$, —OC(=O)N($R^{13}$)$_2$, —$NR^{13}$C(=O)$R^{13}$, —$NR^{14}$C(=O)$OR^{13a}$, —$NR^{13}$C(=O)N($R^{13}$)$_2$, —$NR^{14}SO_2$N($R^{13}$)$_2$, —$NR^{14}SO_2R^{13a}$, —$SO_3H$, —$SO_2R^{13a}$, —$SR^{13}$, —S(=O)$R^{13a}$, —$SO_2$N($R^{13}$)$_2$, —N($R^{13}$)$_2$, —NHC(=NH)$NHR^{13}$, —C(=NH)$NHR^{13}$, =$NOR^{13}$, $NO_2$, —C(=O)$NHOR^{13}$, —C(=O)$NHNR^{13}R^{13a}$, =$NOR^{13}$, —B($R^{34}$)($R^{35}$), —$OCH_2CO_2H$, 2-(1-morpholino)ethoxy, —SC(=NH)$NHR^{13}$, $N_3$, —Si($CH_3$)$_3$, ($C_1$–$C_5$ alkyl)$NHR^{16}$;
—($C_0$–$C_6$ alkyl)X;

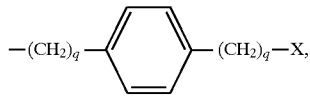

where q is independently 0,1;

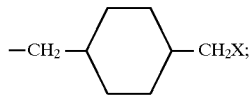

—($CH_2$)$_m$S(O)$_{p'}$($CH_2$)$_2$X, where m=1,2 and p'=0–2; wherein X is defined below; and
$R^3$ and $R^4$ may also be taken together to form

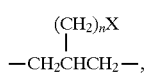

where
n=0,1 and X is

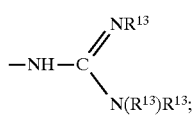

$R^3$ and $R^5$ can alternatively be taken together to form —($CH_2$)$_t$— or —$CH_2$S(O)$_{p'}$C($CH_3$)$_2$—, where t=2–4 and p'=0–2; or
$R^4$ and $R^5$ can alternatively be taken together to form —($CH_2$)$_u$—, where u=2–5;
$R^{16}$ is selected from:

an amine protecting group;
1–2 amino acids;
1–2 amino acids substituted with an amine protecting group;

K is a D-isomer or L-isomer amino acid of structure —N($R^6$)CH($R^7$)C(=O)—, wherein:
$R^6$ is H or $C_1$–$C_8$ alkyl;
$R^7$ is selected from:
—($C_1$–$C_7$ alkyl)X;

wherein each q is independently 0–2 and substitution on the phenyl is at the 3 or 4 position;

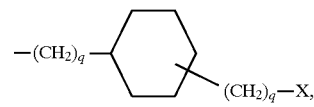

wherein each q is independently 0–2 and substitution on the cyclohexyl is at the 3 or 4 position;

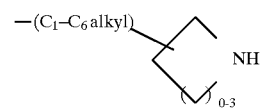

—($CH_2$)$_m$O—($C_1$–$C_4$ alkyl)-X, where m=1 or 2;
—($CH_2$)$_m$S(O)$_{p'}$—($C_1$–$C_4$ alkyl)-X, where m=1 or 2 and p'=0–2; and X is selected from:

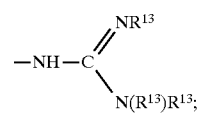

—N($R^{13}$)$R^{13}$; —C(=NH)($NH_2$); —SC(=NH)—$NH_2$;
—NH—C(=NH)(NHCN); —NH—C(=NCN)($NH_2$);
—NH—C(=N—$OR^{13}$)($NH_2$);

$R^6$ and $R^7$ can alternatively be taken together to form

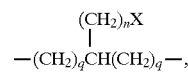

wherein each q is independently 1 or 2 and wherein n=0 or 1 and X is —$NH_2$ or

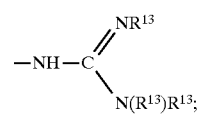

L is —Y($CH_2$)$_v$C(=O)—, wherein:
Y is NH, N($C_1$–$C_3$ alkyl), O, or S; and v=1 or 2;

M is a D-isomer or L-isomer amino acid of structure

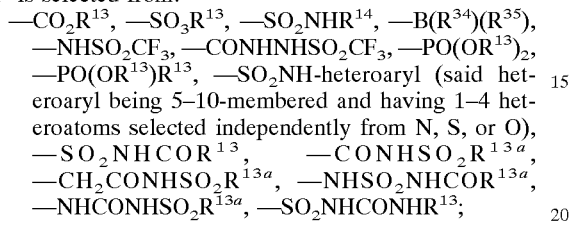

wherein:
q' is 0–2;
$R^{17}$ is H, $C_1$–$C_3$ alkyl;
$R^8$ is selected from:
—$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$;

$R^{34}$ and $R^{35}$ are independently selected from:
—OH,
—F,
—$N(R^{13})_2$, or
$C_1$–$C_8$-alkoxy;
$R^{34}$ and $R^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O.

[2] Included in the present invention are those reagents in [1] above, wherein:
$R^{31}$ is bonded to $(C(R^{23})R^{22})_{n''}$ and $(C(R^{21})R^1)_{n'}$ at 2 different atoms on said carbocyclic ring.

[3] Included in the present invention are those reagents in [1] above, wherein:
n" is 0 and n' is 0;
n" is 0 and n' is 1;
n" is 0 and n' is 2;
n" is 1 and n' is 0;
n" is 1 and n' is 1;
n" is 1 and n' is 2;
n" is 2 and n' is 0;
n" is 2 and n' is 1; or
n" is 2 and n' is 2.

[4] Included in the present invention are those reagents in [1] above, wherein:
wherein $R^6$ is methyl, ethyl, or propyl.

[5] Included in the present invention are those reagents in [1] above, wherein:
$R^{32}$ is selected from:
—C(=O)—;
—C(=S)—
—S(=O)$_2$—;
$R^1$ and $R^{22}$ are independently selected from the following groups:
hydrogen,
$C_1$–$C_8$ alkyl substituted with 0–2 $R^{11}$,
$C_2$–$C_8$ alkenyl substituted with 0–2 $R^{11}$,
$C_2$–$C_8$ alkynyl substituted with 0–2 $R^{11}$,
$C_3$–$C_8$ cycloalkyl substituted with 0–2 $R^{11}$,
$C_6$–$C_{10}$ bicycloalkyl substituted with 0–2 $R^{11}$;
a bond to $L_n$;
aryl substituted with 0–2 $R^{12}$;
a 5–10-membered heterocyclic ring system containing 1–4 heteroatoms independently selected from N, S, or O, said heterocyclic ring being substituted with 0–2 $R^{12}$;
=O, F, Cl, Br, I, —$CF_3$, —CN, —$CO_2R^{13}$, —C(=O)$R^{13}$, —C(=O)N($R^{13}$)$_2$, —CHO, —$CH_2OR^{13}$, —OC(=O)$R^{13}$, —OC(=O)$OR^{13a}$, —$OR^{13}$, —OC(=O)N($R^{13}$)$_2$, —$NR^{13}$C(=O)$R^{13}$, —$NR^{14}$C(=O)$OR^{13a}$, —$NR^{13}$C(=O)N($R^{13}$)$_2$, —$NR^{14}SO_2N(R^{13})_2$, —$NR^{14}SO_2R^{13a}$, —$SO_3H$, —$SO_2R^{13a}$, —$SR^{13}$, —S(=O)$R^{13a}$, —$SO_2N(R^{13})_2$, —N($R^{13}$)$_2$, —NHC(=NH)NHR$^{13}$, —C(=NH)NHR$^{13}$, $NO_2$;

$R^1$ and $R^{21}$ can alternatively join to form a 5–7 membered carbocyclic ring substituted with 0–2 $R^{12}$;
when n' is 2, $R^1$ or $R^{21}$ can alternatively be taken together with $R^1$ or $R^{21}$ on an adjacent carbon atom to form a direct bond, thereby to form a double or triple bond between said carbon atoms;

$R^{22}$ and $R^{23}$ can alternatively join to form a 3–7 membered carbocyclic ring substituted with 0–2 $R^{12}$;
when n" is 2, $R^{22}$ or $R^{23}$ can alternatively be taken together with $R^{22}$ or $R^{23}$ on an adjacent carbon atom to form a direct bond, thereby to form a double or triple bond between said carbon atoms;

$R^1$ and $R^2$, where $R^{21}$ is H, can alternatively join to form a 5–8 membered carbocyclic ring substituted with 0–2 $R^{12}$;

$R^{11}$ is selected from one or more of the following:
=O, F, Cl, Br, I, —$CF_3$, —CN, —$CO_2R^{13}$, —C(=O)$R^{13}$, —C(=O)N($R^{13}$)$_2$, —CHO, —$CH_2OR^{13}$, —OC(=O)$R^{13}$, —OC(=O)$OR^{13a}$, —$OR^{13}$, —OC(=O)N($R^{13}$)$_2$, —$NR^{13}$C(=O)$R^{13}$, —$NR^{14}$C(=O)$OR^{13a}$, —$NR^{13}$C(=O)N($R^{13}$)$_2$, —$NR^{14}SO_2N(R^{13})_2$, —$NR^{14}SO_2R^{13a}$, —$SO_3H$, —$SO_2R^{13a}$, —$SR^{13}$, —S(=O)$R^{13a}$, —$SO_2N(R^{13})_2$, —N($R^{13}$)$_2$, —NHC(=NH)NHR$^{13}$, —C(=NH)NHR$^{13}$, =NOR$^{13}$, $NO_2$;
$C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, $C_1$–$C_4$ alkyl (substituted with —$NR^{13}R^{14}$, —$CF_3$, $NO_2$, —$SO_2R^{13}$, or —S(=O)$R^{13a}$)
aryl substituted with 0–2 $R^{12}$,
a 5–10-membered heterocyclic ring system containing 1–4 heteroatoms independently selected from N, S, or O, said heterocyclic ring being substituted with 0–2 $R^{12}$;

$R^3$ is H or $CH_3$;
$R^5$ is H, $C_1$–$C_8$ alkyl, $C_3$–$C_6$ cycloalkyl, $C_3$–$C_6$ cycloalkylmethyl, $C_3$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, $(CH_2)_sNHR^{16}$, where s=3–5;
a bond to $L_n$;
$R^3$ and $R^5$ can alternatively be taken together to form —$(CH_2)_t$— (t=2–4) or —$CH_2SC(CH_3)_2$—; or
$R^7$ is selected from:

—(C$_1$–C$_7$ alkyl)X;

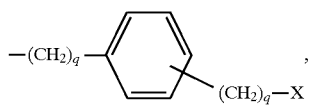

wherein
each q is
independently 0–2 and substitution on the phenyl is at the 3 or 4 position;

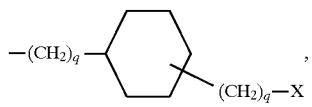

wherein each q is independently 0–2 and substitution on the cyclohexyl is at the 3 or 4 position;

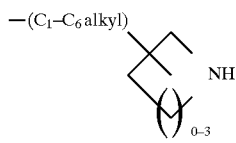

—(CH$_2$)$_m$O—(C$_1$–C$_4$ alkyl)-X, where m=1 or 2;
—(CH$_2$)$_m$S—(C$_1$–C$_4$ alkyl)-X, where m=1 or 2; and
X is selected from:
—NH—C(=NH)(NH$_2$), —NHR$^{13}$, —C(=NH)(NH$_2$),
—SC(NH)—NH$_2$;
R$^6$ and R$^7$ can alternatively be taken together to form

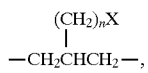

where
n=0 or 1 and X is —NH$_2$ or —NH—C(=NH)(NH$_2$);
L is —Y(CH$_2$)$_v$C(=O)—, wherein:
Y is NH, N(C$_1$–C$_3$ alkyl), O, or S; and v=1 or 2;
M is a D-isomer or L-isomer amino acid of structure

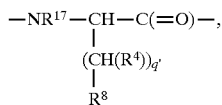

wherein:
q' is 0–2;
R$^{17}$ is H, C$_1$–C$_3$ alkyl;
R$^8$ is selected from:
—CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$;
R$^{34}$ and R$^{35}$ are independently selected from:
—OH,
—F,
—NR$^{13}$R$^{14}$, or
C$_1$–C$_8$-alkoxy;
R$^{34}$ and R$^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O.

[6] Included in the present invention are those reagents in [1] above, wherein:
R$^{31}$ is selected from the group consisting of:
(a) a 6 membered saturated, partially saturated or aromatic carbocyclic ring substituted with 0–3 R$^{10}$ or R$^{10a}$, and optionally bearing a bond to L$_n$;
(b) a 8–11 membered saturated, partially saturated, or aromatic fused bicyclic carbocyclic ring substituted with 0–3 R$^{10}$ or R$^{10a}$, and optionally bearing a bond to L$_n$; or
(c) a 14 membered saturated, partially saturated, or aromatic fused tricyclic carbocyclic ring substituted with 0–3 R$^{10}$ or R$^{10a}$, and optionally bearing a bond to L$_n$.

[7] Included in the present invention are those reagents in [1] above, wherein:
R$^{31}$ is selected from the group consisting of:
(a) a 6 membered saturated, partially saturated, or aromatic carbocyclic ring of formulae:

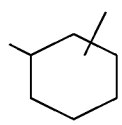

wherein any of the bonds forming the carbocyclic ring may be a single or double bond, and wherein said carbocyclic ring is substituted with 0–3 R$^{10}$, and optionally bears a bond to L$_n$;
(b) a 10 membered saturated, partially saturated, or aromatic bicyclic carbocyclic ring of formula:

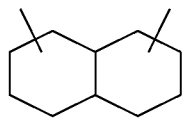

wherein any of the bonds forming the carbocyclic ring may be a single or double bond, wherein said carbocyclic ring is substituted independently with 0–4 R$^{10}$, and optionally bears a bond to L$_n$;
(c) a 9 membered saturated, partially saturated, or aromatic bicyclic carbocyclic ring of formula:

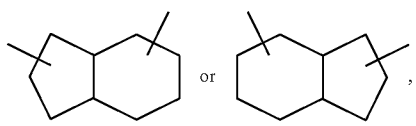

wherein any of the bonds forming the carbocyclic ring may be a single or double bond, wherein said carbocyclic ring is substituted independently with 0–4 $R^{10}$, and optionally bears a bond to $L_n$.

[8] Included in the present invention are those reagents in [1] above, wherein:

$R^{31}$ is selected from (the dashed bond may be a single or double bond):

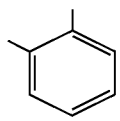

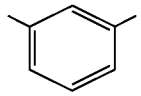

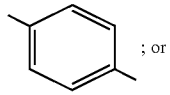; or

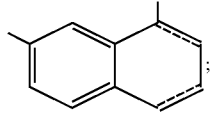

wherein $R^{31}$ may be independently substituted with 0–3 $R^{10}$ or $R^{10a}$, and optionally bears a bond to $L_n$;
n" is 0 or 1; and
n' is 0–2.

[9] Included in the present invention are those reagents in [1] above, wherein:

$R^1$ and $R^{22}$ are independently selected from:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —C(=O)NHOR$^{13a}$, —C(=O)NH(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —($C_1$–$C_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S(=O)R$^{13a}$).

[10] Included in the present invention are those reagents in [1] above, wherein:

$R^{31}$ is selected from:

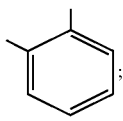

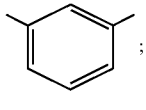

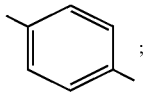

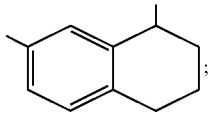

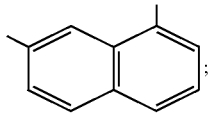

wherein $R^{31}$ may be independently substituted with 0–3 $R^{10}$ or $R^{10a}$, and may optionally bear a bond to $L_n$;
$R^{32}$ is —C(=O)—;
n" is 0 or 1;
n' is 0–2;
$R^1$ and $R^{22}$ are independently selected from H, $C_1$–$C_4$ alkyl, phenyl, benzyl, phenyl—($C_2$–$C_4$)alkyl, $C_1$–$C_4$ alkoxy; and a bond to $L_n$;
$R^{21}$ and $R^{23}$ are independently H or $C_1$–$C_4$ alkyl;
$R^2$ is H or $C_1$–$C_8$ alkyl;
$R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;
$R^{13a}$ is $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;
when two $R^{13}$ groups are bonded to a single N, said $R^{13}$ groups may alternatively be taken together to form —(CH$_2$)$_{2-5}$— or —(CH$_2$)O(CH$_2$)—;
$R^{14}$ is OH, H, $C_1$–$C_4$ alkyl, or benzyl;
$R^{10}$ and $R^{10a}$ are selected independently from: $C_1$–$C_5$ alkyl, phenyl, halogen, or $C_1$–$C_4$ alkoxy;
J is β-Ala or an L-isomer or D-isomer amino acid of structure —N(R$^3$)C(R$^4$)(R$^5$)C(=O)—, wherein:
$R^3$ is H or CH$_3$;
$R^4$ is H or $C_1$–$C_3$ alkyl;
$R^5$ is H, $C_1$–$C_8$ alkyl, $C_3$–$C_6$ cycloalkyl, $C_3$–$C_6$ cycloalkylmethyl, $C_3$–$C_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, —(CH$_2$)$_s$NHC(=NH)(NH$_2$), —(CH$_2$)$_s$NHR$^{16}$, where s=3–5; and a bond to $L_n$; or
$R^3$ and $R^5$ can alternatively be taken together to form —(CH$_2$)$_t$— (t=2–4) or —CH$_2$SC(CH$_3$)$_2$—; or
$R^4$ and $R^5$ can alternatively be taken together to form —(CH$_2$)$_u$—, where u=2–5;
$R^{16}$ is selected from:
an amine protecting group;

1–2 amino acids; or
1–2 amino acids substituted with an amine protecting group;

K is an L-isomer amino acid of structure —N(R$^6$)CH(R$^7$)C(=O)—, wherein:
R$^6$ is H or C$_1$–C$_8$ alkyl;
R$^7$ is

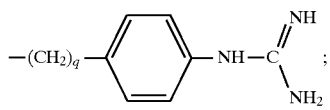

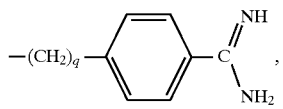

where q=0 or 1;
—(CH$_2$)$_r$X, where r=3–6;

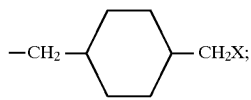

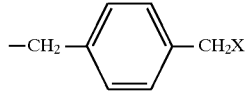

—(CH$_2$)$_m$S(CH$_2$)$_2$X, where m=1 or 2;
—(C$_3$–C$_7$ alkyl)—NH—(C$_1$–C$_6$ alkyl);

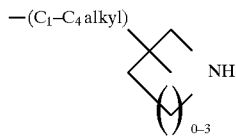

—(CH$_2$)$_m$—O—(C$_1$–C$_4$ alkyl)—NH—(C$_1$–C$_6$ alkyl), where m=1 or 2;
—(CH$_2$)$_m$—S—(C$_1$–C$_4$ alkyl)—NH—(C$_1$–C$_6$ alkyl), where m=1 or 2; and X is —NH$_2$ or —NHC(=NH)(NH$_2$); or
R$^6$ and R$^7$ can alternatively be taken together to form

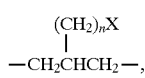

where n=0 or 1 and X is —NH$_2$ or —NHC(=NH)(NH$_2$);

L is —Y(CH$_2$)$_v$C(=O)—, wherein:
Y is NH, O, or S; and v=1 or 2;

M is a D-isomer or L-isomer amino acid of structure

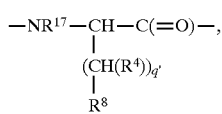

wherein:
q' is 0–2;
R$^{17}$ is H, C$_1$–C$_3$ alkyl;
R$^8$ is selected from:

—CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$.

[11] Included in the present invention are those reagents in [1] above, wherein Q is a 1,3-disubstituted phenyl compound of the formula (II):

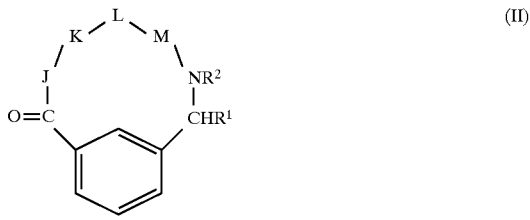

wherein:

the shown phenyl ring in formula (II) may be substituted with 0–3 R$^{10}$, and may optionally bear a bond to L$_n$;

R$^{10}$ is selected independently from: C$_1$–C$_5$ alkyl, phenyl, halogen, or C$_1$–C$_4$ alkoxy;

R$^1$ is H, C$_1$–C$_4$ alkyl, phenyl, phenyl—(C$_1$–C$_4$)alkyl, or a bond to L$_n$;

R$^2$ is H or methyl;

R$^{13}$ is selected independently from: H, C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

R$^{13a}$ is C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

when two R$^{13}$ groups are bonded to a single N, said R$^{13}$ groups may alternatively be taken together to form —(CH$_2$)$_{2-5}$— or —(CH$_2$)O(CH$_2$)—;

R$^{14}$ is OH, H, C$_1$–C$_4$ alkyl, or benzyl;

J is β-Ala or an L-isomer or D-isomer amino acid of structure —N(R$^3$)C(R$^4$)(R$^5$)C(=O)—, wherein:
R$^3$ is H or CH$_3$;
R$^4$ is H or C$_1$–C$_3$ alkyl;
R$^5$ is H, C$_1$–C$_8$ alkyl, C$_3$–C$_6$ cycloalkyl, C$_3$–C$_6$ cycloalkylmethyl, C$_1$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, —(CH$_2$)$_s$NHC(=NH)(NH$_2$), —(CH$_2$)$_s$NHR$^{16}$, where s=3–5, or a bond to L$_n$;

R$^3$ and R$^5$ can alternatively be taken together to form —CH$_2$CH$_2$CH$_2$—; or
R$^4$ and R$^5$ can alternatively be taken together to form —(CH$_2$)$_u$—, where u=2–5;

R$^{16}$ is selected from:
an amine protecting group;
1–2 amino acids; or
1–2 amino acids substituted with an amine protecting group;

K is an L-isomer amino acid of structure —N(R$^6$)CH(R$^7$)C(=O)—, wherein:
R$^6$ is H or C$_1$–C$_8$ alkyl;

$R^7$ is:

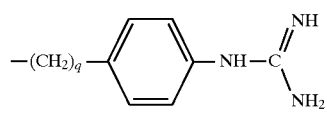

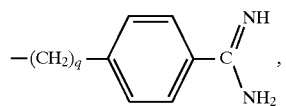

where q=0 or 1;
—$(CH_2)_rX$, where r=3–6;

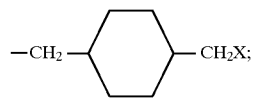

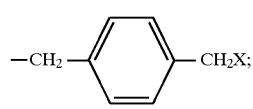

—$(CH_2)_mS(CH_2)_2X$, where m=1 or 2;
—$(C_3$–$C_7$ alkyl)—NH—$(C_1$–$C_6$ alkyl)

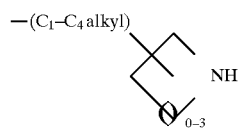

—$(CH_2)_m$—O—$(C_1$–$C_4$ alkyl)—NH—$(C_1$–$C_6$ alkyl),
where m=1 or 2;
—$(CH_2)_m$—S—$(C_1$–$C_4$ alkyl)—NH—$(C_1$–$C_6$ alkyl),
where m=1 or 2; and X is —$NH_2$ or —NHC(=NH)($NH_2$), provided that X is not —$NH_2$ when r=4; or
$R^6$ and R7 are alternatively be taken together to form

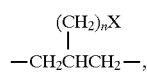

where n=0, 1 and X is —$NH_2$ or —NHC(=NH)($NH_2$);
L is —$Y(CH_2)_vC(=O)$—, wherein:
Y is NH, O, or S; and v=1,2;
M is a D-isomer or L-isomer amino acid of structure

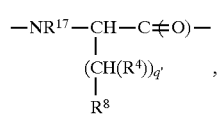

wherein:
q' is 0–2;
$R^{17}$ is H, $C_1$–$C_3$ alkyl;
$R^8$ is selected from:
—$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$.

[12] Included in the present invention are those reagents in [1] above, wherein Q is 1,3-disubstituted phenyl compound of the formula (II):

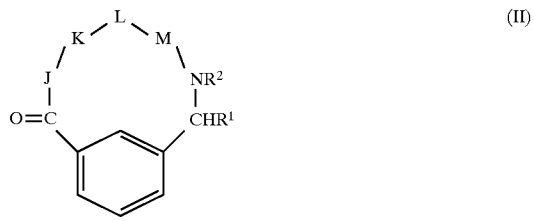

wherein:
the phenyl ring in formula (II) may be substituted with 0–3 $R^{10}$ or $R^{10a}$;
$R^{10}$ or $R^{10a}$ are selected independently from: H, $C_1$–$C_8$ alkyl, phenyl, halogen, or $C_1$–$C_4$ alkoxy;
$R^1$ is H, $C_1$–$C_4$ alkyl, phenyl, benzyl, or phenyl—$(C_2$–$C_4)$ alkyl;
$R^2$ is H or methyl;
$R^{13}$ is selected independently from: H, $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;
J is β-Ala or an L-isomer or D-isomer amino acid of structure —$N(R^3)C(R^4)(R^5)C(=O)$—, wherein:
$R^3$ is H or $CH_3$;
$R^4$ is H;
$R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, $(CH_2)_sNHR_{16}$, where s=3–5; or a bond to $L_n$;
$R^3$ and $R^5$ can alternatively be taken together to form —$CH_2CH_2CH_2$—;
$R^{16}$ is selected from:
an amine protecting group;
1–2 amino acids;
1–2 amino acids substituted with an amine protecting group;
K is an L-isomer amino acid of structure —$N(R^6)CH(R^7)C(=O)$—, wherein:
$R^6$ is H or $C_3$–$C_8$ alkyl;
$R^7$ is

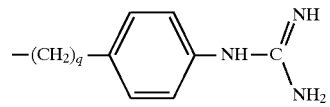

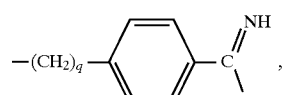

where q=0 or 1;
—$(CH_2)_rX$, where r=3–6;

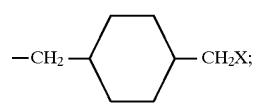

-continued

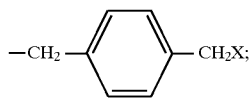

—$(CH_2)_mS(CH_2)_2X$, where m=1 or 2;
—$(C_4–C_7$ alkyl)—NH—$(C_1–C_6$ alkyl)

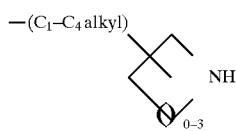

—$(CH_2)_m$—O—$(C_1–C_4$ alkyl)—NH—$(C_1–C_6$ alkyl), where m=1 or 2;
—$(CH_2)$—S—$(C_1–C_4$ alkyl)—NH—$(C_1–C_6$ alkyl), where m=1 or 2; and X is —$NH_2$ or —$NHC(=NH)(NH_2)$, provided that X is not —$NH_2$ when r=4; or L is —$YCH_2C(=O)$—, wherein:
Y is NH or O;

M is a D-isomer or L-isomer amino acid of structure

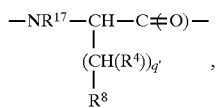

wherein:
q' is 1;
$R^{17}$ is H, $C_1–C_3$ alkyl;
$R^8$ is selected from:
—$CO_2H$ or —$SO_3R^{13}$.

[13] Included in the present invention are those reagents in [1] above, wherein:
the phenyl ring in formula (II) bears a bond to $L_n$, and may be further substituted with 0–2 $R^{10}$ or $R^{10a}$;
$R^{10}$ or $R^{10a}$ are selected independently from: H, $C_1–C_8$ alkyl, phenyl, halogen, or $C_1–C_4$ alkoxy;
$R^1$ is H;
$R^2$ is H;
J is β-Ala or an L-isomer or D-isomer amino acid of formula —$N(R^3)CH(R^5)C(=O)$—, wherein:
$R^3$ is H and $R^5$ is H, $CH_3$, $CH_2CH_3$, $CH(CH_3)_2$, $CH(CH_3)CH_2CH_3$, $CH_2CH_2CH_3$, $CH_2CH_2CH_2CH_3$, $CH_2CH_2SCH_3$, $CH_2CH(CH_3)_2$, $(CH_2)_4NH_2$, $(C_3–C_5$ alkyl)$NHR^{16}$; or
$R^3$ is $CH_3$ and $R^5$ is H; or
$R^3$ and $R^5$ can alternatively be taken together to form —$CH_2CH_2CH_2$—;
$R^{16}$ is selected from:
an amine protecting group;
1–2 amino acids;
1–2 amino acids substituted with an amine protecting group;
K is an L-isomer amino acid of formula —$N(CH_3)CH(R^7)C(=O)$—, wherein:
$R^7$ is —$(CH_2)_3NHC(=NH)(NH_2)$;
L is —$NHCH_2C(=O)$—; and M is a D-isomer or L-isomer amino acid of structure

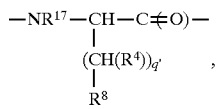

wherein:
q' is 1;
$R^4$ is H or $CH_3$;
$R^{17}$ is H;
$R^8$ is
—$CO_2H$;
—$SO_3H$.

[14] Included in the present invention are those reagents in [1] above, wherein:
the phenyl ring in formula (II) bears a bond to $L_n$;
$R^1$ and $R^2$ are independently selected from H, methyl;
J is selected from D-Val, D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala, $N^ε$-p-azidobenzoyl-D-Lys, $N^ε$-p-benzoylbenzoyl-D-Lys, $N^ε$-tryptophanyl-D-Lys, $N^ε$-o-benzylbenzoyl-D-Lys, $N^ε$-p-acetylbenzoyl-D-Lys, $N^ε$-dansyl-D-Lys, $N^ε$-glycyl-D-Lys, $N^ε$-glycyl-p-benzoylbenzoyl-D-Lys, $N^ε$-p-phenylbenzoyl-D-Lys, $N^ε$-m-benzoylbenzoyl-D-Lys, $N^ε$-o-benzoylbenzoyl-D-Lys;
K is selected from NMeArg, Arg;
L is selected from Gly, β-Ala, Ala;
M is selected from Asp; αMeAsp; βMeAsp; NMeAsp; D-Asp.

[15] Included in the present invention are those reagents in [1] above, wherein:
$R^{31}$ is a phenyl ring and bears a bond to $L_n$;
$R^1$ and $R^2$ are independently selected from H, methyl;
J is selected from: D-Val, D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala;
K is selected from NMeArg;
L is Gly;
M is selected from Asp; αMeAsp; βMeAsp; NMeAsp; D-Asp.

[16] Included in the present invention are those reagents in [1]–[15] above, wherein $C_h$ is selected from the group:

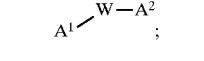

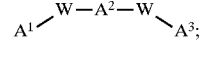

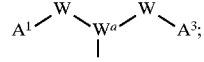

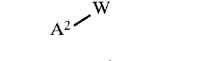

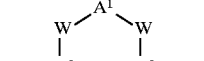

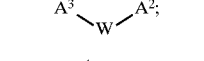

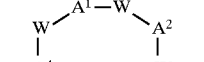

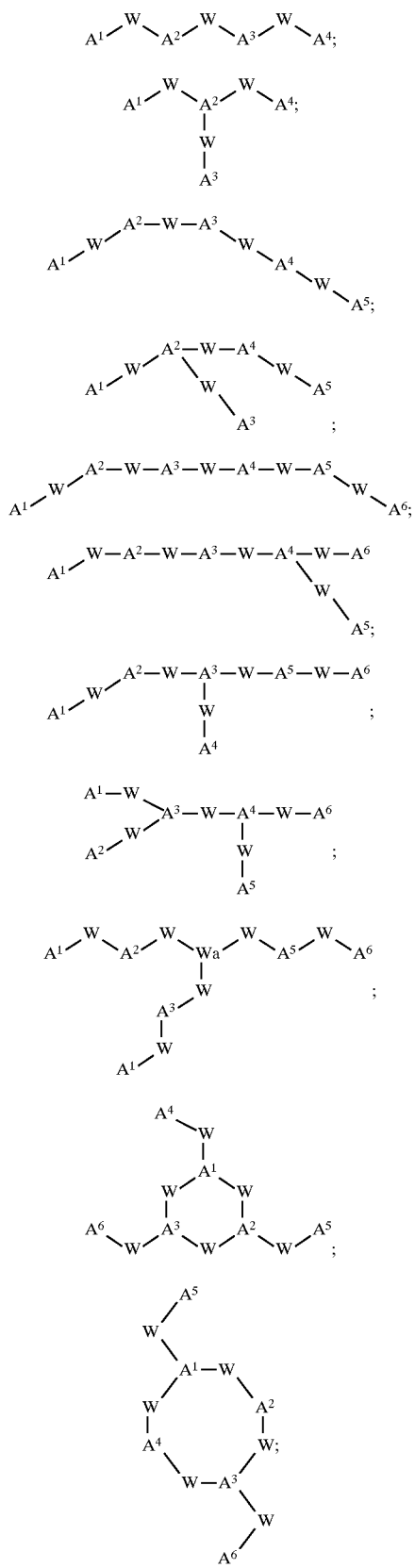
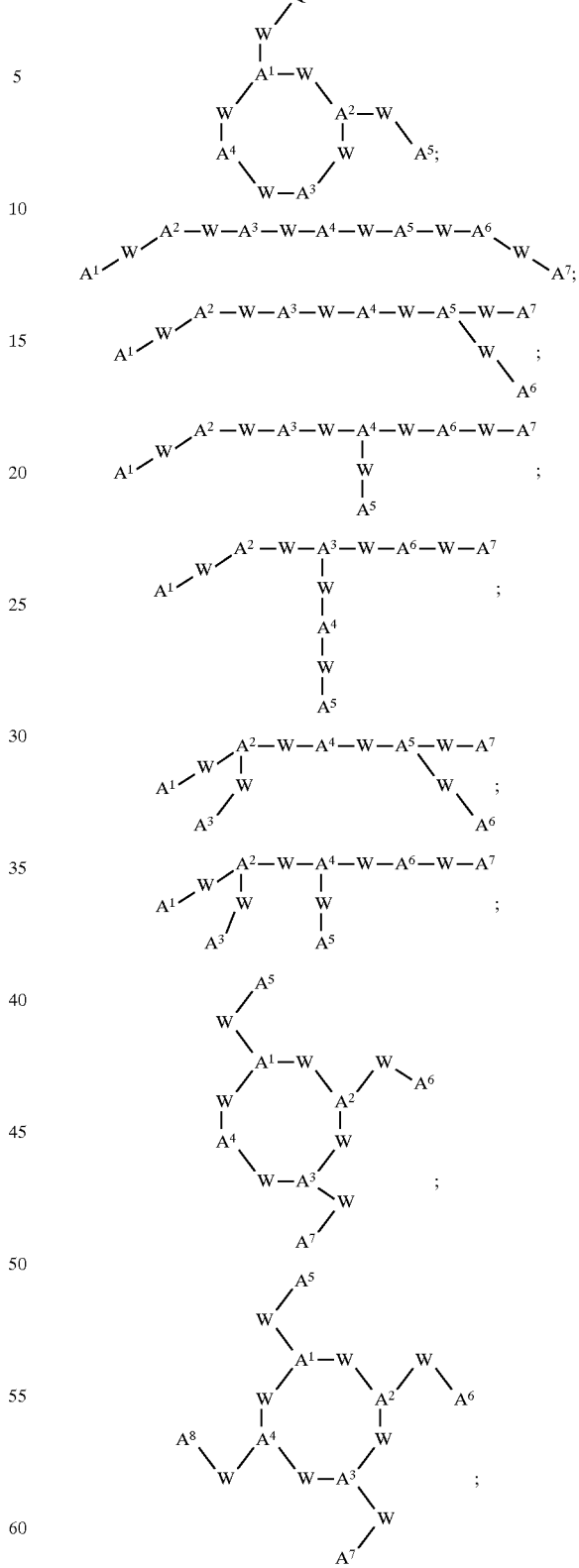
wherein:
$A^1$, $A^2$, $A^3$, $A^4$, $A^5$, $A^6$, $A^7$ and $A^8$ are independently selected at each occurrence from the group: $NR^{40}R^{41}$, S, SH, S(Pg), O, OH, $PR^{42}R^{43}$, $P(O)R^{42}R^{43}$, $P(S)R^{42}R^{43}$, $P(NR^{44})R^{42}R^{43}$;

W is a bond, CH, or a spacer group selected from the group: $C_1$–$C_{10}$ alkyl substituted with 0–3 $R^{52}$, aryl substituted with 0–3 $R^{52}$, cycloaklyl substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$W^a$ is a $C_1$–$C_{10}$ alkyl group or a $C_3$–$C_{14}$ carbocycle;

$R^{40}$, $R^{41}$, $R^{42}$, $R^{43}$, and $R^{44}$ are each independently selected from the group: a bond to $L_n$, hydrogen, $C_1$–$C_{10}$ alkyl substituted with 0–3 $R^{52}$, aryl substituted with 0–3 $R^{52}$, cycloaklyl substituted with 0–3 $R^{52}$, aralkyl substituted with 0–3 $R^{52}$, alkaryl substituted with 0–3 $R^{52}$ and an electron, provided that when one of $R^{40}$ or $R^{41}$ is an electron, then the other is also an electron, and provided that when one of $R^{42}$ or $R^{43}$ is an electron, then the other is also an electron; additionally, $R^{40}$ and $R^{41}$ may combine to form $=C(C_1$–$C_3$ alkyl)($C_1$–$C_3$ alkyl);

$R^{52}$ is independently selected at each occurrence from the group: a bond to $L_n$, =O, F, Cl, Br, I, —$CF_3$, —CN, —$CO_2R^{53}$, —C(=O)$R^{53}$, —C(=O)N($R^{53}$)$_2$, —CHO, —$CH_2OR^{53}$, —OC(=O)$R^{53}$, —OC(=O)$OR^{53a}$, —$OR^{53}$, —OC(=O)N($R^{53}$)$_2$, —$NR^{53}$C(=O)$R^{53}$, —$NR^{54}$C(=O)$OR^{53a}$, —$NR^{53}$C(=O)N($R^{53}$)$_2$, —$NR^{54}SO_2$N($R^{53}$)$_2$, —$NR^{54}SO_2R^{53a}$, —$SO_3H$, —$SO_2R^{53a}$, —$SR^{53}$, —S(=O)$R^{53a}$, —$SO_2$N($R^{53}$)$_2$, —N($R^{53}$)$_2$, —NHC(=NH)$NHR^{53}$, —C(=NH)$NHR^{53}$, =$NOR^{53}$, $NO_2$, —C(=O)$NHOR^{53}$, —C(=O)$NHNR^{53}R^{53a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{53}$, a 5–10-membered heterocyclic ring system containing 1–4 heteroatoms independently selected from N, S, and O;

$R^{53}$, $R^{53a}$, and $R^{54}$ are independently selected at each occurrence from the group: a bond to $L_n$, $C_1$–$C_6$ alkyl, phenyl, benzyl, $C_1$–$C_6$ alkoxy, halide, nitro, cyano, and trifluoromethyl; and Pg is a thiol protecting group capable of being displaced upon reaction with a radionuclide.

[17] Included in the present invention are those reagents in [1]–[15] above, wherein $C_h$ is selected from the group:

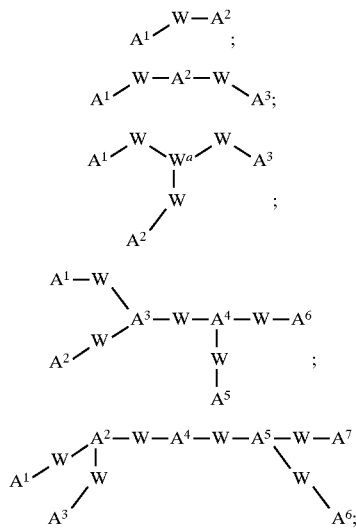

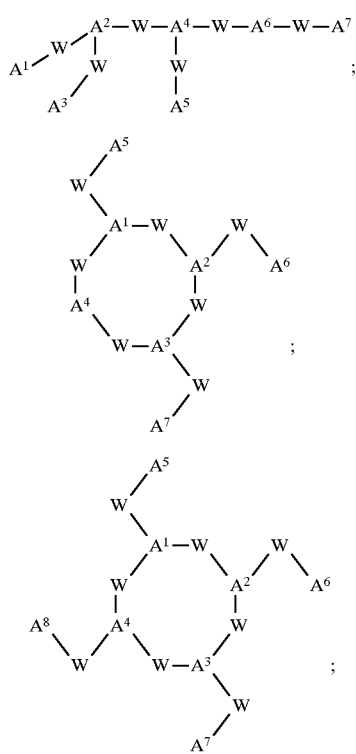

wherein:

$A^1$, $A^2$, $A^3$, $A^4$, $A^5$, $A^6$, $A^7$ and $A^8$ are independently selected at each occurrence from the group: $NR^{40}R^{41}$, S, SH, S(Pg), OH;

W is a bond, CH, or a spacer group selected from the group: $C_1$–$C_3$ alkyl substituted with 0–3 $R^{52}$;

$W^a$ is a methylene group or a $C_3$–$C_6$ carbocycle;

$R^{40}$, $R^{41}$, $R^{42}$, $R^{43}$, and $R^{44}$ are each independently selected from the group: a bond to $L_n$, hydrogen, $C_1$–$C_{10}$ alkyl substituted with 0–3 $R^{52}$, heterocycle substituted with 0–3 $R^t$ and an electron, provided that when one of $R^{40}$ or $R^{41}$ is an electron, then the other is also an electron, and provided that when one of $R^{42}$ or $R^{43}$ is an electron, then the other is also an electron; additionally, $R^{40}$ and $R^{41}$ may combine to form, $=C(C_1$–$C_3$ alkyl)($C_1$–$C_3$ alkyl);

$R^{52}$ is independently selected at each occurrence from the group: a bond to $L_n$, =O, F, Cl, Br, I, —$CF_3$, —CN, —$CO_2R^{53}$, —C(=O)$R^{53}$, —C(=O)N($R^{53}$)$_2$, —CHO, —$CH_2OR^{53}$, —OC(=O)$R^{53}$, —OC(=O)$OR^{53a}$, —$OR^{53}$, —OC(=O)N($R^{53}$)$_2$, —$NR^{53}$C(=O)$R^{53}$, —$NR^{54}$C(=O)$OR^{53a}$, —$NR^{53}$C(=C)N($R^{53}$)$_2$, —$NR^{54}SO_2$N($R^{53}$)$_2$, —$NR^{54}SO_2R^{53a}$, —$SO_3H$, —$SO_2R^{53a}$, —$SR^{53}$, —S(=O)$R^{53a}$, —$SO_2$N($R^{53}$)$_2$, —N($R^{53}$)$_2$, —NHC(=NH)$NHR^{53}$, —C(=NH)$NHR^{53}$, =$NOR^{53}$, $NO_2$, —C(=O)$NHOR^{53}$, —C(=O)$NHNR^{53}R^{53a}$, —$OCH_2CO_2H$, 2-(1-morpholino)ethoxy, $R^{53}$, $R^{53a}$, and $R^{54}$ are independently selected at each occurrence from the group: a bond to $L_n$, $C_1$–$C_6$ alkyl.

[18] Included in the present invention are those reagents in [1]–[15] above, of formula:

$(QL_n)_dC_h$, wherein d is 1; and $C_h$ is selected from:

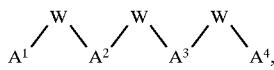

wherein:
$A^1$ and $A^4$ are SH or SPg;
$A^2$ and $A^3$ are $NR^{41}$;
W is independently selected from the group:
$CHR^{52}$, $CH_2CHR^{52}$, $CH_2CH_2CHR^{52}$ and $CHR^{52}C=O$; and
$R^{41}$ and $R^{52}$ are independently selected from hydrogen and a bond to $L_n$, and,

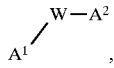

wherein:
$A^1$ is $NH_2$ or $N=C(C_1-C_3\ alkyl)(C_1-C_3\ alkyl)$;
W is a bond;
$A^2$ is $NHR^{40}$, wherein $R^{40}$ is heterocycle substituted with $R^{52}$, wherein the heterocycle is selected from the group: pyridine, pyrazine, proline, furan, thiofuran, thiazole, and diazine, and $R^{52}$ is a bond to $L_n$.

[19] Included in the present invention are those reagents in [1]–[15] above, of formula:

wherein d is 1; and
wherein $C_h$ is:

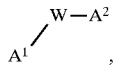

wherein:
$A^1$ is $NH_2$ or $N=C(C_1-C_3\ alkyl)(C_1-C_3\ alkyl)$;
W is a bond;
$A^2$ is $NHR^{40}$, wherein $R^{40}$ is heterocycle substituted with $R^{52}$, wherein the heterocycle is selected from pyridine and thiazole, and $R^{52}$ is a bond to $L_n$.

[20] Included in the present invention are those reagents in [1]–[15] above, wherein $L_n$ is:
a bond between Q and $C_h$; or,
a compound of formula:

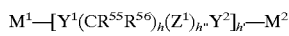

wherein:
$M^1$ is $-[(CH_2)_g Z^1]_{g'}-(CR^{55}R^{56})_{g''}-$;
$M^2$ is $-(CR^{55}R^{56})_{g''}-[Z^1(CH_2)_g]_{g'}-$;
g is independently 0–10;
g' is independently 0–1;
g" is 0–10;
h is 0–10;
h' is 0–10;
h" is 0–1
$Y^1$ and $Y^2$, at each occurrence, are independently selected from:
a bond, O, $NR^{56}$, $C=O$, $C(=O)O$, $OC(=O)O$, $C(=O)NH-$, $C=NR^{56}$, S, SO, $SO_2$, $SO_3$, $NHC(=O)$, $(NH)_2C(=O)$, $(NH)_2C=S$;

$Z^1$ is independently selected at each occurrence from a $C_6-C_{14}$ saturated, partially saturated, or aromatic carbocyclic ring system, substituted with 0–4 $R^{57}$; a heterocyclic ring system, optionally substituted with 0–4 $R^{57}$;

$R^{55}$ and $R^{56}$ are independently selected at each occurrence from:
hydrogen;
$C_1-C_{10}$ alkyl substituted with 0–5 $R^{57}$;
$(C_1-C_{10}\ alkyl)aryl$ wherein the aryl is substituted with 0–5 $R^{57}$;

$R^{57}$ is independently selected at each occurrence from the group: hydrogen, OH, $NHR^{58}$, $C(=O)R^{58}$, $OC(=O)R^{58}$, $OC(=O)OR^{58}$, $C(=O)OR^{58}$, $C(=O)NR^{58}-$, $C\equiv N$, $SR^{58}$, $SOR^{58}$, $SO_2R^{58}$, $NHC(=O)R^{58}$, $NHC(=O)NHR^{58}$, $NHC(=S)NHR^{58}$; or, alternatively, when attached to an additional molecule Q, $R^{57}$ is independently selected at each occurrence from the group: O, $NR^{58}$, $C=O$, $C(=O)O$, $OC(=O)O$, $C(=O)N-$, $C=NR^{58}$, S, SO, $SO_2$, $SO_3$, $NHC(=O)$, $(NH)_2C(=O)$, $(NH)_2C=S$; and, $R^{58}$ is independently selected at each occurrence from the group: hydrogen; $C_1-C_6$ alkyl; benzyl, and phenyl.

[21] Included in the present invention are those reagents in [1]–[15] above, wherein $L_n$ is:
a compound of formula:

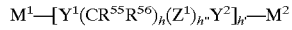

wherein:
$M^1$ is $-[(CH_2)_g Z^1]_{g'}-(CR^{55}R^{56})_{g''}-$;
$M^2$ is $-(CR^{55}R^{56})_{g''}-[Z^1(CH_2)_g]_{g'}-$;
g is independently 0–10;
g' is independently 0–1;
g" is 0–10;
h is 0–10;
h' is 0–10;
h" is 0–1
$Y^1$ and $Y^2$, at each occurrence, are independently selected from:
a bond, O, $NR^{56}$, $C=O$, $C(=O)O$, $OC(=O)O$, $C(=O)NH-$, $C=NR^{56}$, S, SO, $SO_2$, $SO_3$, $NHC(=O)$, $(NH)_2C(=O)$, $(NH)_2C=S$;

$Z^1$ is independently selected at each occurrence from a $C_6-C_{14}$ saturated, partially saturated, or aromatic carbocyclic ring system, substituted with 0–4 $R^{57}$; a heterocyclic ring system, optionally substituted with 0–4 $R^{57}$;

$R^{55}$ and $R^{56}$ are independently selected at each occurrence from:
hydrogen;
$C_1-C_{10}$ alkyl substituted with 0–5 $R^{57}$;
$(C_1-C_{10}\ alkyl)aryl$ wherein the aryl is substituted with 0–5 $R^{57}$;

$R^{57}$ is independently selected at each occurrence from the group: hydrogen, OH, $NHR^{58}$, $C(=O)R^{58}$, $OC(=O)R^{58}$, $OC(=O)OR^{58}$, $C(=O)OR^{58}$, $C(=O)NR^{58}-$, $C\equiv N$, $SR^{58}$, $SOR^{58}$, $SO_2R^{58}$, $NHC(=O)R^{58}$, $NHC(=O)NHR^{58}$, $NHC(=S)NHR^{58}$; or, alternatively, when attached to an additional molecule Q, R57 is independently selected at each occurrence from the group: O, $NR^{58}$, $C=O$, $C(=O)O$, $OC(=O)O$, $C(=O)N-$, $C=NR^{58}$, S, SO, $SO_2$, $SO_3$, $NHC(=O)$, $(NH)_2C(=O)$, $(NH)_2C=S$, and $R^{57}$ is attached to an additional molecule Q; and, R[58] is independently selected at each occurrence from the group:hydrogen; $C_1$–$C_6$ alkyl; benzyl, and phenyl.

[22] Included in the present invention are those reagents in [1]–[15] above, wherein $L_n$ is:

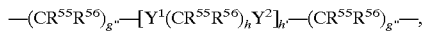

wherein:
g" is 0–10;
h is 0–10;
h' is 1–10;
Y[1] and Y[2], at each occurrence, are independently selected from:
  a bond, O, NR[56], C=O, C(=O)O,
  OC(=O)O,
  C(=O)NH—, C=NR[56], S, SO, SO$_2$, SO$_3$,
  NHC(=O), (NH)$_2$C(=O), (NH)$_2$C=S;
R[55] and R[56] are independently selected at each occurrence from:
  hydrogen;
  $C_1$–$_{10}$ alkyl substituted with 0–5 R[57];
  ($C_1$–$C_{10}$ alkyl)aryl wherein the aryl is substituted with 0–5 R[57];
R[57] is independently selected at each occurrence from the group: hydrogen, OH, NHR[58], C(=O)R[58], OC(=O)R[58], OC(=O)OR[58], C(=O)OR[58], C(=O)NR[58]—, C≡N, SR[58], SOR[58], SO$_2$R[58], NHC(=O)R[58], NHC(=O)NHR[58], NHC(=S)NHR[58]; or, alternatively, when attached to an additional molecule Q, R57 is independently selected at each occurrence from the group: O, NR[58], C=O, C(=O)O, OC(=O)O, C(=O)N—, C=NR[58], S, SO, SO$_2$, SO$_3$, NHC(=O), (NH)$_2$C(=O), (NH)$_2$C=S, and R[57] is attached to an additional molecule Q; and,
R[58] is independently selected at each occurrence from the group:hydrogen; $C_1$–$C_6$ alkyl; benzyl, and phenyl.

[23] Included in the present invention are those reagents in [1]–[15] above, wherein $L_n$ is:

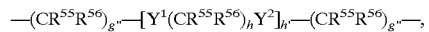

wherein:
g" is 0–5;
h is 0–5;
h' is 1–5;
Y[1] and Y[2], at each occurrence, are independently selected from:
  O, NR[56], C=O, C(=O)O, OC(=O)O, C(=O)NH—,
  C=NR[56], S, SO, SO$_2$, SO$_3$, NHC(=O), (NH)$_2$C(=O), (NH)$_2$C=S;
R[55] and R[56] are independently selected at each occurrence from:
  hydrogen;
  $C_1$–$C_{10}$ alkyl;
  ($C_1$–$C_{10}$ alkyl)aryl.

[24] Included in the present invention are those reagents in [1]–[15] above, wherein $L_n$ is:

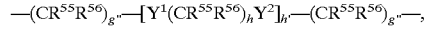

wherein:
g" is 1–5;
h is 0–5;
h' is 1–5;
Y[1] and Y[2], at each occurrence, are independently selected from:
  O, NR[56], C=O, C(=O)O, OC(=O)O, C(=O)NH—,
  C=NR[56], S, NHC(=O), (NH)$_2$C(=O), (NH)$_2$C=S;
R[55] and R[56] are independently selected at each occurrence from:
  hydrogen.

[25] Included in the present invention are those reagents in [1] above, which are:

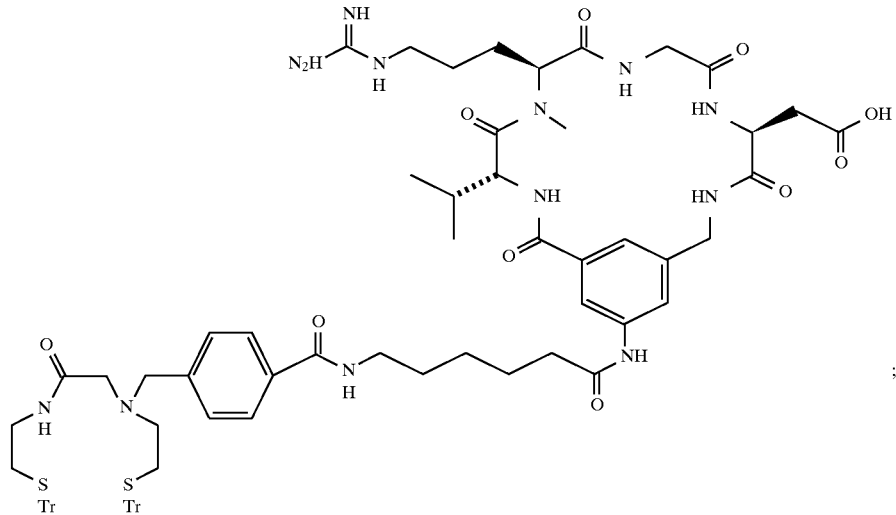

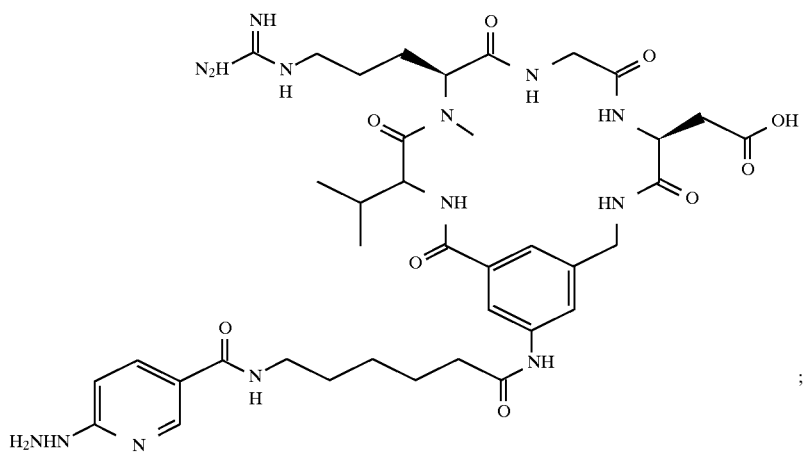;
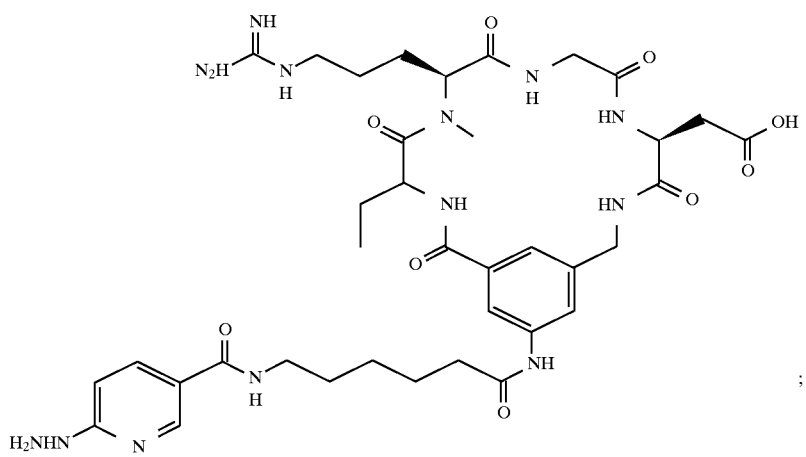;
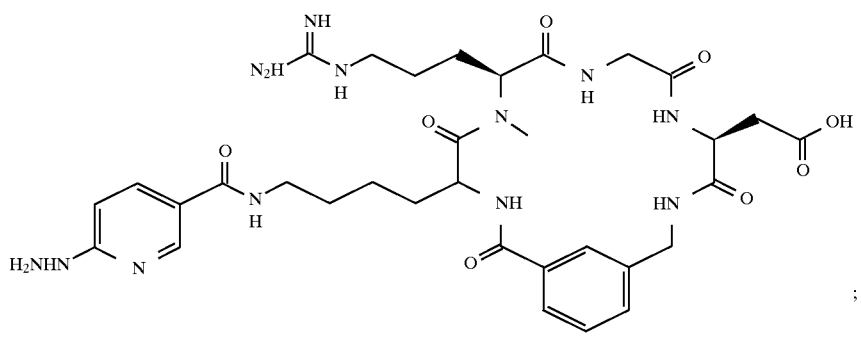;

-continued

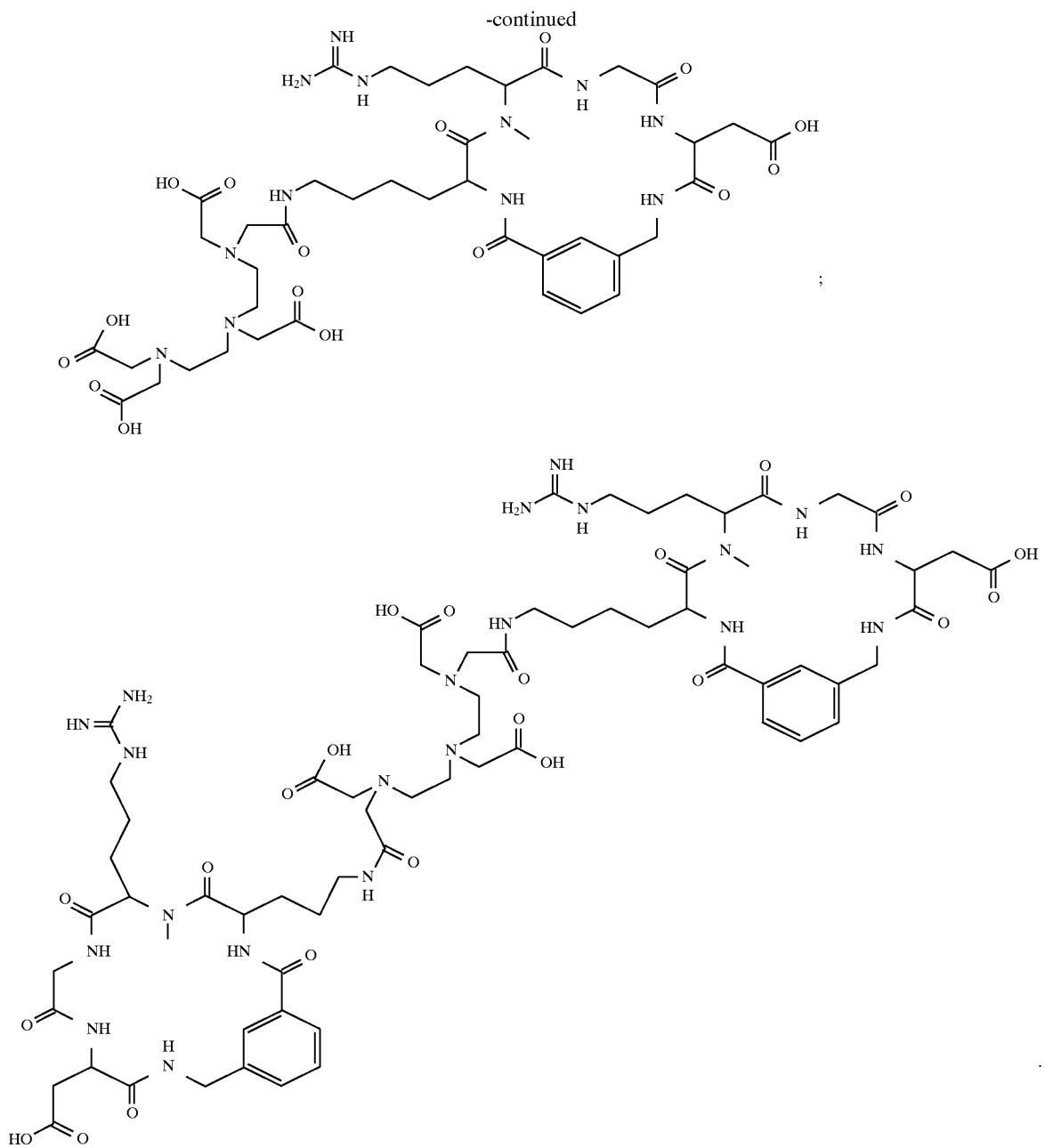

[26] Also included in the present invention is a kit for preparing a radiopharmaceutical comprising a predetermined quantity of a sterile, pharmaceutically acceptable reagent of [23].

[27] Also included in the present invention is a kit for preparing a radiopharmaceutical comprising a predetermined quantity of a sterile, pharmaceutically acceptable reagent of [24].

[28] Also included in the present invention is a kit for preparing a radiopharmaceutical comprising a predetermined quantity of a sterile, pharmaceutically acceptable reagent of [25].

[29] Also included in the present invention is a radiopharmaceutical comprising a complex of a reagent of [1]–[15] and a radionuclide selected from the group $^{99m}Tc$, $^{94m}TC$, $^{95}Tc$, $^{111}In$, $^{62}Cu$, $^{43}Sc$, $^{45}Ti$, $^{67}Ga$, $^{68}Ga$, $^{97}Ru$, $^{72}As$, $^{82}Rb$, and $^{201}Tl$.

[30] Also included in the present invention is a radiopharmaceutical comprising a complex of a reagent of [16] and a radionuclide selected from the group $^{99m}Tc$, $^{94m}Tc$, $^{95}Tc$, $^{111}In$, $^{62}Cu$, $^{43}Sc$, $^{45}Ti$, $^{67}Ga$, $^{68}Ga$, $^{97}Ru$, $^{72}As$, $^{82}Rb$, and $^{201}Tl$.

[31] Also included in the present invention is a radiopharmaceutical comprising a complex of a reagent of [17] and a radionuclide selected from the group $^{99m}Tc$, $^{94m}Tc$, $^{95}Tc$, $^{111}In$, $^{62}Cu$, $^{43}Sc$, $^{45}Ti$, $^{67}Ga$, $^{68}Ga$, $^{97}Ru$, $^{72}As$, $^{82}Rb$, and $^{201}Tl$.

[32] Also included in the present invention is a radiopharmaceutical comprising a complex of a reagent of [18] and a radionuclide selected from the group $^{99m}Tc$, $^{94m}Tc$, $^{95}Tc$, $^{111}In$, $^{62}Cu$, $^{43}Sc$, $^{45}Ti$, $^{67}Ga$, $^{68}Ga$, $^{97}Ru$, $^{72}As$, $^{82}Rb$, and $^{201}Tl$.

[33] Also included in the present invention is a radiopharmaceutical comprising a complex of a reagent of [19] and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

[34] Also included in the present invention is a radiopharmaceutical comprising a complex of a reagent of [20] and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

[35] Also included in the present invention is a radiopharmaceutical comprising a complex of a reagent of [21] and a radionuclide selected from the group $^{99m}$Tc, $^{111}$In, and $^{62}$Cu.

[36] Also included in the present invention is a radiopharmaceutical comprising a complex of a reagent of [22] and a radionuclide selected from the group $^{99m}$Tc, $^{111}$In, and $^{62}$Cu.

[37] Also included in the present invention is a radiopharmaceutical comprising a complex of a reagent of [23] and a radionuclide selected from the group $^{99m}$Tc, $^{111}$In, and $^{62}$Cu.

[38] Also included in the present invention is a radiopharmaceutical comprising a complex of a reagent of [24] and a radionuclide selected from the group $^{99m}$Tc, and $^{111}$In.

[39] Also included in the present invention are the radiopharmaceuticals of [29] which are:

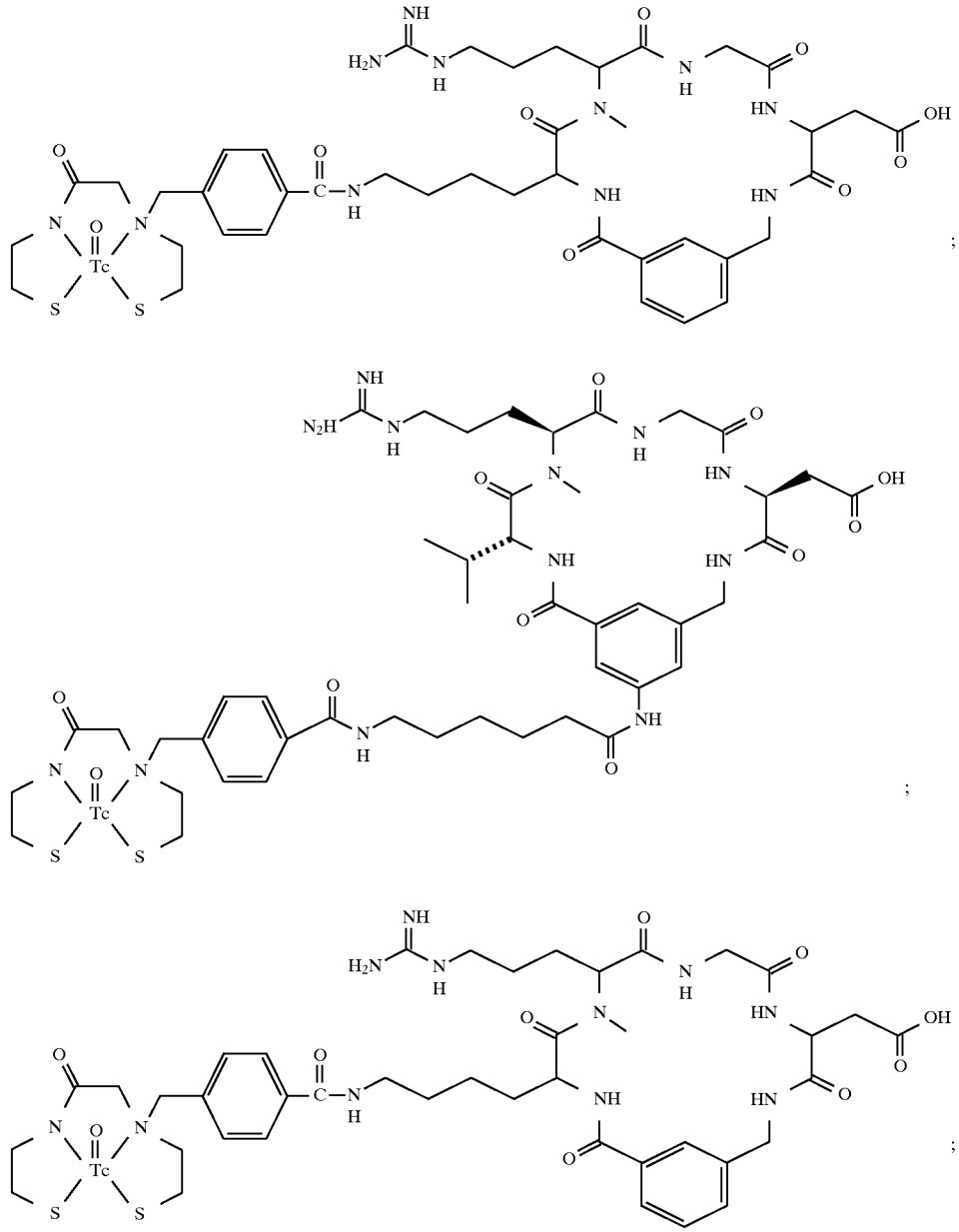

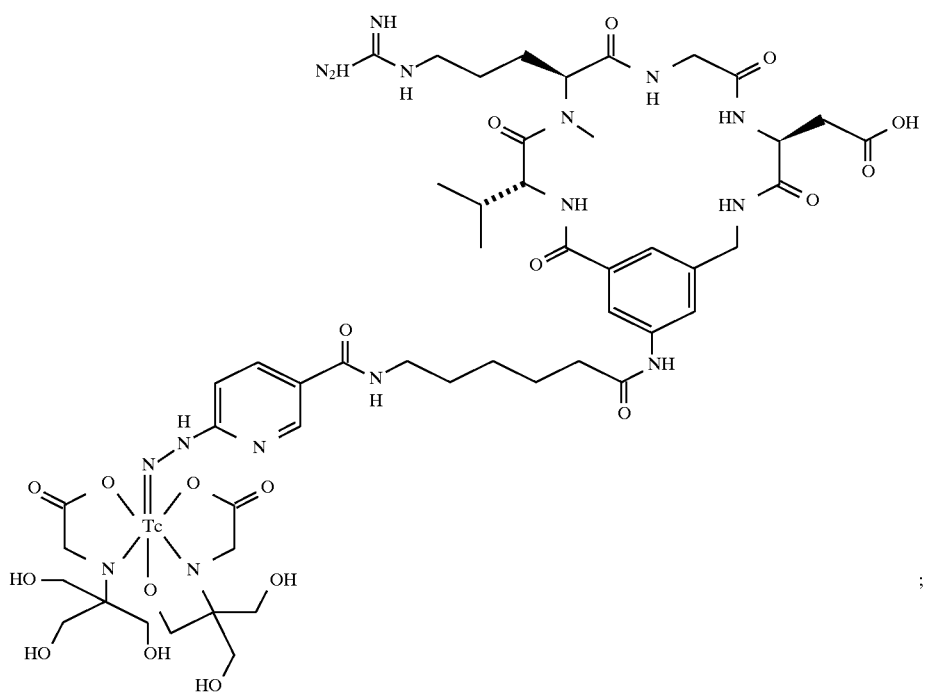
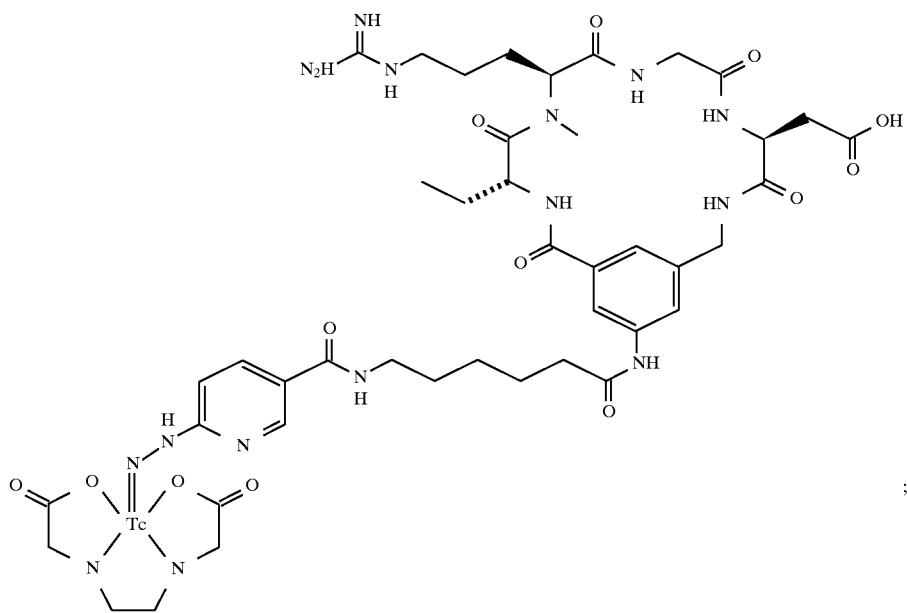

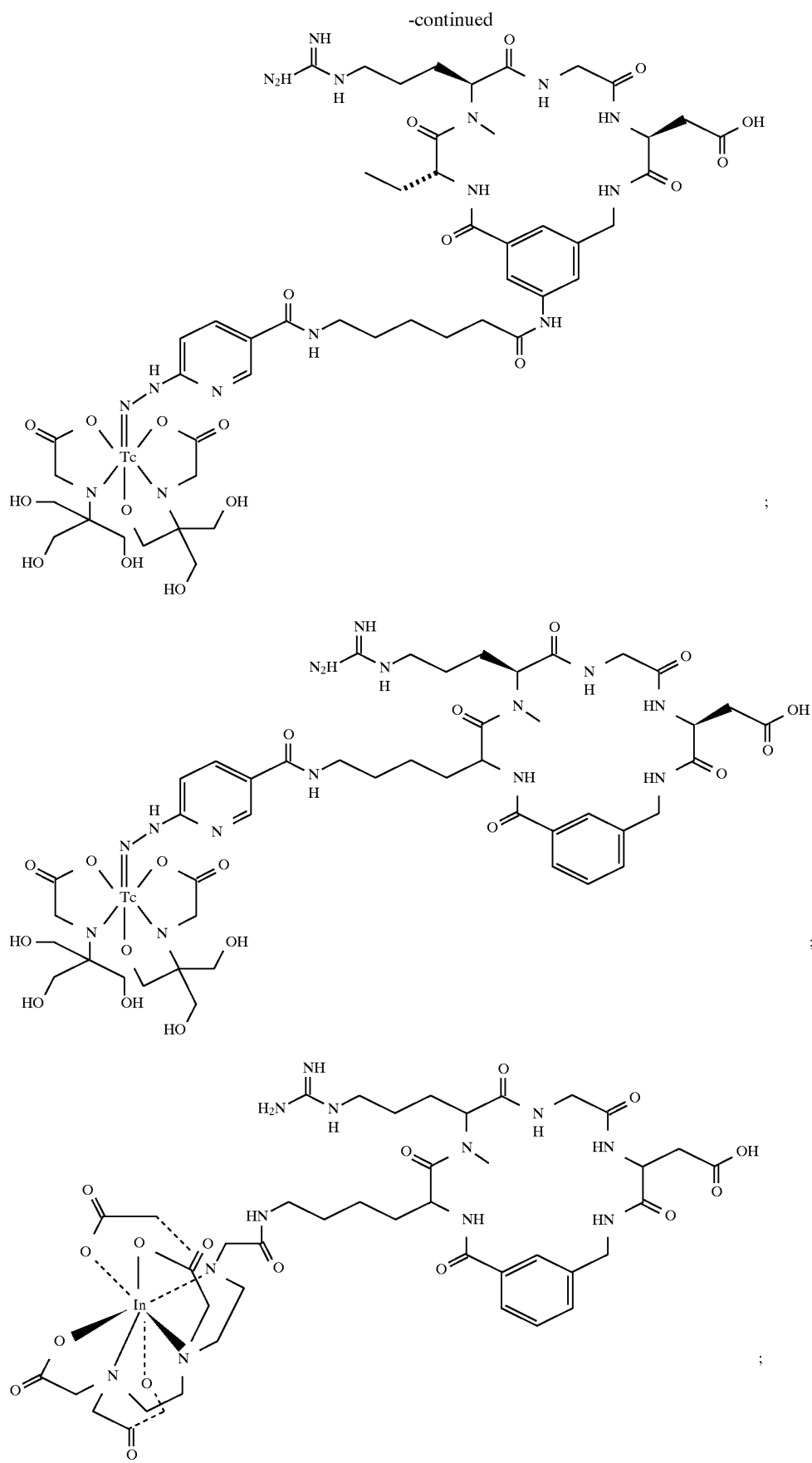

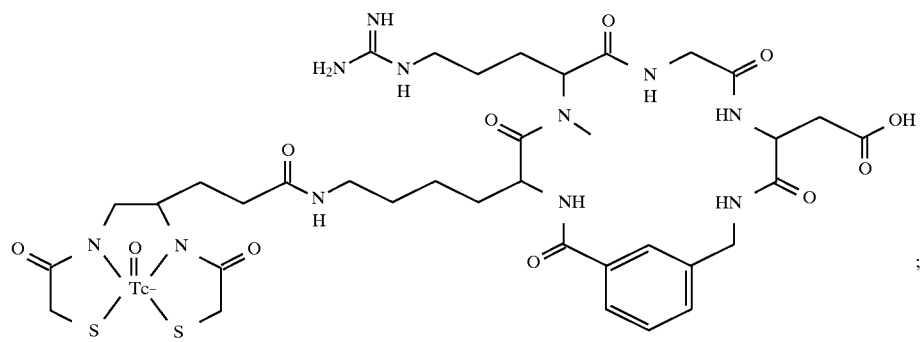
;
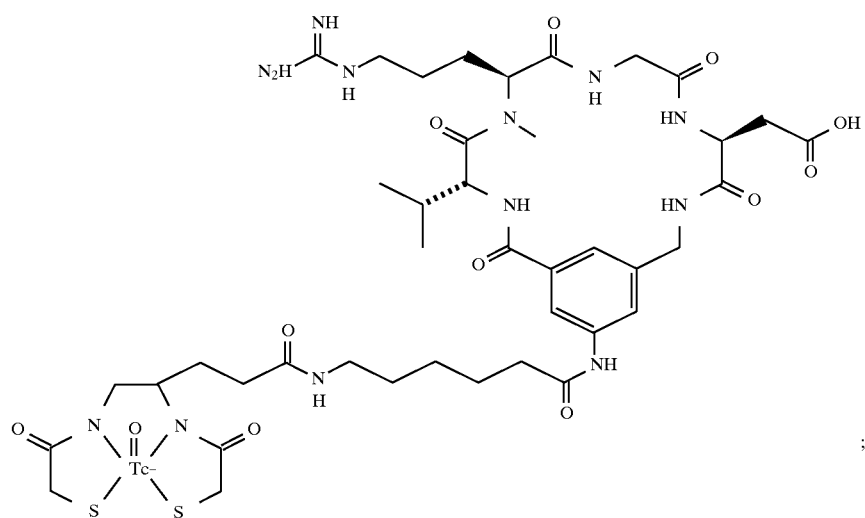
;
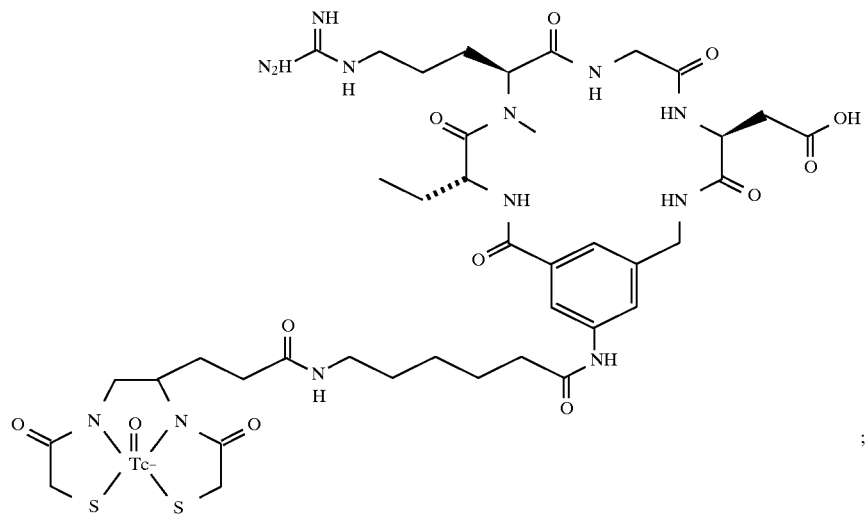
;

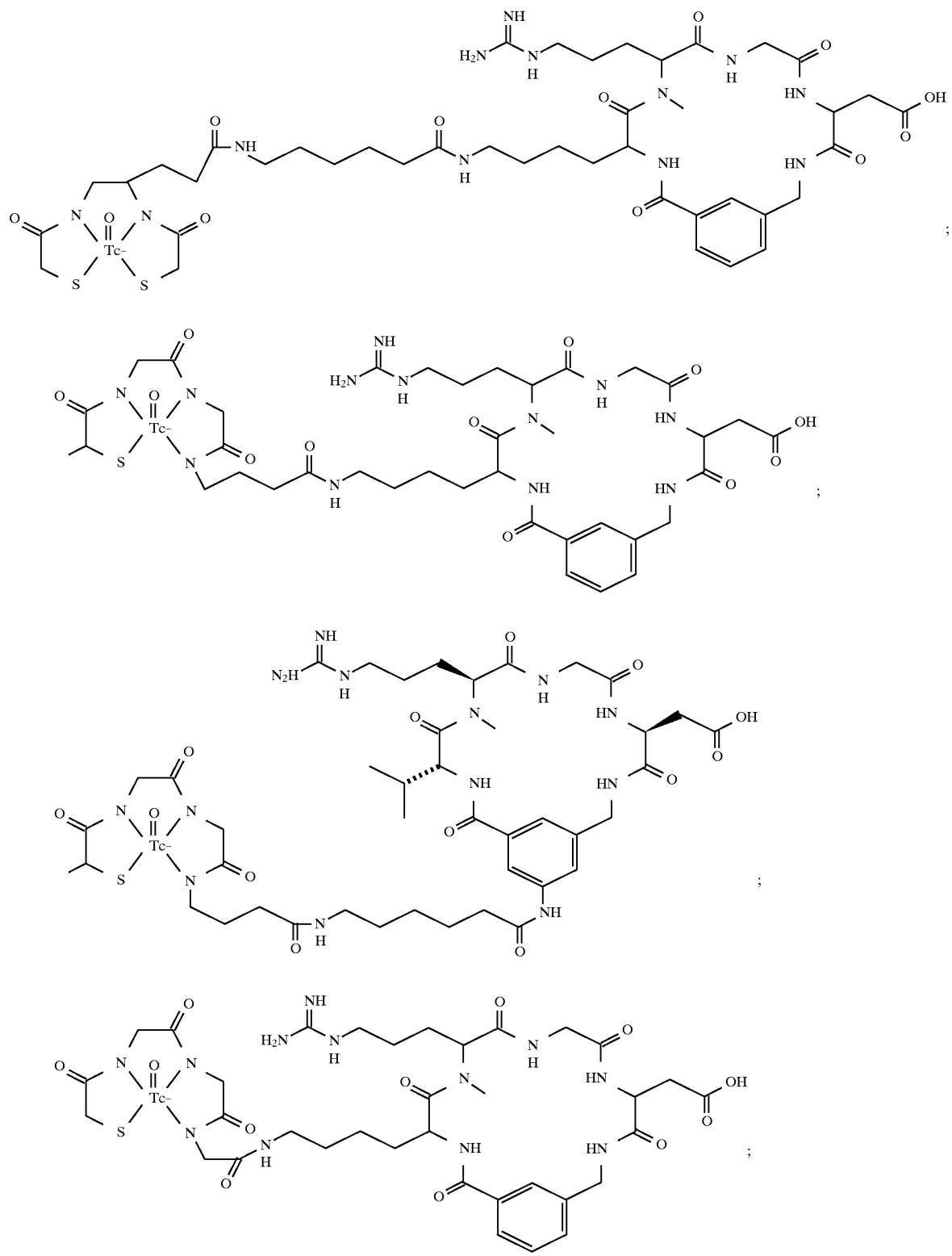

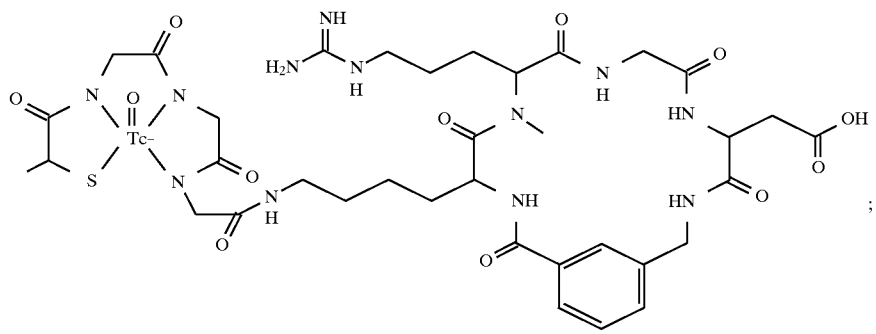
;
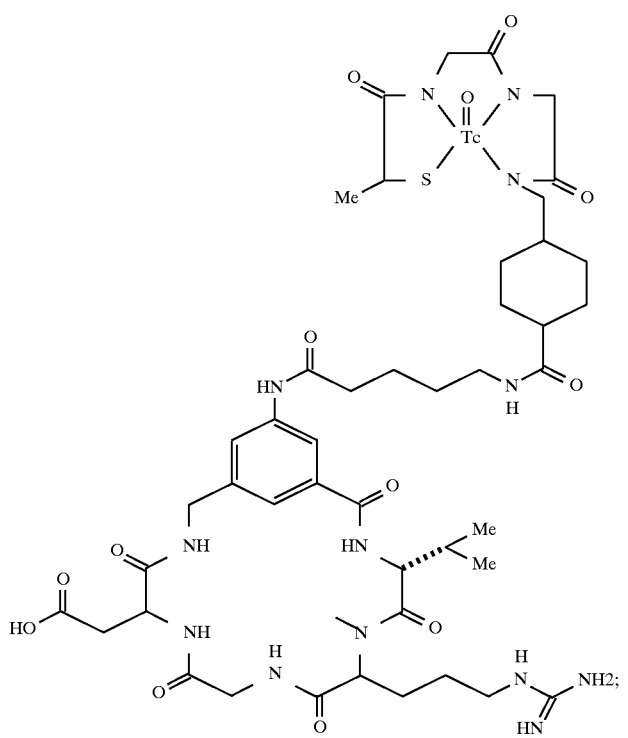
;
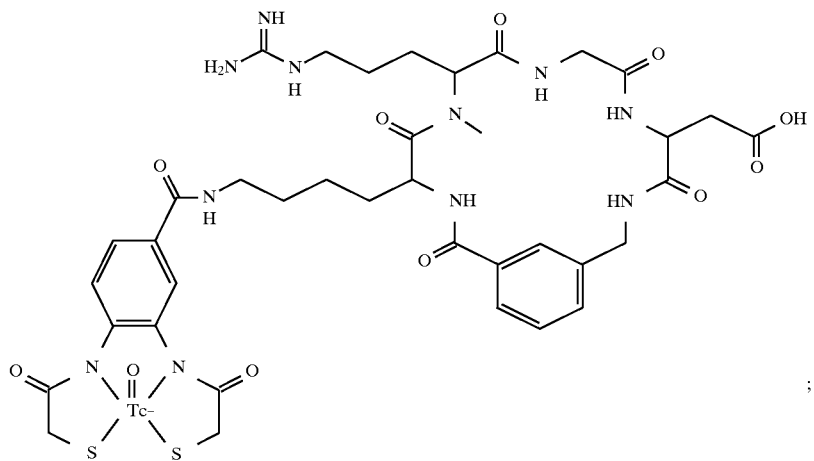
; and

-continued

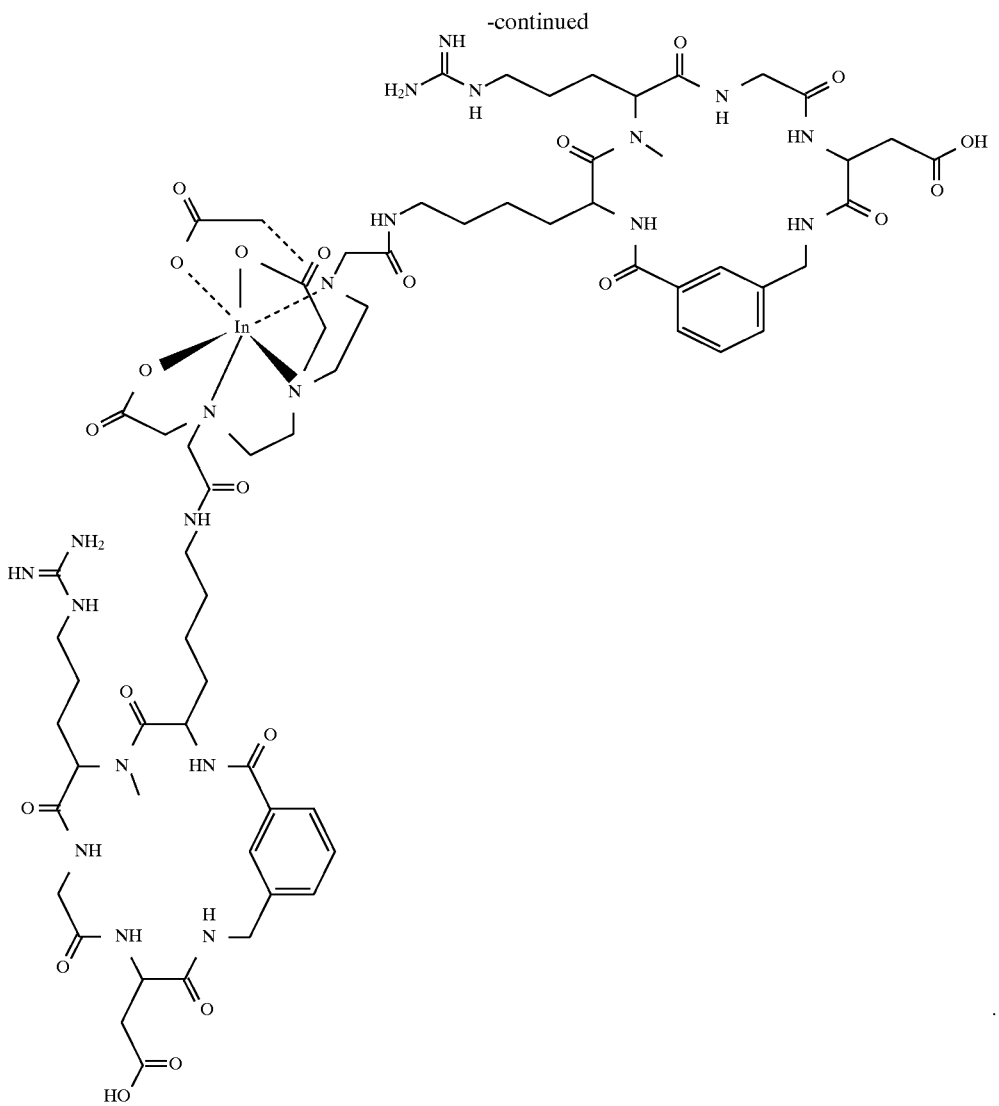

[40] Also included in the present invention is a method for visualizing sites of platelet deposition in a mammal by radioimaging, comprising (i) administering to said mammal an effective amount of a radiopharmaceutical of [29], and (ii) scanning the mammal using a radioimaging device.

[41] Also included in the present invention is a method for visualizing sites of platelet deposition in a mammal by radioimaging, comprising (i) administering to said mammal an effective amount of a radiopharmaceutical of [30], and (ii) scanning the mammal using a radioimaging device.

[42] Also included in the present invention is a method for visualizing sites of platelet deposition in a mammal by radioimaging, comprising (i) administering to said mammal an effective amount of a radiopharmaceutical of [31], and (ii) scanning the mammal using a radioimaging device.

[43] Also included in the present invention is a method for visualizing sites of platelet deposition in a mammal by radioimaging, comprising (i) administering to said mammal an effective amount of a radiopharmaceutical of [32], and (ii) scanning the mammal using a radioimaging device.

[44] A method for visualizing sites of platelet deposition in a mammal by radioimaging, comprising (i) administering to said mammal an effective amount of a radiopharmaceutical of [133], and (ii) scanning the mammal using a radioimaging device.

[45] A method for visualizing sites of platelet deposition in a mammal by radioimaging, comprising (i) administering to said mammal an effective amount of a radiopharmaceutical of [34], and (ii) scanning the mammal using a radioimaging device.

[46] A method for visualizing sites of platelet deposition in a mammal by radioimaging, comprising (i) administering to said mammal an effective amount of a radiopharmaceutical of [35], and (ii) scanning the mammal using a radioimaging device.

[47] A method for visualizing sites of platelet deposition in a mammal by radioimaging, comprising (i) administering to said mammal an effective amount of a radiopharmaceutical of [36], and (ii) scanning the mammal using a radioimaging device.

[48] A method for visualizing sites of platelet deposition in a mammal by radioimaging, comprising (i) administering to said mammal an effective amount of a radiopharmaceutical of [37], and (ii) scanning the mammal using a radioimaging device.

[49] A method for visualizing sites of platelet deposition in a mammal by radioimaging, comprising (i) administering to said mammal an effective amount of a radiopharmaceutical of [38], and (ii) scanning the mammal using a radioimaging device.

[50] A method for visualizing sites of platelet deposition in a mammal by radioimaging, comprising (i) administering to said mammal an effective amount of a radiopharmaceutical of claim 39, and (ii) scanning the mammal using a radioimaging device.

[51] The present invention is also directed to direct radiolabeled compounds of formula (I):

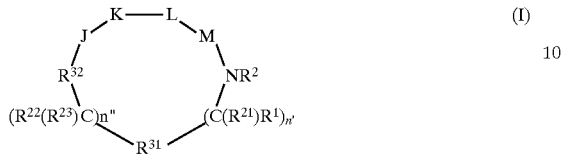

or a pharmaceutically acceptable salt or prodrug form thereof wherein:

$R^{31}$ is a $C_6$–$C_{14}$ saturated, partially saturated, or aromatic carbocyclic ring system substituted with 0–4 $R^{10}$ or $R^{10a}$;

$R^{32}$ is selected from:
—C(=O)—;
—C(=S)—
—S(=O)$_2$—;
—S(=O)—;
—P(=Z)(ZR$^{13}$)—;
Z is S or O;
n" and n' are independently 0–2;
$R^1$ and $R^{22}$ are independently selected from the following groups:
hydrogen,
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
aryl substituted with 0–2 $R^{12}$;
a 5–10-membered heterocyclic ring system containing 1–4 heteroatoms independently selected from N, S, and O, said heterocyclic ring being substituted with 0–2 $R^{12}$;
=O, F, Cl, Br, I, —CF$_3$, —CN, —CO$_2$R$^{13}$, —C(=O) R$^{13}$, —C(=O)N(R$^{13}$)$_2$, —CHO, —CH$_2$OR$^{13}$, —OC (=O)R$^{13}$, —OC(=O)OR$^{13a}$, —OR$^{13}$, —OC(=O) N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC (=NH)NHR$^{13}$, —C(=NH)NHR$^{13}$, =NOR$^{13}$, NO$_2$, —C(=O) NHOR$^{13}$, —C(=O)NHNR$^{13}$R$^{13a}$, —OCH$_2$CO$_2$H, 2-(1-morpholino)ethoxy;

$R^1$ and $R^{21}$ can alternatively join to form a 3–7 membered carbocyclic ring substituted with 0–2 $R^{12}$;
when n' is 2, $R^1$ or $R^{21}$ can alternatively be taken together with $R^1$ or $R^{21}$ on an adjacent carbon atom to form a direct bond, thereby to form a double or triple bond between said carbon atoms;
$R^{22}$ and $R^{23}$ can alternatively join to form a 3–7 membered carbocyclic ring substituted with 0–2 $R^{12}$;
when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;
$R^1$ and $R^2$, where $R^{21}$ is H, can alternatively join to form a 5–8 membered carbocyclic ring substituted with 0–2 $R^{12}$;
$R^{11}$ is selected from one or more of the following:
=O, F, Cl, Br, I, —CF$_3$, —CN, —CO$_2$R$^{13}$, —C(=O) R$^{13}$, —C(=O)N(R$^{13}$)$_2$, —CHO, —CH$_2$OR$^{13}$, —OC (=O)R$^{13}$, —OC(=O)OR$^{13a}$, —OR$^{13}$, —OC(=O) N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC (=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, $C_3$–$C_6$ cycloalkoxy, $C_1$–$C_4$ alkyl(alkyl being substituted with 1–5 groups selected independently from: —NR$^{13}$R$^{14}$, —CF$_3$, NO$_2$, —SO$_2$R$^{13a}$, or —S(=O) R$^{13a}$),
aryl substituted with 0–2 $R^{12}$,
a 5–10-membered heterocyclic ring system containing 1–4 heteroatoms independently selected from N, S, and O, said heterocyclic ring being substituted with 0–2 $R^{12}$;
$R^{12}$ is selected from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O) OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N (R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, ethoxy, $C_1$–$C_4$ alkyl (alkyl being substituted with —N(R$^{13}$)$_2$, —CF$_3$, NO$_2$, or —S(=O)R$^{13a}$);

$R^{13}$ is selected independently from: H, $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;
$R^{13a}$ is $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;
when two $R^{13}$ groups are bonded to a single N, said $R^{13}$ groups may alternatively be taken together to form —(CH$_2$)$_{2-5}$— or —(CH$_2$)O(CH$_2$)—;
$R^{14}$ is OH, H, $C_1$–$C_4$ alkyl, or benzyl;
$R^{21}$ and $R^{23}$ are independently selected from:
hydrogen;
$C_1$–$C_4$ alkyl, optionally substituted with 1–6 halogen;
benzyl;
$R^2$ is H or $C_1$–$C_8$ alkyl;
$R^{10}$ and $R^{10a}$ are selected independently from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)N (R$^{13}$)$_2$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC (=O)N(R$^{13}$)$_2$, —NR$^{13}$C(=O)R$^{13}$, —NR$^{13}$C(=O) OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —(=O) R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl (including —$C_vF_w$ where v=1 to 3 and w=1 to (2v+1)), $C_1$–$C_4$ haloalkoxy, —$OCH_2CO_2H$, 2-(1-morpholino)ethoxy, $C_1$–$C_4$ alkyl (alkyl being substituted with —$N(R^{13})_2$, —$CF_3$, $NO_2$, or —$S(=O)R^{13a}$);

J is β-Ala or an L-isomer or D-isomer amino acid of structure
—$N(R^3)C(R^4)(R^5)C(=O)$—, wherein:

$R^3$ is H or $C_1$–$C_8$ alkyl;
$R^4$ is H or $C_1$–$C_3$ alkyl;
$R^5$ is selected from:
  hydrogen;
  $C_1$–$C_8$ alkyl substituted with 0–2 $R^{11}$;
  $C_2$–$C_8$ alkenyl substituted with 0–2 $R^{11}$;
  $C_2$–$C_8$ alkynyl substituted with 0–2 $R^{11}$;
  $C_3$–$C_{10}$ cycloalkyl substituted with 0–2 $R^{11}$;
  aryl substituted with 0–2 $R^{12}$;
  a 5–10-membered heterocyclic ring system containing 1–4 heteroatoms independently selected from N, S, or O, said heterocyclic ring being substituted with 0–2 $R^{12}$;
  =O, F, Cl, Br, I, —$CF_3$, —CN, —$CO_2R^{13}$, —$C(=O)R^{13}$, —$C(=O)N(R^{13})_2$, —CHO, —$CH_2OR^{13}$, —$OC(=O)R^{13}$, —$OC(=O)OR^{13a}$, —$OR^{13}$, —$OC(=O)N(R^{13})_2$, —$NR^{13}C(=O)R^{13}$, —$NR^{14}C(=O)OR^{13a}$, —$NR^{13}C(=O)N(R^{13})_2$, —$NR^{14}SO_2N(R^{13})_2$, —$NR^{14}SO_2R^{13a}$, —$SO_3H$, —$SO_2R^{13a}$, —$SR^{13}$, —$S(=O)R^{13a}$, —$SO_2N(R^{13})_2$, —$N(R^{13})_2$, —$NHC(=NH)NHR^{13}$, —$C(=NH)NHR^{13}$, =$NOR^{13}$, $NO_2$, —$C(=O)NHOR^{13}$, —$C(=O)NHNR^{13}R^{13a}$, =$NOR^{13}$, —$B(R^{34})(R^{35})$, —$OCH_2CO_2H$, 2-(1-morpholino)ethoxy, —$SC(=NH)NHR^{13}$, $N_3$, —$Si(CH_3)_3$, ($C_1$–$C_5$ alkyl)$NHR^{16}$;
  —($C_0$–$C_6$ alkyl)X;

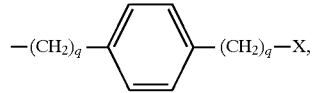

where q is independently 0,1;

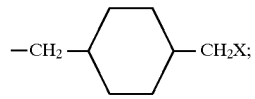

—$(CH_2)_mS(O)_{p'}(CH_2)_2X$, where m=1,2 and p'=0–2; wherein X is defined below; and
$R^3$ and $R^4$ may also be taken together to form

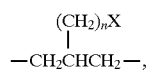

where
n=0,1 and X is

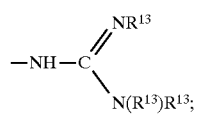

$R^3$ and $R^5$ can alternatively be taken together to form —$(CH_2)_t$— or —$CH_2S(O)_{p'}C(CH_3)_2$—, where t=2–4 and p'=0–2; or $R^4$ and $R^5$ can alternatively be taken together to form —$(CH_2)_u$—, where u=2–5;

$R^{16}$ is selected from:
  an amine protecting group;
  1–2 amino acids;
  1–2 amino acids substituted with an amine protecting group;

K is a D-isomer or L-isomer amino acid of structure —$N(R^6)CH(R^7)C(=O)$—, wherein:

$R^6$ is H or $C_1$–$C_8$ alkyl;
$R^7$ is selected from:
  —($C_1$–$C_7$ alkyl)X;

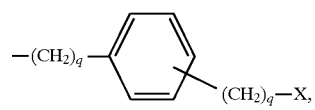

wherein each q is independently 0–2 and substitution on the phenyl is at the 3 or 4 position;

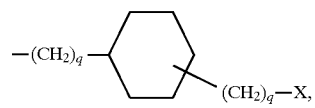

wherein each q is independently 0–2 and substitution on the cyclohexyl is at the 3 or 4 position;

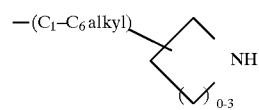

—$(CH_2)_mO$—($C_1$–$C_4$ alkyl)-X, where m=1 or 2;
  —$(CH_2)_mS(O)_{p'}$—($C_1$–$C_4$ alkyl)-X, where m=1 or 2 and p'=0–2; and X is selected from:

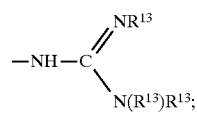

—$N(R^{13})R^{13}$; —$C(=NH)(NH_2)$; —$SC(=NH)$—$NH_2$; —NH—$C(=NH)(NHCN)$; —NH—$C(=NCN)(NH_2)$; —NH—$C(=N$—$OR^{13})(NH_2)$;

$R^6$ and $R^7$ can alternatively be taken together to form

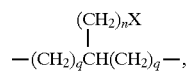

wherein each q is independently 1 or 2 and wherein n=0 or 1 and X is —$NH_2$ or

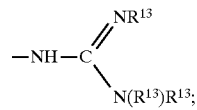

L is —$Y(CH_2)_vC(=O)$—, wherein:
Y is NH, $N(C_1$–$C_3$ alkyl), O, or S; and v=1 or 2;

M is a D-isomer or L-isomer amino acid of structure

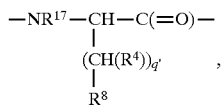

wherein:
q' is 0–2;
$R^{17}$ is H, $C_1$–$C_3$ alkyl;
$R^8$ is selected from:
—$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$;
$R^{34}$ and $R^{35}$ are independently selected from:
—OH,
—F,
—$N(R^3)_2$, or
$C_1$–$C_8$-alkoxy;
$R^{34}$ and $R^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O; and
wherein the radiolabel is selected from the group: $^{123}I$, $^{125}I$, $^{131}I$, $^{18}F$, $^{11}C$, $^{13}N$, $^{15}O$, $^{75}Br$.

[52] Included in the present invention are those direct radiolabeled compounds in [51] above, wherein:
$R^{31}$ is bonded to $(C(R^{23})R^{22})_{n''}$ and $(C(R^{21})R^1)_{n'}$ at 2 different atoms on said carbocyclic ring.

[53] Included in the present invention are those direct radiolabeled compounds in [51] above, wherein:
n" is 0 and n' is 0;
n" is 0 and n' is 1;
n" is 0 and n' is 2;
n" is 1 and n' is 0;
n" is 1 and n' is 1;
n" is 1 and n' is 2;
n" is 2 and n' is 0;
n" is 2 and n' is 1; or
n" is 2 and n' is 2.

[54] Included in the present invention are those direct radiolabeled compounds in [51] above, wherein $R^6$ is methyl, ethyl, or propyl.

[55] Included in the present invention are those direct radiolabeled compounds in [51] above, wherein:
$R^{31}$ is selected from the group consisting of:
(a) a 6 membered saturated, partially saturated or aromatic carbocyclic ring substituted with 0–3 $R^{10}$ or $R^{10a}$;
(b) a 8–11 membered saturated, partially saturated, or aromatic fused bicyclic carbocyclic ring substituted with 0–4 $R^{10}$ or $R^{10a}$; or (c) a 14 membered saturated, partially saturated, or aromatic fused tricyclic carbocyclic ring substituted with 0–4 $R^{10}$ or $R^{10a}$.

[56] Included in the present invention are those direct radiolabeled compounds in [51] above, wherein:
$R^{31}$ is selected from the group consisting of:
(a) a 6 membered saturated, partially saturated, or aromatic carbocyclic ring of formula:

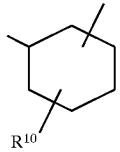

wherein any of the bonds forming the carbocyclic ring may be a single or double bond, and wherein said carbocyclic ring is substituted independently with 0–4 $R^{10}$;

(b) a 10 membered saturated, partially saturated, or aromatic bicyclic carbocyclic ring of formula:

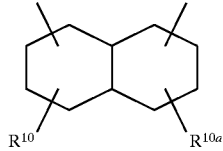

wherein any of the bonds forming the carbocyclic ring may be a single or double bond,
and wherein said carbocyclic ring is substituted independently with 0–4 $R^{10}$ or $R^{10a}$;

(c) a 9 membered saturated, partially saturated, or aromatic bicyclic carbocyclic ring of formula:

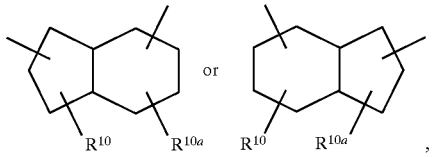

wherein any of the bonds forming the carbocyclic ring may be a single or double bond,
and wherein said carbocyclic ring is substituted independently with 0–4 $R^{10}$ or $R^{10a}$.

[57] Included in the present invention are those direct radiolabeled compounds in [51] above, wherein:
$R^{31}$ is selected from (the dashed bond may be a single or double bond):

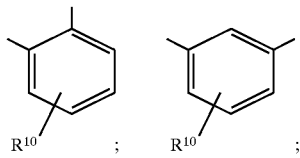

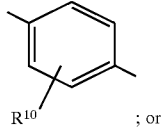

-continued

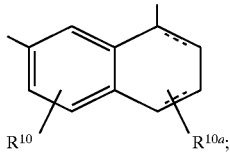

n" is 0 or 1; and
n' is 0–2.

[58] Included in the present invention are those direct radiolabeled compounds in [51] above, wherein:

$R^1$ and $R^{22}$ are independently selected from:
  phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —($C_1$–$C_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S(=O)R$^{13a}$).

[59] Included in the present invention are those direct radiolabeled compounds in [51] above, wherein:

$R^{31}$ is selected from:

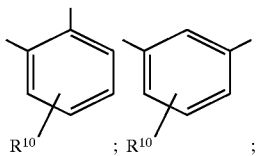

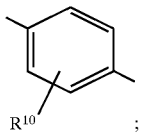

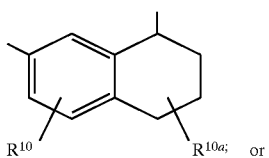

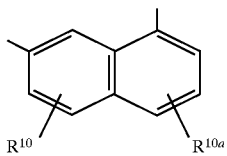

wherein $R^{31}$ may be substituted independently with 0–3 $R^{10}$ or $R^{10a}$;
$R^{32}$ is —C(=O)—;
n" is 0 or 1;
n' is 0–2;
$R^1$ and $R^{22}$ are independently selected from H, $C_1$–$C_4$ alkyl, phenyl, benzyl, phenyl—($C_2$–$C_4$)alkyl, $C_1$–$C_4$ alkoxy;

$R^{21}$ and $R^{23}$ are independently H or $C_1$–$C_4$ alkyl;

$R^2$ is H or $C_1$–$C_8$ alkyl;

$R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_3$–$C_{10}$ alkyl)aryl, or $C_3$–$C_{10}$ alkoxyalkyl;

13a is $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;
  when two $R^{13}$ groups are bonded to a single N, said $R^{13}$ groups may alternatively be taken together to form —(CH$_2$)$_{2-5}$— or —(CH$_2$)O(CH$_2$)—;

$R^{14}$ is OH, H, $C_1$–$C_4$ alkyl, or benzyl;

$R^{10}$ and $R^{10a}$ are selected independently from: $C_1$–$C_5$ alkyl, phenyl, halogen, or $C_1$–$C_4$ alkoxy;

J is β-Ala or an L-isomer or D-isomer amino acid of structure —N(R$^3$)C(R$^4$)(R$^5$)C(=O)—, wherein:
  $R^3$ is H or CH$_3$;
  $R^4$ is H or $C_1$–$C_3$ alkyl;
  $R^5$ is H, $C_1$–$C_8$ alkyl, $C_3$–$C_6$ cycloalkyl, $C_3$–$C_6$ cycloalkylmethyl, $C_3$–$C_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, —(CH$_2$)$_s$NHC(=NH)(NH$_2$), —(CH$_2$)$_s$NHR$^{16}$, where s=3–5; or $R^{16}$ is selected from:
  an amine protecting group;
  1–2 amino acids; or
  1–2 amino acids substituted with an amine protecting group;

$R^3$ and $R^5$ can alternatively be taken together to form —(CH$_2$)$_t$—(t=2–4) or —CH$_2$SC(CH$_3$)$_2$—; or $R^4$ and $R^5$ can alternatively be taken together to form —(CH$_2$)$_u$—, where u=2–5;

K is an L-isomer amino acid of structure —N(R$^6$)CH(R$^7$)C(=O)—, wherein:
  $R^6$ is H or $C_1$–$C_8$ alkyl;
  $R^7$ is

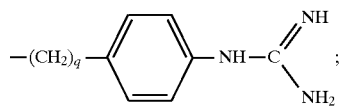

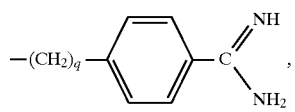

where q=0 or 1;
—(CH$_2$)$_r$X, where r=3–6;

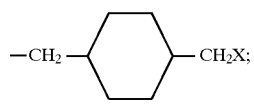

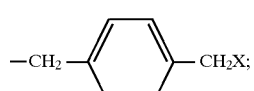

—(CH$_2$)$_m$S(CH$_2$)$_2$X, where m=1 or 2;
—($C_3$–$C_7$ alkyl)—NH—($C_1$–$C_6$ alkyl) —($C_1$–$C_4$ alkyl)

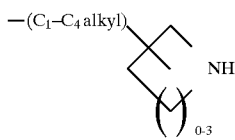

—(CH$_2$)$_m$—O—(C$_1$–C$_4$ alkyl)—NH—(C$_1$–C$_6$ alkyl), where m=1 or 2;
—(CH$_2$)$_m$—S—(C$_1$–C$_4$ alkyl)—NH—(C$_1$–C$_6$ alkyl), where m=1 or 2; and
X is —NH$_2$ or —NHC(=NH)(NH$_2$); or
R$^6$ and R$^7$ can alternatively be taken together to form

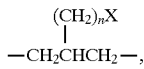

where n=0 or 1 and X is —NH$_2$ or —NHC(=NH)(NH$_2$);
L is —Y(CH$_2$)$_v$C(=O)—, wherein:
Y is NH, O, or S; and v=1 or 2;
M is a D-isomer or L-isomer amino acid of structure

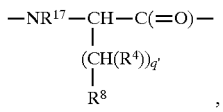

wherein:
q' is 0–2;
R$^{17}$ is H, C$_1$–C$_3$ alkyl;
R$^8$ is selected from:
—CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$.

[60] Included in the present invention are those direct radiolabeled compounds in [51] above, that are radiolabeled 1,3-disubstituted phenyl compounds of the formula (II):

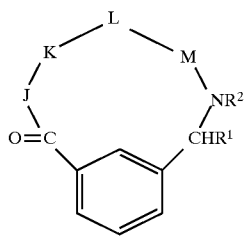

(II)

wherein:
the shown phenyl ring in formula (II) may be further substituted with 0–3 R$^{10}$;
R$^{10}$ is selected independently from: C$_1$–C$_5$ alkyl, phenyl, halogen, or C$_1$–C$_4$ alkoxy;
R$^1$ is H, C$_1$–C$_4$ alkyl, phenyl, or phenyl—(C$_1$–C$_4$)alkyl;
R$^2$ is H or methyl;
R$^{13}$ is selected independently from: H, C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;
R$^{13a}$ is C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

when two R$^{13}$ groups are bonded to a single N, said R$^{13}$ groups may alternatively be taken together to form —(CH$_2$)$_{2-5}$— or —(CH$_2$)O(CH$_2$)—;
R$^{14}$ is OH, H, C$_1$–C$_4$ alkyl, or benzyl;
J is β-Ala or an L-isomer or D-isomer amino acid of structure —N(R$^3$)C(R$^4$)(R$^5$)C(=O)—, wherein:
R$^3$ is H or CH$_3$;
R$^4$ is H or C$_1$–C$_3$ alkyl;
R$^5$ is H, C$_1$–C$_8$ alkyl, C$_3$–C$_6$ cycloalkyl, C$_3$–C$_6$ cycloalkylmethyl, C$_1$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, —(CH$_2$)$_s$NHC(=NH)(NH$_2$), —(CH$_2$)$_s$NHR$^{16}$, where s=3–5; or
R$^{16}$ is selected from:
an amine protecting group;
1–2 amino acids; or
1–2 amino acids substituted with an amine protecting group;
R$^3$ and R$^5$ can alternatively be taken together to form —CH$_2$CH$_2$CH$_2$—; or R$^4$ and R$^5$ can alternatively be taken together to form —(CH$_2$)$_u$—, where u=2–5;
K is an L-isomer amino acid of structure —N(R$^6$)CH(R$^7$)C(=O)—, wherein:
R$^6$ is H or C$_1$–C$_8$ alkyl;
R$^7$ is:

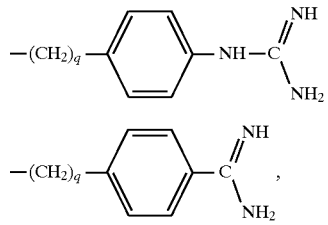

where q=0 or 1;
—(CH$_2$)$_r$X, where r=3–6;

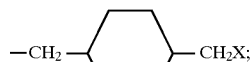

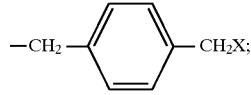

—(CH$_2$)$_m$S(CH$_2$)$_2$X, where m=1 or 2;
—(C$_3$–C$_7$ alkyl)—NH—(C$_1$–C$_6$ alkyl)

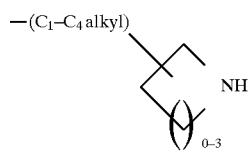

—(CH$_2$)$_m$—O—(C$_1$–C$_4$ alkyl)—NH—(C$_1$–C$_6$ alkyl), where m=1 or 2;
—(CH$_2$)$_m$—S—(C$_1$–C$_4$ alkyl)—NH—(C$_1$–C$_6$ alkyl), where m=1 or 2; and
X is —NH$_2$ or —NHC(=NH)(NH$_2$), provided that X is not —NH$_2$ when r=4; or $R^6$ and $R^7$ are alternatively be taken together to form

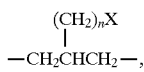

where n=0,1 and X is —$NH_2$ or —$NHC(=NH)(NH_2)$;
L is —$Y(CH_2)_vC(=O)$—, wherein:
Y is NH, O, or S; and v=1,2;
M is a D-isomer or L-isomer amino acid of structure

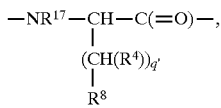

wherein:
q' is 0–2;
$R^{17}$ is H, $C_1$–$C_3$ alkyl;
$R^8$ is selected from:
—$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$.

[61] Included in the present invention are those direct radiolabeled compounds in [51] above, that are radiolabeled 1,3-disubstituted phenyl compounds of the formula (II):

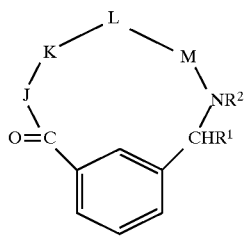

(II)

wherein:
the phenyl ring in formula (II) may be further substituted with 0–3 $R^{10}$ or $R^{10a}$;
$R^{10}$ or $R^{10a}$ are selected independently from: H, $C_1$–$C_8$ alkyl, phenyl, halogen, or $C_1$–$C_4$ alkoxy;
$R^1$ is H, $C_1$–$C_4$ alkyl, phenyl, benzyl, or phenyl—$(C_2$–$C_4)$ alkyl;
$R^2$ is H or methyl;
$R^{13}$ is selected independently from: H, $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;
J is β-Ala or an L-isomer or D-isomer amino acid of structure —$N(R^3)C(R^4)(R^5)C(=O)$—, wherein:
$R^3$ is H or $CH_3$;
$R^4$ is H;
$R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, $(CH_2)_sNHR^{16}$, where s=3–5;
$R^3$ and $R^5$ can alternatively be taken together to form —$CH_2CH_2CH_2$—;
$R^{16}$ is selected from:

an amine protecting group;
1–2 amino acids;
1–2 amino acids substituted with an amine protecting group;
K is an L-isomer amino acid of structure —$N(R^6)CH(R^7)C(=O)$—, wherein:
$R^6$ is H or $C_3$–$C_8$ alkyl;
$R^7$ is

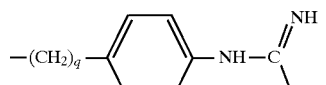

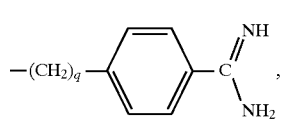

where q=0 or 1;
—$(CH_2)_rX$, where r=3–6;

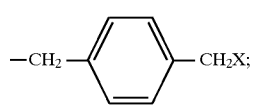

—$(CH_2)_mS(CH_2)_2X$, where m=1 or 2;
—$(C_4$–$C_7$ alkyl)—NH—$(C_1$–$C_6$ alkyl)

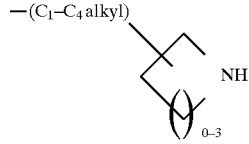

—$(CH_2)_m$—O—$(C_1$–$C_4$ alkyl)—NH—$(C_1$–$C_6$ alkyl), where m=1 or 2;
—$(CH_2)_m$—S—$(C_1$–$C_4$ alkyl)—NH—$(C_1$–$C_6$ alkyl), where m=1 or 2; and
X is —$NH_2$ or —$NHC(=NH)(NH_2)$, provided that X is not —$NH_2$ when r=4; or
L is —$YCH_2C(=O)$—, wherein:
Y is NH or O;
M is a D-isomer or L-isomer amino acid of structure

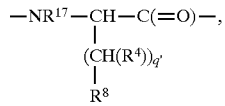

wherein:
q' is 1;
$R^{17}$ is H, $C_1$–$C_3$ alkyl;
$R^8$ is selected from:
—$CO_2H$ or —$SO_3R^{13}$.

[62] Included in the present invention are those direct radiolabeled compounds in of formula (II) above, wherein:
the phenyl ring in formula (II) may be further substituted with 0–2 $R^{10}$ or $R^{10a}$;
$R^{10}$ or $R^{10a}$ are selected independently from: H, $C_1$–$C_8$ alkyl, phenyl, halogen, or $C_1$–$C_4$ alkoxy;

R¹ is H;
R² is H;
J is β-Ala or an L-isomer or D-isomer amino acid of
  formula —N(R³)CH(R⁵)C(=O)—, wherein:
  R³ is H and R⁵ is H, CH₃, CH₂CH₃, CH(CH₃)₂,
    CH(CH₃)CH₂CH₃, CH₂CH₂CH₃, CH₂CH₂CH₂CH₃,
    CH₂CH₂SCH₃, CH₂CH(CH₃)₂, (CH₂)₄NH₂, (C₃–C₅
    alkyl)NHR¹⁶; or
  R³ is CH₃ and R⁵ is H; or
  R³ and R⁵ can alternatively be taken together to form
    —CH₂CH₂CH₂—;
R¹⁶ is selected from:
  an amine protecting group;
  1–2 amino acids;
  1–2 amino acids substituted with an amine protecting
    group;
K is an L-isomer amino acid of formula
  —N(CH₃)CH(R⁷)C(=O)—, wherein:
  R⁷ is —(CH₂)₃NHC(=NH)(NH₂);
L is —NHCH₂C(=O)—; and
M is a D-isomer or L-isomer amino acid of structure

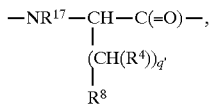

wherein:
  q' is 1;
R⁴ is H or CH₃;
R¹⁷ is H;
R⁸ is
  —CO₂H;
  —SO₃H.

[63] Included in the present invention are those direct
radiolabeled compounds in of formula (II) above, wherein:
  R¹ and R² are independently selected from H, methyl;
  J is selected from D-Val, D-2-aminobutyric acid, D-Leu,
    D-Ala, Gly, D-Pro, D-Ser, D-Lys, β-Ala, Pro, Phe,
    NMeGly, D-Nle, D-Phg, D-Ile, D-Phe, D-Tyr, Ala,
    Nᵉ-p-azidobenzoyl-D-Lys, Nᵉ-p-benzoylbenzoyl-D-
    Lys, Nᵉ-tryptophanyl-D-Lys, Nᵉ-o-benzylbenzoyl-D-
    Lys, Nᵉ-p-acetylbenzoyl-D-Lys, Nᵉ-dansyl-D-Lys,
    Nᵉ-glycyl-D-Lys, Nᵉ-glycyl-p-benzoylbenzoyl-D-Lys,
    Nᵉ-p-phenylbenzoyl-D-Lys, Nᵉ-m-benzoylbenzoyl-D-
    Lys, Nᵉ-o-benzoylbenzoyl-D-Lys;
  K is selected from NMeArg, Arg;
  L is selected from Gly, β-Ala, Ala;
  M is selected from Asp; αMeAsp; βMeAsp; NMeAsp;
    D-Asp.

[64] Included in the present invention are those direct
radiolabeled compounds in of formula (II) above, wherein:
  R¹ and R² are independently selected from H, methyl;
  J is selected from: D-Val, D-2-aminobutyric acid, D-Leu,
    D-Ala, Gly, D-Pro, D-Ser, D-Lys, β-Ala, Pro, Phe,
    NMeGly, D-Nle, D-Phg, D-Ile, D-Phe, D-Tyr, Ala;
  K is selected from NMeArg;
  L is Gly;
  M is selected from Asp; αMeAsp; βMeAsp; NMeAsp;
    D-Asp.

[65] Included in the present invention are those direct
radiolabeled compounds of [51] that are:
  the radiolabeled compound of formula (II) wherein R¹
    and R² are H; J is D-Val; K is NMeArg; L is Gly; and
    M is Asp;
  the radiolabeled compound of formula (II) wherein R¹
    and R² are H; J is D-2-aminobutyric acid; K is NMe-
    Arg; L is Gly; and M is Asp;
  the radiolabeled compound of formula (II) wherein R¹
    and R² are H; J is D-Leu; K is NMeArg; L is Gly; and
    M is Asp;
  the radiolabeled compound of formula (II) wherein R¹
    and R² are H; J is D-Ala; K is NMeArg; L is Gly; and
    M is Asp;
  the radiolabeled compound of formula (II) wherein R¹
    and R² are H; J is Gly; K is NMeArg; L is Gly; and M
    is Asp;
  the radiolabeled compound of formula (II) wherein R¹
    and R² are H; J is D-Pro; K is NMeArg; L is Gly; and
    M is Asp;
  the radiolabeled compound of formula (II) wherein R¹
    and R² are H; J is D-Lys; K is NMeArg; L is Gly; and
    M is Asp;
  the radiolabeled compound of formula (II) wherein R¹
    and R² are H; J is β-Ala; K is NMeArg; L is Gly; and
    M is Asp;
  the radiolabeled compound of formula (II) wherein R¹
    and R² are H; J is NMeGly; K is NMeArg; L is Gly; and
    M is Asp;
  the radiolabeled compound of formula (II) wherein R¹ is
    methyl (isomer 1); R² are H; J is D-Val; K is NMeArg;
    L is Gly; and M is Asp;
  the radiolabeled compound of formula (II) wherein R¹ is
    methyl (isomer 2); R² are H; J is D-Val; K is NMeArg;
    L is Gly; and M is Asp;
  the radiolabeled compound of formula (II) wherein R¹ is
    phenyl (isomer 1); R² are H; J is D-Val; K is NMeArg;
    L is Gly; and M is Asp;
  the radiolabeled compound of formula (II) wherein J=D-
    Met, K=NMeArg, L=Gly, M=Asp, R¹=H, R²=H;
  the radiolabeled compound of formula (II) wherein J=D-
    Abu, K=diNMe-guanidinyl-Orn, L=Gly, M=Asp,
    R¹=H, R²=H;
  the radiolabeled compound of formula (II) wherein J=D-
    Abu, K=diNMe-Lys, L=Gly, M=Asp, R¹=H, R²=H;
  the radiolabeled compound of formula (II) wherein R¹
    and R² are H; J is Nᵉ-p-azidobenzoyl-D-Lysine; K is
    NMeArg; L is Gly; and M is Asp;
  the radiolabeled compound of formula (II) wherein R¹
    and R² are H; J is Nᵉ-p-benzoylbenzoyl-D-Lysine; K is
    NMeArg; L is Gly; and M is Asp;
  the radiolabeled compound of formula (II) wherein R¹
    and R² are H; J is Nᵉ-tryptophanyl-D-Lysine; K is
    NMeArg; L is Gly; and M is Asp;
  the radiolabeled compound of formula (II) wherein R¹
    and R² are H; J is Nᵉ-o-benzylbenzoyl-D-Lysine; K is
    NMeArg; L is Gly; and M is Asp.
  The radiolabeled compound of formula (II) wherein R¹
    and R² are H; J is Nᵉ-p-acetylbenzoyl-D-Lysine; K is
    NMeArg; L is Gly; and M is Asp;
  the radiolabeled compound of formula (II) wherein R¹
    and R² are H; J is Nᵉ-dansyl-D-Lysine; K is NMeArg;
    L is Gly; and M is Asp;
  the radiolabeled compound of formula (II) wherein R¹
    and R² are H; J is Nᵉ-glycyl-D-Lysine; K is NMeArg;
    L is Gly; and M is Asp;
  the radiolabeled compound of formula (II) wherein R¹
    and R² are H; J is Nᵉ-glycyl-p-benzoylbenzoyl-D-
    Lysine; K is NMeArg; L is Gly; and M is Asp;

the radiolabeled compound of formula (II) wherein $R^1$ and $R^2$ are H; J is $N^\epsilon$-p-phenylbenzoyl-D-Lysine; K is NMeArg; L is Gly; and M is Asp;

the radiolabeled compound of formula (II) wherein $R^1$ and $R^2$ are H; J is $N^\epsilon$-m-benzoylbenzoyl-D-Lysine; K is NMeArg; L is Gly; and M is Asp;

the radiolabeled compound of formula (II) wherein $R^1$ and $R^2$ are H; J is $N^\epsilon$-o-benzoylbenzoyl-D-Lysine; K is NMeArg; L is Gly; and M is Asp;

the radiolabeled compound of formula (III) wherein $R^1$ and $R^2$ are H; J is D-Val; K is NMeArg; L is Gly; and M is Asp;

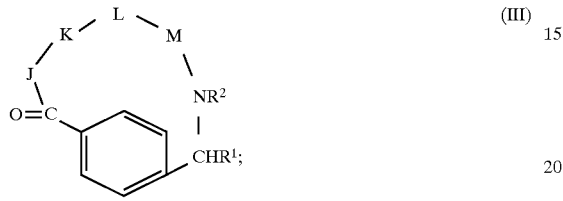

(III)

the radiolabeled compound of formula (II) wherein $R^1$ and $R^2$ are H; J is D-Val; K is D-NMeArg; L is Gly; and M is Asp;

the radiolabeled compound of formula (II) wherein $R^1$ and $R^2$ are H; J is D-Nle; K is NMeArg; L is Gly; and M is Asp;

the radiolabeled compound of formula (II) wherein $R^1$ and $R^2$ are H; J is D-Phg; K is NMeArg; L is Gly; and M is Asp;

the radiolabeled compound of formula (II) wherein $R^1$ and $R^2$ are H; J is D-Phe; K is NMeArg; L is Gly; and M is Asp;

the radiolabeled compound of formula (V) wherein $R^1$ and $R^2$ are H; J is D-Ile; K is NMeArg; L is Gly; and M is Asp;

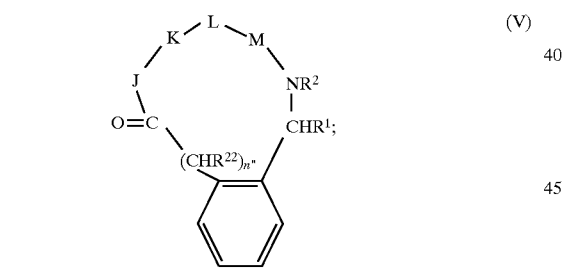

(V)

the radiolabeled compound of formula (V) wherein n"=1; $R^1$, $R^2$, and $R^{22}$ are H; J is D-Val; K is NMeArg; L is Gly; and M is Asp;

the radiolabeled compound of formula (V) wherein n"=0; $R^1$ and $R^2$ are H; J is D-Val; K is NMeArg; L is Gly; and M is Asp;

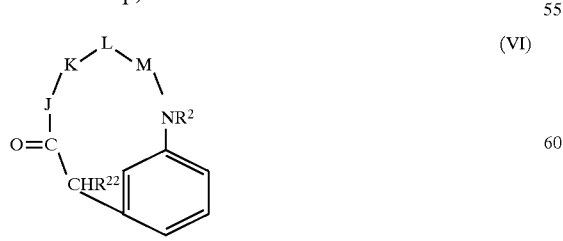

(VI)

the radiolabeled compound of formula (VI) wherein $R^2$ and $R^{22}$ are H; J is D-Val; K is NMeArg; L is Gly; and M is Asp;

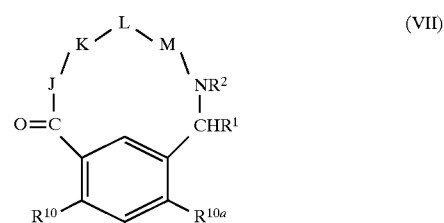

(VII)

the radiolabeled compound of formula (VII) wherein $R^1$, $R^2$, and $R^{10}$ are H; $R^{10a}$ is Cl; J is D-Val; K is NMeArg; L is Gly; and M is Asp;

the radiolabeled compound of formula (VII) wherein $R^1$, $R^2$, and $R^{10}$ are H; $R^{10a}$ is I; J is D-Val; K is NMeArg; L is Gly; and M is Asp;

the radiolabeled compound of formula (VII) wherein $R^1$, $R^2$, and $R^{10}$ are H; $R^{10a}$ is I; J is D-Abu; K is NMeArg; L is Gly; and M is Asp;

the radiolabeled compound of formula (VII) wherein $R^1$, $R^2$, and $R^{10}$ are H; $R^{10a}$ is Me; J is D-Val; K is NMeArg; L is Gly; and M is Asp;

the radiolabeled compound of formula (VII) wherein $R^1$, $R^2$, and $R^{10a}$ are H; $R^{10}$ is Cl; J is D-Val; K is NMeArg; L is Gly; and M is Asp;

the radiolabeled compound of formula (VII) wherein $R^1$, $R^2$, and $R^{10a}$ are H; $R^{10}$ is MeO; J is D-Val; K is NMeArg; L is Gly; and M is Asp;

the radiolabeled compound of formula (VII) wherein $R^1$, $R^2$, and $R^{10a}$ are H; $R^{10}$ is Me; J is D-Val; K is NMeArg; L is Gly; and M is Asp;

the radiolabeled compound of formula (VII) wherein $R^1$, $R^2$, and $R^{10}$ are H; $R^{10a}$ is Cl; J is D-Abu; K is NMeArg; L is Gly; and M is Asp;

the radiolabeled compound of formula (VII) wherein $R^1$, $R^2$, and $R^{10}$ are H; $R^{10a}$ is I; J is D-Abu; K is NMeArg; L is Gly; and M is Asp.

The radiolabeled compound of formula (VII) wherein $R^1$, $R^2$, and $R^{10}$ are H; $R^{10a}$ is Me; J is D-Abu; K is NMeArg; L is Gly; and M is Asp;

the radiolabeled compound of formula (II) wherein $R^1$ and $R^2$ are H; J is D-Tyr; K is NMeArg; L is Gly; and M is Asp;

the radiolabeled compound of formula (II) wherein $R^1$ and $R^2$ are H; J is D-Val; K is NMeAmf; L is Gly; and M is Asp;

the radiolabeled compound of formula (II) wherein $R^1$ and $R^2$ are H; J is D-Val; K is NMeArg; L is Gly; and M is βMeAsp;

the radiolabeled compound of formula (II) wherein $R^1$ is H; $R^2$ is $CH_3$; J is D-Val; K is NMeArg; L is Gly; and M is Asp;

the radiolabeled compound of formula (III) wherein $R^1$ and $R^2$ are H; J is D-Val; K is NMeArg; L is Gly; and M is Asp;

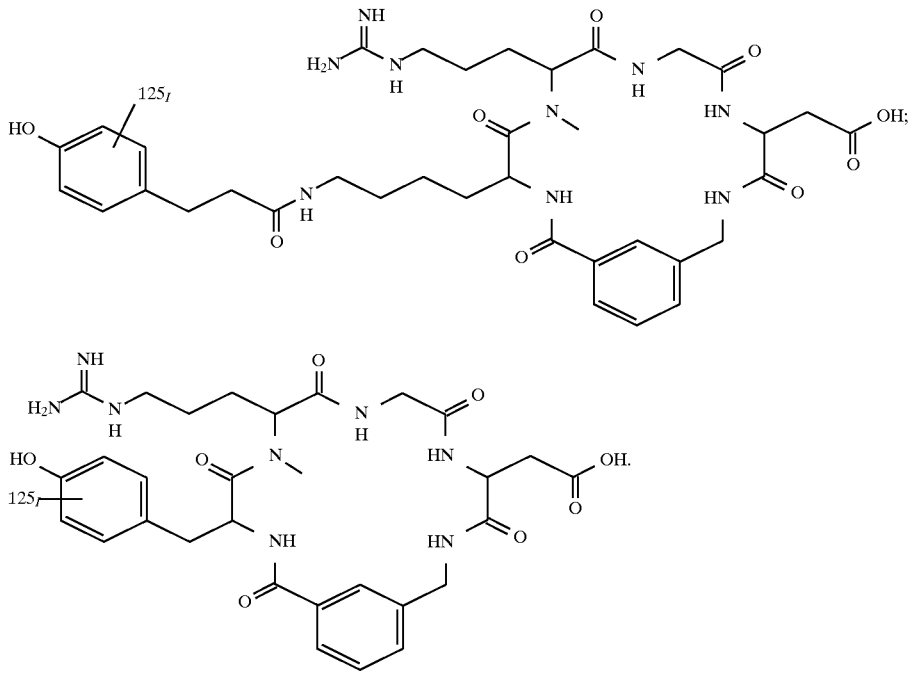

[66] Included in the present invention are those radiolabeled compound as in one of [51]–[65] wherein the radiolabel is selected from the group: $^{18}F$, $^{11}C$, $^{123}I$, and $^{125}I$.

[67] Included in the present invention are those radiolabeled compounds of [66] wherein the radiolabel is $^{123}I$.

[68] Included in the present invention is a radiopharmaceutical composition comprising a radiopharmaceutically acceptable carrier and a radiolabeled compound of any of [51]–[67].

[69] Included in the present invention is a method of determining platelet deposition in a mammal comprising administering to said mammal a radiopharmaceutical composition comprising a compound of any of [51]–[67], and imaging said mammal.

[70] Included in the present invention is a method of diagnosing a disorder associated with platelet deposition in a mammal comprising administering to said mammal a radiopharmaceutical composition comprising a compound of any of [51]–[67], and imaging said mammal.

As noted above, the cyclic compounds of the present invention are radiolabeled. By "radiolabeled", it is meant that the subject cyclic platelet glycoprotein IIb/IIIa compounds contain a radioisotope which is suitable for administration to a mammalian patient. Suitable radioisotopes are known to those skilled in the art and include, for example, isotopes of halogens (such as chlorine, fluorine, bromine and iodine), and metals including technetium and indium. Preferred radioisotopes include 11C, 18F, $^{123}I$, $^{125}I$, $^{131}I$, $^{99m}Tc$, $^{94m}Tc$, $^{95}Tc$, $^{111}In$, $^{62}Cu$, $^{43}Sc$, $^{45}Ti$, $^{67}Ga$, $^{68}Ga$, $^{97}Ru$, $^{72}As$, $^{82}Rb$, and $^{201}Tl$. Most preferred are the isoptopes $^{123}I$, $^{111}In$, and $^{99m}Tc$. Radiolabeled compounds of the invention may be prepared using standard radiolabeling procedures well known to those skilled in the art. Suitable synthesis methodology is described in detail below. As discussed below, the cyclic platelet glycoprotein IIb/IIIa compounds of the invention may be radiolabeled either directly (that is, by incorporating the radiolabel directly into the compounds) or indirectly (that is, by incorporating the radiolabel into the compounds through a chelating agent, where the chelating agent has been incorporated into the compounds). Also, the radiolabeling may be isotopic or nonisotopic. With isotopic radiolabeling, one group already present in the cyclic compounds described above is substituted with (exchanged for) the radioisotope. With nonisotopic radiolabeling, the radioisotope is added to the cyclic compounds without substituting with (exchanging for) an already existing group. Direct and indirect radiolabeled compounds, as well as isotopic and nonisotopic radiolabeled compounds are included within the phrase "radiolabeled compounds" as used in connection with the present invention. Such radiolabeling should also be reasonably stable, both chemically and metabolically, applying recognized standards in the art. Also, although the compounds of the invention may be labeled in a variety of fashions with a variety of different radioisotopes, as those skilled in the art will recognize, such radiolabeling should be carried out in a manner such that the high binding affinity and specificity of the unlabeled cyclic platelet GPIIb/IIIa compounds of the invention to the GPIIb/IIIa receptor is not significantly affected. By not significantly affected, it is meant that the binding affinity and specificity is not affected more than about 3 log units, preferably not more than about 2 log units, more preferably not more than about 1 log unit, even more preferably not more than about 500%, and still even more preferably not more than about 250%, and most preferably the binding affinity and specificity is not affected at all.

For radiolabeled compounds, the label may appear at any position on Q. Preferred radiolabeled compounds of the invention are radiolabeled compounds wherein the radiolabel is located on the carbocyclic ring system of $R^{31}$, the $R^5$ substituent on J, and at $R^1$ or $R^{22}$. Even more preferred radiolabeled compounds of the invention are those of formula (II), wherein the radiolabel is located on the carbocyclic ring system of $R^{31}$, or the $R^5$ substituent on J. With regard to the preferred and more preferred direct radiolabeled compounds, the preferred radiolabel is a halogen label, especially an iodine radiolabel. For indirect radiolabeled compounds, the preferred metal nuclides are $^{99m}Tc$ and $^{111}$In. Preferred linking groups, $L_n$, and metal chelators, $C_h$, are described below.

It has been discovered that the radiolabeled compounds of the invention are useful as radiopharmaceuticals for non-invasive imaging to diagnose present or potential thromboembolic disorders, such as arterial or venous thrombosis, including, for example, unstable angina, myocardial infarction, transient ischemic attack, stroke, atherosclerosis, diabetes, thrombophlebitis, pulmonary emboli, or platelet plugs, thrombi or emboli caused by prosthetic cardiac devices such as heart valves. The radiolabeled compounds of the invention are useful with both newly formed and older thrombi. The radiolabeled compounds of the invention may also be used to diagnose other present or potential conditions where there is overexpression of the GPIIb/IIIa receptors, such as with metastatic cancer cells. The subject compounds may be effectively employed in low doses, thereby minimizing any risk of toxicity. Also, the subject compounds are of a much smaller size than, for example, the radiolabeled 7E3 antibodies known in the art, allowing easier attainment of suitable target/background (T/B) ratio for detecting thrombi. The use of the radiolabeled compounds of the invention is further described in the utility section below.

In the present invention it has also been discovered that the radiolabeled compounds above are useful as inhibitors of glycoprotein IIb/IIIa (GPIIb/IIIa), and thus the radiolabeled compounds of the invention may also be employed for therapeutic purposes, in addition to the diagnostic usage described above. As discussed above, GPIIb/IIIa mediates the process of platelet activation and aggregation. The radiolabeled compounds of the present invention inhibit the activation and aggregation of platelets induced by all known endogenous platelet agonists.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis, from optically active starting materials. Two distinct isomers (cis and trans) of the peptide bond are known to occur; both can also be present in the compounds described herein, and all such stable isomers are contemplated in the present invention. Unless otherwise specifically noted, the L-isomer of the amino acid is used at positions J, K, L, and M of the compounds of the present invention. Except as provided in the preceding sentence, all chiral, diastereomeric, racemic forms and all geometric isomeric forms of a structure are intended, unless the specific stereochemistry or isomer form is specifically indicated. The D and L-isomers of a particular amino acid are designated herein using the conventional 3-letter abbreviation of the amino acid, as indicated by the following examples: D-Leu, D-Leu, L-Leu, or L-Leu.

When any variable (for example, $R^1$ through $R^8$, m, n, p, X, Y, etc.) occurs more than one time in any constituent or in any formula, its definition on each occurrence is independent of its definition at every other occurrence. Thus, for example, if a group is shown to be substituted with 0–2 $R^{11}$, then said group may optionally be substituted with up to two $R^{11}$ and $R^{11}$ at each occurrence is selected independently from the defined list of possible $R^{11}$. Also, by way of example, for the group —N($R^{13}$)$_2$, each of the two $R^{13}$ substituents on N is independently selected from the defined list of possible $R^{13}$.

When a bond to a substituent is shown to cross the bond connecting two atoms in a ring, then such substituent may be bonded to any atom on the ring.

Combinations of substituents and/or variables are permissible only if such combinations result in stable compounds.

By "stable compound" or "stable structure" is meant herein a compound that is sufficiently robust to survive isolation to a useful degree of purity from a reaction mixture, and formulation into an efficacious therapeutic agent.

The term "substituted", as used herein, means that an one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl and adamantyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The phrase "boronic acid" as used herein means a group of the formula —B($R^{34}$)($R^{35}$), wherein $R^{34}$ and $R^{35}$ are independently selected from: —OH; —F; —N$R^{13}R^{14}$; or $C_1$–$C_8$-alkoxy; or $R^{34}$ and $R^{35}$ can alternatively be taken together to form: a cyclic boron ester where said chain or ring contains from 2 to 20 carbon atoms and, optionally, 1–4 heteroatoms independently selected from N, S, or O; a divalent cyclic boron amide where said chain or ring contains from 2 to 20 carbon atoms and, optionally, 1–4 heteroatoms independently selected from N, S, or O; a cyclic boron amide-ester where said chain or ring contains from 2 to 20 carbon atoms and, optionally, 1–4 heteroatoms independently selected from N, S, or O. Such cyclic boron esters, boron amides, or boron amide-esters may also be optionally substituted with 1–5 groups independently selected from $R^{11}$.

Boron esters include boronic acid protecting groups, including moieties derived from diols, for example pinanediol and pinacol to form pinanediol boronic acid ester and the pinacol boronic acid, ester respectively. Other illustrations of diols useful for deriving boronic acid esters are perfluoropinacol, ethylene glycol, diethylene glycol, 1,2-ethanediol, 1,3-propanediol, 1,2-propanediol, 1,2- butanediol, 1,4-butanediol, 2,3-butanediol, 2,3-hexanediol, 1,2-hexanediol, catechol, 1,2-diisopropylethanediol, 5,6-decanediol, 1,2-dicyclohexylethanediol.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl. As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic ring system" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H,6H-1,5,2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4-oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$. Examples of groups that, when administered to a mammalian subject, are cleaved to form a free hydroxyl, amino or sulfhydryl, include hydroxy, amine or sulfhydryl protecting groups, respectively.

As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The term "amino acid" as used herein means an organic compound containing both a basic amino group and an acidic carboxyl group. Included within this term are modified and unusual amino acids, such as those disclosed in, for example, Roberts and Vellaccio (1983) *The Peptides,* 5: 342–429, the teaching of which is hereby incorporated by reference. Modified or unusual amino acids which can be used to practice the invention include, but are not limited to, D-amino acids,hydroxylysine, 4-hydroxyproline, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, 4-aminopiperidine-4-carboxylic acid, 6-aminocaproic acid, trans-4-(aminomethyl) cyclohexanecarboxylic acid, 2-, 3-, and 4-(aminomethyl) benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a linear compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

A "pseudopeptide" or "peptide mimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue.

A "pseudopeptide residue" means that portion of an pseudopeptide or peptide mimetic (as defined herein) that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The terms "$L_n$", "linking group" and "linker", used interchangeably throughout, designate the group of atoms separating Q from the metal chelator, $C_h$.

The terms "activated $L_n$ group", "activated $L_n$", "activated linking group" and "activated linker", used interchangeably throughout, refer to a linking group that bears one or more reactive group capable of reacting with, and forming a bond with, a chelator or a Q.

The terms "$C_h$", "metal chelator", and "chelator"0 are used interchangeably throughout to designate a chemical moiety capable of binding to or completing with a metal nuclide.

The term "cyclizing moiety" means the intermediate compound that serves as the precursor to the $R^{31}$ group of Q.

The term "ring substituted cyclizing moiety" is a cyclizing moiety bearing a substituent group one or more of its carbocyclic or heterocyclic rings.

The term "linker modified cyclizing moiety" refers to a cyclizing moiety that bears an activated $L_n$ group.

The term "cyclic compound intermediate" means the intermediate compound that serves as the precursor to the Q group in the claimed compounds.

The term "linker modified cyclic compound intermediate" means a cyclic compound intermediate that bears an activated $L_n$ group.

The compounds of the present invention can be prepared in a number of ways well known to one skilled in the art of organic synthesis. Preferred methods include but are not limited to those methods described below.

The following abbreviations are used herein:

| | |
|---|---|
| Acm | acetamidomethyl |
| D-Abu | D-2-aminobutyric acid |
| Aca | 6-aminocaproamide(6-aminohexanamide) |
| b-Ala, b-Ala or bAla | 3-aminopropionic acid |
| Boc | t-butyloxycarbonyl |
| Boc-iodo-Mamb | t-butyloxycarbonyl-3-aminomethyl-4-iodo-benzoic acid |
| Boc-Mamb | t-butyloxycarbonyl-3-aminomethylbenzoic acid |
| Boc-ON | [2-(tert-butyloxycarbonyloxylimino)-2-phenylacetonitrile |
| $Cl_2Bzl$ | dichlorobenzyl |
| CBZ, Cbz or Z | Carbobenzyloxy |
| DCC | dicyclohexylcarbodiimide |
| DIEA | diisopropylethylamine |
| di-NMeOrn | N-aMe-N-gMe-ornithine |
| DMAP | 4-dimethylaminopyridine |
| HBTU | 2-(1H-Benzotriazol-1-yl)-1,1,3,3-tetramethyluronium hexafluorophosphate |
| NMeArg or MeArg | a-N-methyl arginine |
| NMeAmf | N-Methylaminomethylphenylalanine |
| NMeASP | a-N-methyl aspartic acid |
| NMeGly or MeGly | N-methyl glycine |
| NMe-Mamb | N-methyl-3-aminomethylbenzoic acid |
| NMM | N-methylmorpholine |
| OcHex | O-cyclohexyl |
| OBzl | O-benzyl |
| oSu | O-succinimidyl |
| pNP | p-nitrophenyl |
| TBTU | 2-(1H-Benzotriazol-1-yl)-1,1,3,3-tetramethyluronium tetrafluoroborate |
| Teoc | 2-(Trimethylsilyl)ethyloxycarbonyl |
| Tos | tosyl |
| Tr | trityl |

The following conventional three-letter amino acid abbreviations are used herein; the conventional one-letter amino acid abbreviations are not used herein:

Ala=alanine
Arg=arginine
Asn=asparagine
Asp=aspartic acid
Cys=cysteine
Gln=glutamine
Glu=glutamic acid
Gly=glycine
His=histidine
Ile=isoleucine
Leu=leucine
Lys=lysine
Met=methionine
Nle=norleucine
Phe=phenylalanine
Phg=phenylglycine
Pro=proline
Ser=serine
Thr=threonine
Trp=tryptophan
Tyr=tyrosine
Val=valine The compounds of the present invention can be synthesized using standard synthetic methods known to those skilled in the art. Preferred methods include but are not limited to those methods described below.

Generally, peptides are elongated by deprotecting the a-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

The compounds of the invention may also be synthesized using automated peptide synthesizing equipment. In addition to the foregoing, procedures for peptide synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Sythesis" Springer-Verlag, New York (1984), the disclosures of which are hereby incorporated by reference.

The coupling between two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole These coupling reactions may be performed in either solution (liquid phase) or solid phase.

The functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference.

The a-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) J. Org. Chem. 45, 1295–1300) chloro or bromomethyl resin, hydroxymethyl resin, and aminomethyl resin. Many of these resins are commercially available with the desired C-terminal amino acid already incorporated.

The a-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tertbutyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred a-amino protecting group is either Boc or Fmoc. Many amino acid derivatives suitably protected for peptide synthesis are commercially available.

The a-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-identified groups. Those skilled in the art will appreciate that the selection and use of appropriate protecting groups for these side chain functionalities will depend upon the amino acid and presence of other protecting groups in the peptide. The selection of such a protecting group is important in that it must not be removed during the deprotection and coupling of the a-amino group.

For example, when Boc is chosen for the a-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the a-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation and cyclization of the peptide is completed all of the protecting groups are removed. For the liquid phase synthesis the protecting groups are removed in whatever manner as dictated by the choice of protecting groups. These procedures are well known to those skilled in the art.

When a solid phase synthesis is used, the peptide should be removed from the resin without simultaneously removing protecting groups from functional groups that might interfere with the cyclization process. Thus, if the peptide is to be cyclized in solution, the cleavage conditions need to be chosen such that a free a-carboxylate and a free a-amino group are generated without simultaneously removing other protecting groups. Alternatively, the peptide may be removed from the resin by hydrazinolysis, and then coupled by the azide method. Another very convenient method involves the synthesis of peptides on an oxime resin, followed by intramolecular nucleophilic displacement from the resin, which generates a cyclic peptide (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide can also be accomplished by other acid reagents such as trifluoromethanesulfonic acid/ trifluoroacetic acid mixtures.

Unusual amino acids used in this invention can be synthesized by standard methods familiar to those skilled in the art ("The Peptides: Analysis, Sythesis, Biology, Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated here by reference.

The compounds of the present invention may be prepared using the procedures further detailed below.

Representative materials and methods that may be used in preparing the compounds of the invention are described further below.

Manual solid phase peptide synthesis was performed in 25 mL polypropylene filtration tubes purchased from BioRad Inc., or in 60 mL hour-glass reaction vessels purchased from Peptides International. Oxime resin (substitution level=0.96 mmol/g) was prepared according to published procedures (DeGrado and Kaiser (1980) *J. Org. Chem.* 45, 1295), or was purchased from Novabiochem (substitution level=0.62 mmol/g). All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 3-cyanobenzoic acid and [2-(tert-butyloxycarbonyloxylimino)-phenylacetonitrile] (Boc-ON) were purchased from Aldrich Chemical Company. Dimethylformamide (DMF), ethyl acetate, chloroform (CHCl$_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were purchased from EM Science. Palladium on carbon catalyst (10% Pd) was purchased from Fluka Chemical Company. Absolute ethanol was obtained from Quantum Chemical Corporation. Thin layer chromatography (TLC) was performed on Silica Gel 60 F$_{254}$ TLC plates (layer thickness 0.2 mm) which were purchased from EM Separations. TLC visualization was accomplished using UV light, iodine, ninhydrin spray and/or Sakaguchi spray. Melting points were determined using a Thomas Hoover or Electrothermal 9200 melting point apparatus and are uncorrected. HPLC analyses were performed on either a Hewlett Packard 1090, Waters Delta Prep 3000, Rainin, or DuPont 8800 system. NMR spectra were recorded on a 300 MHz General Electric QE-300, Varian 300, or Varian 400 spectrometer. Fast atom bombardment mass spectrometry (FAB-MS) was performed on a VG Zab-E double-focusing mass spectrometer using a Xenon FAB gun as the ion source or a Finnigan MAT 8230.

Boc-D-2-aminobutyric acid (Boc-D-Abu) was prepared by a modification of procedures previously reported in the literature (Itoh, Hagiwara, and Kamiya (1975) *Tett. Lett.*, 4393), as shown in the scheme below.

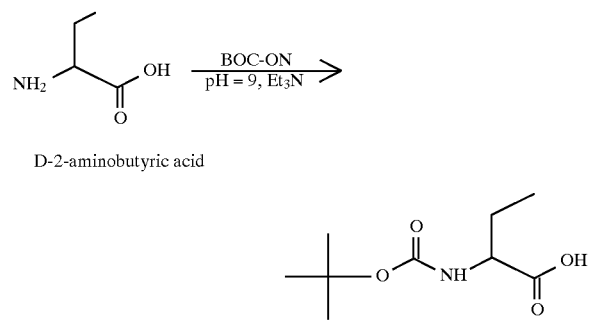

D-2-aminobutyric acid

D-2-aminobutyric acid (1.0 g, 9.70 mmol) was dissolved in 20 ml H$_2$O and a solution of Boc-ON (2.62 g, 10.6 mmol) in 20 ml acetone was added. A white precipitate formed which dissolved upon addition of triethylamine (3.37 ml, 24.2 mmol) to give a pale yellow solution (pH=9, wet pH paper). The solution was stirred at room temperature overnight at which time the acetone was removed under reduced pressure. The remaining aqueous layer was extracted with ether three times, acidified to pH 2 with concentrated HCl, and then extracted with ethyl acetate three times. The combined organic layers were dried over anhydrous magnesium sulfate and evaporated under reduced pressure to give t-butyloxycarbonyl-D-2-aminobutyric acid as an oil (2.05 g, greater than quantitative yield, contains solvent), which was used without further purification. $^1$H NMR (CDCl$_3$) 0.98 (t, 3H), 1.45 (s, 9H), 1.73 (m, 1H), 1.90 (m, 1H), 4.29 (m, 1H), 5.05 (m, 1H).

Synthesis of R$^{31}$ Cyclizing Moieties

This section teaches the synthesis of certain cyclizing moieties that serve as intermediates to the R$^{31}$ groups in Q. Later sections teach the synthesis of other cyclizing moieties.

Synthesis of Boc-aminomethylbenzoic Acid, Boc-aminophenylacetic Acid And Boc-aminomethylphenylacetic Acid Derivatives Boc-aminomethylbenzoic acid derivatives useful as cyclizing moieties in the synthesis of the compounds of the invention are prepared using standard procedures, for example, as described in *Tett. Lett.*, 4393 (1975); *Modern Synthetic Reactions*, H. O. House (1972); or Harting et al. *J. Am. Chem. Soc.*, 50: 3370 (1928), and as shown schematically below.

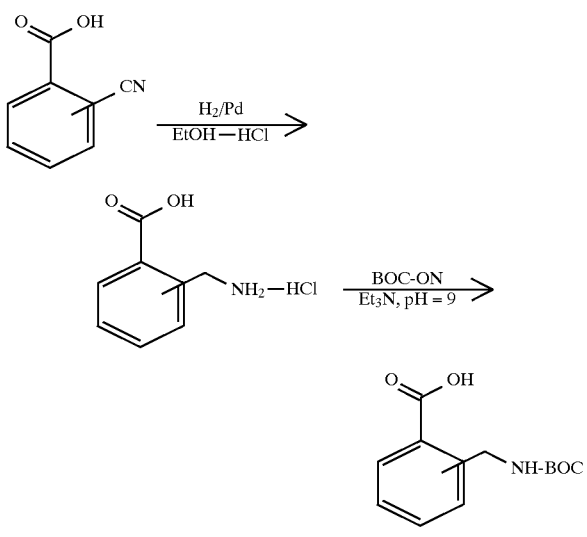

3-Aminomethylbenzoic acid.HCl

3-Cyanobenzoic acid (10.0 g, 68 mmol) was dissolved in 200 ml ethanol by heating in a 35°–50° C. water bath. Concentrated HCl (6.12 ml, 73 mmol) was added and the solution was transferred to a 500 ml nitrogen-flushed round bottom flask containing palladium on carbon catalyst (1.05 g, 10% Pd/C). The suspension was stirred under an atmosphere of hydrogen for 38 hours, filtered through a scintered glass funnel, and washed thoroughly with $H_2O$. The ethanol was removed under reduced pressure and the remaining aqueous layer, which contained a white solid, was diluted to 250 ml with additional $H_2O$. Ethyl ether (250 ml) was added and the suspension was transferred to a separatory funnel. Upon vigorous shaking, all solids dissolved and the aqueous layer was then washed two times with ether, evaporated under reduced pressure to a volume of 150 ml, and lyophilized to give the title compound (3-aminomethylbenzoic acid.HCl) (8.10 g, 64%) as a beige solid. $^1H$ NMR ($D_2O$) 4.27 (s, 2H), 7.60 (t, 1H), 7.72 (d,1H), 8.06 (d, 2H).

t-Butyloxycarbonyl-3-aminomethylbenzoic Acid (Boc-Mamb)

The title compound was prepared according to a modification of standard procedures previously reported in the literature (Itoh, Hagiwara, and Kamiya (1975) *Tett. Lett.,* 4393). 3-Aminomethylbenzoic acid (hydrochloride salt) (3.0 g, 16.0 mmol) was dissolved in 60 ml $H_2O$. To this was added a solution of Boc-ON (4.33 g, 17.6 mmol) in 60 ml acetone followed by triethylamine (5.56 ml, 39.9 mmol). The solution turned yellow and the pH was adjusted to 9 (wet pH paper) by adding an additional 1.0 ml (7.2 mmol) triethylamine. The solution was stirred overnight at room temperature at which time the acetone was removed under reduced pressure and the remaining aqueous layer was washed three times with ether. The aqueous layer was then acidified to pH 2 with 2N HCl and then extracted three times with ethyl acetate. The combined organic layers were washed three times with $H_2O$, dried over anhydrous magnesium sulfate, and evaporated to dryness under reduced pressure. The material was recrystallized from ethyl acetate/hexane to give two crops of the title compound (2.58 g, 64%) as an off-white solid. mp 123°–125° C.; $^1H$ NMR ($CDCl_3$) 1.47 (s, 9H), 4.38 (br s, 2H), 4.95 (br s, 1H), 7.45 (t, 1H), 7.55 (d, 1H), 8.02 (d, 2H).

Synthesis of t-Butyloxycarbonyl-3-aminophenylacetic Acid t-Butyloxycarbonyl-3-aminophenylacetic acids useful as intermediates in the synthesis of the compounds of the invention are prepared using standard procedures, for example, as described in Collman and Groh (1982) *J. Am. Chem. Soc.,* 104: 1391, and as shown schematically below.

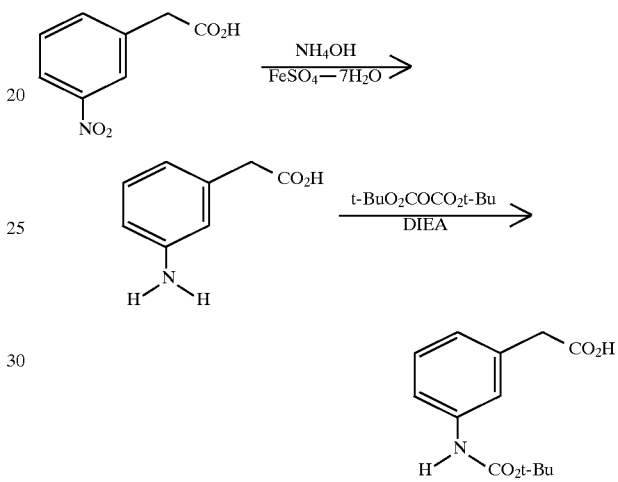

t-Butyloxycarbonyl-3-aminophenylacetic Acid

A solution of 3-aminophenylacetic acid (Aldrich, 10 g, 66 mmol), di-tert-butyl dicarbonate (15.8 g, 72 mmol), and DIEA (8.6 g, 66 mmol) in 50 ml of dichloromethane was stirred overnight at room temperature. The reaction mixture was concentrated, partitioned between dichloromethane-$H_2O$, the water layer was separated, acidified to pH 3 with 1N HCl, and extracted with dichloromethane. The extracts were washed with $H_2O$, brine, dried over anhydrous sodium sulfate, and evaporated to dryness under reduced pressure. This material was purified by recrystallization from heptane to provide the title compound (3.7 g, 22%) as a white solid. mp 105° C.; $^1H$ NMR ($CDCl_3$) 7.35 (s, 1H), 7.25 (m, 3H), 6.95 (m, 1H), 6.60 (br s, 1H), 3.65 (s, 2H), 1.50 (s, 9H).

Synthesis of 2-Aminomethylbenzoic Acid.HCl and 2-Aminomethylphenylacetic Acid.HCl 2-Aminomethylbenzoic acid.HCl and 2-aminomethylphenylacetic acid.HCl useful as intermediates in the synthesis of the compounds of the invention are prepared using standard procedures, for example, as described in Naito et al *J. Antibiotics,* 30: 698 (1977); or Young and Sweet *J. Am. Chem. Soc.,* 80: 800 (1958), and as shown schematically below.

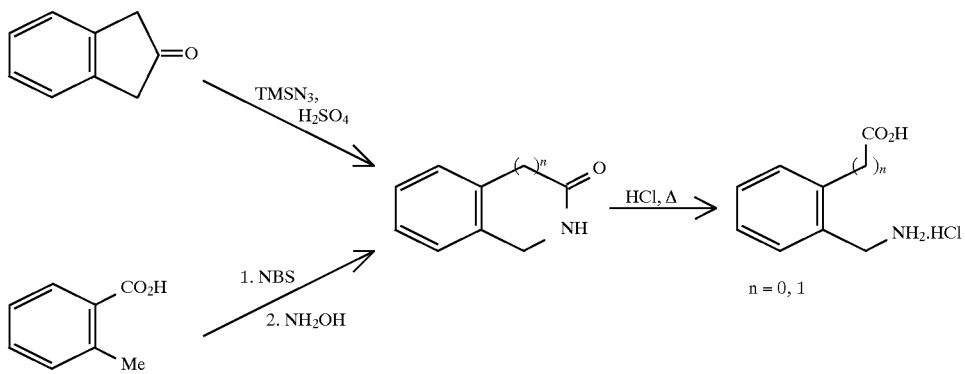

2-Aminomethylphenylacetic Acid d-Lactam

The title compound was prepared by modification of procedures previously reported in the literature (Naito et al. (1977) *J. Antibiotics*, 30: 698). To an ice-cooled suspension of 2-indanone (10.8 g, 82 mmol) and azidotrimethylsilane (9.4 g, 82 mmol) in 115 ml of chloroform was added 25 ml of concentrated sulfuric acid at a rate to maintain the temperature between 30°–40° C. After an additional 3 hours, the reaction mixture was poured onto ice, and the water layer was made basic with concentrated ammonium hydroxide. The chloroform layer was separated, washed with $H_2O$, brine, dried over anhydrous magnesium sulfate, and evaporated to dryness under reduced pressure. This material was purified by sublimation (145° C., <1 mm), followed by recrystallization from benzene to give the title compound (5.4 g, 45%) as pale yellow crystals. mp 149°–150° C.; $^1$H NMR ($CDCl_3$) 7.20 (m, 5H), 4.50 (s, 2H), 3.60 (s, 2H).

2-Aminomethylphenylacetic Acid.HCl

The title compound was prepared by modification of procedures previously reported in the literature (Naito et al. (1977) *J. Antibiotics*, 30: 698). A mixture of 2-aminomethylphenylacetic acid d-lactam (6.4 g, 44 mmol) and 21 ml of 6N HCl was heated to reflux for 4 hours. The reaction mixture was treated with activated carbon (Norit A), filtered, evaporated to dryness, and the residual oil triturated with acetone. Filtration provided the title compound (5.5 g, 62%) as colorless crystals. mp 168° C. (dec); $^1$H NMR ($D_6$-DMSO) 12.65 (br s, 1H), 8.35 (br s, 3H), 7.50 (m, 1H), 7.35 (m, 3H), 4.05 (ABq, 2H), 3.80 (s, 2H).

2-Aminomethylbenzoic Acid g-Lactam

The title compound was prepared by modification of procedures previously reported in the literature (Danishefsky et al. (1975) *J. Org. Chem.*, 40: 796). A mixture of methyl o-toluate (45 g, 33 mol), N-bromosuccinimide (57 g, 32 mol), and dibenzoyl peroxide (0.64 g) in 175 ml of carbon tetrachloride was heated to reflux for 4 hours. The cooled reaction mixture was filtered, evaporated to dryness under reduced pressure, dissolved in 250 ml of methanol, and concentrated ammonium hydroxide (75 ml, 1.11 mol) was added. The reaction mixture was heated to reflux for 5 hours, concentrated, filtered, and the solid washed with $H_2O$ followed by ether. This material was purified by recrystallization from $H_2O$ to give the title compound (11.0 g, 26%) as a white solid. mp 150° C.; $^1$H NMR ($CDCl_3$) 7.90 (d, 1H), 7.60 (t, 1H), 7.50 (t, 2H), 7.00 (br s, 1H), 4.50 (s, 2H).

2-Aminomethylbenzoic Acid.HCl

The title compound was prepared using the general procedure described above for 2-aminomethylphenylacetic acid.HCl. The lactam (3.5 g, 26 mmol) was converted to the title compound (2.4 g, 50%) as colorless crystals. mp 233° C. (dec); $^1$H NMR (D6-DMSO) 13.40 (br s, 1H), 8.35 (br s, 3H), 8.05 (d, 1H), 7.60 (m, 3H), 4.35 (br s, 2H).

Synthesis of Cyclic Compound Intermediates

This section teaches the synthesis of certain cyclic compound intermediates. These are the intermediate compounds that serve as the precursor to the Q group in the claimed compounds, $(QL_n)_dC_h$; $(Q)_dL_n$—$C_n$. These compounds may be directly labeled with radioisotopes, or may be modified by attaching linker group(s) and chelator(s).

t-Butyloxycarbonyl-3-aminomethylbenzoic acid (Boc-Mamb) is coupled to oxime resin by a modification of the method described by DeGrado and Kaiser (1980) *J. Org. Chem.* 45, 1295 using 1 equivalent of the 3-aminomethylbenzoic acid (with respect to the substitution level of the resin), 1 equivalent of HBTU, and 3 equivalent of NMM. Alternatively, Boc-Mamb (1 equivalent) may be coupled to the oxime resin using 1 equivalent each of DCC and DMAP in methylene chloride. Coupling times range from 15 to 96 hours. The substitution level is then determined using either the picric acid test (Sarin, Kent, Tam, and Merrifield, (1981) *Anal. Biochem.* 117, 145–157) or the quantitative ninhydrin assay (Gisin (1972) *Anal. Chim. Acta* 58, 248–249). Unreacted oxime groups are blocked using 0.5M trimethylacetylchloride/0.5M diisopropylethylamine in DMF for 2 hours. Deprotection of the Boc protecting group is accomplished using 25% TFA in DCM for 30 minutes. The remaining amino acids or amino acid derivatives are coupled using between a two and ten fold excess (based on the loading of the first amino acid or amino acid derivative) of the appropriate amino acid or amino acid derivatives and HBTU in approximately 8 ml of DMF. The resin is then neutralized in situ using 3 eq. of NMM (based on the amount of amino acid used) and the coupling times range from 1 hour to several days. The completeness of coupling is monitored by qualitative ninhydrin assay, or picric acid assay in cases where the amino acid was coupled to a secondary amine. Amino acids are recoupled if necessary based on these results.

After the linear peptide had been assembled, the N-terminal Boc group is removed by treatment with 25% TFA in DCM for 30 minutes. The resin is then neutralized by treatment with 10% DIEA in DCM. Cyclization with concomitant cleavage of the peptide is accomplished using the method of Osapay and Taylor ((1990) *J. Am. Chem. Soc.*, 112, 6046) by suspending the resin in approximately 10 ml/g of DMF, adding one equivalent of HOAc (based on the loading of the first amino acid), and stirring at 50°–60° C. for 60 to 72 hours. Following filtration through a scintered glass funnel, the DMF filtrate is evaporated, redissolved in HOAc or 1:1 acetonitrile: $H_2O$, and lyophilized to obtain protected, cyclized material. Alternatively, the material may be dissolved in methanol and precipitated with ether to obtain the protected, cyclized material. This is then treated using standard procedures with anhydrous hydrogen fluoride (Stewart and Young (1984) "Solid Phase Peptide Synthesis", 2nd. edition, Pierce Chemical Co., 85) containing 1 ml/g m-cresol or anisole as scavenger at 0° C. for 20 to 60 minutes to remove side chain protecting groups. The crude product may be purified by reversed-phase HPLC using a 2.5 cm preparative Vydac C18 column with a linear acetonitrile gradient containing 0.1% TFA to produce pure cyclized material. The following N-a-Boc-protected amino acids may be used for the syntheses: Boc-Arg(Tos), Boc-N-a-MeArg(Tos), Boc-Gly, Boc-Asp(OcHex), Boc-3-aminomethyl-4-iodo-benzoic acid, Boc-D-Ile, Boc-NMeAsp(OcHex), Boc-NMe-Mamb, Boc-D-Phg, Boc-D-Asp(OBzl), Boc-L-Asp(OcHex), Boc-aMe-Asp(OcHex), Boc-bMe-Asp(OcHex), Boc-L-Ala, Boc-L-Pro, Boc-D-Nle, Boc-D-Leu, Boc-D-Val, Boc-D-2-aminobutyric acid (Boc-D-Abu), Boc-Phe, Boc-D-Ser(Bzl), Boc-D-Ala, Boc-3-aminomethylbenzoic acid (Boc-Mamb), Boc-D-Lys(2-ClZ), Boc-b-Ala, Boc-D-Pro, Boc-D-Phe, Boc-D-Tyr(Cl2Bzl), Boc-NMe-Amf(CBZ), Boc-aminotetralincarboxylic acid, Boc-aminomethylnaphthoic acid, Boc-4-aminomethylbenzoic acid, or Boc-NMeGly.

Preferable N-a-Boc-protected amino acids useful in these syntheses are Boc-Arg(Tos), Boc-N-a-MeArg(Tos), Boc-Gly, Boc-Asp(OcHex), Boc-D-Leu, Boc-D-Val, Boc-D-2-aminobutyric acid (Boc-D-Abu), Boc-Phe, Boc-D-Ser(Bzl), Boc-D-Ala, Boc-3-aminomethylbenzoic acid (Boc-Mamb), Boc-D-Lys(2–ClZ), Boc-Ala,Boc-D-Pro, or Boc-NMeGly.

The synthesis of the compounds of the invention is further exemplified below. The Tables below set forth representative compounds of the present invention.

Cyclic Compound Intermediate 1 cyclo-(Gly-NMeArg-Gly-Asp-Mamb); the compound of formula (II) wherein J=Gly, K=NMeArg, L=Gly, M=Asp, $R^1=R^2=H$ The title compound was prepared using the general procedure described below for cyclo-(D-Val-NMeArg-Gly-Asp-Mamb). The peptide was prepared on a 0.336 mmol scale to give the protected cyclic peptide (218 mg, 84%). The peptide (200 mg) and 200 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (158 mg, greater than quantitative yield; calculated as the acetate salt). Purification was accomplished by reversed-phase HPLC on a preparative Vydac C18 column (2.5 cm) using a 0.23%/min. gradient of 2 to 11% acetonitrile containing 0.1% TFA and then lyophilized to give the TFA salt of the title compound as a fluffy white solid (21% recovery, overall yield 16.3%). Mass spectrum: M+H=533.26.

Cyclic Compound Intermediate 2 cyclo-(D-Ala-NMeArg-Gly-Asp-Mamb); the compound of formula (II) wherein J=D-Ala, K=NMeArg, L=Gly, M=Asp, $R^1=R^2H$ The title compound was prepared using the general procedure described below for cyclo-(D-Val-NMeArg-Gly-Asp-Mamb). Recoupling of the Boc-N-MeArg(Tos) residue was found to be necessary. The peptide was prepared on a 0.244 mmol scale to give the protected cyclic peptide (117 mg, 61%). The peptide (110 mg) and 110 mL of m-cresol were treated with anhydrous hydrogen fluoride at 0° C. for 1 hour. The crude material was precipitated with ether, redissolved in aqueous HOAc, and lyophilized to generate the title compound as a pale yellow solid. Purification was accomplished by reversed-phase HPLC on a preparative Vydac C18 column (2.5 cm) using a 0.25%/min. gradient of 2 to 11% acetonitrile containing 0.1% TFA and then lyophilized to give the TFA salt of the title compound as a fluffy white solid. Mass spectrum: M+H=547.23.

Cyclic Compound Intermediate 3 cyclo-(D-Abu-NMeArg-Gly-Asp-Mamb); the compound of formula (II) wherein J=D-Abu, K=NMeArg, L=Gly, M=Asp, $R^1=R^2=H$ The title compound was prepared using the general procedure described below for Cyclic Compound Intermediate 4. The peptide was prepared on a 0.101 mmol scale to give the protected cyclic peptide (51 mg, 63%). The peptide (43 mg) and 50 µL of m-cresol were treated with anhydrous hydrogen fluoride at 0° C. for 30 minutes. The crude material was precipitated with ether, redissolved in aqueous HOAc, and lyophilized to generate the title compound as a pale yellow solid (23 mg, 68.7%; calculated as the acetate salt). Purification was accomplished by reversed-phase HPLC on a preparative Vydac C18 column (2.5 cm) using a 0.23%/min. gradient of 7 to 14% acetonitrile containing 0.1% trifluoroacetic acid and then lyophilized to give the TFA salt of the title compound as a fluffy white solid (31% recovery; overall yield 12.4%).

Mass spectrum: M+H=561.46.

Cyclic Compound Intermediate 3a cyclo-(Abu-NMeArg-Gly-Asp-Mamb); the compound of formula (II) wherein J=Abu, K=NMeArg, L=Gly, M=Asp, $R^1=H$, $R^2=H$ The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. TBTU was used as the coupling reagent. The peptide was prepared on a 0.596 mmol scale to give the protected cyclic peptide (182 mg,38.4%). The peptide (176 mg) and 0.176 mL of anisole were treated with anhydrous hydrogen fluoride at 0° C. for 20 minutes. The crude material was precipitated with ether, redissolved in aqueous acetonitrile, and lyophilized to generate the title compound (116 mg; 90.4%; calculated as the fluoride salt). Purification was accomplished by reversed-phase HPLC on a preparative Vydac C18 column (2.5 cm) using a 0.45%/min. gradient of 9 to 27% acetonitrile containing 0.1% TFA and then lyophilized to give the TFA salt of the title compound as a fluffy white solid (1.92% recovery, overall yield 0.574%); FAB-MS: [M+H]=561.39.

Cyclic Compound Intermediate 4 cyclo-(D-Val-NMeArg-Gly-Asp-Mamb); the compound of formula (II) wherein J=D-Val, K=NMeArg, L=Gly, M=Asp, $R^1=R^2=H$ To a 25 ml polypropylene tube fitted with a frit was added Boc-Mamb (0.126 g, 0.5 mmol) and 6 ml of DMF. To this was added HBTU (0.194 g, 0.5 mmol), oxime resin (0.52 g, substitution level=0.96 mmol/g), and N-methylmorpholine (0.165 ml, 1.50 mmol). The suspension was mixed at room temperature for 24 hours. The resin was then washed thoroughly (10–12 ml volumes) with DMF (3×), MeOH (1×), DCM (3×), MeOH (2×) and DCM (3×). The substitution level was determined to be 0.389 mmol/g by quantitative ninhydrin assay. Unreacted oxime groups were blocked by treatment with 0.5M trimethylacetylchloride/0.5M DIEA in DMF for 2 hours.

The following steps were then performed: (Step 1) The resin was washed with DMF(3×), MeOH (1×), DCM (3×), MeOH (2×), and DCM (3×). (Step 2) The t-Boc group was deprotected using 25% TFA in DCM for 30 minutes. (Step 3) The resin was washed with DCM (3×), MeOH (1×), DCM (2×), MeOH (3×) and DMF(3×) (Step 4) Boc-Asp(OcHex) (0.613 g, 1.94 mmol), HBTU (0.753 g, 1.99 mmol), 8 ml of DMF, and N-methylmorpholine (0.642 ml, 5.84 mmol) were added to the resin and the reaction allowed to proceed for 2.5 hours. (Step 5) The coupling reaction was found to be complete as assessed by the qualitative ninhydrin assay. Steps 1–5 were repeated until the desired sequence had been attained. The coupling of Boc-D-Val to NMeArg was monitored by the picric acid test.

After the linear peptide was assembled, the N-terminal t-Boc group was removed by treatment with 25% TFA in DCM (30 min.) The resin was washed thoroughly with DCM (3×), MeOH (2×) and DCM (3×), and then neutralized with 10% DIEA in DCM (2×1 min.) The resin was washed thoroughly with DCM (3×) and MeOH (3×) and then dried. Half of the resin (0.101 mmol) was cyclized by treating with 6 ml of DMF containing HOAc (5.8 mL, 0.101 mmol) and heating at 50° C. for 72 hours. The resin was then filtered through a scintered glass funnel and washed thoroughly with DMF. The DMF filtrate was evaporated to an oil, redissolved in 1:1 acetonitrile: $H_2O$, and lyophilized to give the protected cyclic peptide (49 mg, 60%). The peptide (42 mg) was treated with anhydrous hydrogen fluoride at 0° C., in the presence of 50 mL of m-cresol as scavenger, for 30 minutes to remove side chain protecting groups. The crude material was precipitated with ether, redissolved in aqueous HOAc, and lyophilized to generate the title compound as a pale yellow solid (23 mg, 70%; calculated as the acetate salt). Purification was accomplished using reversed-phase HPLC with a preparative Vydac C18 column (2.5 cm) and a 0.23%/minute gradient of 7 to 18% acetonitrile containing 0.1% trifluoroacetic acid to give the TFA salt of the title compound as a fluffy white solid (24% recovery; overall yield 9.4%); FAB-MS: [M+H]=575.45.

Solution Phase Synthesis of Cyclic Compound Intermediate

The following abbreviations are used below for TLC solvent systems: chloroform/methanol 95:5=CM; chloroform/acetic acid 95:5=CA; chloroform/methanol/acetic acid 95:5=CMA BocNMeArg(Tos)-Gly-OBzl 25 mmol BocNMeArg(Tos) (11.07 g, Bachem), 30 mmol Gly-OBzl tosylate (10.10 g, Bachem), 25 mmol HBTU (O-Benzotriazole-N,N,N',N',—tetramethyl-uronium-hexafluorophosphate; 9.48 g; Advanced Chemtech), and 75 mmol DIEA (diisopropylethylamine; Aldrich) were dissolved in 25 ml $CH_2Cl_2$. The reaction was allowed to proceed 1 hr, the solvent was evaporated under reduced pressure at 50° to a syrup, which was dissolved in 400 ml ethyl acetate. This solution was extracted with (150 ml each) 2×5% citric acid, 1×water, 2×sat. $NaHCO_3$, 1×sat. NaCl. The organic layer was dried over $MgSO_4$, and the solvent evaporated under reduced pressure. The resulting oil was triturated with petroleum ether and dried under high vacuum for a minimum of 1 hr. yield 14.7 g (99.5%); TLC $R_{f(CM)}$=0.18 $R_{f(CA)}$=0.10; NMR is consistent with structure; FABMS M+H$^+$=590.43 (expected 590.26).

NMeArg(Tos)-Gly-OBzl 14.5 g (BocNMeArg(Tos)-Gly-OBzl (24.5 mmol) was dissolved in 30 ml TFA, allowed to react for 5 min., and the solvent evaporated at 1 mm mercury pressure at r.t. The resulting syrup was dissolved in 400 ml ice cold ethyl acetate, and extracted with 100 ml ice cold sat. $NaHCO_3$, the aqueous phase was extracted twice with 200 ml ethyl acetate, and the combined organic phases were extracted once with 25 ml sat. NaCl. The solvent was evaporated under reduced pressure giving a viscous oil that was triturated with 300 ml ether. The resulting solid was filtered and washed with ether, giving a hygroscopic compound that was dried in a vacuum desiccator: yield 10.33 g (86.2%); TLC $R_{f(CM)}$=0.03; $R_{f(CMA)}$=0.20; NMR is consistent with structure; FABMS M+H$^+$=490.21 (expected 490.20).

Boc-D-Val-NMeArg(Tos)-Gly-OBzl 9.80 mmol NMeArg(Tos)-Gly-OBzl (4.80 g), 9.82 mmol Boc-D-Val (2.13 g, Bachem), and 10.0 mmol HBTU (3.79 g) were dissolved in 10 ml methylene chloride. The flask was placed on an ice bath, and 20 mmol DIEA (3.48 ml) was added. The reaction was allowed to proceed at 0° for 15 min and 2 days at r.t. The reaction mixture was diluted with 400 ml ethyl acetate, extracted (200 ml each) 2×5% citric acid, 1×sat. NaCl, dried over $MgSO_4$ and evaporated under reduced pressure. The resulting oil was triturated with 50, then 30 ml ether for 30 min with efficient mixing: yield 4.58 g (69%); TLC $R_{f(CM)}$=0.27 (also contains a spot near the origin, which is an aromatic impurity that is removed during trituration of the product in the next step); NMR is consistent with structure; FABMS M+H$^+$=689.59 (expected 689.43).

Boc-D-Val-NMeArg(Tos)-Gly 4.50 g Boc-D-Val-NMeArg(Tos)-Gly-OBzl (4.44 mmol) dissolved in 80 ml methanol was purged with $N_2$ for 10 min. 1.30 g Pd/C catalyst (10% Fluka lot #273890) was then added, and then $H_2$ was passed directly over the surface of the reaction. TLC showed the reaction to be complete within approximately 0.5 hr. After 1 hr. the catalyst was removed by filtering through a bed of Celite, and the solvent removed at 40° under reduced pressure. The resulting solid was triturated well with 50 ml refluxing ether, filtered, and washed with petroleum ether: yield 3.05 g (78%); TLC $R_{f(CM)}$=0.03; $R_{f(CMA)}$=0.37; NMR is consistent with structure; FABMS M+H$^+$=599.45 (expected 599.29).

4-Nitrobenzophenone Oxime (Ox)

50 g 4-nitrobenzophenone (220 mmol, Aldrich) and 30.6 g hydroxylamine hydrochloride (Aldrich, 440 mmol) were heated at reflux in 0.5 L methanol/pyridine (9:1) for 1 hr. The reaction mixture was evaporated under reduced pressure, dissolved in 500 ml ether, and extracted with 200 ml each of 5% citric acid (2 times) and sat. NaCl (1 time), dried over $MgSO_4$, evaporated under reduced pressure and triturated with ether giving 44.35 g (83%) of the oxime as a mixture of the cis and trans isomers: TLC $R_{f(CM)}$=0.50; $R_{f(CMA)}$=0.82; NMR is consistent with structure; FABMS M+H$^+$=242.07 (expected 242.07).

BocMamb-Ox 22 mmol BocMamb (5.522 g), 20 mmol nitrobenzophenone oxime (4.84 g), and 20 mmol DMAP (4-dimethylaminopyridine; Aldrich) were dissolved in 40 ml $CH_2Cl_2$. The flask was placed on an ice bath, and 21 mmol DCC (Dicyclohexylcarbodiimide; 4.33 g) was added. The reaction was allowed to proceed on ice for 30 min and at r.t. over night. The dicyclohexylurea formed was filtered, and washed with 40 ml methylene chloride. The filtrate was evaporated under reduced pressure at r.t. to a syrup, and dissolved in 400 ml ethyl acetate. This solution was extracted with (150 ml each) 2×5% citric acid, 1×water, 2×sat. NaHCO₃, 1×sat. NaCl. The organic layer was dried over MgSO₄, and the solvent evaporated under reduced pressure. The resulting oil was triturated with petroleum ether and dried under high vacuum for a minimum of 1 hr.: yield 7.51 g (79%); TLC R$_{f(CM)}$=0.41; R$_{f(CMA)}$=0.66; NMR is consistent with structure; FABMS M+H⁺=476.30 (expected 47.18).

TFA.MAMB-Ox

BocMamb-Ox, 7.4 g (15.5 mmol) was dissolved in 30 ml methylene chloride plus 10 ml TFA (25% TFA). The reaction was allowed to proceed at r.t. for 1 hr, and the solvent evaporated under reduced pressure at r.t. for 10 min, then at 40° for 15 min. The resulting syrup was triturated with ether (200 ml) at −5°. The resulting crystals were filtered after 1 hr and washed well with ether: yield 7.22 g (95%); R$_{f(CMA)}$= 0.25; NMR is consistent with structure; FABMS M+H⁺= 376.22 (expected 376.12).

Boc-Asp(OcHex)-Mamb-Ox 20 mmol Boc-Asp(OcHex) (6.308 g, Bachem) and 44 mmol DIEA (7.66 ml) were dissolved in 20 ml DMF. 20 mmol HBTU (7.58 g, Advanced Chemtech) was added, and the reaction allowed to proceed for 2 minutes with vigorous stirring. TFA.Mamb-Ox (7.13 g, 15 mmol) was added, and the reaction allowed to proceed overnight at r.t. The solvent was removed under reduced pressure giving an oil, which was dissolved in 500 ml ethyl acetate, and this solution was extracted with (150 ml each) 2×5% citric acid, 1×water, 2×sat. NaHCO₃, 1×sat. NaCl. The organic layer was dried over MgSO₄, and the solvent evaporated under reduced pressure. The resulting oil was triturated with petroleum ether and dried under high vacuum: yield 9.76 g (97%); TLC R$_{f(CM)}$=0.55; NMR is consistent with structure; FABMS M+H⁺673.45 (expected 673.23).

TFA Asp(OcHex)-MAMB-Ox b 15mmol Boc-Asp(OcHex)-MAMB-Ox was dissolved in 50 ml 35% TFA in CH₂Cl₂, and allowed to react 90 min. The solvent was evaporated under reduced pressure at r.t. for 10 min, then at 40° for 15 min. To remove traces of TFA, 25 ml DMF was added and the solvent evaporated at 50°. The resulting syrup was triturated with ether (200 ml), then dried under high vacuum: yield 9.61 g (93%); R$_{f(CMA)}$=0.45; NMR is consistent with structure; FABMS M+H⁺=573.56 (expected 573.23).

Boc-D-Val-NMeArg (Tos)-Gly-Asp(OcHex)-MAMB-Ox 10.0 mmol each TFA Asp(OcHex)-MAMB-Ox, Boc-D-Val-NMeArg(Tos)-Gly, and HBTU, plus 30 mmol DIEA were dissolved in 20 ml DMF. After 4 hr., the solvent was removed under reduced pressure, and the residue taken up in 600 ml ethyl acetate, which was extracted with 300 ml each of 5% citric acid, water and sat. NaCl. The organic layer was dried over MgSO₄, evaporated under reduced pressure, triturated with ether and dried in vacuo: yield 9.90 g (86%); R$_{f(CM)}$=0.10; NMR is consistent with structure; FABMS M+H⁺=1153.22 (expected 1153.47).

TFA.D-Val-NMeArg(Tos)-Gly-Asp(OcHex)-MAMB-Ox

This compound was prepared from Boc-D-Val-NMeArg (Tos)-Gly-Asp(OcHex)-MAMB-Ox (9.8 g, 8.5 mmol) by treatment with TFA/CH₂Cl₂ (1:1) for 45 min. The solvent was evaporated and the product triturated with ether: yield 9.73 g (98%); R$_{f(CM)}$=0.10; NMR is consistent with structure; FABMS M+H⁺=1053.22 (expected 1053.4).

cyclo(.D-Val-NMeArg(Tos)-Gly-Asp(OcHex)-MAMB)

TFA.D-Val-NMeArg(Tos)-Gly-Asp(OcHex)-MAMB-Ox (1.80 g, 1.54 mmol), and 2 mmol each of DIEA and acetic acid were dissolved in 200 ml DMF. The mixture was heated to 50° for 2 days, then evaporated under reduced pressure. The syrup was dissolved in 400 ml ethyl acetate/n-butanol (1:1), and extracted with 200 ml each of 5% citric acid (3×) and sat. NaCl (1×). The organic layer was dried over MgSO₄ and triturated twice with 200 ml ether: yield 1.07 g (86%); R$_{f(CM)}$=0.10; NMR is consistent with structure; FABMS M+H⁺=811.25 (expected 811.38).

cyclo(.D-Val-NMeArg-Gly-Asp-MAMB)

0.50 g cyclo(D-Val-NMeArg(Tos)-Gly-Asp(OcHex)-MAMB) was treated with 5 ml HF at 0° C., in the presence of 0.5 ml of anisole for 30 min. The HF was removed under reduced pressure and the crude peptide triturated with ether, ethyl acetate and ether. The resulting solid was dissolved in 10% acetic acid and lyophilized: yield 0.321 g (82% calculated as the acetate salt). The product was purified with a recovery of approximately 40% using the same method as described for the material synthesized by the solid phase procedure.

Crystallization of Cyclic Compound Intermediate 4
Preparation of Salt Forms of the Compound of
Cyclic Compound Intermediate 4

It has been discovered that the compounds of the present invention may be isolated by crystallization of the compound from organic and aqueous solvents.

The zwitterion of Cyclic Compound Intermediate 4 was converted to the mesyl (methanesulfonate) salt of Cyclic Compound Intermediate 4 (Cyclic Compound Intermediate 4 (methane-sulfonate)) by refluxing the zwitterion with stirring in isopropanol at 25 mg/ml and slowly adding a solution of 1.0 molar equivalent methanesulfonic acid (correcting for the water content of the zwitterion) dissolved in isopropanol. The heat was turned off and the solution cooled to 5° C. in an ice bath. After stirring 1 hour, the solution was filtered and the solid rinsed three times with cold isopropanol and dried under vacuum to constant weight.

The following salts of the compound of Cyclic Compound Intermediate 4 were prepared using the same procedure, by adding 1.0 equivalent of the appropriate acid:

Cyclic Compound Intermediate 4 (biphenylsulfonate): zwitterion+1.0 equivalent biphenylsulfonic acid.

Cyclic Compound Intermediate 4 (a-naphthalenesulfonate): zwitterion+1.0 equiv. a-naphthalenesulfonic acid.

Cyclic Compound Intermediate 4 (b-naphthalenesulfonate): zwitterion+1.0 equiv. b-naphthalenesulfonic acid.

Cyclic Compound Intermediate 4 (benzenesulfonate): zwitterion+1.0 equiv. benezene-sulfonic acid.

Cyclic Compound Intermediate 4 (p-toluenesulfonate): zwitterion+1.0 equiv. p-toluene-sulfonic acid.

The following salts of the compound of Cyclic Compound Intermediate 4 were prepared by crystallization of the compound from aqueous systems.

Cyclic Compound Intermediate 4 (sulfate): 10 mg amorphous Cyclic Compound Intermediate 4 (made by lyophilizing the zwitterion from a solution of 2 molar equivalents of acetic acid in water) dissolved per ml 1N H₂SO₄, pH adjusted to 2.5. On standing at room temperature, a precipitate formed. This was filtered through a sintered glass funnel and dried under vacuum to constant weight.

Cyclic Compound Intermediate 4 (methanesulfonate (mesyl)): 100 mg amorphous Cyclic Compound Intermediate 4 dissolved per ml water+1.2 molar equiv. methanesulfonic acid (this was obtained as a 4M aqueous solution). On standing at room temperature, a large flat crystal was formed.

Cyclic Compound Intermediate 4 (benzenesulfonate):
100 mg zwitterion dissolved per ml water+1.2 equiv. benzenesulfonic acid added. On standing at room temperature, a precipitate formed. This was filtered through a sintered glass funnel, rinsed with a small volume of isopropanol, and dried under vacuum to constant weight.

Cyclic Compound Intermediate 4 (p-toluenesulfonate): 100 mg zwitterion dissolved per ml water+1.2 molar equiv. toluenesulfonic acid added. On standing at room temperature, a precipitate formed. This was filtered through a sintered glass funnel and dried under vacuum to constant weight.

Cyclic Compound Intermediate 4b cyclo-(D-Val-D-NMeArg-Gly-Asp-Mamb); J=D-Val, K=D-NMeArg, L=Gly, M=Asp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.596 mmol scale to give the protected cyclic peptide (186 mg, 38.6%). The peptide (183 mg) and 0.183 mL of anisole were treated with anhydrous hydrogen fluoride at 0° C. for 30 minutes. The crude material was precipitated with ether, redissolved in aqueous acetonitrile, and lyophilized to generate the title compound (145 mg, greater than quantitative yield; calculated as the fluoride salt). Purification was accomplished by reversed-phase HPLC on a preparative Vydac C18 column (2.5 cm) using a 0.23%/min. gradient of 9 to 22.5% acetonitrile containing 0.1% TFA and then lyophilized to give the TFA salt of the title compound as a fluffy white solid (14.8% recovery, overall yield 5.3%); FAB-MS: [M+H]=575.31.

Cyclic Compound Intermediate 5 cyclo-(D-Leu-NMeArg-Gly-Asp-Mamb); the compound of formula (II) wherein J=D-Leu, K=NMeArg, L=Gly, M=Asp, $R^1$=$R^2$=H The title compound was prepared using the general procedure described above for cyclo-(D-Val-NMeArg-Gly-Asp-Mamb). The peptide was prepared on a 0.115 mmol scale to give the protected cyclic peptide (92.4 mg, 98%). The peptide (92.4 mg) and 93 mL of m-cresol were treated with anhydrous hydrogen fluoride at 0° C. for 20 minutes. The crude material was precipitated with ether, redissolved in aqueous HOAc, and lyophilized to generate the title compound as a pale yellow solid (45.7 mg, 63%; calculated as the acetate salt). Purification was accomplished by reversed-phase HPLC on a preparative Vydac C18 column (2.5 cm) using a 0.23%/min. gradient of 7 to 21% acetonitrile containing 0.1% TFA and then lyophilized to give the TFA salt of the title compound as a fluffy white solid (29% recovery, overall yield 16.5%); FAB-MS: [M+H]=589.48.

Cyclic Compound Intermediate 7 cyclo-(D-Nle-NMeArg-Gly-Asp-Mamb); the compound of formula (II) wherein J=D-Nle, K NMeArg, L=Gly, M=Asp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.586 mmol scale to give the protected cyclic peptide (305 mg, 63.3%). The peptide (295 mg) and 0.295 mL of anisole were treated with anhydrous hydrogen fluoride at 0° C. for 30 minutes. The crude material was precipitated with ether, redissolved in aqueous acetonitrile, and lyophilized to generate the title compound (207 mg, 95.4%; calculated as the fluoride salt). Purification was accomplished by reversed-phase HPLC on a preparative Vydac C18 column (2.5 cm) using a 0.23%/min. gradient of 5.4 to 18% acetonitrile containing 0.1% TFA and then lyophilized to give the TFA salt of the title compound as a fluffy white solid (44% recovery, overall yield 22.9%); FAB-MS: [M+H]=589.26.

Cyclic Compound Intermediate 11 cyclo-(D-Phg-NMeArg-Gly-Asp-Mamb); the compound of formula (II) wherein J=D-Phg, K=NMeArg, L=Gly, M=Asp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.611 mmol scale to give the protected cyclic peptide (296 mg, 57.4%). The peptide (286 mg) and 0.286 mL of anisole were treated with anhydrous hydrogen fluoride at 0° C. for 30 minutes. The crude material was precipitated with ether, redissolved in aqueous acetonitrile, and lyophilized to generate the title compound (210 mg, 98.9%; calculated as the fluoride salt). Purification was accomplished by reversed-phase HPLC on a preparative Vydac C18 column (2.5 cm) using a 0.23%/min. gradient of 5.4 to 18% acetonitrile containing 0.1% TFA and then lyophilized to give the TFA salt of the title compound as a fluffy white solid (24.2% recovery, overall yield 11.9%); FAB-MS: [M+H]=609.27.

Cyclic Compound Intermediate 12 cyclo-(D-Phe-NMeArg-Gly-Asp-Mamb); the compound of formula (II) wherein J=D-Phe, K=NMeArg, L=Gly, M=Asp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.611 mmol scale to give the protected cyclic peptide (140 mg, 26.7%). The peptide (135 mg) and 0.135 mL of anisole were treated with anhydrous hydrogen fluoride at 0° C. for 30 minutes. The crude material was precipitated with ether, redissolved in aqueous acetonitrile, and lyophilized to generate the title compound (108 mg, greater than quantitative yield; calculated as the fluoride salt). Purification was accomplished by reversed-phase HPLC on a preparative Vydac C18 column (2.5 cm) using a 0.23%/min. gradient of 7.2 to 22.5% acetonitrile containing 0.1% TFA and then lyophilized to give the TFA salt of the title compound as a fluffy white solid (35% recovery, overall yield 8.7%); FAB-MS: [M+H]=623.28.

Solid Phase Synthesis of Cyclic Compound Intermediate 13f cyclo-(D-Lys-NMeArg-Gly-Asp-Mamb); the compound of formula (II) wherein J=D-Lys, K=NMeArg, L=Gly, M=Asp, $R^1$=$R^2$=H The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.586 mmol scale to give the protected cyclic peptide (349 mg, 58.9%). The peptide (334 mg) and 334 mL of anisole were treated with anhydrous hydrogen fluoride at 0° C. for 30 minutes. The crude material was precipitated with ether, redissolved in aqueous acetonitrile, and lyophilized to generate the title compound as a pale yellow solid (168 mg, 79.1%; calculated as the difluoride salt). Purification was accomplished by reversed-phase HPLC on a preparative Vydac C18 column (2.5 cm) using a 0.23%/min. gradient of 5.4 to 14.4% acetonitrile containing 0.1% TFA and then lyophilized to give the TFA salt of the title compound as a fluffy white solid (33.6% recovery, overall yield 12.1%); FAB-MS: [M+H]=604.32

Solution Phase Synthesis of Cyclic Compound Intermediate 13f

A Scheme depicting the synthesis described below appears immediately after the description.
Cyclo-(D-Lys-NMeArg-Gly-Asp-Mamb); the compound of formula (II) wherein J=D-Lys, K=NMe Arg, L=Gly, M=Asp, $R^1=R^2=H$
Part A Boc-Asp(OBzl)

To a solution of Boc-Asp(OBzl) (45.80 g, 140 mmol) and HOSu (N-hydroxysuccinimide; 16.10 g, 140 mmol) in 300 ml p-dioxane at 5°–10° C. was added DCC (30.20 g, 140 mmol). The solution was stirred for 30 minutes at 5°–10° C. then the solids were filtered and washed with dioxane (3×50 ml). The combined organics were concentrated under reduced pressure to give a clear oil which crystallized to a colorless solid (42.98 g, 73%) when triturated with ethyl ether (3×100 ml). NMR is consistent with structure; MP=98°–99° C.; DCI-MS: [M+NH$_4$]=438.
Part B Boc-Asp(OBzl)-Mamb 3-Aminomethylbenzoic acid.HCl (Mamb; 13.08 g, 70.0 mmol) was dissolved in 120 ml DMF and DIEA (24.32 ml, 140 mmol) was added, changing the pH from 4 to 7.5. The white suspension was stirred for 30 min at room temperature before a solution of Boc-Asp(OBzl)-OSu (29.40 g, 70.0 mmol) in DMF (50 ml) was added. The mixture was allowed to stir 24 hr, during which time it turned to a gold solution. The solution was added to 5% citric acid (2000 ml) and cooled to 5° C. for 3 hr. The solids were then collected by filtration, washed with ice cold water (200 ml) and ice cold ethyl ether (100 ml), and dried under reduced pressure to give the title compound as a colorless solid (29.62 g, 92%); MP=149°–151° C.; DCI-MS: [M+NH$_4$]=474.
Part C HCl.H-Asp(OBzl)-Mamb Boc-Asp(OBzl)-Mamb (7.92 g, 17.4 mmol) was dissolved in 4N HCl in dioxane (50 ml), stirred for 2 hr, and the solution concentrated under reduced pressure to give the title compound as a colorless solid (6.80 g, 99%). DCI-MS: [M+NH$_4$]=374.
Part D Boc-D-Lys(Tfa)-NMeArg(Tos)-Gly-OBzl NMeArg(Tos)-Gly-OBzl (14.40 g, 29.4 mmol), Boc-D-Lys(Tfa) (10.00 g, 29.4 mmol), and HBTU (11.37 g, 62.0 mmol) were dissolved in methylene chloride (40 ml). After cooling to 0° C., DIEA (10.44 g, 62.0 mmol) was added and the reaction was allowed to proceed 20 minutes at 0° C. and 2 days at room temperature. The reaction mixture was diluted with ethyl acetate (800 ml), extracted with 200 ml portions of 0.2N HCl (1×), sat. NaHCO$_3$ (1×), and saturated NaCl (2×), dried (MgSO$_4$), and evaporated under reduced pressure to a yellow solid. Purification by flash chromatography (silica gel; 5:1 EtOAc:acetonitrile) gave the title compound as a colorless solid (20.34 g, 85%). MP 78°–85° C.; DCI-MS: [M+NH$_4$]=831.
Part E Boc-D-Lys(Tfa)-NMeArg(Tos)-Gly A solution of Boc-D-Lys(Tfa)-NMeArg(Tos)-Gly-OBzl (11.00 g, 13.5 mmol) in methanol (200 ml) was placed in a Parr shaker bottle, purged with N$_2$ for 10 minutes, and treated with 10% palladium on carbon catalyst (10% Pd/C, 3.6 g). The shaker bottle was further purged with 7 pressurization-evacuation cycles, repressurized, and allowed to shake 90 minutes, during which time the calculated amount of hydrogen was consumed. The catalyst was removed by filtration through a bed of Celite and the filtrate was concentrated under reduced pressure yielding a solid. Trituration with refluxing ethyl ether (75 ml) gave pure product (9.18 g, 94%) as a colorless solid. DCI-MS: [M+H] =724.
Part F Boc-D-Lys(Tfa)-NMeArg(Tos)-Gly-OSu Boc-D-Lys(Tfa)-NMeArg(Tos)-Gly (8.00 g, 11.0 mmol), HOSu (1.25 g, 10.8 mmol) and DCC (2.22 g, 10.8 mmol) were dissolved in DMF (75 ml) and stirred at room temperature for 2 days. The solids were removed by filtration and washed with DMF (2×15 ml). The filtrate was concentrated under reduced pressure and the resulting syrup dried under reduced pressure at 40° C. to give a tan solid (6.50 g, 72%). MP=66°–69° C.; FAB-MS: [M+H]=821.
Part G Boc-D-Lys(Tfa)-N-MeArg(Tos)-Gly-Asp(OBzl)-Mamb A suspension of Boc-D-Lys(Tfa)-N-MeArg(Tos)-Gly-OSu (8.85 g, 10.8 mmol) and HCl.Asp(OBzl)-Mamb (4,24 g, 10.8 mmol) in 4:1 dioxane:DMF (100 ml) was treated with DIEA (1.39 g, 10.8 mmol) over 10 minutes. The resulting mixture was stirred 2 days at room temperature and concentrated under reduced pressure to a syrup. This syrup was dissolved in ethyl acetate (300 ml) and washed with 75 ml portions of 0.2N HCl (3×), sat. NaHCO$_3$ (2×), H$_2$O (1×), and saturated NaCl (1×). The organic layer was dried (MgSO$_4$) and concentrated under reduced pressure at 40° C. to a sticky amber solid (9.13 g, 78%). MP=90°–93° C.; FAB-MS: [M+H]=1062.
Part H HCl.D-Lys(Tfa)-N-MeArg(Tos)-Gly-Asp(OBzl)-Mamb Boc-D-Lys(Tfa)-N-MeArg(Tos)-Gly-Asp(OBzl)-Mamb (8.30 g, 7.8 mmol) was partially dissolved in 4N HCl in dioxane (50 ml), stirred at room temperature for 30 min, and concentrated under reduced pressure to give a yellow solid. Trituration with warm EtOAc (60 ml) afforded the product (7.65 g, 98%) as a yellow solid. FAB-MS: [M+H]=962.
Part I Cyclo-(D-Lys(Tfa)-N-MeArg(Tos)-Gly-Asp(OBzl)-Mamb)

HCl.D-Lys(Tfa)-N-MeArg(Tos)-Gly-Asp(OBzl)-Mamb (3.00 g, 3.0 mmol), DIEA (0.77 g, 6.0 mmol), and TBTU (0.98 g, 3.0 mmol) were dissolved in DMF (100 ml). The reaction was stirred at room temperature for 22 hours, and the pH was maintained at 7–8 by the addition of DIEA as necessary. The reaction was concentrated under reduced pressure and the resulting oil dissolved in 3.75:1 ethyl acetate:1-butanol (110 ml). The organic solution was washed with 50 ml portions of 0.2N HCl (2×), saturated NaHCO$_3$ (1×), H$_2$O (1×), and saturated NaCl (1×), dried (MgSO$_4$), concentrated to a brown oil. Triturated with ethyl ether (100 ml) gave a brown solid which was purified by flash chromatography (silica gel; 5:1 EtOAc:EtOH) to give the title compound (1.62 g, 57%) as a colorless solid. MP=128°–130° C.; FAB-MS: [M+H]944.

Part J

Cyclo-(D-Lys(Tfa)-N-MeArg-Gly-Asp-Mamb)

Cyclo-(D-Lys(Tfa)-N-MeArg(Tos)-Gly-Asp(OBzl)-Mamb) (0.85 g, 0.9 mmol) was dissolved in TFA (10 ml) and cooled to –10° C. Triflic acid (trifluoromethanesulfonic acid; 10 ml) was slowly added to the stirred reaction while maintaining the temperature at –5° C. Anisole (2 ml) was added and stirring was continued for 3 hours at –5° C. The temperature of the reaction was decreased to –78° C., ethyl ether (200 ml) was added, and the reaction was stirred for 1 hour. The white sticky solids were removed by filtration and washed with ice cold ether (50 ml). The solids were dissolved in 1:1 acetone:H$_2$O (10 ml) and lyophilized to give the product (0.63 g, 100%) as a fluffy colorless solid. FAB-MS: [M+H]=700.

Part K

Cyclo-(D-Lys-N-MeArg-Gly-Asp-Mamb)

Cyclo-(D-Lys(Tfa)-N-MeArg-Gly-Asp-Mamb) (0.63 g, 0.9 mmol) was dissolved in 1.0M aqueous piperdine (10 ml) at 0° C. and the reaction was allowed to slowly warm to room temperature over 3 hours. The solution was lyophilized to give a yellow solid. Purification was accomplished by preparative HPLC with a Vydac protein-peptide C-18 column (2.1 cm) using a 0.36%/min. gradient of 9 to 18% acetonitrile containing 0.1% TFA, and then lyophilized to give the title compound (0.20 g, 90%) as a colorless fluffy solid. MP=138°–142° C.; FAB-MS: [M+H]=604.

Solution Phase Synthesis of 13f

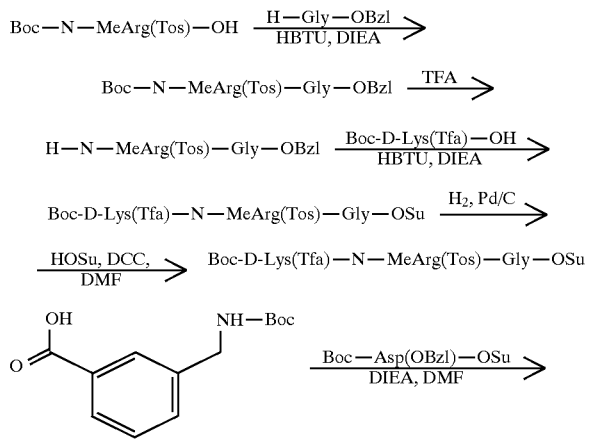

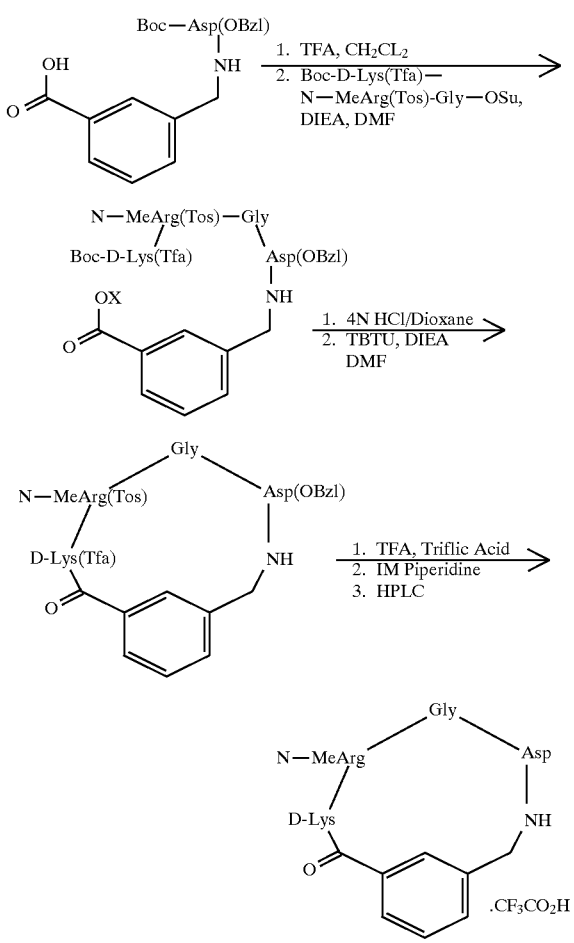

Cyclic Compound Intermediate 13r
cyclo-(D-Ile-NMeArg-Gly-Asp-Mamb); the compound of formula (II) wherein J=D-Ile, K=NMeArg, L=Gly, M=Asp, R$^1$=H, R$^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.611 mmol scale to give the protected cyclic peptide (349 mg, 69.2%). The peptide (342 mg) and 0.342 mL of anisole were treated with anhydrous hydrogen fluoride at 0° C. for 30 minutes. The crude material was precipitated with ether, redissolved in aqueous acetonitrile, and lyophilized to generate the title compound (227 mg, 90%; calculated as the fluoride salt). Purification was accomplished by reversed-phase HPLC on a preparative Vydac C18 column (2.5 cm) using a 0.23%/min. gradient of 10.8 to 19.8% acetonitrile containing 0.1% TFA and then lyophilized to give the TFA salt of the title compound as a fluffy white solid (22.5% recovery, overall yield 12.1%); FAB-MS: [M+H]=589.34.

Cyclic Compound Intermediate 17
cyclo-(D-Met-NMeArg-Gly-Asp-Mamb); the compound of formula (II) wherein J=D-Met, K=NMeArg, L=Gly, M=Asp, R$^1$=H, R$^2$=H The title compound was prepared using the general procedure described for cyclo-(D-Val-NMeArg-Gly-Asp- Mamb) (Cyclic Compound Intermediate 4). The DCC/DMAP method was used for the attachment of Boc-Mamb to the resin. The peptide was prepared on a 0.179 mmol scale to give the protected cyclic peptide (105 mg, 69.7%). The peptide (105 mg) and 0.105 mL of anisole were treated with anhydrous hydrogen fluoride at 0° C. for 20 minutes. The crude material was precipitated with ether, redissolved in aqueous acetonitrile, and lyophilized to generate the title compound (72 mg; 92.3% yield; calculated as the fluoride salt). Purification was accomplished by reversed-phase HPLC on a preparative Vydac C18 column (2.5 cm) using a 0.23%/min. gradient of 14.4 to 23.4% acetonitrile containing 0.1% TFA and then lyophilized to give the TFA salt of the title compound as a fluffy white solid (13.2% recovery, overall yield 7.4%); FAB-MS: [M+H]=607.3.

Cyclic Compound Intermediate 18 cyclo-(NMeGly-NMeArg-Gly-Asp-Mamb); the compound of formula (II) wherein J=NMeGly, K=NMeArg, L=Gly, M=Asp, $R^1=R^2=H$ The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.43 mmol scale to give the protected cyclic peptide (205 mg, 60%). The peptide (200 mg) and 200 mL of m-cresol were treated with anhydrous hydrogen fluoride at 0° C. for 30 minutes. The crude material was precipitated with ether, redissolved in aqueous HOAc, and lyophilized to generate (18) as a pale yellow solid (148 mg, 97%; calculated as the acetate salt). Purification was accomplished by reversed-phase HPLC on a preparative Vydac C18 column (2.5 cm) using a 0.23%/min. gradient of 7 to 22% acetonitrile containing 0.1% TFA and then lyophilized to give the TFA salt of (18) as a fluffy white solid (14.7% recovery, overall yield 7.9%); FAB-MS: [M+H]=547.34.

Cyclic Compound Intermediate 24 cyclo-(Pro-NMeArg-Gly-Asp-Mamb); the compound of formula (II) wherein J=Pro, K=NMeArg, L=Gly, M=Asp, $R^1=R^2=H$ The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.43 mmol scale to give the protected cyclic peptide (170 mg, 48.8%). The peptide (164 mg) and 164 mL of m-cresol were treated with anhydrous hydrogen fluoride at 0° C. for 30 minutes. The crude material was precipitated with ether, redissolved in aqueous HOAc, and lyophilized to generate (24) as a pale yellow solid (101 mg, 79% ; calculated as the acetate salt). Purification was accomplished by reversed-phase HPLC on a preparative Vydac C18 column (2.5 cm) using a 0.23%/min. gradient of 7 to 22% acetonitrile containing 0.1% TFA and then lyophilized to give the TFA salt of (24) as a fluffy white solid (5.8% recovery, overall yield 2.1%); FAB-MS: [M+H]=573.46.

Cyclic Compound Intermediate 25 cyclo-(D-Pro-NMeArg-Gly-Asp-Mamb); the compound of formula (II) wherein J=D-Pro, K=NMeArg, L=Gly, M=Asp, $R^1=R^2=H$ The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.43 mmol scale to give the protected cyclic peptide (211 mg, 60.8%). The peptide (200 mg) and 200 mL of m-cresol were treated with anhydrous hydrogen fluoride at 0° C. for 30 minutes. The crude material was precipitated with ether, redissolved in aqueous HOAc, and lyophilized to generate (25) as a pale yellow solid (145 mg, 93.3%; calculated as the acetate salt). Purification was accomplished by reversed-phase HPLC on a preparative Vydac C18 column (2.5 cm) using a 0.23%/min. gradient of 7 to 22% acetonitrile containing 0.1% TFA and then lyophilized to give the TFA salt of (25) as a fluffy white solid (6.4% recovery, overall yield 3.3%); FAB-MS: [M+H]=573.35.

Cyclic Compound Intermediate 28c cyclo-(b-Ala-NMeArg-Gly-Asp-Mamb); the compound of formula (II) wherein J=b-Ala, K=NMeArg, L=Gly, M=Asp, $R^1=R^2=H$ The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.586 mmol scale to give the protected cyclic peptide (264 mg, 57.5%). The peptide (258 mg) and 258 mL of anisole were treated with anhydrous hydrogen fluoride at 0° C. for 30 minutes. The crude material was precipitated with ether, redissolved in aqueous acetonitrile, and lyophilized to generate the title compound as a pale yellow solid (231 mg, greater than quantitative yield; calculated as the fluoride salt). Purification was accomplished by reversed-phase HPLC on a preparative Vydac C18 column (2.5 cm) using a 0.23%/min. gradient of 5.4 to 14.4% acetonitrile containing 0.1% TFA and then lyophilized to give the TFA salt of the title compound as a fluffy white solid (53.2% recovery, overall yield 32.5%); FAB-MS: [M+H]=547.28.

Cyclic Compound Intermediate 28f cyclo-(D-Tyr-NMeArg-Gly-Asp-Mamb); the compound of formula (II) wherein J=D-Tyr, K=NMeArg, L=Gly, M=Asp, $R^1=H$, $R^2=H$ The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.313 mmol scale to give the protected cyclic peptide (342 mg, greater than quantitative yield). The peptide (331 mg) and 0.330 mL of anisole were treated with anhydrous hydrogen fluoride at 0° C. for 30 minutes. The crude material was precipitated with ether, redissolved in aqueous acetonitrile, and lyophilized to generate the title compound (218 mg, greater than quantitative yield; calculated as the fluoride salt). Purification was accomplished by reversed-phase HPLC on a preparative Vydac C18 column (2.5 cm) using a 0.23%/min. gradient of 9 to 18% acetonitrile containing 0.1% TFA and then lyophilized to give the TFA salt of the title compound as a fluffy white solid (11.3% recovery, overall yield 10.8%); FAB-MS: [M+H]=639.54.

Cyclic Compound Intermediate 29 cyclo-(Gly-Arg-Gly-Asp-Mamb); the compound of formula (II) wherein J=Gly, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.283 mmol scale and half was cyclized to give the protected cyclic peptide (62 mg, 58%). The peptide (60 mg) and 60 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (48 mg,

Cyclic Compound Intermediate 30 cyclo-(D-Ala-Arg-Gly-Asp-Mamb); the compound of formula (II) wherein J=D-Ala, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.189 mmol scale to give the protected cyclic peptide (211 mg, >quantitative yield). The peptide (195 mg) and 195 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (125 mg, 83%; calculated as the acetate salt). Purification was accomplished by reversed-phase HPLC on a preparative Vydac C18 column (2.5 cm) using a 0.23%/min. gradient of 2 to 11% acetonitrile containing 0.1% TFA and then lyophilized to give the TFA salt of the title compound as a fluffy white solid (12.5% recovery, overall yield 13.8%); FAB-MS: [M+H]=533.26.

Cyclic Compound Intermediate 31 cyclo-(Ala-Arg-Gly-Asp-Mamb); the compound of formula (II) wherein J=Ala, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.324 mmol scale to give the protected cyclic peptide (191 mg, 76.4%). The peptide (100 mg) and 100 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (75 mg, 97.4%; calculated as the acetate salt). Purification was accomplished by reversed-phase HPLC on a preparative Vydac C18 column (2.5 cm) using a 0.23%/min. gradient of 2 to 11% acetonitrile containing 0.1% TFA and then lyophilized to give the TFA salt of the title compound as a fluffy white solid (15.5% recovery, overall yield 10.5%); FAB-MS: [M+H]=533.25.

Cyclic Compound Intermediate 32 cyclo-(D-Val-Arg-Gly-Asp-Mamb); the compound of formula (II) wherein J=D-Val, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.193 mmol scale to give the protected cyclic peptide (199 mg, >quantitative yield). The peptide (193 mg) and 193 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (130 mg, 86%; calculated as the acetate salt). Purification was accomplished by reversed-phase HPLC on a preparative Vydac C18 column (2.5 cm) using a 0.23%/min. gradient of 2 to 13% acetonitrile containing 0.1% TFA and then lyophilized to give the TFA salt of the title compound as a fluffy white solid (57% recovery, overall yield 58.1%); FAB-MS: [M+H]=561.22.

Cyclic Compound Intermediate 33 cyclo-(D-Leu-Arg-Gly-Asp-Mamb); the compound of formula (II) wherein J=D-Leu, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.202 mmol scale to give the protected cyclic peptide (152 mg, 93%). The peptide (150 mg) and 150 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (78 mg, 66%; calculated as the acetate salt). Purification was accomplished by reversed-phase HPLC on a preparative Vydac C18 column (2.5 cm) using a 0.23%/min. gradient of 5 to 18% acetonitrile containing 0.1% trifluoroacetic acid and then lyophilized to give the TFA salt of the title compound as a fluffy white solid (26% recovery, overall yield 14.8%); FAB-MS: [M+H]=575.45.

Cyclic Compound Intermediate 34 cyclo-(D-Abu-Arg-Gly-Asp-Mamb); the compound of formula (II) wherein J=D-Abu, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.193 mmol scale to give the protected cyclic peptide (210 mg, >quantitative yield). The peptide (206 mg) and 206 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (158 mg, 99%; calculated as the acetate salt). Purification was accomplished by reversed-phase HPLC on a preparative Vydac C18 column (2.5 cm) using a 0.23%/min. gradient of 2 to 11% acetonitrile containing 0.1% TFA and then lyophilized to give the TFA salt of the title compound as a fluffy white solid (57% recovery, overall yield 72.2%); FAB-MS: [M+H]=547.21.

Cyclic Compound Intermediate 35 cyclo-(D-Ser-Arg-Gly-Asp-Mamb); the compound of formula (II) wherein J=D-Ser, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.193 mmol scale to give the protected cyclic peptide (224 mg, >quantitative yield). The peptide (210 mg) and 210 ml of m-cresol were treated with anhydrous hydrogen fluoride at 0° C. for 1 hour. The crude material was precipitated with ether, redissolved in aqueous HOAc, and lyophilized to generate the title compound as a pale yellow solid (145 mg, 89%; calculated as the acetate salt). Purification was accomplished by reversed-phase HPLC on a preparative Vydac C18 column (2.5 cm) using a 0.23%/min. gradient of 2 to 13% acetonitrile containing 0.1% TFA and then lyophilized to give the TFA salt of the title compound as a fluffy white solid (22% recovery, overall yield 27%); FAB-MS: [M+H]=549.31.

Cyclic Compound Intermediate 36 cyclo-(D-Phe-Arg-Gly-Asp-Mamb); the compound of formula (II) wherein J=D-Phe, K=Arg, L=Gly, M=Asp, $R^1=R^2=H$ The title compound was prepared using the general procedure described above for cyclo-(D-Val-NMeArg-Gly-

---

>quantitative yield; calculated as the acetate salt). Purification was accomplished by reversed-phase HPLC on a preparative Vydac C18 column (2.5 cm) using a 0.30%/min. gradient of 0 to 9% acetonitrile containing 0.1% TFA and then lyophilized to give the TFA salt of the title compound as a fluffy white solid (36% recovery, overall yield 19.9%); FAB-MS: [M+H]=519.26.

Asp-Mamb). The peptide was prepared on a 0.266 mmol scale to give the protected cyclic peptide (202 mg, 90%). The peptide (157 mg) and 157 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (125 mg, >quantitative yield; calculated as the acetate salt). Purification was accomplished by reversed-phase HPLC on a preparative Vydac C18 column (2.5 cm) using a 0.23%/min. gradient of 7 to 23% acetonitrile containing 0.1% TFA and then lyophilized to give the TFA salt of the title compound as a fluffy white solid (35% recovery, overall yield 29.3%); FAB-MS: [M+H]= 609.25

Cyclic Compound Intermediate 37 cyclo-(Phe-Arg-Gly-Asp-Mamb); the compound of formula (II) wherein J=Phe, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.335 mmol scale to give the protected cyclic peptide (306 mg, >quantitative yield). The peptide (275 mg) and 275 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (214 mg, 98%; calculated as the acetate salt). Purification was accomplished by reversed-phase HPLC on a preparative Vydac C18 column (2.5 cm) using a 0.23%/min. gradient of 9 to 23% acetonitrile containing 0.1% TFA and then lyophilized to give the TFA salt of the title compound as a fluffy white solid (32% recovery, overall yield 31.5%); FAB-MS: [M+H]= 609.26

Cyclic Compound Intermediate 40 cyclo-(D-Val-NMeAmf-Gly-Asp-Mamb); the compound of formula (II) wherein J=D-Val, K=NMeAmf, L=Gly, M=Asp, $R^1=R^2=H$ The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.586 mmol scale to give the protected cyclic peptide (189 mg, 39.9%). The peptide (189 mg) and 0.189 mL of anisole were treated with anhydrous hydrogen fluoride at 0° C. for 30 minutes. The crude material was precipitated with ether, redissolved in aqueous acetonitrile, and lyophilized to generate the title compound (212 mg, greater than quantitative yield; calculated as the fluoride salt). Purification was accomplished by reversed-phase HPLC on a preparative Vydac C18 column (2.5 cm) using a 0.23%/min. gradient of 10.8 to 22.5% acetonitrile containing 0.1% TFA and then lyophilized to give the TFA salt of the title compound as a fluffy white solid (8.1% recovery, overall yield 4.1%); FAB-MS: [M+H]= 595.23.

Cyclic Compound Intermediate 48a

The title compound may be synthesized using procedures described in Mosher et al. Tett. Lett. 29: 3183–3186, and as shown schematically below. This same procedure is a generally useful method for converting a primary amine into a guanidine functionality.

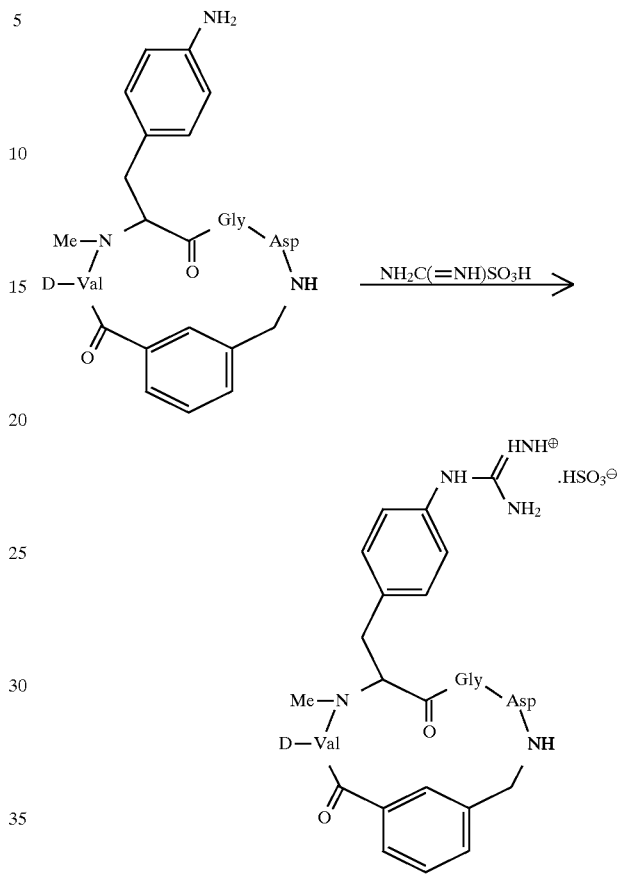

Cyclic Compound Intermediates 42–45

The synthesis of Cyclic Compound Intermediates 42–45 is shown schematically below.

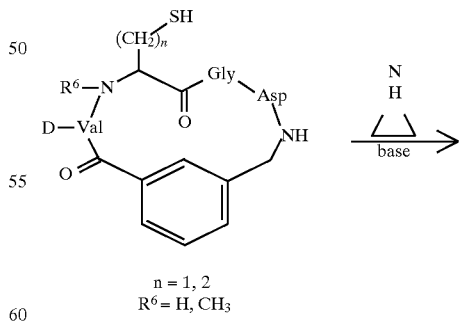

n = 1, 2
$R^6$ = H, $CH_3$

-continued

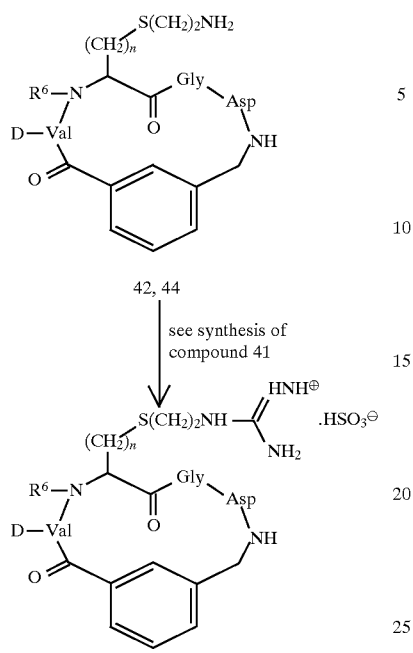

Cyclic Compound Intermediate 46 and 47

Cyclic Compound Intermediates 46 and 47 are prepared according to standard procedures, for example, as described in Garigipati, *Tett. Lett.* (1990) 31: 1969–1972 and in Canadian Patent 2008311, as is shown schematically below. The aspartic acid group may be protected (e.g., with a phenacyl protection group) to avoid side reactions.

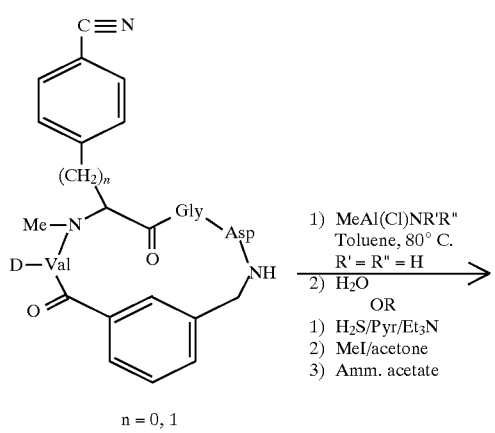

-continued

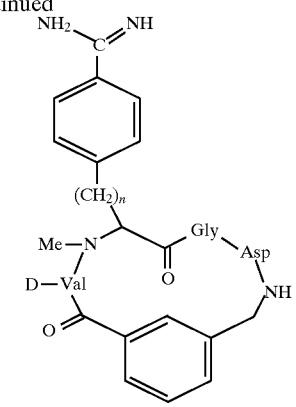

Cyclic Compound Intermediate 54 cyclo-(D-Val-NMeArg-b-Ala-Asp-Mamb); J=D-Val, K=NMeArg, L=b-Ala, M=Asp, $R^1=R^2=H$ The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.586 mmol scale to give the protected cyclic peptide (227 mg, 46.9%). The peptide (219 mg) and 219 mL of anisole were treated with anhydrous hydrogen fluoride at 0° C. for 30 minutes. The crude material was precipitated with ether, redissolved in aqueous acetonitrile, and lyophilized to generate (54) as a pale yellow solid (150 mg, 93.2%; calculated as the fluoride salt). Purification was accomplished by reversed-phase HPLC on a preparative Vydac C18 column (2.5 cm) using a 0.23%/min. gradient of 7.2 to 16.2% acetonitrile containing 0.1% TFA and then lyophilized to give the TFA salt of (54) as a fluffy white solid (43.6% recovery, overall yield 16.5%); FAB-MS: [M+H]= 589.32.

Cyclic Compound Intermediate 55–58

The synthesis of Cyclic Compound Intermediates 55–58 is shown schematically below.

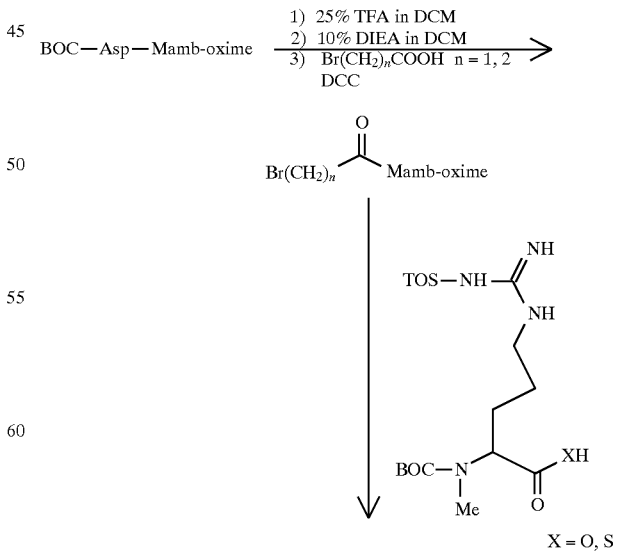

-continued

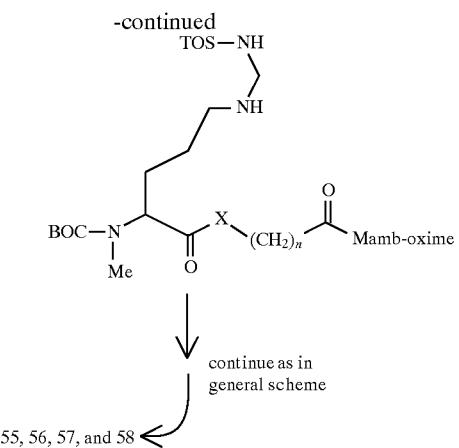

continue as in general scheme
55, 56, 57, and 58

Cyclic Compound Intermediate 58c cyclo-(D-Val-NMeArg-L-Ala-Asp-Mamb); the compound of formula (II) wherein J=D-Val, K=NMeArg, L=L-Ala, M=Asp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.611 mmol scale to give the protected cyclic peptide (375 mg, 74.6%). The peptide (360 mg) and 0.360 mL of anisole were treated with anhydrous hydrogen fluoride at 0° C. for 30 minutes. The crude material was precipitated with ether, redissolved in aqueous acetonitrile, and lyophilized to generate the title compound (220 mg, 83%; calculated as the fluoride salt). Purification was accomplished by reversed-phase HPLC on a preparative Vydac C18 column (2.5 cm) using a 0.23%/min. gradient of 9 to 18% acetonitrile containing 0.1% TFA and then lyophilized to give the TFA salt of the title compound as a fluffy white solid (19.9% recovery, overall yield 10.6%); FAB-MS: [M+H]=589.31.

Cyclic Compound Intermediate 63 and 63a cyclo-(D-Val-NMeArg-Gly-a-MeAsp-Mamb); the compounds of formula (II) wherein J is D-Val; K is NMeArg; L is Gly; M is a-MeAsp; $R^1$=$R^2$=H The title compound was prepared using the general procedure described for cyclo-(D-Val-NMeArg-Gly-Asp-Mamb). The DCC/DMAP method was used for attachment of Boc-Mamb to the oxime resin. The peptide was prepared on a 0.794 mmol scale to give the protected cyclic peptide (237 mg, 36.1%). The peptide (237 mg) and 0.237 mL of anisole were treated with anhydrous hydrogen fluoride at 0° C. for 30 minutes. The crude material was precipitated with ether, redissolved in aqueous acetonitrile, and lyophilized to generate the title compound (165 mg, 94.3%; calculated as the fluoride salt). Purification was accomplished by reversed-phase HPLC on a preparative Vydac $C_{18}$ column (2.5 cm) using a 0.23%/min. gradient of 9 to 18% acetonitrile containing 0.1% TFA and then lyophilized to give the TFA salt of the title compound as a fluffy white solid; isomer #1 (8.36% recovery, overall yield 2.5%); FAB-MS: [M+H] =589.29; isomer #2 (9.16% recovery, overall yield 2.7%); FAB-MS: [M+H]=589.27.

Cyclic Compound Intermediates 64 and 64a cyclo-(D-Val-NMeArg-Gly-B-MeAsp-Mamb); the compounds of formula (II) wherein J=D-Val, K=NMeArg, L=Gly, M=B-MeAsp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.611 mmol scale to give the protected cyclic peptide (201 mg, 40.0%). The peptide (200 mg) and 0.200 mL of anisole were treated with anhydrous hydrogen fluoride at 0° C. for 30 minutes. The crude material was precipitated with ether, redissolved in aqueous acetonitrile, and lyophilized to generate the title compound (162 mg, greater than quantitative yield; calculated as the fluoride salt). Purification was accomplished by reversed-phase HPLC on a preparative Vydac C18 column (2.5 cm) using a 0.23%/min. gradient of 9 to 18% acetonitrile containing 0.1% TFA and then lyophilized to give the TFA salt of the title compound as a fluffy white solid; isomer #1 (12.7% recovery, overall yield 4.8%); FAB-MS: [M+H] =589.43; isomer #2 (13.9% recovery, overall yield 5.3%); FAB-MS: [M+H]=589.45.

Cyclic Compound Intermediate 64b cyclo-(D-Val-NMeArg-Gly-NMeAsp-Mamb); the compound of formula (II) wherein J=D-Val, K=NMeArg, L=Gly, M=NMeAsp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.611 mmol scale to give the protected cyclic peptide (232 mg, 46.1%). The peptide (225 mg) and 0.225 mL of anisole were treated with anhydrous hydrogen fluoride at 0° C. for minutes. The crude material was precipitated with ether, redissolved in aqueous acetonitrile, and lyophilized to generate the title compound (160 mg, 96.4%; calculated as the fluoride salt). Purification was accomplished by reversed-phase HPLC on a preparative Vydac C18 column (2.5 cm) using a 0.23%/min. gradient of 9 to 18% acetonitrile containing 0.1% TFA and then lyophilized to give the TFA salt of the title compound as a fluffy white solid (28.2% recovery, overall yield 10.9%); FAB-MS: [M+H]=589.42.

Cyclic Compound Intermediate 64c cyclo-(D-Val-NMeArg-Gly-D-Asp-Mamb); the compound of formula (II) wherein J=D-Val, K=NMeArg, L=Gly, M=D-Asp, $R^1$=H, $R^2$=H The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.611 mmol scale to give the protected cyclic peptide (257 mg, 51.9%). The peptide (250 mg) and 0.250 mL of anisole were treated with anhydrous hydrogen fluoride at 0° C. for 30 minutes. The crude material was precipitated with ether, redissolved in aqueous acetonitrile, and lyophilized to generate the title compound (192 mg, greater than quantitative yield; calculated as the fluoride salt). Purification was accomplished by reversed-phase HPLC on a preparative Vydac C18 column (2.5 cm) using a 0.23%/min. gradient of 9 to 18% acetonitrile containing 0.1% TFA and then lyophilized to give the TFA salt of the title compound as a fluffy white solid (44.4% recovery, overall yield 20.7%); FAB-MS: [M+H]=575.42.

Cyclic Compound Intermediate 89e cyclo-(D-Abu-di-NMeOrn-Gly-Asp-Mamb); the compound of formula (II) wherein J=D-Abu, K=di-NMeOrn, L=Gly, M=Asp, $R^1$=$R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. The peptide was prepared on a 0.498 mmol scale to give the protected cyclic peptide (150 mg, 39.3%). The peptide (150 mg) and 0.150 mL of anisole were treated with anhydrous hydrogen fluoride at 0° C. for 30 minutes. The crude material was precipitated with ether, redissolved in aqueous acetonitrile, and lyophilized to generate the title compound (93 mg, 86%; calculated as the fluoride salt).

Purification was accomplished by reversed-phase HPLC on a preparative Vydac C18 column (2.5 cm) using a 0.45%/min. gradient of 3.6 to 18% acetonitrile containing 0.1% TFA and then lyophilized to give the TFA salt of the title compound as a fluffy white solid (49.3% recovery, overall yield 14.2%); FAB-MS: [M+H]=533.34.

Cyclic Compound Intermediate 89f cyclo-(D-Abu-NMeArg-Gly-D-Asp-Mamb); compound of formula (II) wherein J=D-Abu, K NMeArg, L=Gly, M=D-Asp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. TBTU was used as the coupling reagent. The peptide was prepared on a 0.596 mmol scale to give the protected cyclic peptide (273 mg, 57.6%). The peptide (263 mg) and 0.263 mL of anisole were treated with anhydrous hydrogen fluoride at 0° C. for 20 minutes. The crude material was precipitated with ether, redissolved in aqueous acetonitrile, and lyophilized to generate the title compound (218 mg; greater than quantitative yield; calculated as the fluoride salt). Purification was accomplished by reversed-phase HPLC on a preparative Vydac C18 column (2.5 cm) using a 0.23%/min. gradient of 10.8 to 19.8% acetonitrile containing 0.1% TFA and then lyophilized to give the TFA salt of the title compound as a fluffy white solid (40.4% recovery, overall yield 21.9%); FAB-MS: [M+H]=561.37.

Cyclic Compound Intermediate 89g cyclo-(D-Abu-D-NMeArg-Gly-Asp-Mamb); the compound of formula (II) J=D-Abu, K=D-NMeArg, L=Gly, M=Asp, $R^1$=H, $R^2$=H The title compound was prepared using the general procedure described for cyclo-(D-Val-NMeArg-Gly-Asp-Mamb) (Cyclic Compound Intermediate 4). The DCC/DMAP method was used for attachment of Boc-Mamb to the oxime resin. TBTU was used as the coupling reagent. The peptide was prepared on a 0.596 mmol scale to give the protected cyclic peptide (241 mg, 50.8%). The peptide (235 mg) and 0.235 mL of anisole were treated with anhydrous hydrogen fluoride at 0° C. for 20 minutes. The crude material was precipitated with ether, redissolved in aqueous acetonitrile, and lyophilized to generate the title compound (168 mg; 98.3%; calculated as the fluoride salt). Purification was accomplished by reversed-phase HPLC on a preparative Vydac C18 column (2.5 cm) using a 0.23%/min. gradient of 12.6 to 21.6% acetonitrile containing 0.1% TFA and then lyophilized to give the TFA salt of the title compound as a fluffy white solid (2.3% recovery, overall yield 0.99%); FAB-MS: [M+H]=561.36.

Cyclic Compound Intermediate 89h

Cyclo-(D-Ala-p-guanidinyl-Phe-Gly-Asp-Mamb);

the compound of formula (II) wherein J=D-Ala, K=p-guanidinyl-Phe, L=Gly, M=Asp $R^1$=H, $R^2$=H

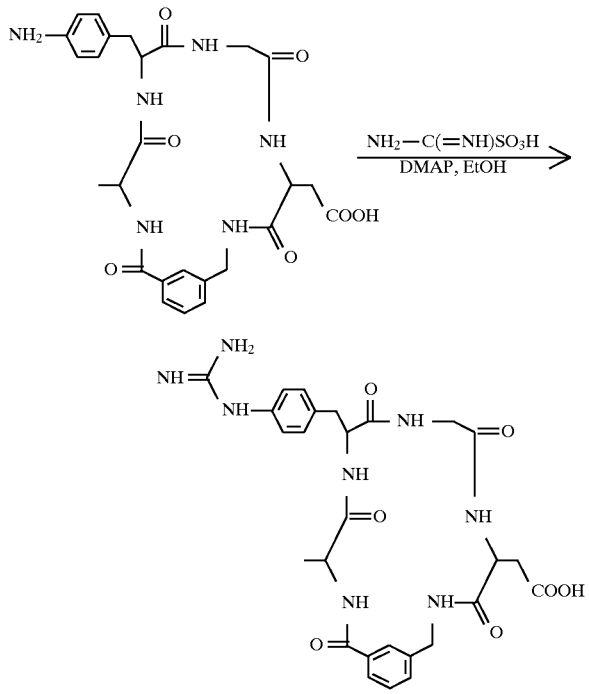

Dissolved 25 mg (38.3 mmoles) of cyclo-(D-Ala-p-amino-Phe-Gly-Asp-Mamb) (TFA salt), 14.3 mg (114.9 umoles) formamidine sulfonic acid, and 18.7 mg (153.2 umoles) of 4-dimethyl-aminopyridine in 5 ml of ethanol in a 10 ml round bottom flask. Refluxed the mixture for 3 hours, then added an additional 14.3 mg of formamidine sulfonic acid and 18.7 mg of 4-dimethyl-aminopyridine. After refluxing for an additional 3 hours, the reaction was found to be ~75% complete by reversed-phase HPLC. The ethanol was evaporated under reduced pressure, and the residue was purified on a preparative Vydac C18 column (2.5 cm) using a 0.45%/min. gradient of 0 to 18% acetonitrile containing 0.1% TFA. Lyophilization afforded the TFA salt of the title compound as a white solid (28% recovery), overall yield 26.4%); FAB-MS: [M+H]=581.30.

Cyclic Compound Intermediate 89i cyclo-(D-Abu-(DiNMe,guanidinyl-Orn)-Gly-Asp-Mamb); the compound of formula (II) wherein J=D-Abu, K=diNMe, guanidinyl-Orn, L=Gly, D=Asp, $R^1$=H, $R^2$=H

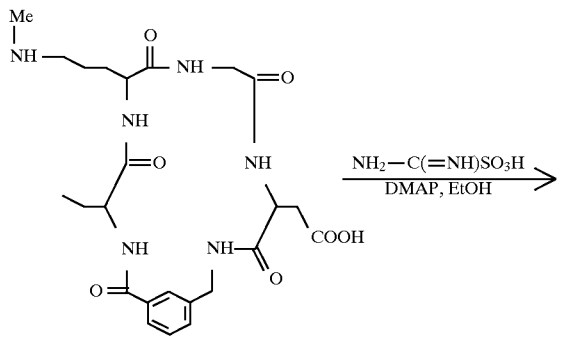

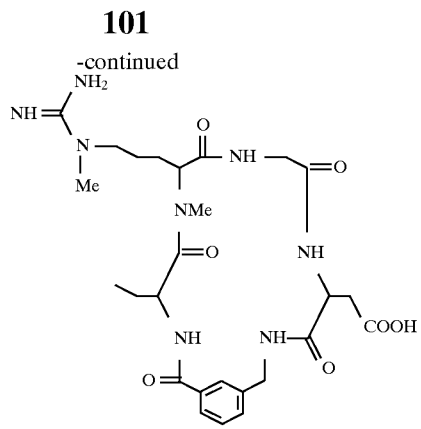

Dissolved 10.53 mg (16.3 mmoles) of cyclo-(D-Abu-diNMeOrn-Gly-Asp-Mamb) (TFA salt), 6.08 mg (48.99 umoles) formamidine sulfonic acid, and 8.00 mg (65.57 umoles) of 4-dimethyl-aminopyridine in 2.5 ml of ethanol in a 10 ml round bottom flask. Refluxed the mixture for 2 hours and then stirred at room temperature overnight. Refluxed for one hour, added an additional 6.08 mg of formamidine sulfonic acid and 8.00 mg of 4-dimethylaminopyridine and then refluxed for an additional 2 hours. Evaporated the ethanol under reduced pressure and purified the residue on a preparative Vydac C18 column (2.5 cm) using a 0.45%/min. gradient of 3.6 to 18% acetonitrile containing 0.1% TFA. Lyophilization afforded the TFA salt of the title compound as a white solid (57.2% recovery), overall yield 53.5%); FAB-MS: [M+H]=575.34.

Cyclic Compound Intermediates 89j cyclo-(D-Abu-Di-NMeLys-Gly-Asp-Mamb); the compound of formula (II) wherein J=D-Abu, K=Di-NMeLys, L=Gly, M=Asp, $R^1$=H, $R^2$=H cyclo-(D-Abu-NMeLys-Gly-Asp-Mamb); the compound of formula (II) wherein J=D-Abu, K=NMeLys, L=Gly, M=Asp, $R^1$=H, $R^2$=H Di-N-methyl amino acid derivatives may be prepared using methods which have been described previously (Olsen, *J. Org. Chem.* (1970) 35: 1912) or, alternatively, through the use of $NaH/CH_3I$. The mono-NMe-Lysine amino acid was obtained as a side product during the synthesis of the corresponding di-NMe-lysine derivative. The title compounds were prepared using conventional solution phase peptide chemistry techniques described previously. Cyclo-(D-Abu-diNMeLys-Gly-Asp-Mamb) was obtained in 0.31% overall yield, FAB-MS: [M+H]=547.3. Cyclo-(D-Abu-NMeLys-Gly-Asp-Mamb) was obtained in 0.25% overall yield, FAB-MS: [M+H]=533.3.

Cyclic Compound Intermediate 90 cyclo-(D-Val-NMeArg-Gly-Asp-2-aminomethylphenylacetic acid)

The title compound was prepared by a modification of the general solution-phase chemistry route. This approach employed an amino acid succinimide ester coupling to the aromatic cyclizing moiety, and the dinitrobenzophenone oxime as shown schematically below in the Scheme below (n=1).

Scheme

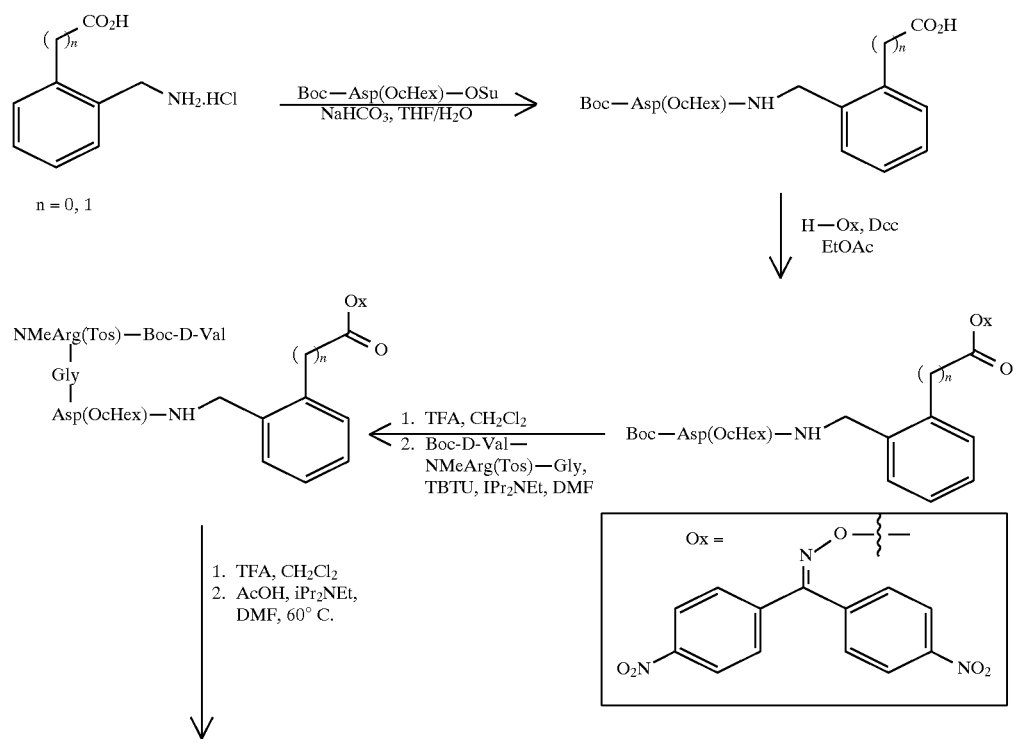

-continued
Scheme

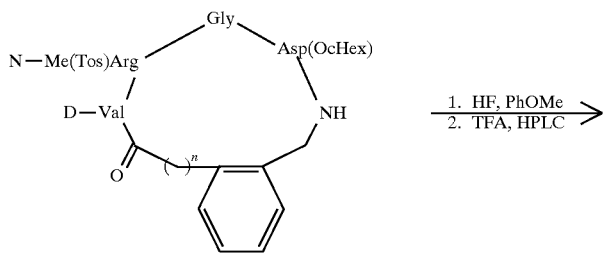 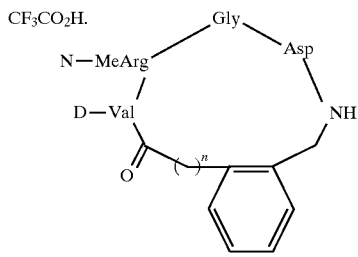

Boc-Asp(OcHex)-2-aminomethylphenylacetic Acid

To a suspension of 2-aminomethylphenylacetic acid.HCl (4.0 g, 20 mmol) in H₂O (20 ml) was added NaHCO₃ (5.0 g, 60 mmol), followed by a solution of Boc-Asp(OcHex)-OSu (7.5 g, 18 mmol) in THF (20 ml). The reaction mixture was stirred at room temperature for 3 hours, filtered, diluted with H₂O, acidified with 1N HCl, and extracted with ethyl acetate. The extracts were washed with H₂O, brine, dried over anhydrous magnesium sulfate, and evaporated to dryness under reduced pressure. This material was triturated with ether to provide the title compound (7.0 g, 83%) as a white powder. $^1$H NMR (D$_6$-DMSO) 12.40 (br s, 1H), 8.30 (br t, 1H), 7.20 (m, 5H), 4.65 (m, 1H), 4.35 (q, 1H), 4.25 (m, 2H), 3.65 (s, 2H), 2.70 (dd, 1H), 2.55 (dd, 1H), 1.70 (m, 4H), 1.40 (s, 9H), 1.35 (m, 6H).

4,4'-Dinitrobenzophenone Oxime

The title compound was prepared by modification of procedures previously reported in the literature (Chapman and Fidler (1936) J. Chem. Soc, 448; Kulin and Leffek (1973) Can. J. Chem., 51: 687). A solution of chromic anhydride (20 g, 200 mmol) in 125 ml of H₂O was added dropwise over 4 hours, to a suspension of bis(4-nitrophenyl) methane (25 g, 97 mmol) in 300 ml of acetic acid heated to reflux. The reaction mixture was heated at reflux for 1 hour, cooled to room temperature, and poured into water. The solid was collected by filtration, washed with H₂O, 5% sodium bicarbonate, H₂O, and air-dryed to provide a 1:1 mixture of bis(4-nitrophenyl)methane/4,4'-dinitrobenzophenone via $^1$H NMR. This material was oxidized with a second portion of chromic anhydride (20 g, 200 mmol), followed by an identical work-up procedure to provide the crude product. Trituration with 200 ml of benzene heated to reflux for 16 hours provided 4,4'-dinitrobenzophenone (20.8 g, 79%) as a yellow powder.

A solution of hydroxylamine hydrochloride (10.2 g, 147 mmol) was added to a suspension of 4,4'-dinitrobenzophenone (19 g, 70 mmol) in 100 ml of ethanol. The reaction mixture was heated to reflux for 2 hours, cooled to room temperature, and the solid collected by filtration. Recrystallization from ethanol provided the title compound (14.0 g, 70%) as pale yellow crystals. mp 194° C.; $^1$H NMR (D$_6$-DMSO) 12.25 (s, 1H), 8.35 (d, 2H), 8.20 (d, 2H), 7.60 (d, 4H).

4.4'-Dinitrobenzophenone Oxime Boc-Asp (OcHex)-2-aminomethylphenylacetate

To an ice-cooled solution of Boc-Asp(OcHex)-2-aminomethylphenylacetic acid (3.5 g, 7.6 mmol) and 4,4'-dinitrobenzophenone oxime (2.2 g, 7.5 mmol) in 50 ml of ethyl acetate and 5 ml of DMF was added DCC (1.6 g, 7.8 mmol). The reaction mixture was stirred at room temperature for 8 hours, filtered, diluted with ethyl acetate, washed with saturated sodium bicarbonate solution, H₂O, brine, dried over anhydrous magnesium sulfate, and evaporated to dryness under reduced pressure. This material was purified by column chromatography on silica gel (EM Science, 230–400 mesh) using 10:1 dichloromethane/ethyl acetate to give the title compound (4.3 g, 78%) as pale yellow crystals. $^1$H NMR (D$_6$-DMSO) 8.30 (dd, 5H), 7.80 (d, 2H), 7.65 (d, 2H), 7.15 (m, 5H), 4.65 (m, 1H), 4.35 (q, 1H), 4.15 (m, 2H), 3.90 (s, 2H), 2.70 (dd, 1H), 2.50 (dd, 1H), 1.70 (m, 4H), 1.40 (s, 9H), 1.35 (m, 6H).

4,4'-Dinitrobenzophenone Oxime Boc-D-Val-NMeArg(Tos)-Gly-Asp(OcHex)-2-aminomethylphenylacetate To a solution of 4,4'-dinitrobenzophenone oxime Boc-Asp(OcHex)-2-aminomethylphenylacetate (1.5 g, 2 mmol) in 4 ml of dichloromethane was added 2 ml of trifluoroacetic acid. The reaction mixture was stirred at room temperature for 1 hour, diluted with dichloromethane, and evaporated to dryness under reduced pressure. The oily residue was concentrated under high vacuum to remove traces of excess trifluoroacetic acid.

To a solution of the crude TFA salt and Boc-D-Val-NMeArg(Tos)-Gly (1.2 g, 2 mmol) in 5 ml of DMF was added TBTU (640 mg, 2 mmol) and DIEA (780 mg, 6 mmol). The reaction mixture was stirred at room temperature for 16 hours, concentrated under high vacuum, diluted with ethyl acetate, washed with 5% citric acid, H₂O, brine, dried over anhydrous magnesium sulfate, and evaporated to dryness under reduced pressure. This material was triturated with ether to provide the title compound (2.3 g, 95%) as a yellow powder. This material was used without further purification.

cyclo-(D-Val-NMeArg(Tos)-Gly-Asp (OcHex)-2-aminomethylphenylacetic acid)

To a solution of 4,4'-dinitrobenzophenone oxime Boc-D-Val-NMeArg(Tos)-Gly-Asp(OcHex)-2-aminomethylphenylacetate (1.2 g, 1 mmol) in 4 ml of dichloromethane was added 2 ml of trifluoroacetic acid. The reaction mixture was stirred at room temperature for 3 hours, diluted with dichloromethane, and evaporated to dryness under reduced pressure. The oily residue was concentrated under high vacuum to remove traces of excess trifluoroacetic acid.

To a solution of the crude TFA salt in 100 ml of DMF was added acetic acid (0.50 ml, 8.7 mmol) and DIEA (1.52 ml, 8.7 mmol). The reaction mixture was stirred at 60° C. for 3 days, concentrated under high vacuum, diluted with ethyl acetate, and the solution allowed to crystallize overnight.

Filtration provided the title compound (563 mg, 68%) as a yellow powder. $^1$H NMR (D$_6$-DMSO) 8.70 (d, 1H), 8.40 (br s, 1H), 8.30 (br s, 1H), 8.05 (t, 1H), 7.65 (d, 2H), 7.25 (d, 2H), 7.20 (m, 4H), 7.10 (br d, 1H), 6.80 (br s, 1H), 6.60 (br s, 1H), 5.10 (dd, 1H), 4.65 (m, 1H), 4.55 (m, 1H), 4.40 (m, 2H), 3.85 (m, 2H), 3.65 (d, 1H), 3.45 (m, 2H), 3.05 (m, 2H), 2.80 (s, 3H), 2.80 (m, 1H), 2.60 (dd, 1H), 2.30 (s, 3H), 1.70 (m, 6H), 1.30 (m, 9H), 0.95 (d, 3H), 0.80 (d, 3H); DCI (NH$_3$)-MS: [M+H]=825.

cyclo-(D-Val-NMeArg-Gly-Asp-2-aminomethylphenylacetic acid)

A mixture of 352 mg (0.43 mmol) of cyclo-(D-Val-NMeArg(Tos)-Gly-Asp(OcHex)-2-aminomethylphenylacetic acid) and 352 µl of anisole was treated at 0° C. with 5 ml of HF for 20 minutes. The excess HF was removed under reduced pressure, the residue triturated with ether, dissolved in 50% acetonitrile/H$_2$O, and lyophilized to provide the crude cyclic peptide.HF salt as an off-white powder. Purification was accomplished by reversed-phase HPLC on a preparative Vydac C18 column (2.5 cm) using a 0.8%/minute gradient of 10 to 38% acetonitrile containing 0.1% trifluoroacetic acid to give the TFA salt of the title compound (225 mg, 75%) as a fluffy white solid; $^1$H NMR (D$_6$-DMSO) 8.70 (d, 1H), 8.35 (d, 1H), 8.20 (t, 1H), 8.00 (t, 1H), 7.45 (t, 1H), 7.20 (m, 3H), 7.10 (m, 1H), 7.00 (br s, 4H), 5.10 (dd, 1H), 4.50 (dt, 1H), 4.40 (m, 2H), 3.85 (dt, 2H), 3.65 (d, 1H), 3.50 (dd, 1H), 3.45 (d, 1H), 3.10 (m, 2H), 2.90 (s, 3H), 2.75 (dd, 1H), 2.55 (dd, 1H), 2.00 (m, 1H), 1.85 (m, 1H), 1.65 (m, 1H), 1.30 (m, 2H), 0.95 (d, 3H), 0.85 (d, 3H); FAB-MS: [M+H]=589.

Cyclic Compound Intermediate 91 cyclo-(D-Val-NMeArg-Gly-Asp-2-aminomethylbenzoic acid)

The title compound was prepared by the general solution-phase procedure described above for cyclo-(D-Val-NMeArg-Gly-Asp-2-aminomethylphenylacetic acid), and as shown schematically above in the Cyclic Compound Intermediate 90 Scheme (n=0). The cyclic peptide (192 mg, 0.24 mmol) was deprotected with excess HF in the presence of anisole as scavenger. Purification was accomplished by reversed-phase HPLC on a preparative Vydac C18 column (2.5 cm) using a 0.8%/minute gradient of 10 to 38% acetonitrile containing 0.1% trifluoroacetic acid to give the TFA salt of the title compound (20 mg, 12%) as a fluffy white solid; $^1$H NMR (D$_6$-DMSO) 8.75 (d, 1H), 8.50 (d, 1H), 7.65 (t, 1H), 7.60 (t, 1H), 7.50 (m, 2H), 7.40 (m, 3H), 7.00 (br s, 4H), 5.05 (dd, 1H), 4.50 (t, 1H), 4.30 (m, 2H), 4.10 (dd, 1H), 3.70 (m, 2H), 3.15 (q, 2H), 3.05 (s, 3H), 2.80 (dd, 1H), 2.55 (dd, 1H), 2.10 (m, 1H), 1.95 (m, 1H), 1.60 (m, 1H), 1.40 (m, 2H), 1.05 (d, 3H), 0.95 (d, 3H); FAB-MS: [M+H]=575.

Cyclic Compound Intermediate 92 cyclo-(D-Val-NMeArg-Gly-Asp-3-aminophenylacetic acid)

The title compound was prepared by the general solution-phase procedure described above for cyclo-(D-Val-NMeArg-Gly-Asp-Mamb), and as shown schematically in the Scheme above. The cyclic peptide (360 mg, 0.44 mmol) was deprotected with excess HF in the presence of anisole as scavenger. Purification was accomplished by reversed-phase HPLC on a preparative LiChrospher RP-18 column (5 cm) using a 2.3%/minute gradient of 22 to 90% acetonitrile containing 0.1% trifluoroacetic acid to give the TFA salt of the title compound (150 mg, 50%) as a fluffy white solid; $^1$H NMR (D$_6$-DMSO) 12.40 (br s, 1H), 8.95 (s, 1H), 8.55 (m, 2H), 8.45 (t, 1H), 7.90 (d, 1H), 7.50 (m, 1H), 7.20 (t, 1H), 7.00 (br s, 4H), 6.90 (m, 2H), 5.15 (dd, 1H), 4.65 (q, 1H), 4.55 (t, 1H), 3.65 (m, 2H), 3.60 (dd, 1H), 3.10 (m, 2H), 2.85 (s, 3H), 2.85 (d, 1H), 2.70 (dd, 2H), 2.00 (m, 2H), 1.75 (m, 1H), 1.35 (m, 2H), 0.90 (d, 3H), 0.85 (d, 3H); FAB-MS: [M+H]=575.

Cyclic Compound Intermediate 87, 88 cyclo-(D-Val-NMeArg-Gly-Asp-4-aminomethylbenzoic acid); the compound of formula (III) wherein J=D-Val, K=NMeArg, L=Gly, M=Asp, R$^1$=H, R$^2$=H The title compound was prepared using the general procedure described above for cyclo-(D-Val-NMeArg-Gly-Asp-Mamb). The DCC/DMAP method was used for attachment of Boc-4-aminomethylbenzoic acid to the oxime resin. The peptide was prepared on a 0.43 mmol scale to give the protected cyclic peptide (212mg, 60.8%). The peptide (200 mg) and 200 mL of m-cresol were treated with anhydrous hydrogen fluoride at 0° C. for 30 minutes. The crude material was precipitated with ether, redissolved in aqueous HOAc, and lyophilized to generate the crude peptide as a pale yellow solid (152 mg, 97% calculated as the acetate salt). Purification was accomplished by reversed-phase HPLC on a preparative Vydac C18 column (2.5 cm) using a 0.23%/min. gradient of 7 to 22% acetonitrile containing 0.1% TFA. Two peaks were isolated to give isomer #1 (87) (17.1% recovery, overall yield 9.3%) and isomer #2 (88) (13.4% recovery, overall yield 7.3%); FAB-MS: [M+H]= 575.41 (isomer #1; 87); 575.44 (isomer #2; 88).

R$^1$ or R$^2$ Substituted Intermediates

Cyclic compound intermediates which incorporate substituents at R$^1$ or R$^2$ are synthesized from the corresponding substituted cyclizing moieties. The following Schemes, discussions, and examples teach the preparation of this class of cyclizing moiety and the corresponding cyclic compound intermediates.

t-Butyloxycarbonyl-N-methyl-3-aminomethylbenzoic Acid (Boc-NMeMamb)

The title compound can be prepared according to standard procedures, for examples, as disclosed in Olsen, *J. Org. Chem.* (1970) 35: 1912), and as shown schematically below.

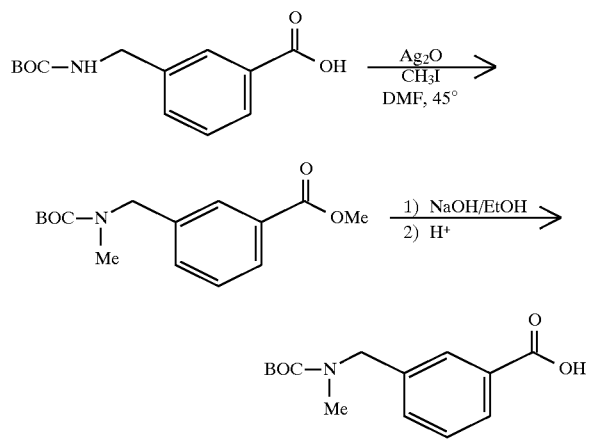

Synthesis of Aminomethylbenzoic Acid Analogs

Cyclizing moieties of the formula below may be prepared using standard synthetic procedures, for example, as shown in the indicated reaction schemes shown below.
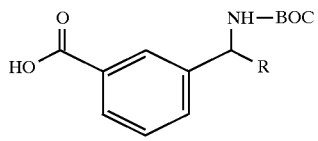
For R=CH$_3$, CH$_2$CH$_3$, CH$_2$CH$_2$CH$_3$, CH$_2$CH$_2$CH$_2$CH$_3$, CH(CH$_3$)$_2$, C(CH$_3$)$_3$, CH(CH$_3$)CH$_2$CH$_3$, benzyl, cyclopentyl, cyclohexyl; see Scheme 1.
For R=CH$_3$, CH$_2$CH$_2$CH$_2$CH$_3$, phenyl; see Scheme 2.
For R=CH$_3$, phenyl; see Scheme 3 and 4.
Scheme 1:
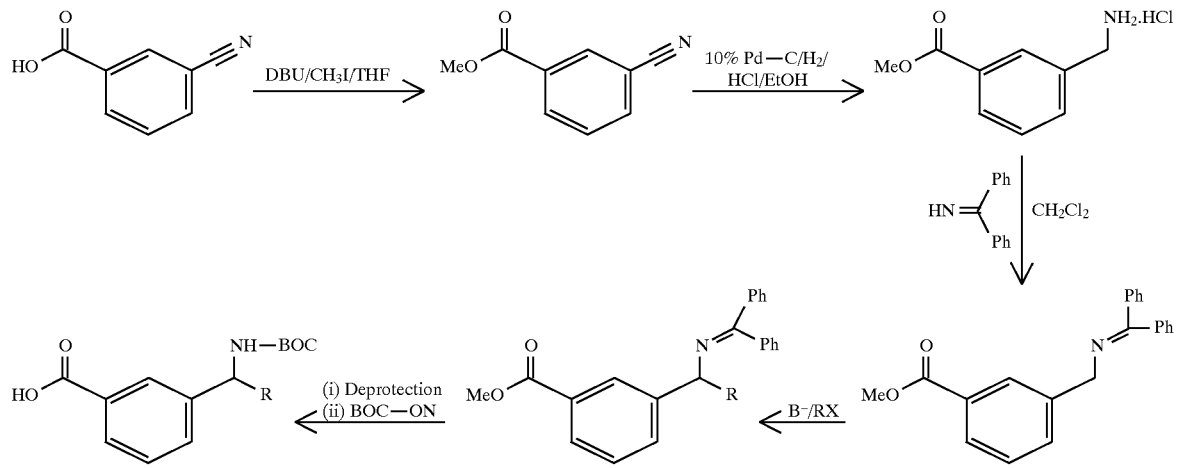
Scheme 2:
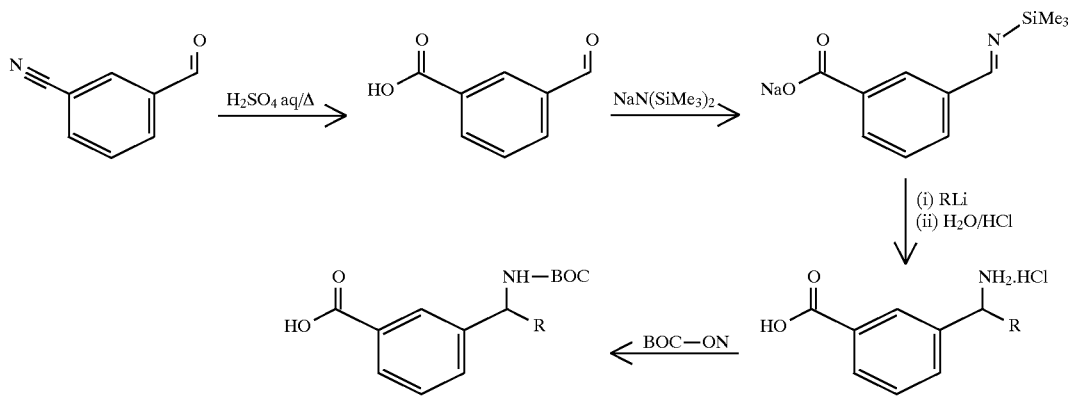

Scheme 3:

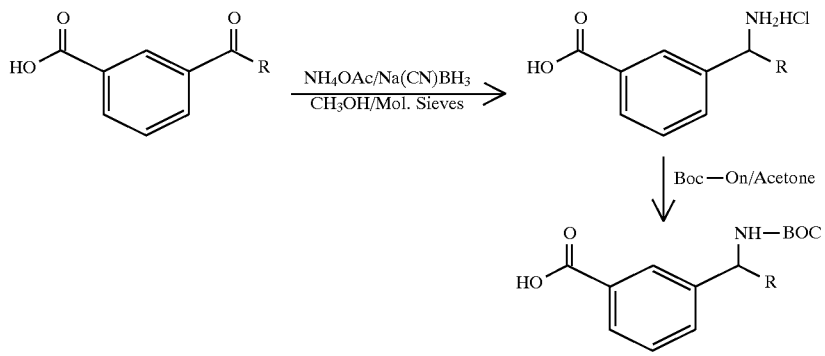

Scheme 4:

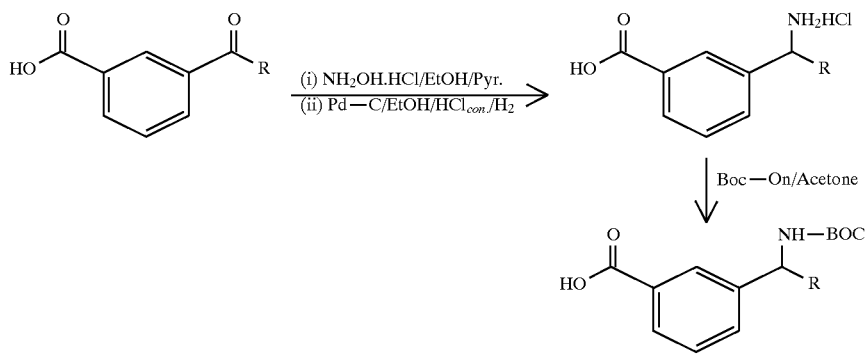

3-[1'-(t-butyloxycarbonyl)amino]ethylbenzoic acid
(BOC-MeMAMB)

The title compound for the purpose of this invention was prepared according to the Scheme 4 above.

3-Acetylbenzoic acid (0.50 g, 3 mmol), hydroxylamine hydrochloride (0.70 g, 10 mmol) and pyridine (0.70 ml, 9 mmol) were refluxed in 10 ml ethanol, for 2 h. Reaction mixture was concentrated, residue triturated with water, filtered and dried. Oxime was isolated as a white solid (0.51 g; 94.4% yield). $^1$HNMR (CD$_3$OD) 7.45–8.30(m, 4H), 2.30 (s, 3H). MS (CH$_4$-CI) [M+H–O]=164.

A solution of the oxime (0.51 g, 3 mmol) in ethanol, containing 10% Pd on carbon (1.5 g) and conc. HCl (0.25 ml, 3 mmol) was hydrogenated at 30 psi H$_2$ pressure in a Parr hydrogenator for 5 h. Catalyst was filtered and the filtrate concentrated. Residue was triturated with ether. Amine hydrochloride was isolated as a white solid (0.48 g; 85.7% yield). $^1$H NMR (CD$_3$OD) 7.6–8.15(m, 4H), 4.55(q, 1H), 1.70(s, 3H). MS [M+H]=166.

Amine hydrochloride (0.40 g, 2 mmol) was dissolved in 15 ml water. A solution of BOC-ON (0.52 g, 2.1 mmol) in 15 ml acetone was added, followed by the addition of triethylamine (0.8 ml, 6 mmol). Reaction was allowed to proceed for 20 h. Reaction mixture was concentrated, partitioned between ethyl acetate and water. Aqueous layer was acidified to pH 2 using 10% HCl solution. Product was extracted in ethyl acetate, which after the usual work up and recrystallization from ethyl acetate/hexane, gave the title compound as a white solid (0.30 g; 57% yield). m.p. 116°–118° C. $^1$HNMR (CDCl$_3$) 7.35–8.2(m, 4H), 4.6(bs, 1.5H), 1.50(d, 3H), 1.40(s, 9H). MS (NH$_3$—CI) [M+NH$_4$]=283.

3-[1'-(t-butyloxycarbonyl)amino]benzylbenzoic acid
(BOC-PhMAMB)

The title compound for the purpose of this invention was prepared according to the Scheme 4 (above), by the procedure similar to that for the methyl derivative.

A solution of 3-benzoylbenzoic acid (2.00 g, 9 mmol), hydroxylamine hydrochloride (2.00 g, 29 mmol) and pyridine (2.00 ml, 25 mmol) in ethanol was refluxed for 12 h. After the usual extractive work up, white solid was obtained (2.41 g). The product still contained traces of pyridine, but was used in the next step without further purification.

The crude product (2.00 g, ~8 mmol) was dissolved in 200 ml ethanol. 10% Pd—C (2.00 g) and con. HCl (1.3 ml, 16 mmol) were added. Reaction mixture was hydrogenated at 30 psi for 1 h. The catalyst was filtered and the reaction mixture concentrated. Upon trituration of the residue with ether and drying under vacuum, amine hydrochloride was obtained as a white solid (2.12 g; 97% yield). $^1$HNMR (CD$_3$OD) 7.4–8.15(m, 10H), 5.75(s, 1H). MS (CH$_4$-CI) [M+H–OH]=211.

Amine hydrochloride (1.00 g, 4 mmol) was converted to its BOC-derivative by a procedure similar to the methyl case. 0.60 g (48% yield) of the recrystallized (from ethanol/hexane) title compound was obtained as a white solid. m.p. 190°–192° C. $^1$HNMR (CD$_3$OD) 7.2–8.0(m, 10H), 5.90 (2s, 1H, 2 isomers), 1.40(s, 9H). MS (NH$_3$-CI) [M+NH$_4$–C$_4$H$_8$]=289.

Cyclic Compound Intermediates 68 and 68a
cyclo-(D-Val-NMeArg-Gly-Asp-MeMamb); the compound of formula (II) wherein J=D-Val, K=NMeArg, L=Gly, M=Asp, R$^1$=CH$_3$, R$^2$=H MeMAMB cyclizing moiety was prepared via Scheme 4 (described earlier). The title compound was made by following the solution phase synthetic route to attach MeMAMB to the tripeptide. Cyclization gave the protected cyclic peptide. Deprotection was achieved by treatment of the peptide (390 mg) and anisol (0.390 ml) with anhydrous HF at 0° C. for 30 minutes. The crude material was precipitated with ether, redissolved in 10% aqueous acetic acid, and lyophilized to give a mixture of the two isomers (330 mg; greater than quantitative yield; calculated as the acetate salt). Purification and the separation of the isomers was accomplished by Reverse-Phase HPLC on a preparative Vydac C18 column (2.5 cm) using a 0.48%/min gradient of 7 to 23% acetonitrile containing 0.1% TFA. Fractions collected at retention time 24.1 min and 26.8 min were lyophilized to give the TFA salts of the isomers 1 and 2 respectively. FAB-MS (Isomer 1): [M+H]=589.31; FAB-MS (isomer 2): [M+H]=589.31.

Cyclic Compound Intermediates 76 and 76a cyclo-(D-Val-NMeArg-Gly-Asp-PhMamb); the compound of formula (II) wherein J=D-Val, K=NMeArg, L=Gly, M=Asp, $R^1$=Ph, $R^2$=H PhMAMB cyclizing moiety was prepared via Scheme 4 (described earlier). The title compound was made by following the solution phase synthetic route to attach PhMAMB to the tripeptide. Cyclization gave the protected cyclic peptide. Deprotection was achieved by treatment of the peptide (470 mg) and anisol (0.470 ml) with anhydrous HF at 0° C. for 30 minutes. The crude material was precipitated with ether, redissolved in 10% aqueous acetic acid, and lyophilized to give a mixture of the two isomers (310 mg; 82.4% overall recovery). Purification and the separation of the isomers was accomplished by Reverse-Phase HPLC on a preparative Vydac C18 column (2.5 cm) using a 0.55%/min gradient of 18 to 36% acetonitrile containing 0.1% TFA. Fractions collected at retention time 22 min and 24.6 min were lyophilized to give the TFA salts of the isomers 1 and 2 respectively. FAB-MS (Isomer 1): [M+H]=651.33; FAB-MS (isomer 2): [M+H]=651.33.

Cyclic Compound Intermediate 79 cyclo-(D-Val-NMeArg-Gly-Asp-NMeMamb); the compound of formula (II) wherein J=D-Val, K=NMeArg, L=Gly, M=Asp, $R^1$=H, $R^2$=$CH_3$ The title compound was prepared using the general procedure described for cyclo-(D-Val-NMeArg-Gly-Asp-Mamb) (Cyclic Compound Intermediate 4). The DCC/DMAP method was used for attachment of Boc-NMeMamb to the oxime resin. The peptide was prepared on a 0.456 mmol scale to give the protected cyclic peptide (406 mg, greater than quantitative yield). The peptide (364 mg) and 0.364 mL of anisole were treated with anhydrous hydrogen fluoride at 0° C. for 30 minutes. The crude material was precipitated with ether, redissolved in aqueous acetonitrile, and lyophilized to generate the title compound (251 mg, 93.5%; calculated as the fluoride salt). Purification was accomplished by reversed-phase HPLC on a preparative Vydac C18 column (2.5 cm) using a 0.23%/min. gradient of 9 to 18% acetonitrile containing 0.1% TFA and then lyophilized to give the TFA salt of the title compound as a fluffy white solid (34.2% recovery, overall yield 29.9%); FAB-MS: [M+H]=589.33.

Ring-Substituted $R^{31}$ Cyclizing Moieties

Cyclizing moieties possessing an aromatic ring that bears a substituent group may be prepared using the methods taught in the following examples and Schemes.

Synthesis of 4, 5, and 6-Substituted 3-Aminomethylbenzoic Acid.HCl, and 4, 5, and 6-Substituted t-Butyloxycarbonyl-3-aminomethylbenzoic Acid Derivatives 4, 5, and 6-Substituted 3-aminomethylbenzoic acid.HCl, and 4, 5, and 6-substituted t-butyloxycarbonyl-3-aminomethylbenzoic acid derivatives useful as intermediates in the synthesis of the compounds of the invention are prepared using standard procedures, for example, as described in Felder et al *Helv. Chim. Acta,* 48: 259 (1965); de Diesbach *Helv. Chim. Acta,* 23: 1232 (1949); Truitt and Creagn *J. Org. Chem.,* 27: 1066 (1962); or Sekiya et al *Chem. Pharm. Bull.,* 11: 551 (1963), and as shown schematically below.

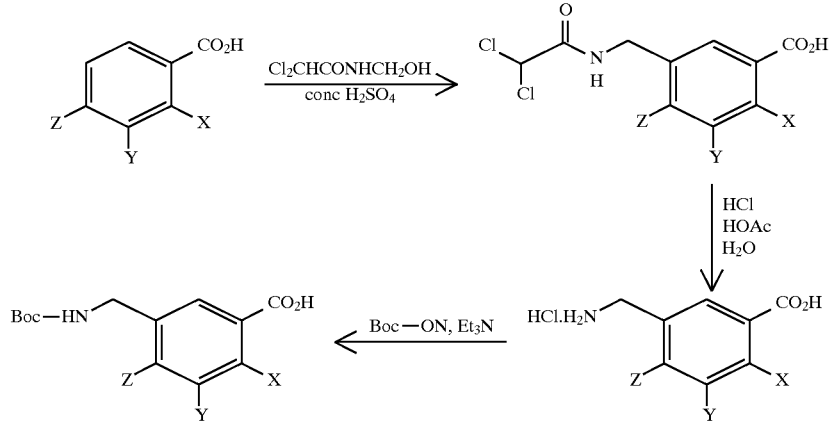

Synthesis of 4-Chloro-3-aminomethylbenzoic Acid.HCl

The title compound was prepared by modification of procedures previously reported in the literature (Felder et al (1965) *Helv. Chim. Acta,* 48: 259). To a solution of 4-chlorobenzoic acid (15.7 g, 100 mmol) in 150 ml of concentrated sulfuric acid was added N-hydroxymethyl dichloroacetamide (23.7 g, 150 mmol) in portions. The reaction mixture was stirred at room temperature for 2 days, poured onto 375 g of ice, stirred for 1 hour, the solid was collected by filtration, and washed with $H_2O$. The moist solid was dissolved in 5% sodium bicarbonate solution, filtered, and acidified to pH 1 with concentrated HCl. The solid was collected by filtration, washed with $H_2O$, and air-dryed overnight to give 4-chloro-3-dichloroacetylaminomethylbenzoic acid (26.2 g, 89%) as a white powder.

A suspension of 4-chloro-3-dichloroacetylaminomethylbenzoic acid (26.2 g, 88 mmol) in 45 ml of acetic acid, 150 ml of concentrated HCl, and 150 ml of $H_2O$ was heated to reflux for 3 hours, filtered while hot, and allowed to cool to room temperature. The solid was collected by filtration, washed with ether, washed with acetone-ether, and air-dryed overnight to give the title compound (7.6 g, 39%) as off-white crystals. mp 278°–9° C.; $^1$H NMR ($D_6$-DMSO) 13.40 (br s, 1H), 8.75 (br s, 3H), 8.20 (s, 1H), 7.95 (dd, 1H), 7.70 (d, 1H), 4.20 (br s, 2H).

t-Butyloxycarbonyl-4-chloro-3-aminomethylbenzoic Acid

A suspension of 4-chloro-3-aminomethylbenzoic acid.HCl (6.7 g, 30 mmol) and triethylamine (9.3 g, 92 mmol) in 50 ml of $H_2O$, was added to a solution of Boc-ON (9.2 g, 38 mmol) in 50 ml of tetrahydrofuran cooled to 0° C. The reaction mixture was stirred at room temperature overnight, and the volatile compounds were removed by concentration under reduced pressure. The residue was diluted with $H_2O$, washed with ether, acidified to pH 3 with 1N HCl, and extracted with ethyl acetate. The extracts were washed with $H_2O$, brine, dried over anhydrous magnesium sulfate, and evaporated to dryness under reduced pressure. This material was triturated with ether-hexane to provide the title compound (7.4 g, 87%) as a white powder. mp 159° C. (dec); $^1$H NMR ($D_6$-DMSO) 13.20 (br s, 1H), 7.90 (s, 1H), 7.80 (dd, 1H), 7.60 (br s, 1H), 7.55 (d, 1H), 4.20 (br d, 2H), 1.40 (s, 9H).

Synthesis of 3-Aminomethyl-6-iodobenzoic Acid.HCl

The title compound was prepared by modification of procedures previously reported in the literature (Felder et al. (1965) Helv. Chim. Acta, 48: 259). To a solution of 6-iodobenzoic acid (24.8 g, 100 mmol) in 150 ml of concentrated sulfuric acid was added N-hydroxymethyl dichloroacetamide (23.7 g, 150 mmol) in portions. The reaction mixture was stirred at room temperature for 7 days, poured onto 375 g of ice, and stirred for 1 hour. The solid was then collected by filtration, and washed with $H_2O$. The moist solid was dissolved in 5% sodium bicarbonate solution, filtered, and acidified to pH 1 with concentrated HCl. The solid was collected by filtration, washed with $H_2O$, and air-dried overnight to give 3-dichloroacetyl-aminomethyl-6-iodobenzoic acid (32.0 g, 82%) as a white powder.

A suspension of 3-dichloroacetylaminomethyl-6-iodobenzoic acid (32.0 g, 82 mmol) in 51 ml of acetic acid, 170 ml of concentrated HCl, and 125 ml of $H_2O$ was heated to reflux for 3 hours, and filtered while hot, and allowed to cool to room temperature. The solid was collected by filtration, washed with ether, washed with acetone-ether, and air-dried overnight to give the title compound (13.2 g, 51%) as a beige powder; 1H NMR (D6-DMSO) 13.50 (br s, 1H), 8.50 (br s, 3H), 8.05 (d, 1H), 7.85 (s, 1H), 7.40 (d, 1H), 4.05 (br s, 2H).

t-Butyloxycarbonyl-3-Aminomethyl-6-Iodobenzoic Acid

A suspension of 3-aminomethyl-6-iodobenzoic acid.HCl (8.0 g, 26 mmol) and triethylamine (8.7 g, 86 mmol) in 32 ml of $H_2O$, was added to a solution of Boc-ON (8.0 g, 32 mmol) in 23 ml of tetrahydrofuran cooled to 0° C. The reaction mixture was stirred at room temperature for overnight, and the volatile compounds were removed by concentration under reduced pressure. The residue was diluted with H2O, washed with ether, acidified to pH 3 with 1N HCl, and extracted with ethyl acetate. The extracts were washed with H2O, brine, dried over anhydrous magnesium sulfate, and evaporated to dryness under reduced pressure. This material was triturated from ether to provide the title compound (5.7 g, 59%) as a white powder; mp 182° C. (dec); 1H NMR (D6-DMSO) 13.35 (br s, 1H), 7.95 (d, 1H), 7.60 (s, 1H), 7.50 (br t, 1H), 7.10 (d, 1H), 4.10 (d, 2H), 1.40 (s, 9H).

Other examples of ring-substituted $R^{31}$ cyclizing moieties prepared using the general procedure described above for t-butyloxycarbonyl-3-aminomethyl-6-iodobenzoic acid are tabulated below.

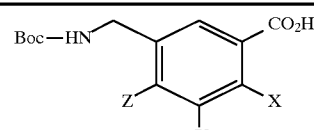

| X | Y | Z | mp. °C. |
|---|---|---|---|
| H | H | Cl | 159 |
| H | H | I | 168 |
| H | H | Me | 155 |
| H | H | MeO | 171 |
| Cl | H | H | 150 |
| I | H | H | 182 |
| Me | H | H | 166 |
| MeO | H | H | 79 |

4-Bromo and 6-Bromo derivatives useful as intermediates in the synthesis of the compounds of the invention may be prepared as described above for t-butyloxycarbonyl-3-aminomethyl-6-iodobenzoic acid. 4-Hydroxy and 6-Hydroxy derivatives useful as intermediates in the synthesis of the compounds of the invention may be prepared as described in Sekiya et al Chem. Pharm. Bull., 11: 551 (1963). 5-Nitro and 5-Amino derivatives useful as intermediates in the synthesis of the compounds of the invention may be prepared as described in Felder et al Helv. Chim. Acta, 48: 259 (1965). The 5-amino derivative may be converted to the 5-iodo, 5-bromo, 5-chloro, or 5-fluoro derivatives via the diazonium salt as described in Org. Syn. Coll. Vol., 2: 130 (1943); 2: 299 (1943); 2: 351 (1943); and 3: 185 (1955).

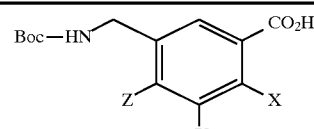

| X | Y | Z |
|---|---|---|
| H | H | Br |
| Br | H | H |
| H | H | HO |
| HO | H | H |
| H | $NO_2$ | H |
| H | $NH_2$ | H |
| H | I | H |

115

-continued

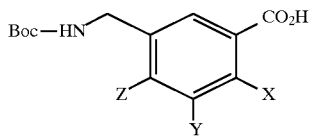

| X | Y | Z |
|---|---|---|
| H | Br | H |
| H | Cl | H |
| H | F | H |

Synthesis of Cyclic Compound Intermediates Using Ring Substituted $R^{31}$ Cyclizing Moieties Cyclic compound intermediates in which the cyclizing moiety contains an aromatic ring bearing a substituent group may be prepared as taught in the following examples.

Cyclic Compound Intermediate 93 cyclo-(D-Val-NMeArg-Gly-Asp-3-aminomethyl-4-chlorobenzoic acid)

The title compound was prepared by the general solution-phase procedure described above for cyclo-(D-Val-NMeArg-Gly-Asp-Mamb). The cyclic peptide (240 mg, 0.28 mmol) was deprotected with excess HF in the presence of anisole as scavenger. Purification was accomplished by reversed-phase HPLC on a preparative LiChrospher RP-18 column (5 cm) using a 1.4%/minute gradient of 22 to 90% acetonitrile containing 0.1% trifluoroacetic acid to give the TFA salt of the title compound (80 mg, 39%) as a fluffy white solid; $^1$H NMR ($D_6$-DMSO) 9.00 (d, 1H), 8.50 (d, 1H), 8.45 (t, 1H), 7.60 (d, 2H), 7.45 (s, 1H), 7.45 (d, 2H), 7.00 (br s, 4H), 5.15 (dd, 1H), 4.45 (m, 2H), 4.20 (m, 2H), 4.10 (d, 1H), 3.55 (d, 1H), 3.10 (m, 2H), 2.90 (s, 3H), 2.65 (dd, 1H), 2.50 (m, 1H), 2.05 (m, 2H), 1.50 (m, 1H), 1.30 (m, 2H), 1.05 (d, 3H), 0.85 (d, 3H); FAB-MS: [M+H]=609.

Cyclic Compound Intermediate 94 cyclo-(D-Val-NMeArg-Gly-Asp-iodo-Mamb); the compound of formula (VII) wherein J=D-Val, K=NMeArg, L=Gly, M=Asp, $R^1=R^2=H$, $R^{10}=H$, $R^{10a}=I$ The title compound was prepared using the general procedure described for cyclo-(D-Val-NMeArg-Gly-Asp-Mamb) (Cyclic Compound Intermediate 4). The DCC/DMAP method was used for attachment of Boc-iodo-Mamb to the oxime resin. The peptide was prepared on a 1.05 mmol scale to give the protected cyclic peptide (460 mg, 46.8%). The peptide (438 mg) and 0.5 mL of anisole were treated with anhydrous hydrogen fluoride at 0° C. for 30 minutes. The crude material was precipitated with ether, redissolved in aqueous acetic acid, and lyophilized to generate the title compound (340 mg, 95.6%; calculated as the acetate salt). Purification was accomplished by reversed-phase HPLC on a preparative Vydac C18 column (2.5 cm) using a 0.23%/min. gradient of 12.6 to 22.5% acetonitrile containing 0.1% TFA and then lyophilized to give the TFA salt of the title compound as a fluffy white solid (39.7% recovery, overall yield 16.6%); 1H NMR (D6-DMSO) ∂9.05 (d, 1H), 8.55 (d, 1H), 8.55 (t, 1H), 7.90 (d, 1H), 7.65 (d, 1H), 7.55 (t, 1H), 7.20 (d, 1H), 7.15 (s, 1H), 7.00 (br s, 4H), 5.15 (dd, 1H), 4.50 (g, 1H), 4.30 (m, 3H), 3.95 (dd, 1H), 3.60 (d, 1H), 3.10 (m, 2H), 3.00 (s, 3H), 2.75 (dd, 1H), 2.55 (dd, 1H), 2.10 (m, 2H), 1.60 (m, 1H), 1.35 (m, 2H), 1.10 (d, 3H), 0.90 (d, 3H); FAB-MS: [M+H]=701.37.

116

Cyclic Compound Intermediate 95 cyclo-(D-Val-NMeArg-Gly-Asp-3-aminomethyl-4-methoxybenzoic acid)

The title compound was prepared by the general solution-phase procedure described above for cyclo-(D-Val-NMeArg-Gly-Asp-Mamb). The cyclic peptide (600 mg, 0.71 mmol) was deprotected with excess HF in the presence of anisole as scavenger. Purification was accomplished by reversed-phase HPLC on a preparative Vydac C18 column (2.5 cm) using a 0.33%/minute gradient of 7 to 18% acetonitrile containing 0.1% trifluoroacetic acid to give the TFA salt of the title compound (104 mg, 32%) as a fluffy white solid; $^1$H NMR ($D_6$-DMSO) 12.40 (br s, 1H), 8.25 (d, 1H), 8.20 (br s, 1H), 8.00 (br s, 2H), 7.85 (d, 1H), 7.75 (s, 1H), 7.65 (br s, 1H), 7.05 (d, 1H), 7.05 (br s, 4H), 5.00 (dd, 1H), 4.60 (q, 1H), 4.30 (d, 1H), 4.25 (d, 2H), 3.85 (s, 3H), 3.85 (dd, 1H), 3.70 (dd, 1H), 3.10 (q, 2H), 3.00 (s, 3H), 2.70 (m, 1H), 2.50 (m, 1H), 2.10 (m, 1H), 1.90 (m, 1H), 1.65 (m, 1H), 1.35 (m, 2H), 1.00 (d, 3H), 0.90 (d, 3H); FAB-MS: $[M+H_2O+H]=623$.

Cyclic Compound Intermediate 96 cyclo-(D-Val-NMeArg-Gly-Asp-3-aminomethyl-4-methylbenzoic acid)

The title compound was prepared by the general solution-phase procedure described above for cyclo-(D-Val-NMeArg-Gly-Asp-Mamb). The cyclic peptide (210 mg, 0.25 mmol) was deprotected with excess HF in the presence of anisole as scavenger. Purification was accomplished by reversed-phase HPLC on a preparative LiChrospher RP-18 column (5 cm) using a 2.3%/minute gradient of 22 to 90% acetonitrile containing 0.1% trifluoroacetic acid to give the TFA salt of the title compound (75 mg, 42%) as a fluffy white solid; $^1$H NMR ($D_6$-DMSO) 12.30 (br s, 1H), 8.85 (d, 1H), 8.55 (d, 1H), 8.30 (t, 1H), 7.75 (d, 1H), 7.55 (m, 2H), 7.40 (s, 1H), 7.20 (s, 1H), 7.00 (br s, 4H), 5.20 (dd, 1H), 4.55 (q, 1H), 4.45 (dd, 1H), 4.30 (m, 2H), 4.05 (dd, 1H), 3.60 (d, 1H), 3.10 (q, 2H), 3.00 (s, 3H), 2.70 (dd, 1H), 2.50 (m, 1H), 2.25 (s, 3H), 2.10 (m, 2H), 1.60 (m, 1H), 1.35 (m, 2H), 1.10 (d, 3H), 0.90 (d, 3H); FAB-MS: [M+H]=589.

Cyclic Compound Intermediate 97 cyclo-(D-Val-NMeArg-Gly-Asp-3-aminomethyl-6-chlorobenzoic acid)

The title compound was prepared by the general solution-phase procedure described above for cyclo-(D-Val-NMeArg-Gly-Asp-Mamb), except that 4,4'-dinitrobenzophenone oxime was employed. The cyclic peptide (550 mg, 0.65 mmol) was deprotected with excess HF in the presence of anisole as scavenger. Purification was accomplished by reversed-phase HPLC on a preparative Vydac C18 column (2.5 cm) using a 0.8%/minute gradient of 10 to 38% acetonitrile containing 0.1% trifluoroacetic acid to give the TFA salt of the title compound (254 mg, 54%) as a fluffy white solid; $^1$H NMR ($D_6$-DMSO) 12.30 (br s, 1H), 9.05 (d, 1H), 8.45 (m, 2H), 7.50 (t, 1H), 7.35 (d, 1H), 7.30 (m, 2H), 7.10 (s, 1H), 7.05 (br s, 4H), 5.15 (dd, 1H), 4.45 (dd, 1H), 4.40 (q, 2H), 4.05 (dt, 2H), 3.55 (dd, 1H), 3.15 (q, 2H), 3.10 (s, 3H), 2.70 (dd, 1H), 2.50 (m, 1H), 2.05 (m, 2H), 1.65 (m, 1H), 1.35 (m, 2H), 1.10 (d, 3H), 0.90 (d, 3H); FAB-MS: [M+H]=609.

Cyclic Compound Intermediate 99 cyclo-(D-Val-NMeArg-Gly-Asp-3-aminomethyl-6-methoxybenzoic acid)

The title compound was prepared by the general solution-phase procedure described above for cyclo-(D-Val- NMeArg-Gly-Asp-Mamb), except that 4,4'-dinitrobenzophenone oxime was employed. The cyclic peptide (256 mg, 0.30 mmol) was deprotected with excess HF in the presence of anisole as scavenger. Purification was accomplished by reversed-phase HPLC on a preparative Vydac C18 column (2.5 cm) using a 0.8%/minute gradient of 10 to 38% acetonitrile containing 0.1% trifluoroacetic acid to give the TFA salt of the title compound (137 mg, 63%) as a fluffy white solid; $^1$H NMR (D$_6$-DMSO) 8.45 (d, 1H), 8.40 (d, 1H), 8.30 (t, 1H), 7.65 (d, 1H), 7.50 (t, 1H), 7.40 (s, 1H), 7.35 (d, 1H), 7.05 (d, 1H), 7.00 (br s, 4H), 5.20 (dd, 1H), 4.55 (dd, 1H), 4.50 (q, 1H), 4.35 (dd, 1H), 4.25 (dd, 1H), 3.95 (dd, 1H), 3.90 (s, 3H), 3.55 (d, 1H), 3.10 (q, 2H), 3.00 (s, 3H), 2.70 (dd, 1H), 2.50 (m, 1H), 2.05 (m, 2H), 1.60 (m, 1H), 1.35 (m, 2H), 1.10 (d, 3H), 0.95 (d, 3H); FAB-MS: [M+H]=605.

Cyclic Compound Intermediate 100 cyclo-(D-Val-NMeArg-Gly-Asp-3-aminomethyl-6-methylbenzoic acid)

The title compound was prepared by the general solution-phase procedure described above for cyclo-(D-Val-NMeArg-Gly-Asp-Mamb), except that 4,4'-dinitrobenzophenone oxime was employed. The cyclic peptide (230 mg, 0.28 mmol) was deprotected with excess HF in the presence of anisole as scavenger. Purification was accomplished by reversed-phase HPLC on a preparative Vydac C18 column (2.5 cm) using a 0.8%/minute gradient of 10 to 38% acetonitrile containing 0.1% trifluoroacetic acid to give the TFA salt of the title compound (54 mg, 27%) as a fluffy white solid; $^1$H NMR (D$_6$-DMSO) 12.30 (br s, 1H), 8.80 (d, 1H), 8.40 (d, 1H), 8.30 (t, 1H), 7.45 (m, 2H), 7.15 (q, 2H), 7.00 (s, 1H), 7.00 (br s, 4H), 5.15 (dd, 1H), 4.45 (m, 3H), 4.05 (m, 2H), 3.55 (dd, 1H), 3.10 (q, 2H), 3.05 (s, 3H), 2.70 (dd, 1H), 2.50 (m, 1H), 2.30 (s, 3H), 2.05 (m, 2H), 1.60 (m, 1H), 1.35 (m, 2H), 1.05 (d, 3H), 0.90 (d, 3H); FAB-MS: [M+H]=589.

Cyclic Compound Intermediate 100a cyclo-(D-Abu-NMeArg-Gly-Asp-3-aminomethyl-6-chlorobenzoic acid)

The title compound was prepared by the general solution-phase procedure described above for cyclo-(D-Val-NMeArg-Gly-Asp-Mamb), except that 4,4'-dinitrobenzophenone oxime was employed. The cyclic peptide (330 mg, 0.40 mmol) was deprotected with excess HF in the presence of anisole as scavenger. Purification was accomplished by reversed-phase HPLC on a preparative Vydac C18 column (2.5 cm) using a 1.0%/minute gradient of 10 to 38% acetonitrile containing 0.1% trifluoroacetic acid to give the TFA salt of the title compound (114 mg, 41%) as a fluffy white solid; $^1$H NMR (D$_6$-DMSO) 9.00 (d, 1H), 8.40 (m, 2H), 7.50 (m, 1H), 7.40 (d, 1H), 7.30 (m, 2H), 7.15 (s, 1H), 7.00 (br s, 4H), 5.15 (dd, 1H), 4.65 (q, 1H), 4.50 (dd, 1H), 4.40 (q, 1H), 4.05 (dd, 1H), 3.95 (dd, 1H), 3.65 (dd, 1H), 3.10 (q, 2H), 3.05 (s, 3H), 2.75 (dd, 1H), 2.50 (m, 1H), 1.95 (m, 1H), 1.75 (m, 2H), 1.60 (m, 1H), 1.35 (m, 2H), 0.95 (t, 3H); FAB-MS: [M+H]=595.4.

Cyclic Compound Intermediate 89d cyclo-(D-Abu-NMeArg-Gly-Asp-iodo-Mamb); the compound of formula (VII) wherein J=D-Abu, K=NMeArg, L=Gly, M=Asp, $R^1$=$R^2$=H, $R^{10}$=H, $R^{10a}$=I The title compound was prepared using the general procedure described above for cyclo-(D-Val-NMeArg-Gly-Asp-Mamb) (Cyclic Compound Intermediate 4). The DCC/DMAP method was used for attachment of Boc-iodo-Mamb to the oxime resin. The peptide was prepared on a 3.53 mmol scale to give the protected cyclic peptide (4.07 g, greater than quantitative yield). The peptide (4.07 g) and 4.0 mL of anisole were treated with anhydrous hydrogen fluoride at 0° C. for 30 minutes. The crude material was precipitated with ether, redissolved in aqueous acetic acid, and lyophilized to generate the title compound (2.97 g, greater than quantitative yield; calculated as the acetate salt). Purification was accomplished by reversed-phase HPLC on a preparative Vydac C18 column (2.5 cm) using a 0.16%/min. gradient of 16.2 to 22.5% acetonitrile containing 0.1% TFA and then lyophilized to give the TFA salt of the title compound as a fluffy white solid (28.7% recovery, overall yield 30.2%); FAB-MS: [M+H]=687.33.

Cyclic Compound Intermediate 100b cyclo-(D-Abu-NMeArg-Gly-Asp-3-aminomethyl-6-iodobenzoic acid)

The title compound was prepared by the general solution-phase procedure described above for cyclo-(D-Val-NMeArg-Gly-Asp-Mamb), except that 4,4'-dinitrobenzophenone oxime was employed. The cyclic peptide (350 mg, 0.38 mmol) was deprotected with excess HF in the presence of anisole as scavenger. Purification was accomplished by reversed-phase HPLC on a preparative Vydac C18 column (2.5 cm) using a 1.0%/minute gradient of 10 to 38% acetonitrile containing 0.1% trifluoroacetic acid to give the TFA salt of the title compound (150 mg, 49%) as a fluffy white solid; $^1$H NMR (D$_6$-DMSO) 8.90 (d, 1H), 8.40 (m, 2H), 7.70 (d, 1H), 7.50 (m, 1H), 7.30 (m, 1H), 7.05 (s, 1H), 7.00 (d, 1H), 7.00 (br s, 4H), 5.15 (dd, 1H), 4.65 (q, 1H), 4.45 (dd, 1H), 4.40 (q, 1H), 4.00 (q, 1H), 3.90 (q, 1H), 3.65 (dd, 1H), 3.10 (q, 2H), 3.05 (s, 3H), 2.70 (dd, 1H), 2.50 (m, 1H), 1.95 (m, 1H), 1.75 (m, 2H), 1.60 (m, 1H), 1.40 (m, 2H), 0.95 (t, 3H); FAB-MS: [M+H]=687.3.

Cyclic Compound Intermediate 100c cyclo-(D-Abu-NMeArg-Gly-Asp-3-aminomethyl-6-methylbenzoic acid)

(the compound of formula (VII) wherein J=D-Abu, K=NMeArg, L=Gly, M=Asp, $R^{10}$=Me)

The title compound was prepared by the general solution-phase procedure described above for cyclo-(D-Val-NMeArg-Gly-Asp-Mamb), except that 4,4'-dinitrobenzophenone oxime was employed. The cyclic peptide (130 mg, 0.16 mmol) was deprotected with excess HF in the presence of anisole as scavenger. Purification was accomplished by reversed-phase HPLC on a preparative Vydac C18 column (2.5 cm) using a 1.0%/minute gradient of 10 to 38% acetonitrile containing 0.1% trifluoroacetic acid to give the TFA salt of the title compound (31 mg, 28%) as a fluffy white solid; $^1$H NMR (D$_6$-DMSO) 8.70 (d, 1H), 8.40 (d, 1H), 8.30 (t, 1H), 7.50 (m, 1H), 7.45 (m, 1H), 7.15 (q, 2H), 7.05 (s, 1H), 7.00 (br s, 4H), 5.15 (dd, 1H), 4.65 (q, 1H), 4.45 (m, 2H), 4.00 (m, 2H), 3.65 (dd, 1H), 3.10 (q, 2H), 3.05 (s, 3H), 2.75 (dd, 1H), 2.50 (m, 1H), 2.30 (s, 3H), 2.00 (m, 1H), 1.75 (m, 2H), 1.60 (m, 1H), 1.35 (m, 2H), 0.95 (t, 3H); FAB-MS: [M+H]=575.4.

Scheme 5: procedure for synthesis of cyclic compound intermediate.

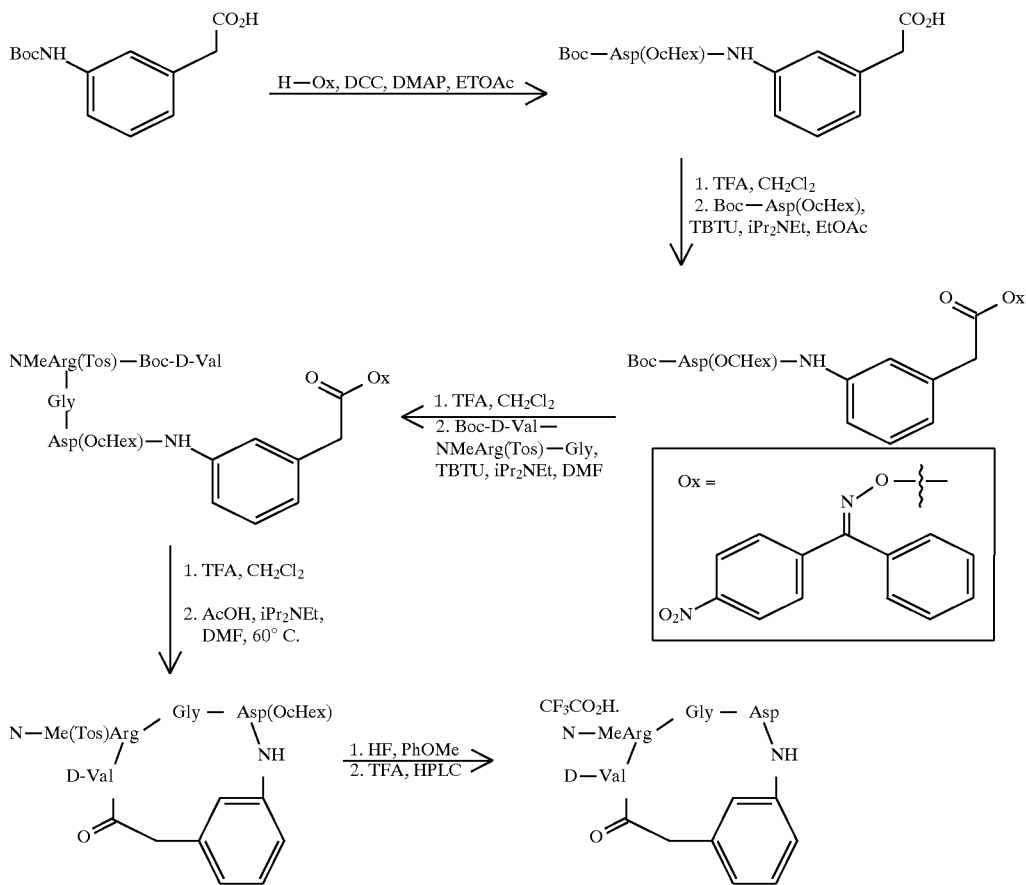

Solid-Phase Synthesis of Cyclic Compound Intermediate 101 cyclo-(D-Val-NMeArg-Gly-Asp-3-aminomethyl-4-iodobenzoic Acid)

The title compound was prepared using the general procedure previously described for cyclo-(D-Val-NMeArg-Gly-Asp-Mamb). The DCC/DMAP method was used for attachment of Boc-iodo-Mamb to the oxime resin. The peptide was prepared on a 1.05 mmol scale to give the protected cyclic peptide (460 mg, 46.8%). The peptide (438 mg) and 0.5 mL of anisole were treated with anhydrous hydrogen fluoride at 0° C. for 30 minutes. The crude material was precipitated with ether, redissolved in aqueous acetic acid, and lyophilized to generate the title compound (340 mg, 95.6%; calculated as the acetate salt). Purification was accomplished by reversed-phase HPLC on a preparative Vydac C18 column (2.5 cm) using a 0.23%/minute gradient of 12.6 to 22.5% acetonitrile containing 0.1% trifluoroacetic acid and then lyophilized to give the TFA salt of the title compound as a fluffy white solid (39.7% recovery, overall yield 16.6%; $^1$H NMR ($D_6$-DMSO) d 9.05 (d, 1H), 8.55 (d, 1H), 8.55 (t, 1H), 7.90 (d, 1H), 7.65 (d, 1H), 7.55 (t, 1H), 7.20 (d, 1H), 7.15 (s, 1H), 7.00 (br s, 4H), 5.15 (dd, 1H), 4.50 (q, 1H), 4.30 (m, 3H), 3.95 (dd, 1H), 3.60 (d, 1H), 3.10 (m, 2H), 3.00 (s, 3H), 2.75 (dd, 1H), 2.55 (dd, 1H), 2.10 (m, 2H), 1.60 (m, 1H), 1.35 (m, 2H), 1.10 (d, 3H), 0.90 (d, 3H); FAB-MS: [M+H]=701.37.

Solution-Phase Synthesis of Cyclic Compound Intermediate 102 cyclo-(D-Val-NMeArg-Gly-Asp-3-aminomethyl-6-iodobenzoic Acid)

The title compound was prepared according to the method of Scheme 6, shown below.

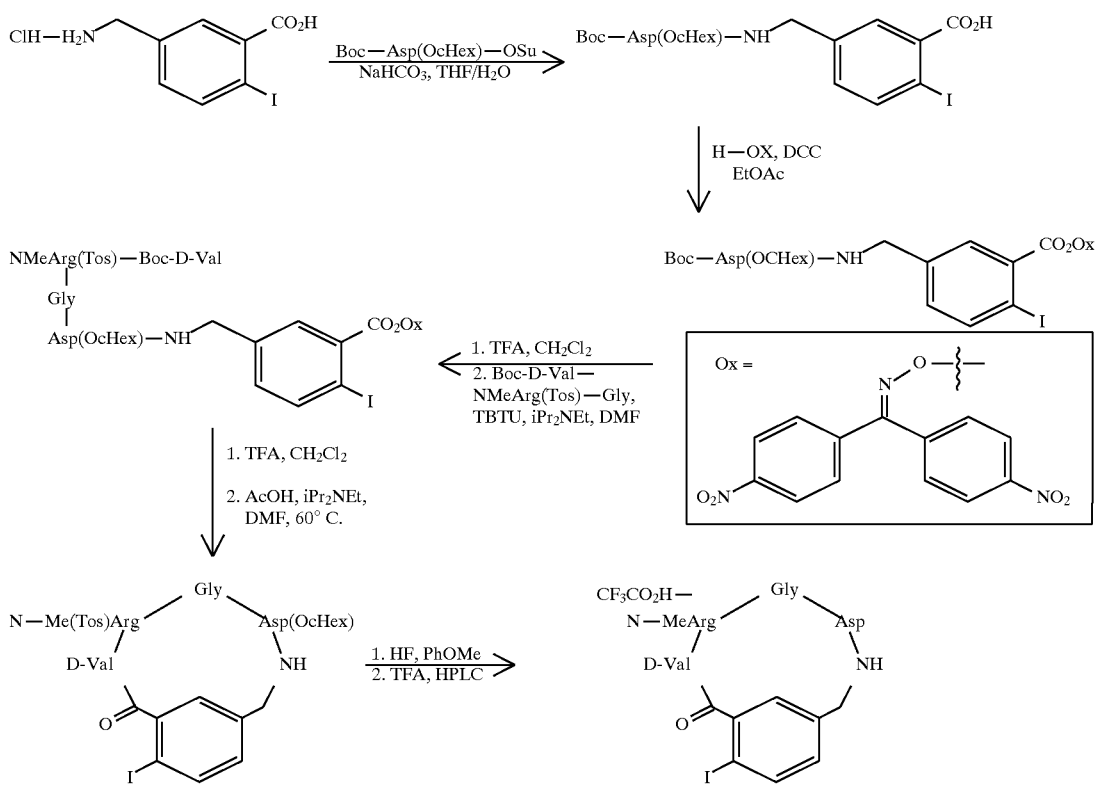

Scheme 6

1. Boc-Asp(OcHex)-3-aminomethyl-6-iodobenzoic Acid

To a suspension of 3-aminomethyl-6-iodobenzoic acid.HCl (4.9 g, 16 mmol) in $H_2O$ (16 ml) was added $NaHCO_3$ (3.9 g, 47 mmol), followed by a solution of Boc-Asp(OcHex)-OSu (5.9 g, 14 mmol) in THF (16 ml). The reaction mixture was stirred at room temperature overnight, filtered, diluted with $H_2O$, acidified with 1N HCl, and extracted with ethyl acetate. The extracts were washed with $H_2O$, brine, dried over anhydrous magnesium sulfate, and evaporated to dryness under reduced pressure. This material was triturated with ether to provide the title compound (6.7 g, 82%) as a white powder. $^1$H NMR d ($D_6$-DMSO) 8.45 (br t, 1H), 7.90 (d, 1H), 7.60 (s, 1H), 7.15 (m, 2H), 4.65 (m, 1H), 4.35 (m, 1H), 4.25 (d, 2H), 2.70 (m, 1H), 2.55 (m, 1H), 1.70 (m, 4H), 1.40 (s, 9H), 1.35 (m, 6H).

2. 4,4'-Dinitrobenzophenone Oxime

The title compound was prepared by modification of procedures previously reported in the literature (Chapman and Fidler (1936) *J. Chem. Soc,* 448; Kulin and Leffek (1973) *Can. J. Chem.,* 51: 687). A solution of chromic anhydride (20 g, 200 mmol) in 125 ml of $H_2O$ was added dropwise over 4 hours, to a suspension of bis(4-nitrophenyl) methane (25 g, 97 mmol) in 300 ml of acetic acid heated to reflux. The reaction mixture was heated at reflux for 1 hour, cooled to room temperature, and poured into water. The solid was collected by filtration, washed with $H_2O$, 5% sodium bicarbonate, $H_2O$, and air-dryed to provide a 1:1 mixture of bis(4-nitrophenyl)methane/4,4'-dinitrobenzophenone via $^1$H NMR. This material was oxidized with a second portion of chromic anhydride (20 g, 200 mmol), followed by an identical work-up procedure to provide the crude product. Trituration with 200 ml of benzene heated to reflux for 16 hours provided 4,4'-dinitrobenzophenone (20.8 g, 79%) as a yellow powder.

A solution of hydroxylamine hydrochloride (10.2 g, 147 mmol) was added to a suspension of 4,4'-dinitrobenzophenone (19 g, 70 mmol) in 100 ml of ethanol. The reaction mixture was heated to reflux for 2 hours, cooled to room temperature, and the solid collected by filtration. Recrystallization from ethanol provided the title compound (14.0 g, 70%) as pale yellow crystals. mp 194° C.; $^1$H NMR ($D_6$-DMSO) d 12.25 (s, 1H), 8.35 (d, 2H), 8.20 (d, 2H), 7.60 (d, 4H).

3. 4,4'-Dinitrobenzophenone Oxime Boc-Asp(OcHex)-3-aminomethyl-6-iodobenzoate To an ice-cooled solution of Boc-Asp(OcHex)-3-aminomethyl-6-iodobenzoic acid (3.3 g, 5.7 mmol) and 4,4'-dinitrobenzophenone oxime (1.7 g, 5.9 mmol) in 32 ml of ethyl acetate was added DCC (1.2 g, 5.8 mmol). The reaction mixture was stirred at room temperature for 3 hours, filtered, diluted with ethyl acetate, washed with saturated sodium bicarbonate solution, $H_2O$, brine, dried over anhydrous magnesium sulfate, and evaporated to dryness under reduced pressure. This material was purified by column chromatography on silica gel (EM Science, 230–400 mesh) using 10:1 dichloromethane/ethyl acetate to give the title compound (1.8 g, 36%) as pale yellow crystals. $^1$H NMR ($D_6$-DMSO) d 8.40 (dd, 5H), 7.90 (m, 5H), 7.45 (s, 1H), 7.20 (m, 2H), 4.65 (m, 1H), 4.35 (m, 1H), 4.20 (m, 2H), 2.75 (dd, 1H), 2.50 (dd, 1H), 1.70 (m, 4H), 1.40 (s, 9H), 1.35 (m, 6H).

4. Boc-D-Val-NMeArg(Tos)-Gly

To a mixture of Boc-NMeArg(Tos) (11.07 g 25 mmol), and Gly-OBzl tosylate (10.10 g, 30 mmol) in 25 ml of dichloromethane was added HBTU (9.48 g, 25 mmol) and DIEA (9.69 g, 75 mmol). The reaction mixture was stirred at room temperature for 1 hour, concentrated under high vacuum, diluted with ethyl acetate, washed with 5% citric acid, H₂O, saturated sodium bicarbonate solution, brine, dried over anhydrous magnesium sulfate, and evaporated to dryness under reduced pressure. The resulting oil was triturated with petroleum ether to provide Boc-NMeArg(Tos)-Gly-OBzl (14.7 g, 100%); FAB-MS: [M+H]=590.43. This material was used without further purification.

A solution of Boc-NMeArg(Tos)-Gly-OBzl (14.5 g, 24.6 mmol) in 30 ml of trifluoroacetic acid was stirred at room temperature for 5 minutes, and evaporated to dryness under reduced pressure. The oily residue was diluted with cold ethyl acetate, washed with cold saturated sodium bicarbonate solution, the aqueous phase was extracted with ethyl acetate. The combined organics were washed with brine, evaporated to dryness under reduced pressure, and the resulting oil triturated with ether. The resulting solid was filtered, washed with ether, and dried in a vacuum desiccator to provide NMeArg(Tos)-Gly-OBzl (10.3 g, 86%); FAB-MS: [M+H]=490.21. This material was used without further purification.

To a solution of NMeArg(Tos)-Gly-OBzl (4.80 g, 9.8 mmol), and Boc-D-Val (2.13 g, 9.8 mmol) in 10 ml of dichloromethane, cooled in an ice-bath, was added HBTU (3.79 g, 10.0 mmol) and DIEA (2.58 g, 20.0 mmol). The reaction mixture was stirred at room temperature for 48 hours, diluted with ethyl acetate, washed with 5% citric acid, brine, dried over anhydrous magnesium sulfate, and evaporated to dryness under reduced pressure. The resulting oil was triturated with ether to provide Boc-D-Val-NMeArg (Tos)-Gly-OBzl (4.58 g, 68%); FAB-MS: [M+H]=689.59. This material was used without further purification.

A solution of Boc-D-Val-NMeArg(Tos)-Gly-OBzl (4.50 g, 6.53 mmol) in 80 ml of methanol was purged with nitrogen gas, 1.30 g of 10% Pd/C was added, and hydrogen gas was passed over the reaction. After 1 hour the catalyst was removed by filtration through a bed of celite, and the solvent removed under reduced pressure. The resulting solid was triturated with ether, filtered, and washed with petroleum ether to provide Boc-D-Val-NMeArg(Tos)-Gly (3.05 g, 78%); ¹H NMR (D₆-DMSO) d 7.90 (br t, 1H), 7.65 (d, 2H), 7.30 (d, 2H), 7.00 (d, 1H), 6.85 (br d, 1H), 6.60 (br s, 1H), 5.00 (dd, 1H), 4.15 (t, 1H), 3.70 (m, 2H), 3.05 (m, 2H), 2.90 (s, 3H), 2.35 (s, 3H), 1.90 (m, 2H), 1.55 (m, 1H), 1.35 (s, 9H), 1.25 (m, 2H), 0.80 (br t, 6H); FAB-MS: [M+H]=599.45.

5. 4,41-Dinitrobenzophenone Oxime Boc-D-Val-NMeArg(Tos)-Gly-Asp(OcHex)-3-aminomethyl-6-iodobenzoate To a solution of 4,4'-dinitrobenzophenone oxime Boc-Asp(OcHex)-3-aminomethyl-6-iodobenzoate (0.5 g, 0.59 mmol) in 1 ml of dichloromethane was added 0.5 ml of trifluoroacetic acid. The reaction mixture was stirred at room temperature for 90 minutes, diluted with dichloromethane, and evaporated to dryness under reduced pressure. The oily residue was concentrated under high vacuum to remove traces of excess trifluoroacetic acid.

To a solution of the crude TFA salt and Boc-D-Val-NMeArg(Tos)-Gly (0.52 g, 0.87 mmol) in 3.8 ml of DMF was added TBTU (0.28 g, 0.87 mmol) and DIEA (0.33 g, 2.58 mmol). The reaction mixture was stirred at room temperature overnight, concentrated under high vacuum, diluted with ethyl acetate, washed with 5% citric acid, H₂O, brine, dried over anhydrous magnesium sulfate, and evaporated to dryness under reduced pressure. This material was triturated with ether to provide the title compound (0.48 g, 61%) as a powder. This material was used without further purification.

6. cyclo-(D-Val-NMeArg(Tos)-Gly-Asp(OcHex)-3-aminomethyl-6-iodobenzoic Acid)

To a solution of 4,4'-dinitrobenzophenone oxime Boc-D-Val-NMeArg(Tos)-Gly-Asp(OcHex)-3-aminomethyl-6-iodobenzoate (0.48 g, 0.36 mmol) in 1 ml of dichloromethane was added 0.5 ml of trifluoroacetic acid. The reaction mixture was stirred at room temperature for 45 minutes, diluted with dichloromethane, and evaporated to dryness under reduced pressure. The oily residue was concentrated under high vacuum to remove traces of excess trifluoroacetic acid.

To a solution of the crude TFA salt in 38 ml of DMF was added acetic acid (0.09 ml, 1.57 mmol) and DIEA (0.26 ml, 1.49 mmol). The reaction mixture was stirred at 60° C. for 3 days, concentrated under high vacuum, diluted with ethyl acetate, washed with 5% citric acid, brine, dried over anhydrous magnesium sulfate, and evaporated to dryness under reduced pressure. This material was purified by column chromatography on silica gel (EM Science, 230–400 mesh) using 10:1 chloroform/isopropanol to give the title compound (0.13 g, 38%) as a powder; ¹H NMR (D₆-DMSO) d 8.95 (d, 1H), 8.50 (t, 1H), 8.45 (d, 1H), 7.70 (d, 1H), 7.60 (d, 2H), 7.30 (d, 3H), 7.05 (d, 1H), 7.00 (s, 1H), 6.80 (br s, 1H), 6.60 (br s, 1H), 5.10 (dd, 1H), 4.65 (m, 1H), 4.45 (m, 1H), 4.35 (m, 1H), 4.00 (m, 1H), 3.55 (dd, 1H), 3.05 (m, 2H), 3.00 (s, 3H), 2.70 (dd, 1H), 2.55 (dd, 1H), 2.35 (s, 3H), 2.05 (m, 1H), 1.90 (m, 1H), 1.75 (m, 1H), 1.65 (m, 1H), 1.35 (m, 13H), 1.15 (d, 3H), 0.85 (d, 3H); FAB(GLYC)-MS: [M+H]=937.

7. cyclo-(D-Val-NMeArg-Gly-Asp-3-aminomethyl-6-iodobenzoic Acid)

The cyclic peptide (490 mg, 0.52 mmol) was deprotected with excess HF in the presence of anisole as scavenger. Purification was accomplished by reversed-phase HPLC on a preparative Vydac C18 column (2.5 cm) using a 0.8%/minute gradient of 10 to 38% acetonitrile containing 0.1% trifluoroacetic acid to give the TFA salt of the title compound (194 mg, 46%) as a fluffy white solid; ¹H NMR (D₆-DMSO) d 12.30 (br s, 1H), 9.00 (d, 1H), 8.40 (m, 2H), 7.70 (d, 1H), 7.50 (m, 1H), 7.30 (m, 1H), 7.05 (d, 1H), 7.00 (s, 1H), 7.00 (br s, 4H), 5.15 (dd, 1H), 4.40 (d, 1H), 4.40 (q, 2H), 4.0 (m, 2H), 3.55 (dd, 1H), 3.15 (q, 2H), 3.10 (s, 3H), 2.70 (dd, 1H), 2.50 (m, 1H), 2.05 (m, 2H), 1.65 (m, 1H), 1.35 (m, 2H), 1.15 (d, 3H), 0.90 (d, 3H); FAB-MS: [M+H]=701.

Table A shows the FAB-MS obtained for certain cyclic compound intermediates.

TABLE A

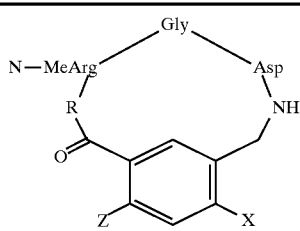

| Cyclic Compound Intermediate Number | R | X | Z | FAB-MS (M+H) |
|---|---|---|---|---|
| 101 | D-Val | I | H | 701.37 |
| 98, 102 | D-Val | H | I | 701 |
| 103 | D-Abu | I | H | 687.33 |
| 104 | D-Abu | H | I | 687.3 |
| 105 | D-Val | Cl | H | 609 |

TABLE A-continued

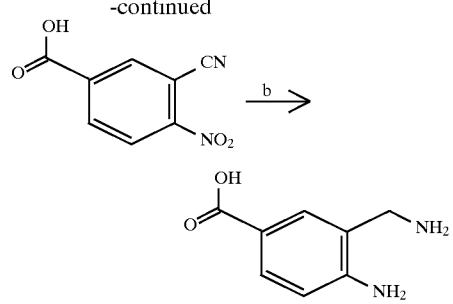

| Cyclic Compound Intermediate Number | R | X | Z | FAB-MS (M+H) |
|---|---|---|---|---|
| 106 | D-Val | H | Cl | 609 |
| 107 | D-Abu | H | Cl | 595.4 |
| 108 | D-Val | Me | H | 589 |
| 109 | D-Val | H | Me | 589 |
| 110 | D-Abu | H | Me | 575.4 |
| 111 | D-Val | MeO | H | 623 (+H$_2$O) |
| 112 | D-Val | H | MeO | 605 |

Other ring substituted cyclizing moieties can be synthesized as taught in the following schemes and discussion. The moiety of the formula above where Z=NH$_2$ can be synthesized by at least two different routes. For example, starting with 4-acetamidobenzoic acid (Aldrich Chemical Co.), a Friedel-Crafts alkylation with N-hydroxymethyldichloroacetamide would give the dichloroacetyl derivative of 3-aminomethyl-4-acetamidobenzoic acid (Felder, Pitre, and Fumagalli (1964), *Helv. Chim. Acta*, 48, 259–274). Hydrolysis of the two amides would give 3-aminomethyl-4-aminobenzoic acid.

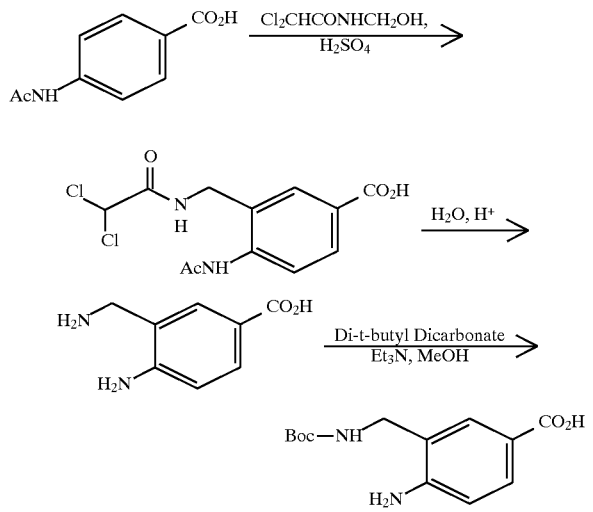

Alternatively, starting with 3-cyano-4-nitrotoluene, oxidation with chromium trioxide followed by reduction will give 3-aminomethyl-4-aminobenzoic acid.

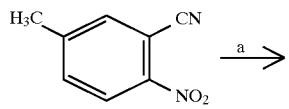

a] CrO$_3$  b] H$_2$-catalyst

The moiety of the formula above where Y=CH$_2$NH$_2$ can be synthesized from 3,5-dicyanotoluene by oxidation of the methyl group with chromium trioxide followed by reduction.

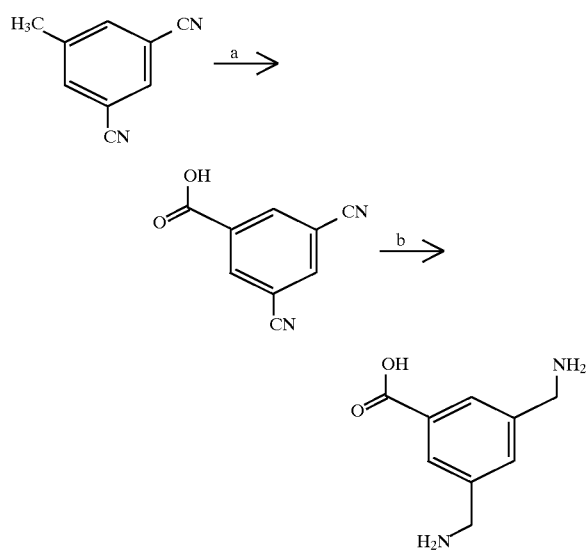

a] CrO$_3$  b] H$_2$-catalyst

The moiety of the formula above where Z=CH$_2$NH$_2$ can be synthesized from 3-cyano-4-methylbenzoic acid (K & K Rare and Fine Chemicals). Bromination using N-bromosuccinimide would give 4-bromomethyl-3-cyanobenzoic acid. A nucleophilic substitution reaction at the bromomethyl position using an amide anion would produce the protected amine. Amide anions which could be used in this reaction include potassium phthalimide (Gabriel synthesis), and the anion of trifluoroacetamide (Usui (1991), *Nippon Kagaku Kaishi*, 206–212) used in this example. Reduction of the nitrile would produce the second aminomethyl group, which would be protected by reaction with di-t-butyl dicarbonate. Removal of the trifluoroacetamide protecting group using aqueous piperidine would give the moiety.

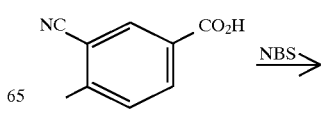

127

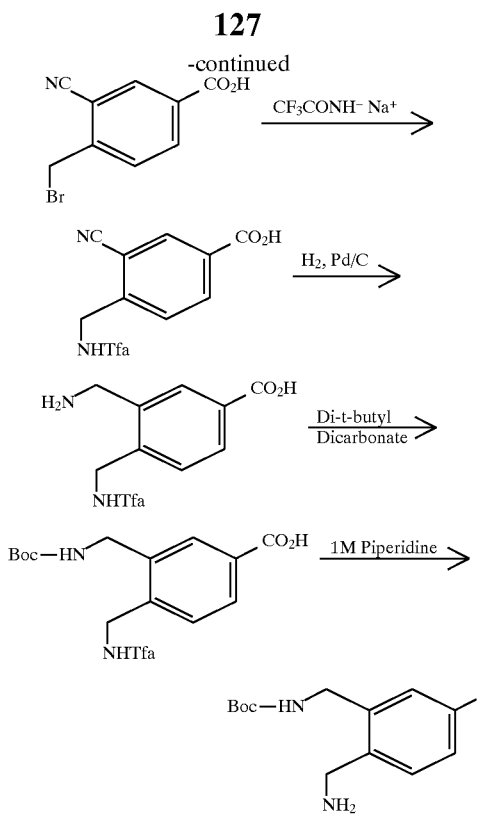

Alternatively, the moiety can be prepared from 4-bromobenzoic acid as shown in the scheme.

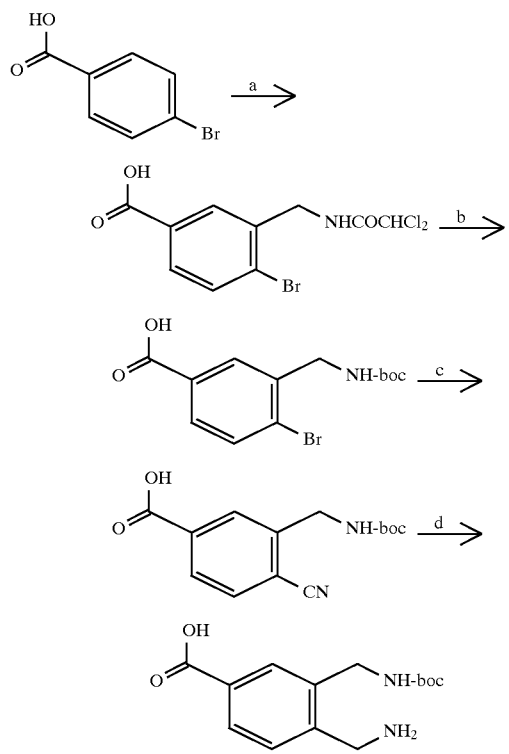

a] $H_2SO_4$, $HOCH_2NHCOCHCl_2$  b] $H^+$, boc-ON
c] CuCN, DMF  d] $H_2$-catalyst These ring substituted cyclizing moieties can be used to synthesize cyclic compound intermediates.

128

Cyclic Compound Intermediate 113

Cyclo(D-Val-NMeArg-Gly-Asp-Mamb(4—$NH_2$)

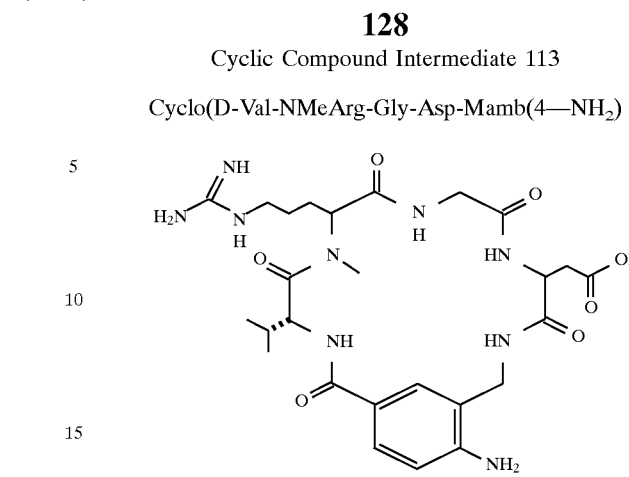

This compound can be prepared using the procedure described above for Cyclo(D-Val-NMeArg-Gly-Asp-Mamb substituting the ring substituted cyclizing moiety where Z=$NH_2$.

Cyclic Compound Intermediates 114, 115 and 116

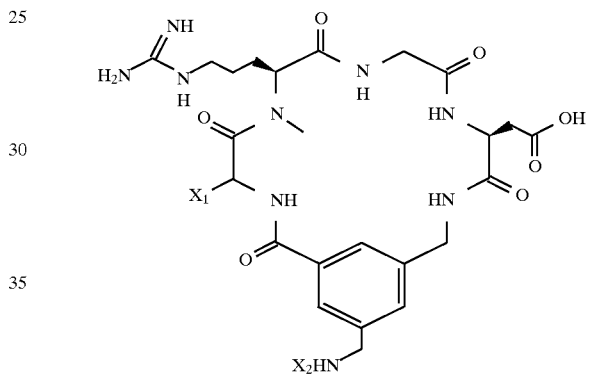

$X_1$ = 2-propyl, ethyl, or p-hydroxyphenylmethyl
$X_2$ = H

Compounds cyclo(D-Val-NMeArg-Gly-Asp-Mamb(5-$CH_2NHX_2$), cyclo(D-Abu-NMeArg-Gly-Asp-Mamb(5-$CH_2NHX_2$), and cyclo(D-Tyr-NMeArg-Gly-Asp-Mamb(5-$CH_2NHX_2$) can be prepared via the methods described above using the ring substituted cyclizing moiety where Y=$CH_2NH_2$.

Cyclic Compound Intermediates 117, 118 and 119.

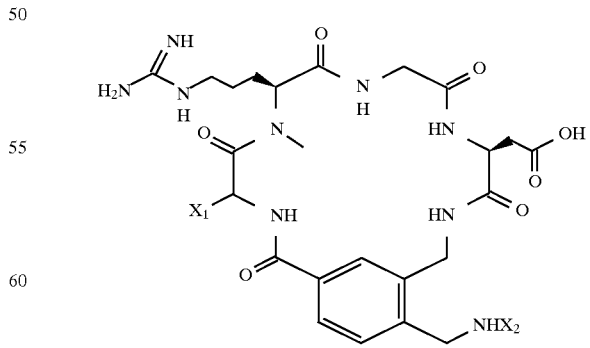

$X_1$ = 2-propyl, ethyl, or p-hydroxyphenylmethyl
$X_2$ = H

Compounds cyclo(D-Val-NMeArg-Gly-Asp-Mamb(4-$CH_2NHX_2$), cyclo(D-Abu-NMeArg-Gly-Asp-Mamb(4-

CH₂NHX₂), and cyclo(D-Tyr-NMeArg-Gly-Asp-Mamb(4-CH₂NHX₂) can be prepared via the procedures described above using the ring substituted cyclizing moiety where Z=CH₂NH₂.

Other R³¹ Cyclizing Moieties

Alternatives to Mamb useful as cyclizing moieties R³¹ in the cyclic peptides of the invention include aminoalkyl-naphthoic acid and aminoalkyl-tetrahydronaphthoic acid residues. Representative aminoalkyl-naphthoic acid and aminoalkyl-tetrahydronaphthoic acid intermediates useful in the synthesis of cyclic peptides of the present invention are described below. The synthesis of these intermediates is outlined below in Scheme 7.

8-Amino-5,6,7,8-tetrahydro-2-naphthoic Acid Hydrochloride (8)

The title compound was prepared according to a modification of standard procedures previously reported in the literature (Earnest, I., Kalvoda, J., Rihs, G., and Mutter, M., Tett. Lett., Vol. 31, No. 28, pp 4011–4014, 1990).

As shown above in Scheme 7, 4-phenylbutyric acid (1) was converted to the ethyl ester (2) which was acylated via aluminum chloride and acetylchloride to give 4-acetylphenylbutyric acid ethyl ester (3). This ester was subjected to saponification to give 4-acetylphenylbutyric acid (4). Subsequently, the acetyl group was oxidized to give 4-carboxyphenylbutyric acid (5) which was converted to the 1-tetralin-7-carboxylic acid (6) using aluminum chloride in

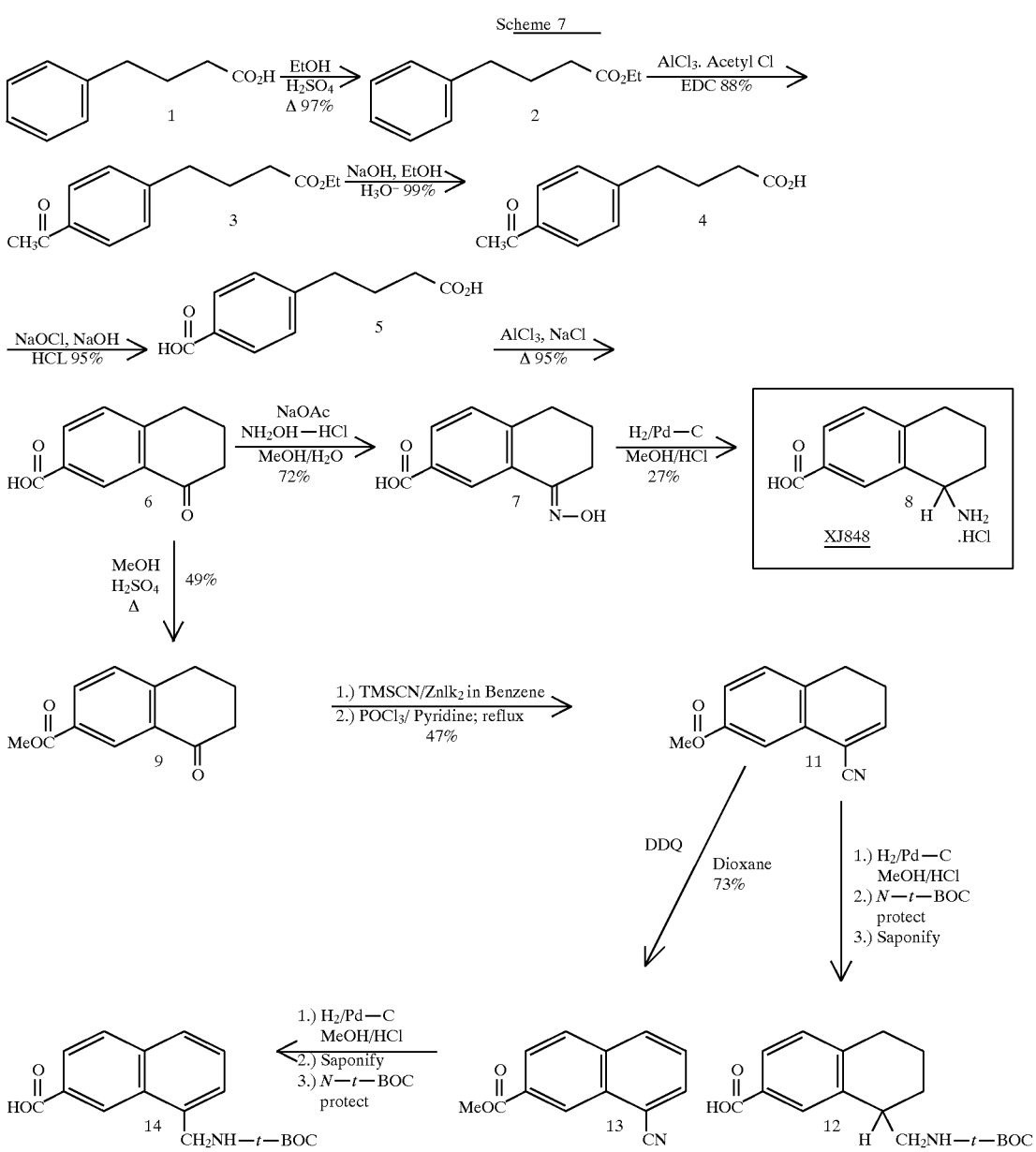

a Friedel-Crafts cyclization with resonably high yield. At that point, the tetralone was split into two portions and some was converted to the oxime (7) using sodium acetate and hydroxylamine hydrochloride. The oxime was subjected to hydrogenolysis to give the racemic mixture of 8-amino-5,6,7,8-tetrahydro-2-naphthoic acid as the hydrochloride (8) for use as an intermediate for incorporation into the cyclic peptide.

Part A

A solution of 4-phenylbutyric acid (50.0 g, 0.3 mol) in ethanol (140 mL) with concentrated sulfuric acid (0.53 mL) was stirred at reflux over 5 hours. The cooled solution was poured into ice water and extracted with ethyl acetate. The combined organic layers were backwashed with brine, dried over anhydrous magnesium sulfate and evaporated to dryness under reduced pressure to give 4-phenylbutyric acid ethyl ester (56.07 g, 0.29 mol, 97%) as a yellow liquid. $^1$H NMR (CDCl$_3$) d 7.3–7.1 (m, 5H), 4.1 (q, 2H, J=7.1 Hz), 2.7 (t, 2H, J=7.7 Hz), 2.3 (t, 2H, J=7.5 Hz), 1.95 (quintet, 2H, J=7.5 Hz), 1.25 (t, 3H, J=7.1 Hz).

Part B

To a solution of aluminum chloride (153 g, 1.15 mol), and acetyl chloride (38.5 mL, 42.5 g, 0.54 mol) in dichloromethane (1500 mL) was added, dropwise, a solution of 4-phenylbutyric acid ethyl ester (50.0 g, 0.26 mol) in dichloromethane (500 mL). All was stirred at ambient temperature for 15 minutes. The solution was poured into cold concentrated hydrochloric acid (2000 mL) and then extracted with dichloromethane. The combined organic layers were backwashed with brine, dried over anhydrous magnesium sulfate and evaporated to dryness under reduced pressure to give 4-acetylphenylbutyric acid ethyl ester (53.23 g, 0.23 mol, 88%) as a dark yellow liquid. $^1$H NMR (CDCl$_3$) d 7.9 (d, 2H, J=8.1 Hz), 7.25 (d, 2H, J=8.4 Hz), 4.1 (q, 2H, J=7.1 Hz), 2.75 (t, 2H, J=7.6 Hz), 2.6 (s, 3H), 2.35 (t, 2H, J=7.6 Hz), 2.0 (quintet, 2H, J=7.5 Hz), 1.25 (t, 3H, J=7.1 Hz).

Part C

To a solution of 4-acetylphenylbutyric acid ethyl ester (50.0 g, 0.21 mol) in ethanol (1250 mL) was added, dropwise, a solution of sodium hydroxide (50.0 g) in water (1250 mL). All was stirred at reflux over 4 hours. The solution was concentrated to half volume and then acidified to a pH equal to 1.0 using hydrochloric acid (1N). The resulting precipitate was collected and washed with water to give 4-acetylphenylbutyric acid (53.76 g, 0.26 mol, 99%) as a white solid. mp=50°–52° C.; $^1$H NMR (CDCl$_3$) d 7.9 (d, 2H, J=8.1 Hz), 7.25 (d, 2H, J=9.1 Hz), 2.75 (t, 2H, J=7.7 Hz), 2.6 (s, 3H), 2.4 (t, H, J=7.3 Hz), 2.0 (quintet, 2H, J=7.4 Hz).

Part D

To a solution of sodium hypochlorite (330 mL, 17.32 g, 0.234 mol) in a solution of sodium hydroxide (50%, 172 mL), warmed to 55° C., was added, portionwise as a solid, 4-acetylphenylbutyric acid (16.0 g, 0.078 mol) while keeping the temperature between 60°–70° C. All was stirred at 55° C. over 20 hours. The cooled solution was quenched by the dropwise addition of a solution of sodium bisulfite (25%, 330 mL). The mixture was then transferred to a beaker and acidified by the careful addition of concentrated hydrochloric acid. The resulting solid was collected, washed with water and dried, then triturated sequentially with chlorobutane and hexane to give 4-carboxyphenylbutyric acid (15.31 g, 0.074 mol, 95%) as a white solid. mp=190°–195° C.; $^1$H NMR (DMSO) d 12.55 (bs, 1H), 8.1 (s, 1H), 7.85 (d, 2H, J=8.1 Hz), 7.3 (d, 2H, J=8.1 Hz), 2.7 (t, 2H, J=7.5 Hz), 2.2 (t, 2H, J=7.4 Hz), 1.8 (quintet, 2H, J=7.5 Hz).

Part E

A mixture of 4-carboxyphenylbutyric acid (10.40 g, 0.05 mol), aluminum chloride (33.34 g, 0.25 mol) and sodium chloride (2.90 g, 0.05 mol) was heated with continual stirring to 190° C. over 30 minutes. As the mixture cooled to 60° C., cold hydrochloric acid (1N, 250 mL) was carefully added. The mixture was extracted with dichloromethane. The combined organic layers were backwashed with dilute hydrochloric acid and water, dried over anhydrous magnesium sulfate and evaporated to dryness under reduced pressure. The resulting solid was triturated with chlorobutane to give 1-tetralon-7-carboxylic acid (9.59 g, 0.05 mol. 100%) as a brown solid. mp=210°–215° C.; $^1$H NMR (DMSO) d 8.4 (s, 1H), 8.1 (d, 2H, J=8.0 Hz), 7.5 (d, 1H, J=7.9 Hz), 3.0 (t, 2H, J=6.0 Hz), 2.65 (t, 2H, J=6.6 Hz), 2.1 (quintet, 2H, J=6.3 Hz).

Part F

A solution of 1-tetralon-7-carboxylic acid (1.0 g, 0.0053 mol) and sodium acetate (1.93 g, 0.024 mol) and hydroxylamine hydrochloride (1.11 g, 0.016 mol) in a mixture of methanol and water (1:1, 15 mL) was stirred at reflux over 4 hours. The mixture was cooled and then added was more water (50 mL). The solid was collected, washed with water and dried, then triturated with hexane to give 1-tetralonoxime-7-carboxylic acid (0.78 g, 0.0038 mol, 72%) as a white solid. mp=205°–215° C.; $^1$H NMR (DMSO) d 11.3 (s, 2H), 8.4 (s, 1H), 7.8 (d, 1H, J=7.7 Hz), 7.3 (d, 1H, J=7.7 Hz), 2.8 (t, 2H, J=5.9 Hz), 2.7 (d, 2H, J=6.6 Hz), 1.9–1.7 (m, 2H).

Part G

A mixture of 1-tetralonoxime-7-carboxylic acid (0.75 g, 0.0037 mol) in methanol (25 mL) with concentrated hydrochloric acid (0.54 mL, 0.20 g, 0.0056 mol) and palladium on carbon catalyst (0.10 g, 5% Pd/C) was shaken for 20 hours at ambient temperature under an atmosphere of hydrogen (60 psi). The reaction mixture was filtered over Celite@ and washed with methanol. The filtrate was evaporated to dryness under reduced pressure and the residue was purified by flash chromatography using hexane:ethyl acetate::1:1 to give the racemic mixture of 8-amino-5,6,7,8-tetrahydro-2-naphthoic acid hydrochloride (0.225 g, 0.001 mol. 27%) as a white solid. mp=289°–291° C.; $^1$H NMR (DMSO) d 8.55 (bs, 3H), 8.2–8.1 (m, 1H), 7.85–7.8 (m, 1H), 7.35–7.25 (m, 1H), 4.5 (m, 1H), 2.9–2.8 (m, 2H), 2.1–1.9 (m, 3H), 1.85–1.7 (m, 1H).

N-(BOC)-8-Aminomethyl-5,6,7,8-tetrahydro-2-naphthoic Acid (12)

As shown above in Scheme 7, the remaining tetralone was then converted to the methyl ester (9). Using a procedure from Gregory, G. B. and Johnson, A. L., JOC, 1990, 55, 1479, the tetralone methyl ester (9) was converted, first, to the cyanohydrin by treatment with trimethylsilylcyanide and zinc iodide and then, via the in situ dehydration with phosphorous oxychloride in pyridine, to the methyl 8-cyano-5,6-dihydro-2-naphthoate (11). This naphthoate was divided into two portions and some was subjected to hydrogenolysis, N-BOC-protection and saponification to give N-(BOC)-8-aminomethyl-5,6,7,8-tetrahydro-2-naphthoic acid (12) as an intermediate for incorporation into the cyclic peptide.

Part A

A mixture of 1-tetralon-7-carboxylic acid (7.0 g, 0.037 mol) in methanol (13.6 mL, 10.8 g, 0.30 mol) with a catalytic amount of hydrochloriic acid (0.07 mL, 0.12 g, 0.0012 mol) was stirred at reflux over 5 hours. The cooled reaction mixture was poured into ice water and extracted with ethyl acetate. The combined organic layers were backwashed with water and brine, dried over anhydrous magnesium sulfate and evaporated to dryness under reduced pressure. The resulting solid was purified by flash chromatography using hexane:ethyl acetate::75:25. The resulting solid was triturated with hexane to give 1-tetralon-7-carboxylic acid methyl ester (3.61 g, 0.018 mol, 49%) as a yellow solid. mp=170°–172° C.; $^1$H NMR (CDCl$_3$) d 8.7 (s, 1H), 8.15 (d, 1H, J=8.1 Hz), 7.35 (d, 1H, J=8.1 Hz), 3.95 (s, 3H), 3.05 (d, 2H, J=6.1 Hz), 2.7 (t, 2H, J=6.4 Hz), 2.15 (quintet, 2H, J=6.2 Hz).

Part B

A solution of 1-tetralon-7-carboxylic acid methyl ester (3.50 g, 0.017 mol), trimethylsilylcyanide (1.98 g, 0.02 mol) and zinc iodide (0.10 g) in benzene (20 mL) was stirred at ambient temperature over 15 hours. Then added, sequentially and dropwise, was pyridine (20 mL) and phosphorous oxychloride (4.0 mL, 6.55 g, 0.0425 mol). The reaction mixture was stirred at reflux over 1 hour then evaporated to dryness under reduced pressure. The residue was taken up in chloroform, backwashed with water, dried over anhydrous magnesium sulfate and evaporated to dryness under reduced pressure to give methyl 8-cyano-5,6-dihydro-2-naphthoate (1.70 g, 0.008 mol, 47%) as a yellow solid. mp=73°–75° C.; $^1$H NMR (CDCl$_3$) d 8.0–7.9 (m, 1H), 7.3–7.2 (m, 1H), 6.95 (t, 1H, J=4.8 Hz), 3.95 (s, 3H), 2.9 (t, 2H, J=8.3 Hz), 2.6–2.4 (m, 3H).

Part C

A mixture of methyl 8-cyano-5,6-dihydro-2-naphthoate (0.80 g, 0.0038 mol) in methanol (25 mL) with concentrated hydrochloric acid (0.56 mL) and palladium on carbon catalyst (0.40 g, 5% Pd/C) was shaken for 20 hours at ambient temperature under an atmosphere of hydrogen (50 psi). The reaction mixture was filtered over Celite and washed with methanol. The filtrate was evaporated to dryness under reduced pressure and the residue was triturated with hexane to give the racemic mixture of methyl 8-aminomethyl-5,6,7,8-tetrahydro-2-naphthoate (0.80 g, 0.0037 mol, 97%) as a white solid. mp=172°–179° C.; $^1$H NMR (DMSO) d 8.2–8.0 (m, 4H), 7.9–7.7 (m, 6H), 7.5–7.2 (m, 4H), 3.9–3.8 (m, 7H), 3.3–2.7(m, 10H), 2.0–1.6 (m, 8H).

Part D

A solution of methyl 8-aminomethyl-5,6,7,8-tetrahydro-2-naphthoate (0.78 g, 0.0036 mol) and triethylamine (0.55 mL, 0.40 g, 0.004 mol) in aqueous tetrahydrofuran (50%, 75 mL) was added, portionwise as a solid, 2-(tert-butoxycarbonyloxyimino)-2-phenylacetonitrile (0.99 g, 0.004 mol). All was stirred at ambient temperature over 3 hours. The solution was concentrated to half volume and extracted with diethylether. The aqueous layer was then acidified to a pH of 1.0 using hydrochloric acid (1N) and then extracted with ethyl acetate. The combined organic layers were dried over anhydrous magnesium sulfate and evaporated to dryness under reduced pressure. The residue was purified by flash chromatography using hexane:ethyl acetate::8:2 to give methyl N-(BOC)-8-aminomethyl-5,6,7,8-tetrahydro-2-naphthoate (0.54 g, 0.0017 mol, 47%) as a white solid. mp=72°–80° C.; $^1$H NMR (DMSO) d 13.8 (s, 1H), 7.8–7.65 (m, 3H), 7.6–7.5 (m, 3H), 7.25–7.20 (m, 1H), 7.15–7.05 (m, 1H), 3.9–3.8 (m, 1H), 3.2–2.8 (m, 4H), 1.8–1.6 (m, 3H), 1.4 (s, 6H).

Part E

To a solution of methyl N-(BOC)-8-aminomethyl-5,6,7,8-tetrahydro-2-naphthoate (0.50 g, 0.0016 mol) in ethanol (12.5 mL) was added, dropwise, a solution of sodium hydroxide (0.50 g) in water (12.5 mL). All was stirred a reflux over 4 hours. The reaction mixture was concentrated to half volume and then acidified to a pH equal to 1.0 using hydrochloric acid (1N). The residue was purified by flash chromatography using a gradient of hexane:ethyl acetate::1:1 to ethyl acetate to ethyl acetate:methanol::9:1 to give the racemic mixture of the title compound, N-(BOC)-2-aminomethyl-5,6,7,8-tetrahydro-2-naphthoic acid (0.19 g, 0.00062 mol, 39%) as a white solid. mp=172°–176° C.; $^1$H NMR (DMSO) d 7.8 (s, 1H), 7.65 (d, 1H, J=8.1 Hz), 7.15 (d, 1H, J=8.1 Hz), 7.1–7.0 (m, 1H), 3.2–3.1 (m, 2H), 3.0–2.7 (m, 4H), 1.8–1.6 (m, 4H), 1.4 (s, 9H).

N-(BOC)-8-aminomethyl-2-naphthoic acid (14)

The remaining naphthoate (11) was treated with 2,3-dichloro-5,6-dicyano-1,4-benzoquinone (DDQ) in dioxane to aromatize the adjacent ring to give the methyl 8-cyano-2-naphthoate (13). Then, the nitrile was reduced via hydrogentation and the methyl ester saponified to the carboxylic acid. This acid was then N-BOC-protected to give N-(BOC)-8-aminomethyl-2-naphthoic acid (14) as an intermediate for incorporation into the cyclic peptide.

Part A

A solution of methyl 8-cyano-5,6-dihydro-2-naphthoate (1.0 g, 0.0047 mol) and 2,3-dichloro-5,6-dicyano-1,4-benzoquinone (1.07 g, 0.0047 mol) in dioxane (50 mL) was stirred at 120° C. over 16 hours. The reaction mixture was poured into ice water and extracted with ethyl acetate. The combined organic layers were dried over anhydrous magnesium sulfate and evaporated to dryness under reduced pressure. The residue was purified by flash chromatography using ethyl acetate to give methyl 8-cyano-2-naphthoate (0.72 g, 0.0034 mol, 73%) as a tan solid. mp=178°–182° C.; $^1$H NMR (CDCl$_3$) d 8.95 (s, 1H), 8.3–8.2 (m, 1H), 8.15–8.10 (m, 1H), 8.0–7.95 (m, 2H), 7.7–7.6 (m, 1H), 4.05 (s, 1H).

Part B

A mixture of methyl 8-cyano-2-naphthoate (1.0 g, 0.0047 mol) in methanol (35 mL) with concentrated hydrochloric acid (0.69 mL) and palladium on carbon catalyst (0.20 g, 5% Pd/C) was shaken for 6 hours at ambient temperature under an atmosphere of hydrogen (50 psi). The reaction mixture was filtered over Celite@ and washed with-methanol. The filtrate was evaporated to dryness under reduced pressure and the residue was triturated with hexane to give methyl 8-aminomethyl-2-naphthoate (0.76 g, 0.0035 mol, 75%) as an oil. $^1$H NMR (DMSO) d 8.75 (s, 1H), 8.5 (bs, 2H), 8.2–8.05 (m, 3H), 7.75–7.70 (m, 2H), 4.6 (s, 2H), 3.95 (m, 3H).

Part C

To a solution of methyl 8-aminomethyl-2-naphthoate (0.75 g, 0.0035 mol) in dry tetrahydrofuran (50 mL), cooled to 0° C., was added a solution of lithium hydroxide (0.5M, 5.83 mL). All was stirred at ambient temperature over 20 hours. Another aliquot of lithium hydroxide was added and all was stirred for an additional 20 hours. The solid was collected and the filtrate was evaporated to dryness under reduced pressure. The solids were triturated with diethyl ether to give 8-aminomethyl-2-naphthoic acid (0.67 g, 0.0033 mol, 95%) as a white solid. mp=223°–225° C.; $^1$H NMR (DMSO) d 8.6 (s, 1H), 8.1–7.9 (m, 1H), 7.8–7.7 (m, 4H), 7.55–7.5 (m, 1H), 7,45–7.35 (m, 2H), 4.2 (s, 2H).

Part D

A solution of 8-aminomethyl-2-naphthoic acid (0.50 g, 0.00025 mol) and triethylamine (0.038 mL, 0.028 g, 0.000275 mol) in aqueous tetrahydrofuran (50%, 5 mL) was added, portionwise as a solid, 2-(tert-butoxycarbonyloxyimino)-2-phenylacetonitrile (0.068 g, 0.000275 mol). All was stirred at ambient temperature over 5 hours. The solution was concentrated to half volume and extracted with diethylether. The aqueous layer was then acidified to a pH of 1.0 using hydrochloric acid (1N) and then extracted with ethyl acetate. The combined organic layers were dried over anhydrous magnesium sulfate and evaporated to dryness under reduced pressure to give the title compound, N-(BOC)-8-aminomethyl-2-naphthoic acid (0.050 g, 0.00017 mol) as a white solid. mp=190°–191° C.; $^1$H NMR (DMSO) d 13.1 (bs, 1H), 8.8 (s, 1H), 8.0 (q, 2H, J=7.9 Hz), 7.9 (d, 1H, J=8.1 Hz), 7.6 (t, 1H, J=7.5 Hz), 7.65–7.55 (m, 2H), 4.6 (d, 2H, J=5.5 Hz), 1.4 (s, 9H).

Cyclic Compound Intermediates 89a and 89b
cyclo-(D-Val-NMeArg-Gly-Asp-aminotetralincarboxylic acid)

The title compound was prepared using the general procedure described for cyclo-(D-Val-NMeArg-Gly-Asp-Mamb) (Cyclic Compound Intermediate 4). The DCC/DMAP method was used for attachment of Boc-aminotetralin-carboxylic acid to the oxime resin. The peptide was prepared on a 0.164 mmol scale to give the protected cyclic peptide (69 mg, 49.3%). The peptide (69 mg) and 0.069 mL of anisole were treated with anhydrous hydrogen fluoride at 0° C. for 30 minutes. The crude material was precipitated with ether, redissolved in aqueous acetonitrile, and lyophilized to generate the title compound (59.7 mg, greater than quantitative yield; calculated as the fluoride salt). Purification was accomplished by reversed-phase HPLC on a preparative Vydac C18 column (2.5 cm) using a 0.23%/min. gradient of 16.2 to 27% acetonitrile containing 0.1% TFA and then lyophilized to give the TFA salt of the title compound as a fluffy white solid. Two isomers were obtained; isomer #1 (12.5% recovery, overall yield 6.2%, FAB-MS: [M+H]=615.34; isomer #2 (18.6% recovery, overall yield 9.3%, FAB-MS: [M+H]=615.35.

Cyclic Compound Intermediate 89c
cyclo-(D-Val-NMeArg-Gly-Asp-aminomethylnaphthoic acid)

The title compound was prepared using the general procedure described for cyclo-(D-Val-NMeArg-Gly-Asp-Mamb) (Cyclic Compound Intermediate 4). The DCC/DMAP method was used for attachment of Boc-aminomethyl-naphthoic acid to the oxime resin. The peptide was prepared on a 0.737 mmol scale to give the protected cyclic peptide (463 mg, 73.1%). The peptide (463 mg) and 0.463 mL of anisole were treated with anhydrous hydrogen fluoride at 0° C. for 20 minutes. The crude material was precipitated with ether, redissolved in aqueous acetonitrile, and lyophilized to generate the title compound (349 mg, greater than quantitative yield; calculated as the fluoride salt). Purification was accomplished by reversed-phase HPLC on a preparative Vydac C18 column (2.5 cm) using a 0.45%/min. gradient of 4.5 to 22.5% acetonitrile containing 0.1% TFA and then lyophilized to give the TFA salt of the title compound as a fluffy white solid (12.1% recovery, overall yield 7.8%); FAB-MS: [M+H]=625.32.

Synthesis of Linker Modified Cyclic Compound Intermediates

Linker modified cyclic compound intermediates can be synthesized either by incorporating an appropriately protected linker into a cyclizing moiety and then synthesizing the linker modified cyclic compound intermediate or by attaching the linker to a cyclic compound intermediate.

Linker Modified Cyclizing Moieties

Linker modified cyclizing moieties can be synthesized either by attaching the linker to a ring substituted cyclizing moiety synthesized as described above or by incorporating an appropriately protected linker into the synthesis of the cyclizing moiety.

For example, the ring substituted cyclizing moiety described above where X=NH$_2$ can be reacted with the succinimidyl linker, RCOOSu (R=—(CH$_2$)$_5$—NH$_2$ or CH$_2$—C$_6$H$_5$—p—NH$_2$), to give a linker attached at position X via an amide group.

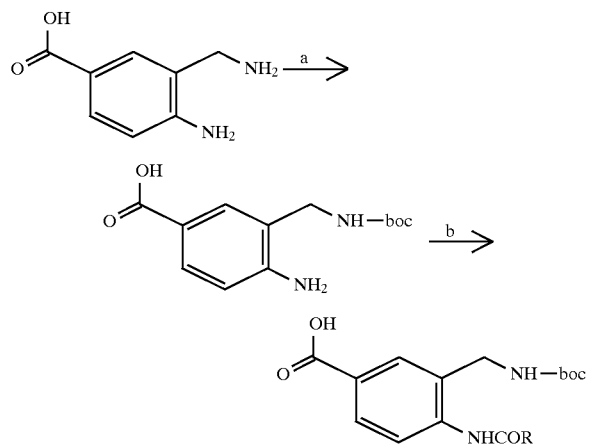

a] Boc—ON  b] RCOOSu

The ring substituted cyclizing moiety with X=OH can be reacted with a linker derived from tetraethylene glycol. This linker consists of four ethylene units separated by ether groups, and bearing a Z-protected amine group at one end of the tether, and a leaving group such as tosylate at the other end of the tether. This will give a linker attached at position X via an ether group.

The ring substituted cyclizing moiety with Z=NH$_2$ can be reacted with (Z—NH(CH$_2$)$_5$CO)$_2$O to give a linker attached at position Z via an amide group.

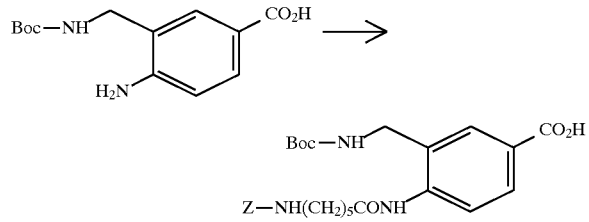

Linkers can be attached to the ring substituted cyclizing moiety with Z=OH. Attachment of the linkers to the ring will require the linker having a leaving group suitable for reaction with a phenolate ion. Such leaving groups include halides, aryl sulfonates (e.g., tosylate) and alkyl tosylates (e.g., mesylate). For example, an alkyl chain bearing a tosyl group at one end of the chain and a protected amine at the other end is used. The literature provides several examples of alkylation at a phenolic group in the presence of a carboxylic acid group (See, for example Brockmann, Kluge, and Muxfeldt (1957), *Ber. Deutsch. Chem. Ges.,* 90, 2302.

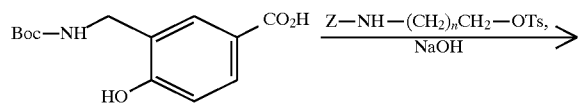

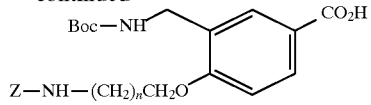

The ring substituted cyclizing moiety with Z=CH$_2$NH$_2$ can be reacted with Z—NH(CH$_2$)$_n$—COOSu to give linkers attached at position Z via an amidomethyl group.

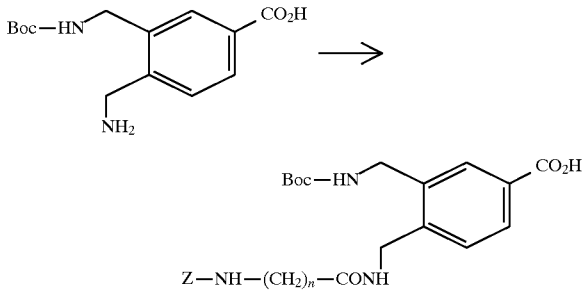

The previous examples have demonstrated the use of linkers which terminate in a protected amine. Linkers that terminate in a carboxylic acid or ester groups may also be desirable. Several such linkers can be attached to the cyclizing moieties described above. For example, in the following scheme, t-Boc protected 3-aminomethyl-4-hydroxybenzoic acid is treated with benzyl chloroacetate and base to introduce a short linker terminating in an ester.

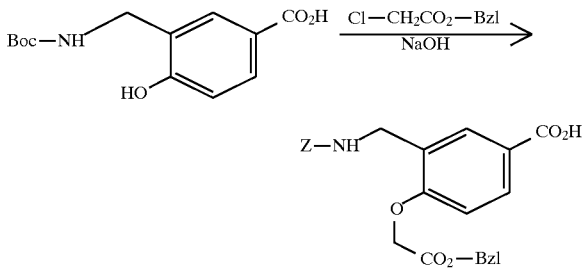

A linker can be attached to the ring substituted cyclizing moiety where Y=NH$_2$. As shown in Scheme 8, hydrolysis of the methyl ester of t-Boc protected methyl 3-aminomethyl-5-aminobenzoate under mild base conditions, followed by treatment with benzyl acrylate (Lancaster Synthesis, Inc.) and acetic acid catalyst would produce the Michael addition product. Even though this linker modified cyclizing moiety contains an unprotected secondary amine, it could be used directly in a solid phase synthesis. However, amine protection, if desired, could be accomplished by treatment with benzyl chloroformate and a mild base.

Scheme 8

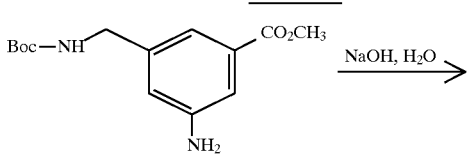

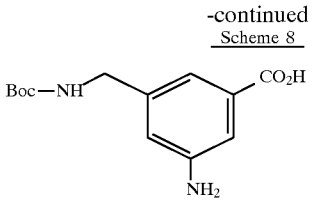

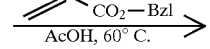

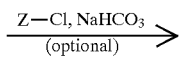

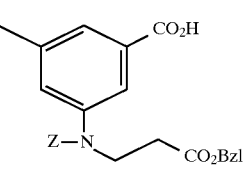

The linker can also be incorporated into the synthesis of the cyclizing moieties. One example is the synthesis of linker modified cyclizing moiety 5-Aca-Mamb.

Synthesis of Boc-Mamb(Z-5-Aca)

This synthesis is depicted in Scheme 9, below.

Part A

Methyl 3-Nitro-5-hydroxymethylbenzoate

To a solution of monomethyl 3-nitroisophthalate (396.0 g, 1.76 mol) in anhydrous THF (1000 ml) was added 2.0M BMS (borane methylsulfide complex) in THF (880 ml, 1.76 mol) dropwise over 1 hour. The resulting solution was heated to reflux for 12 hours, and MeOH (750 ml) was slowly added to quench the reaction. The solution was concentrated to give a yellow solid which was recrystalized from toluene (297.5 g, 80%). $^1$H NMR (CDCl$_3$): 8.71–8.70 (m, 1H), 8.41–8.40 (m, 1H), 8.31–8.30 (m, 1H), 4.86 (s, 2H), 3.96 (s, 3H), 2.47 (s, 1H); MP=76.5°–77.5° C.; DCI-MS: [M+H]=212.

Part B

3-Carbomethoxy-5-nitrobenzyl Methanesulfonate

Methyl 3-nitro-5-hydroxymethylbenzoate (296.0 g, 1.40 mol) and proton sponge (360.8 g, 1.68 mol) were dissolved in ethylene dichloride (150 ml). Triflic anhydride (292.3 g, 1.68 mol) dissolved in ethylene dichloride (800 ml) was added dropwise to the suspension over 90 minutes and the mixture allowed to stir 18 hour under nitrogen. The reaction was quenched with H$_2$O (2000 ml), the two layers were separated, and the organic layer was washed with 1000 ml portions of 1N HCl, H$_2$O, saturated NaHCO$_3$, H$_2$, and saturated NaCl. The organic layer was dried (MgSO$_4$) and concentrated under reduced pressure. The resulting yellow solid was recrystalized from toluene to give the title compound as a tan solid (366.8 g, 91%). $^1$H NMR (CDCl$_3$): 8.84–8.85 (m, 1H), 8.45–8.46 (m, 1H), 8.40–8.39 (m, 1H), 5.35 (s, 2H), 3.98 (s, 3H), 3.10 (s, 3H); MP=96°–97° C.; DCI-MS: [M+NH$_4$]=307.

Part C

Methyl 3-Azidomethyl-5-nitrobenzoate

3-Carbomethoxy-5-nitrobenzyl methanesulfonate (300.0 g, 1.04 mol) and sodium azide (81.0 g, 1.25 mol) were suspended in DMF (1700 ml) and stirred at room temperature for 5 hours. The reaction was diluted with ethyl acetate (2000 ml), washed with 1000 ml portions of $H_2O$ (2×) and saturated NaCl (1×), dried ($MgSO_4$), and concentrated under reduced pressure. The resulting amber syrup was dried under vacuum at 40° C. to yield the title compound as a tan solid (226.5 g, 92%). $^1H$ NMR ($CDCl_3$): 8.60 (s, 1H), 8.26 (s, 1H), 8.20 (s, 1H), 4.52 (s, 2H), 3.88 (s, 3H); MP=44°–46° C.

Part D

Methyl 3-Amino-5-aminomethylbenzoate

A solution of Methyl 3-Azidomethyl-5-nitrobenzoate (15.50 g, 65.7 mmol) and benzene sulfonic acid (22.14 g, 140 mmol) in warm methanol (320 ml) was placed in a Parr shaker bottle and purged with nitrogen for 15 minutes. Palladium on carbon catalyst (10% Pd/C, 4.0 g) was added and the shaker bottle was further purged with 7 pressurization-evacuation cycles, repressurized, and allowed to shake 18 hours, during which time the required amount of hydrogen was consumed. The catalyst was removed by filtration through a bed of Celite and the filtrate was concentrated under reduced pressure yielding a tan oil. Trituration with refluxing EtOAc (2×150 ml) followed by cooling 12 hours at −5° C. gave a tan solid which was collected by filtration, washed with EtOAc (2×50 ml) and dried under vacuum (25.82 g, 80%). $^1H$ NMR ($CD_3OD$): 8.25–8.23 (m, 1H), 8.07–8.06 (m, 1H), 7.86–7.80 (m, 5H), 7.49–7.42 (m, 6H), 4.29 (s, 2H), 3.97 (s, 3H).

Part E

Methyl 3-Amino-5-(t-butoxycarbonylamino) methylbenzoate

A solution of methyl 3-amino-5-aminomethylbenzoate (19.32 g, 39.0 mmol), TEA (7.89 g, 78.0 mmol), and di-t-butyl dicarbonate (8.51 g, 39.0 mmol) in MeOH (350 ml) was allowed to react 24 hours at room temperature and concentrated to yield a colorless solid. Purification by flash chromatography (silica gel; 1:1 hexane:EtOAc) gave the product (9.21 g, 84%) as a colorless solid. $^1H$ NMR ($CD_3OD$): 7.26–7.25 (m, 2H), 6.86–6.85 (m, 1H), 4.16 (s, 2H), 3.88 (s, 3H), 1.48 (s, 9H); MP=57°–65° C. ESI-MS: [M+H]=281.

Part F

Boc-Mamb(Z-5-Aca)-OMe

N-CBZ-e-aminocaproic acid (7.77 g, 29.3 mmol) and TEA (2.97 g, 29.3 mmol) were dissolved in anhydrous THF (250 ml) and cooled to −20° C. Isobutylchloroformate (4.00 g, 29.3 mmol) was added dropwise and the mixture allowed to react for 5 minutes at −20° C. Methyl 3-Amino-5-(t-butoxycarbonylamino)methylbenzoate (8.20 g, 29.3 mmol) dissolved in anhydrous THF (50 ml) was cooled to −20° C. and added to the reaction. The reaction mixture was allowed to slowly warm to room temperatures and was stirred for an additional 2 days. The solids were removed by filtration and the filtrate was concentrated under reduced pressure. The resulting residue was dissolved in EtOAc (125 ml) and washed with two 50 ml portions each of 0.2N HCl, saturated $NaHCO_3$, and saturated NaCl. The organic layer was dried ($MgSO_4$) and concentrated under reduced pressure. The crude product was purified by flash chromatography (silica gel; 1:2 hexane:EtOAc), and recrystallization from $CCl_4$ to give the title compound (10.09 g, 65%) as a colorless solid. $^1H$ NMR ($CDCl_3$): 8.03–7.63 (m, 3H), 7.32–7.28 (m, 5H), 5.12–4.92 (m, 4H), 4.27–4.25 (m, 2H), 3.85 (s, 3H), 3.17–3.12 (m, 2H), 2.34–2.28 (m, 2H), 1.72–1.66 (m, 2H), 1.48–1.53 (m, 2H), 1.43 (s, 9H), 1.36–1.34 (m, 2H); MP=52°–54° C. ESI-MS: [M+H]=528.

Part G

Boc-Mamb(Z-5-Aca)

Boc-Mamb(Z-5-Aca)-OMe (22.58 g, 43.0 mmol) was dissolved in 1:1 1N NaOH:MeOH (500 ml) and allowed to stir 18 hours at room temperature. The reaction was partitioned between EtOAc (300 ml) and $H_2O$ (200 ml) and the two layers were separated. The pH of the aqueous layer was lowered to 4.5, and the resulting oily precipitate was extracted into EtOAc (2×300 ml). The organic extract was dried ($MgSO_4$) and concentrated to a yellow solid. The solid was triturated with refluxing $CCl_4$ (3×100 ml) to give the product (14.17 g, 64%) as a colorless solid. $^1H$ NMR ($CD_3OD$): 8.04 (s, 1H), 7.71–7.66 (m, 2H), 7.30–7.23 (m, 5H), 5.02 (s, 2H), 4.24 (s, 2H), 3.32 (s, 3H), 3.11 (t, J=6.8 Hz, 2H), 2.34 (t, J=6.8 Hz, 2H), 1.74–1.35 (m, 15H); MP=168°–169° C. DCI-MS: [M+$NH_4$]=531.

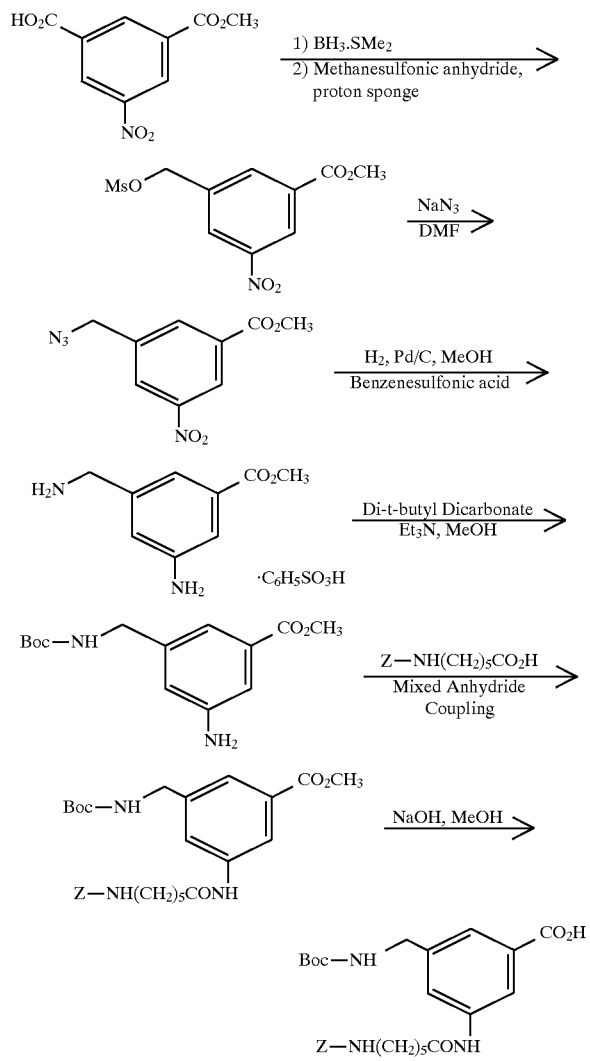

Scheme 9

Scheme 10 teaches how a linker attached to the cyclizing moiety via a reverse amide functional group can also be synthesized. Reduction of the nitro group of monomethyl 3-nitroisophthalate (Fluka) using palladium on carbon would give monomethyl 3-aminoisophthalate, which can be converted to the corresponding nitrile by the Sandmeyer procedure. Treatment of this ester with a mono-protected diamine would yield the corresponding amide. The protecting group on the diamine must be stable to hydrogenation conditions. The Scheme demonstrates the used of the Teoc (2-trimethylsilylethyloxycarbonyl) group, but others familiar to those skilled in the art can also be used. Reduction of the nitrile using palladium on carbon would give the linker modified cyclizing moiety.

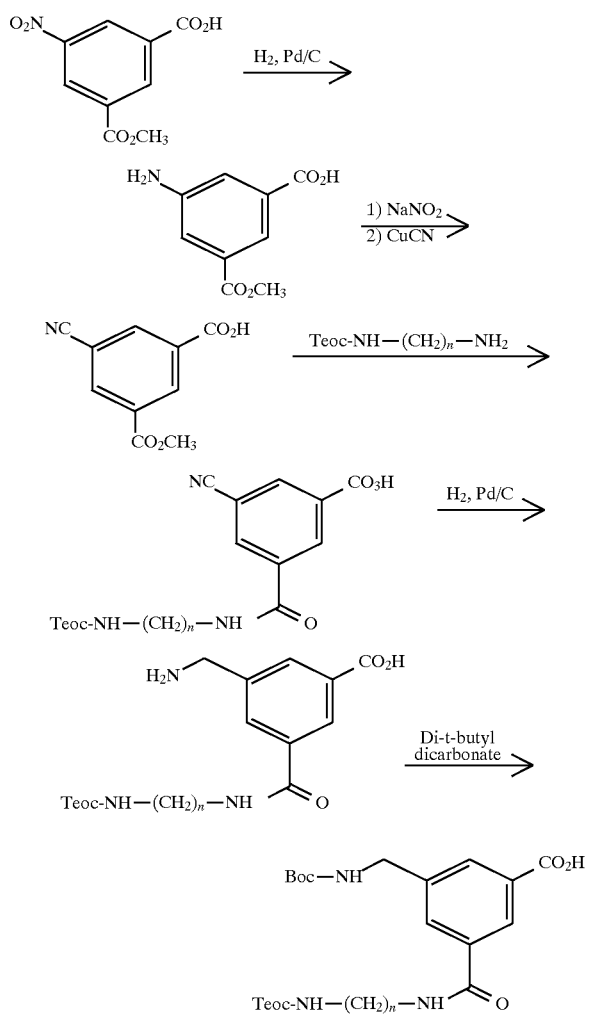

Scheme 10

Linkers attached at position Y of the ring substituted cyclizing moieties via an ether linkage can be synthesized, starting from 3-hydroxy-5-aminobenzoic acid. A Sandmeyer reaction can be used to convert the amine to a 3-hydroxy-5-cyanobenzoic acid. Alkyklation as above introduces the linker. Reduction of the nitrile using palladium on carbon catalyst would provide the aminomethyl group. Protection of the amine with the t-Boc group using di-t-butyl dicarbonate would provide linker modified cyclizing moieties ready for use in a solid phase synthesis. This is shown in Scheme 11.

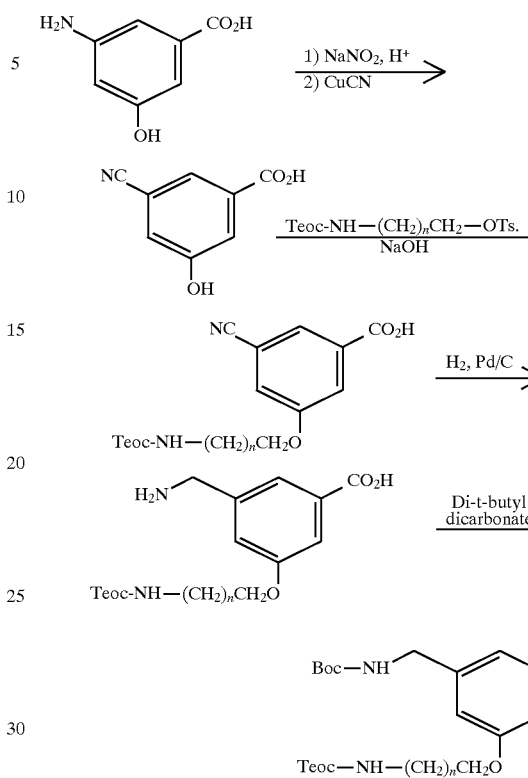

Scheme 11

Linkers terminating in a carboxylic acid group can be synthesized using cyclic anhydrides. Scheme 12 illustrates such a synthesis using succinic anhydride. Reaction of t-Boc protected methyl 3-aminomethyl-5-aminobenzoate with succinic anhydride would give the carboxylic acid linker. Activation of the carboxylic acid and condensation with benzyl carbazate (Lancaster Synthesis, Inc.) would give the protected hydrazide. This hydrazide serves to protect the carboxylic acid during the remainder of the synthesis. Hydrolysis of the methyl ester provides the linker modified cyclizing moiety in a form ready to be used in the solid phase synthesis. After synthesis is complete, removal of the Cbz protecting group from the hydrazide opens the way for the preparation of an azide and azide coupling to the chelator (Hofmann, Magee, and Lindenmann (1950) *J. Amer. Chem. Soc.*, 72, 2814). This is shown in Scheme 12.

Scheme 12

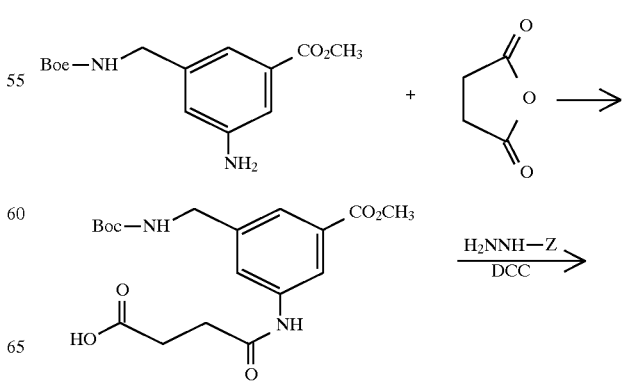

-continued
Scheme 12

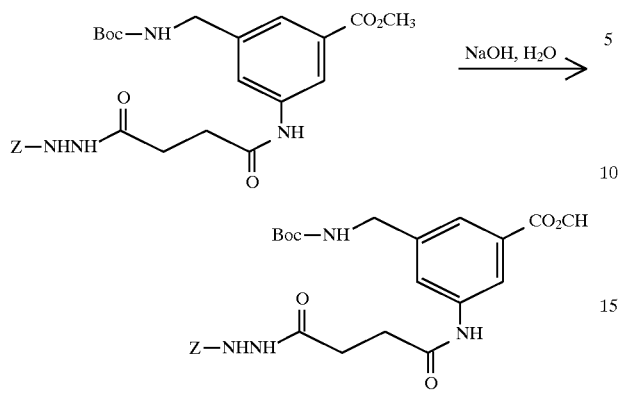

Linkers can also be incorporated into the syntheses of alternate cyclizing moieties. For example, a linker modified heterocyclic cyclizing moiety can be synthesized from 4-amino-6-carbethoxy-1-hydroxymethylpyrimidine (Boger (1994), *J. Amer. Chem. Soc.*, 116, 82–92). The alcohol would be converted to the amine in three steps. First, treatment with toluenesulfonyl chloride and base would give the tosylate, which on treatment with sodium azide would give the azide. Reduction of the azide over palladium on carbon catalyst would yield the diamine. The large difference in nucleophilicity of the two amines will allow the selective protection of the aminomethyl group using di-t-butyl dicarbonate. Attachment of a protected linker, such as Z-5-Aca, to the remaining amine would be accomplished using mixed anhydride or symmetrical anhydride chemistry. Finally, hydrolysis of the ethyl ester would give the linker modified heterocyclic cyclizing moiety ready to be coupled to solid phase synthesis resin. This is shown in Scheme 13.

Scheme 13

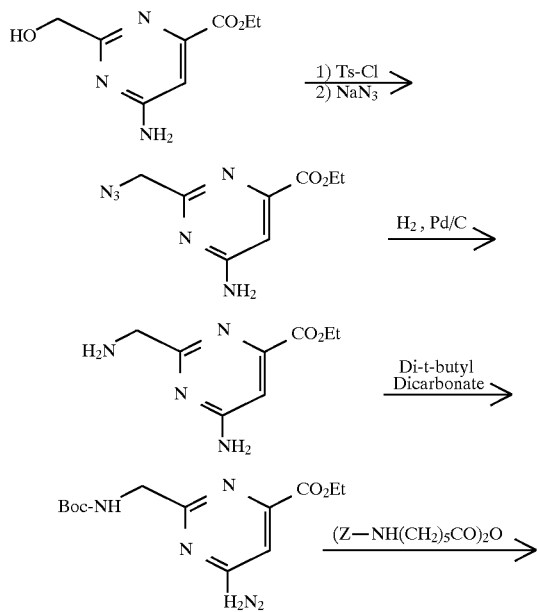

-continued
Scheme 13

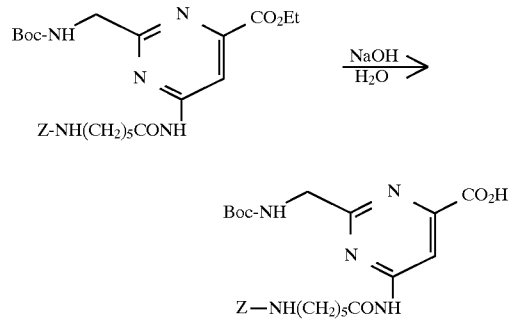

Linkers

The preparation of the tetraethylene glycol tether discussed above is shown in Scheme 14. The synthesis begins with 1-amino-11-azido-3,6,9-trioxaundecane (Bertozzi and Bednarski (1990), *J. Org. Chem.*, 56, 4326– 4329). Reduction of the azide with palladium on carbon catalyst gives the amine, which is protected with the Cbz group (designated as "Z" in Scheme 14, and thereafter). The alcohol is now converted to the tosylate using toluenesulsonyl chloride and base.

Scheme 14

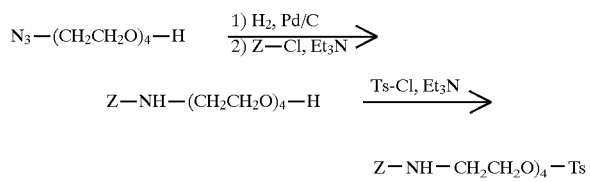

A second type of linker composed of ethylene glycol units is shown in the next Scheme. This linker bears a carboxylic acid group on one end, allowing it to be attached to cyclizing moieties containing amine functional groups. The synthesis begins with the Cbz-protected amino alcohol described above. Treatment of the alcohol with ethyl diazoacetate and rhodium(II) acetate dimer would give the e glycolic acid ester having the tetraethylene glycol tail. Hydrolysis of the ethyl ester would provide the linker ready to be coupled to the cyclizing moiety. This is shown in Scheme 15.

Scheme 15

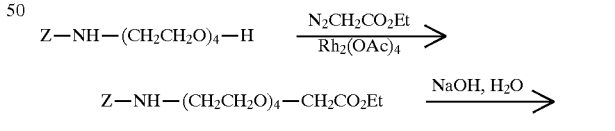

As taught below, these linker modified cyclizing moieties can be used to synthesize linker modified cylic compound intermediates.

Linker Modified Cyclic Compound 1

Cyclo-(D-Val-NMeArg-Gly-Asp-Mamb(5-Aca))

The synthesis of the title compound is depicted in Scheme 16, shown below.

To a 60 ml peptide reaction vessel was added oxime resin (1.61 g, substitution level=0.62 mmol/g). The resin was swelled by washing once with DMF (30 ml). To the reaction vessel was added Boc-Mamb(Z-5-Aca) (513 mg, 1.0 mmol), HBTU (379 mg, 1.0 mmol), and DIEA (0.52 ml, 3 mmol). The suspension was mixed at room temperature for 96 hr. The resin was washed thoroughly with 30 ml portions of DMF (3×), MeOH (1×), DCM (3×), MeOH (2×), and DCM (3×). The substitution level was determined to be 0.381 mmol/g by the picric acid test. Unreacted oxime groups were blocked by treatment with 30 ml of 0.5M trimethylacetylchloride/0.5M DIEA in DMF for 2 hours.

The following steps were then performed: (Step 1) The resin was washed with 30 ml portions of DMF (3×), MeOH (1×), DCM (3×), MeOH (2×), and DCM (3×). (Step 2) The resin was washed with 30 ml of 50% TFA in DCM, and the t-Boc group was deprotected using 30 ml of 50% TFA in DCM for 30 minutes. (Step 3) The resin was washed thoroughly with DCM (3×), MeOH (1×), DCM (2×), MeOH (3×), and DMF (3×). (Step 4) Boc-Asp(OBzl) (0.982 g, 3.04 mmol), HBTU (1.153 g, 3.04 mmol), DIEA (1.59 ml, 9.14 mmol), and DMF (14 ml) were added to the resin and the reaction was allowed to proceed for 22 hours. (Step 5) The completeness of the coupling reaction was monitored by the picric acid test. Steps 1–5 were repeated until the desired sequence had been attained.

After the linear peptide was assembled, the N-terminal t-Boc group was removed first washing with 50% TFA in DCM, followed by treatment with 30 ml of 50% TFA in DCM for 30 minutes. The resin was washed thoroughly with DCM (3×), MeOH (2×), DCM (3×), and then neutralized with 30 ml portions of 10 DIEA in DCM (2×1 min.) The resin was washed with DCM (3×) and MeOH (3×), and dried under vacuum to give 1.965 g of brown resin. The resin was cyclized by suspending in DMF (20 ml) containing HOAc (35 μl, 0.609 mmol) and heating at 50° C. for 72 hours. The resin was filtered in a scintered glass funnel and washed thoroughly with 10 ml of DMF (3×). The DMF filtrate was evaporated, and the resulting oil was redissolved in 1:1 acetonitrile:H$_2$O (20 ml), and lyophilized to give the protected cyclic peptide (342 mg). Purification was accomplished using reversed-phase HPLC with a preparative Vydac C18 column (2.1 cm) and an isocratic mobile phase of 1:1 acetonitrile:H$_2$O containing 0.1% TFA. Lyophilization of the product fraction gave purified protected peptide (127 mg).

The peptide (120 mg, 0.11 mmol) was deprotected by treating with TFA (1 ml) and triflic acid (1 ml) containing anisole (0.2 ml) for three hours at −10°C. The peptide was precipitated by the addition of ether and cooling to −35° C. for 1.5 hours. The peptide was collected by filtration, washed with ether, and dried. The resulting solid was dissolved in 1:1 acetone:H$_2$O (12 ml) and the pH is adjusted to 4–6 by treatment with Bio-Rad AG1-8× acetate ion exchange resin. The resin was filtered and washed with water. The filtrate was lyophilized to give HPLC pure peptide (75 mg, overall yield 13.5%); FAB-MS: [M+H]= 703.3951.

Scheme 16

Linker Modified Cyclic Compound 2

Cyclo-(D-Abu-NMeArg-Gly-Asp-Mamb(5-Aca))

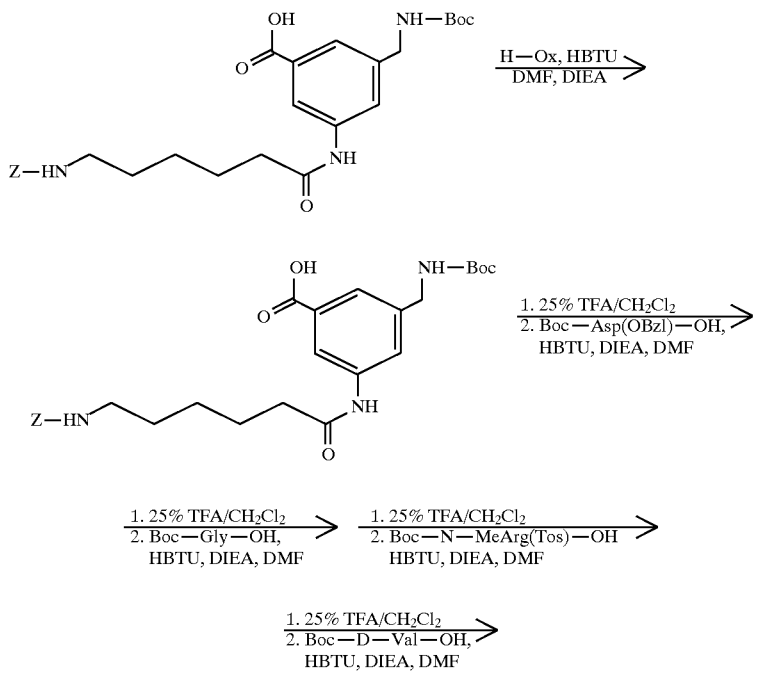

Scheme 16
Linker Modified Cyclic Compound 2
Cyclo-(D-Abu-NMeArg-Gly-Asp-Mamb(5-Aca))

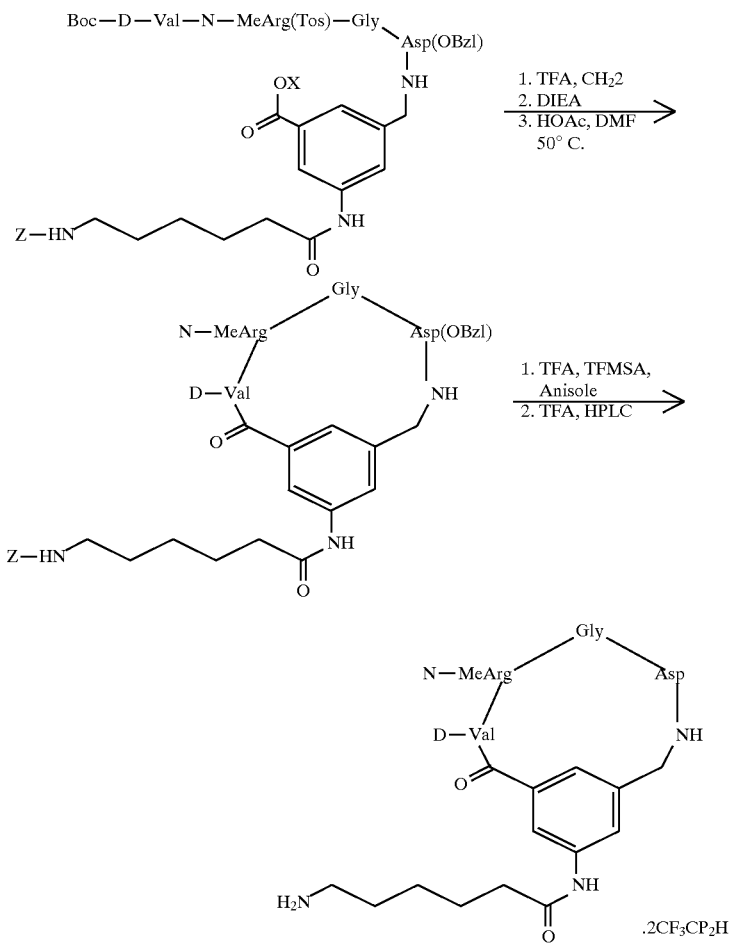

The title compound was prepared using the general procedure described for cyclo-(D-Val-NMeArg-Gly-Asp-Mamb(5-Aca)). The peptide was prepared on a 1.35 mmol scale to give the crude cyclic protected peptide (1.05 g, 73%). The peptide (500 mg) was deprotected by treating with TFA (4 ml) and triflic acid (4 ml) containing anisole (0.8 ml) for three hours at −10° C. The peptide was precipitated by the addition of ether and cooling to −35° C. for 1.5 hours. The peptide was collected by filtration, washed with ether, and dried. The resulting solid was dissolved in 1:1 acetone:$H_2O$ (50 ml) and lyophilized. Purification was accomplished by reversed-phase HPLC on a preparative Vydac $C_{18}$ column (2.1 cm) using a 0.36%/min. gradient of 9 to 18% acetonitrile containing 0.1% TFA and then lyophilized to give the TFA salt of the title compound as a fluffy colorless solid (218 mg, 69% recovery, overall yield 37%); FAB-MS: [M+H]=689.3735.

Linker Modified Cyclic Compounds 3–8

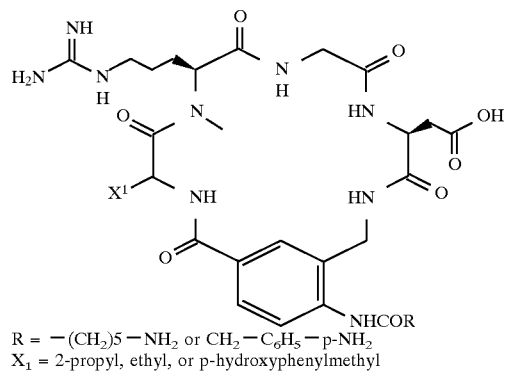

R = —$(CH_2)5$—$NH_2$ or $CH_2$—$C_6H_5$—p-$NH_2$
$X_1$ = 2-propyl, ethyl, or p-hydroxyphenylmethyl Compounds cyclo(D-Val-NMeArg-Gly-Asp-Mamb(4—NHCOR), cyclo(D-Abu-NMeArg-Gly-Asp-Mamb(4—NHCOR), and cyclo(D-Tyr-NMeArg-Gly-Asp-Mamb(4—NHCOR) can be prepared via the procedure described above.

Linkers can be incorporated into the synthesis of cyclic compound intermediates.

Linker Modified Cyclic Compounds 9,10 and 11

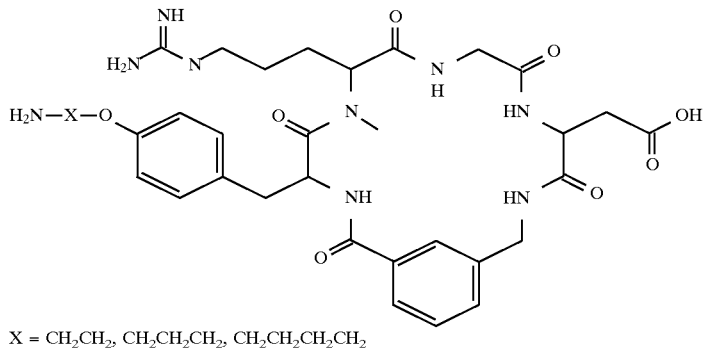

X = CH₂CH₂, CH₂CH₂CH₂, CH₂CH₂CH₂CH₂

Cyclo(O-2-aminoethyl-D-Tyr)-NMeArg-Gly-Asp-Mamb),
Cyclo(O-3-aminopropyl-D-Tyr)-NMeArg-Gly-Asp-Mamb),
Cyclo(O-4-amino-butyl-D-Tyr)-NMeArg-Gly-Asp-Mamb):

These compounds can be prepared using the procedure described above for Cyclo(D-Tyr-NMeArg-Gly-Asp-Mamb) using linker modified D-Tyr. The O-derivatized D-Tyr can be prepared via the alkylation of boc-D-Tyr with the aminoprotected 2-bromoethylamine (or 3-bromopropylamine, 4-bromobutylamine) in the presence of a base.

Linkers can also be attached to cyclic compound intermediates.

Linker Modified Cyclic Compound 12

Cyclo-(D-Lys(5-Aca)-NMeArg-Gly-Asp-Mamb)

The preparation of the title compound is depicted in Scheme 17, shown below.

A solution of cyclo-(D-Lys-NMeArg-Gly-Asp-Mamb) (100 mg, 0.12 mmol), Boc-6-aminocaproic acid hydroxysuccinimide ester (47 mg, 0.144 mmol), and Et₃N (50 µl, 0.36 mmol) in DMF (1.50 ml) was allowed to react at room temperature for 60 minutes. The progress of the reaction was monitored by normal phase TLC (90:8:2 CHCl₃:MeOH:HOAc) using the ninhydrin and Sakaguchi tests. The DMF was removed under reduced pressure. The crude conjugate was treated with TFA (3 ml) at room temperature for 45 minutes to remove the t-Boc protecting group. The TFA was removed under reduced pressure and the conjugate was purified using reversed-phase HPLC with a preparative Vydac C₁₈ column (2.1 cm) using 6% acetonitrile containing 0.1% TFA for 20 minutes, followed by a 3.0%/min. gradient of 6 to 36% acetonitrile containing 0.1% TFA and then lyophilized to give the TFA salt of the title compound as a fluffy colorless solid (80 mg, 70%); FAB-MS: [M+H]=

Scheme 17

Linker Modified Cyclic Compound 13

Cyclo-([3-(4-hydroxyphenyl)propyl-D-Lys] — NMeArg — Gly — Asp-Mamb)

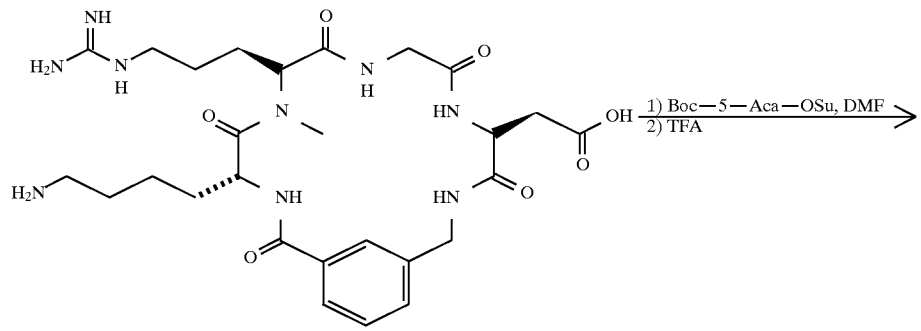

-continued
Scheme 17
Linker Modified Cyclic Compound 13
Cyclo-([3-(4-hydroxyphenyl)propyl-D-Lys]—NMeArg—Gly—Asp-Mamb)

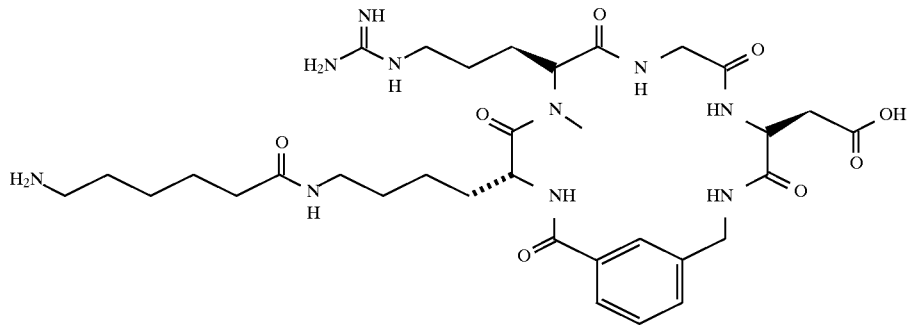

A solution of N-succinimidyl-3-(4-hydroxyphenyl) propionate (Bolton-Hunter reagent; 0.022 g, 0.08 mmol) and DIEA (0.02 ml, 0.10 mmol) in dioxane (5 ml) was added to a solution of cyclo[D-Lys-N-MeArg-Gly-Asp-MAMB] (0.026 g, 0.04 mmol) in pH 9 phosphate buffer (5 ml) and the reaction was allowed to stir for 2 days at room temperature. The solution was lyophilized and the resulting white solid was purified by reversed-phase preparative HPLC on a Vydac C-18 column (2.1 cm) using a 0.36%/min. gradient of 9 to 18% acetonitrile containing 0.1% TFA to give the product (0.018 g, 60%) as a colorless solid. MP=146°–155° C.; ESI-MS: [M]=751.

Linker Modified Cyclic Compound 14

Cyclo((N-E-Tyr-D-Lys)-NMeArg-Gly-Asp-Mamb)

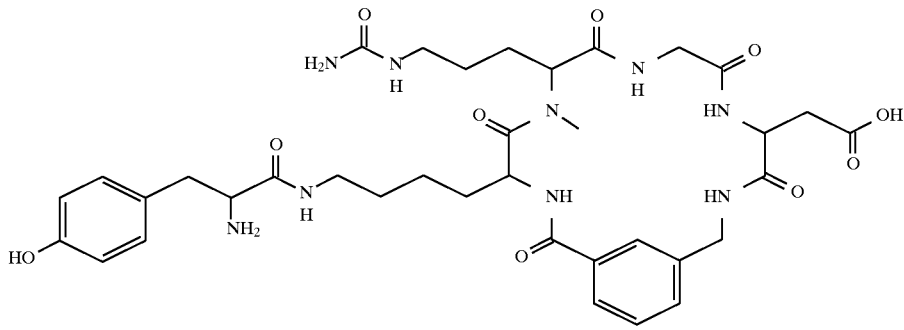

The desired compound can be prepared from the reaction of Cyclo(D-Lys-NMeArg-Gly-Asp-Mamb) with boc-Tyr-OSu in a solvent such as DMF in the presence of a base such as triethylamine, followed by deprotection.

153
Linker Modified Cyclic Compound 15

Cyclo((N-E-(4-aminophenylacetyl)-D-Lys)-
NMeArg-Gly-Asp-Mamb)

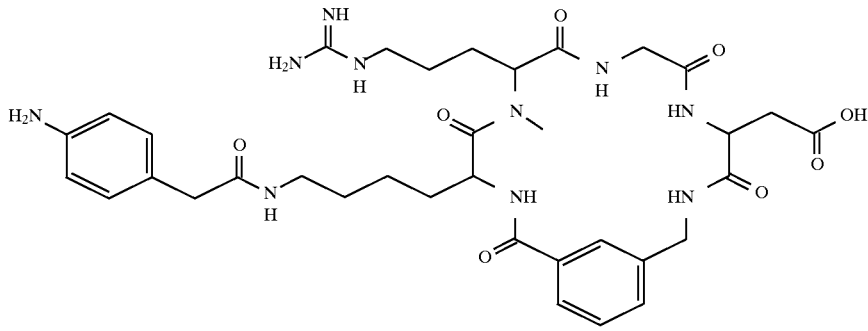

The desired compound can be prepared from the reaction of Cyclo(D-Lys-NMeArg-Gly-Asp-Mamb) with succinimidyl fmoc-4-aminophenylacetate in a solvent such as DMF in the presence of a base such as triethylamine, followed by deprotection.

Linker Modified Cyclic Compound 16

Cyclo((N-E-(4-amino-2-hydroxybenzoyl)-D-Lys)-
NMeArg-Gly-Asp-Mamb)

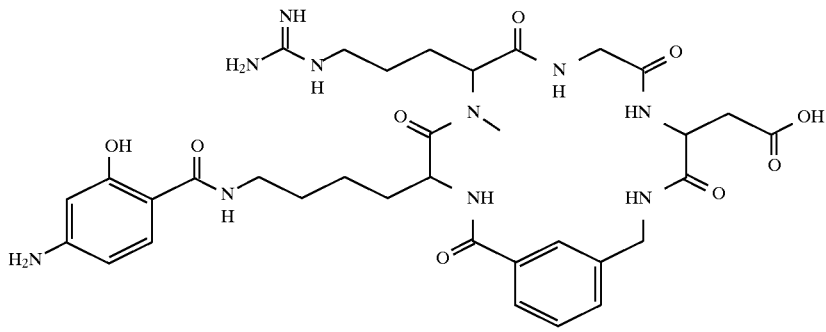

The desired compound can be prepared from the reaction of Cyclo(D-Lys-NMeArg-Gly-Asp-Mamb) with succimidyl 4-amino-2-hydroxybenzoate in a solvent such as DMF or THF in the presence of a base such as triethylamine.

A variety of linker modified cyclic compounds can be synthesized using bifunctional cross-linking reagents developed for the derivatization of proteins. These reagents consist of two electrophilic groups, such as active esters or isocyanates, separated by a spacer. The reagents can be homobifunctional, meaning that the two reactive groups are identical, or heterobifunctional. The spacer can be aliphatic or aromatic and may contain additional functionality to modify the lipophilicity of the conjugates, or to allow cleavage of the chain. The following examples will illustrate the use of several commercially available cross-linking reagents using as a starting point a cyclic compound intermediate synthesized with the 4-aminomethyl Mamb unit.

In the first example, the cyclic compound is treated with an excess of DSS (disuccinimidyl suberate, Pierce Chemical Co.) in either aqueous or organic solvent at a pH of between 7 and 9. These are typical reaction conditions for these cross-linking reagents. The excess of cross-linker minimizes the amount of dimeric species formed. The pH of 7–9 allows the amine to react at a reasonable rate but does not produce any appreciable hydrolysis of the second reactive group and prevents reaction with the guanidino group on arginine. The active ester at the end of the linker is stable enough to allow purification by HPLC or flash chromatography. Once purified, the linker modified cyclic compound can be conjugated to a chelator containing a nucleophilic group, such as an amine or thiol. This is depicted in Scheme 18.

Scheme 18

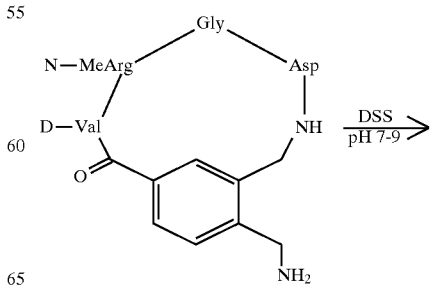

-continued
Scheme 18

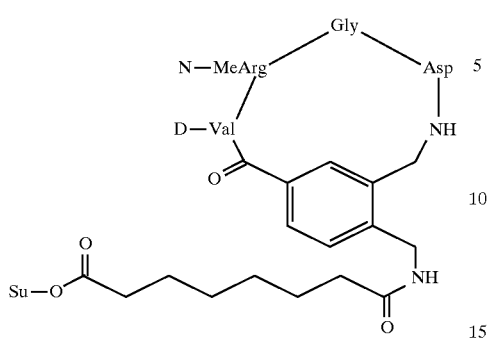

Heterobifunctional reagents are typically used to achieve very selective activatation of peptides and proteins. In the following example SMPB (succinimidyl 4-(p-maleimidophenyl)butyrate, Pierce Chemical Co.) is used to modify an amine-containing cyclic compound and prepare it for coupling to a thiol-containing chelator. Treatment of the cyclic compound with SMPB under slightly basic conditions gives the linker modified cyclic compound in which the linker terminates in a maleimido group. Selectivity is achieved because the maleimido group shows low reactivity towards amine groups, and dimerization is minimized. After purification, the maleimido group can be coupled to a thiol-containing chelator. This is depicted in Scheme 19.

Scheme 19

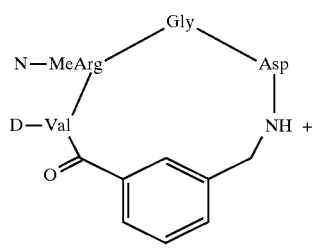

-continued
Scheme 19

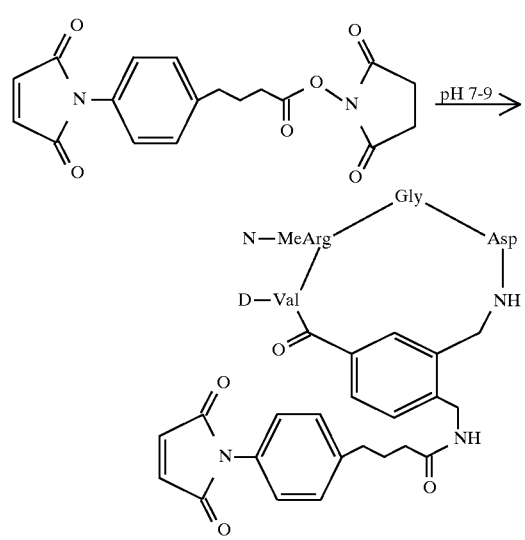

Linkers containing interior functional groups can be prepared with the reagents shown in Scheme 20. EGS (ethylene glycolbis(succinimidylsuccinimidate), Sigma Chemical Co.) is a bis-succinimidyl ester which reacts preferentially with amines. Dimethyl 3,3'-dithiobispropionimidate (DTBP, also called the Wang and Richards reagent, Pierce Chemical Co.) also reacts preferentially with amines. The disulfide is cleaved by thiols. Meares and coworkers have shown (*Int. J. Cancer:* Supplement 2, 1988, 99–102) that $^{111}$In labeled antibody-chelate conjugates joined by a disulfide-containing linker show more rapid clearance of radioactivity from mice than conjugates which did not contain a cleavable linker. The third example of Scheme 20 demonstrates the use of BSOCOES (bis[2-(succinimidooxycarbonyloxy)ethyl] sulfone, Pierce Chemical Co.), a homobifunctional cross-linker which contains an interior sulfone group. This reagent produces a carbamate group on conjugation with an amine.

Scheme 20

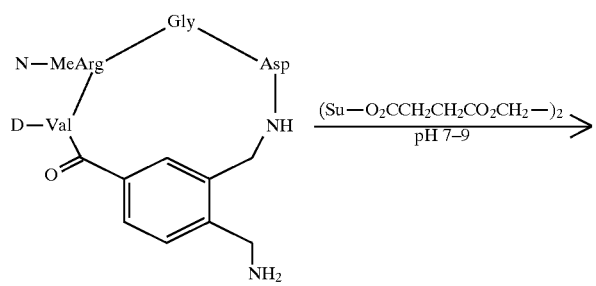

-continued
Scheme 20

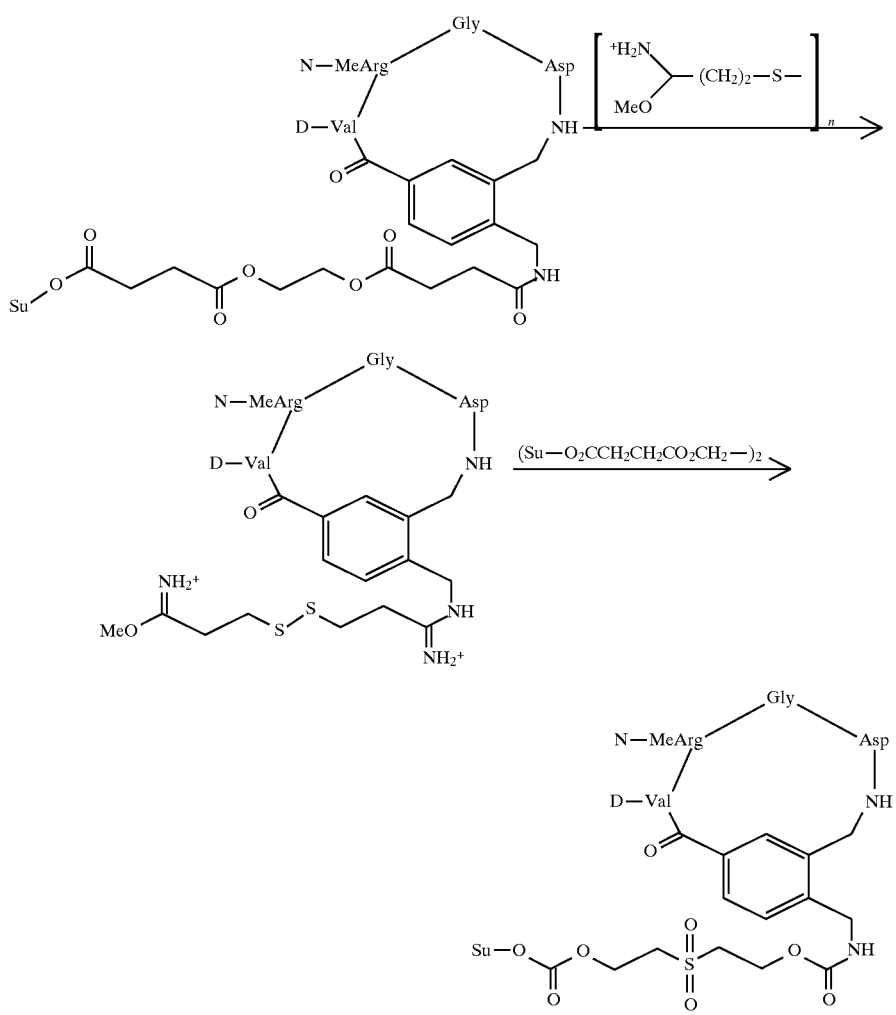

Scheme 21 illustrates the use of bisisocyanates and bisisothiocyanates in the preparation of linker modified cyclic compounds. These reagents react with amines to for urea and thiourea groups, respectively. The reagents would be used in excess to minimize the formation of dimers. The isocyanate and isothiocyanate groups at the end of the linkers are sufficiently stable to allow purification of the products.

Scheme 21

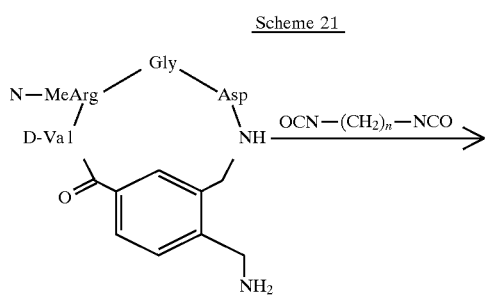

-continued
Scheme 21

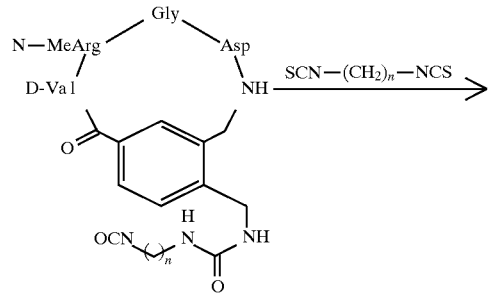

-continued
Scheme 21

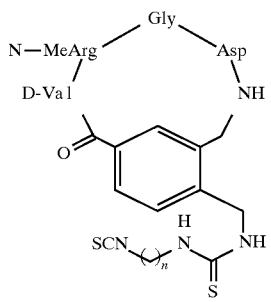

Chelators

The present invention also provides novel reagents useful for the preparation of radiopharmaceuticals. These reagents consist of a chelator, $C_h$, attached via a linking group, $L_n$, to a cyclic compound intermediate, Q. These reagents can be synthesized in several ways, either by attaching a chelator to a linker modified cyclic compound intermediate or by attaching a chelator bearing a linking group to the cyclic compound intermediate. Preferably, the chelator is attached to linker modified cyclic compound intermediate.

Any chelator can be used in this invention provided it forms a stable complex to a radioactive isotope. Typically the radioactive isotope is a metal or transition metal and the complex with the chelator is a metal chelate complex. Examples of metal chelate complexes can be found in a recent review (S. Jurisson et. al., Chem Rev., 1993, 93, 1137–1156) herein incorporated by reference.

The chelators can be attached to the linkers by a variety of means known to those skilled in the art. In general, a reactive group on the linker can react with the chelator or alternatively a reactive group on the chelator can react with the linker. Suitable reactive groups include active esters, isothiocyanates, alkyl and aryl halides, amines, thiols, hydrazines, maleimides, and the like. Several linker modified cyclic compounds bearing reactive groups are described in the examples below.

Representative chelators include: diethylenetriaminepentaacetic acid (DTPA), ethylenediamine-tetraacetic acid (EDTA), 1,4,7,10-tetraazacyclododecane-N,N',N'',N'''-tetraacetic acid (DOTA), 1,4,7,10-tetraaza-cyclododecane-N,N',N''-triacetic acid, hydroxybenzyl-ethylene-diamine diacetic acid, N,N'-bis(pyridoxyl-5-phosphate)ethylene diamine, N,N'-diacetate, 3,6,9-triaza-12- oxa-3,6,9-tricarboxymethylene-10-carboxy-13-phenyl-tridecanoic acid, 1,4,7-triazacyclononane-N,N',N''-triacetic acid, 1,4,8,11-tetraazacyclo-tetradecane-N,N'N'',N'''-tetraacetic acid, 2,3-bis(S-benzoyl)mercaptoacetamidopropanoic acid and the chelators described below. Other chelators may include metal binding regions derived from metal binding proteins such as, for example, metallothionines which are sulfhydryl-rich cytoplasmic proteins present in vertebrates, invertebrates and fungi.

Synthesis of Chelators

Synthesis of 4,5 bis((S-benzoyl)mercaptoacetamido) pentanoic acid (mapt)

The chelator was synthesized as described in Fritzberg et. al., Appl. Radiat. Isot. 1991, 42, 525–530.

Synthesis of (S-benzoyl) mercaptoacetylglycylglycylglycine (MAG₃)

The chelator was synthesized as described in Brandau, W. et al., Appl. Radiat. Isot. 1988, 39, 121–129.

Synthesis of Succinimidyl 6-Boc-hydrazinopyridine-3-carboxylate (SHNH)

The chelator was synthesized as described in Schwartz et. al., 1990, European Patent Application 90301949.5.

Synthesis of N-[4-(Carboxy)benzyl]-N,N'-bis[(2-triphenylmethylthio)ethyl]glycinamide N-hydroxysuccinimide ester The synthesis of the title compound is depicted below in Scheme 22.

Part A

S-Triphenylmethyl-2-aminoethanethiol

A solution of cysteamine hydrochloride (79.5 g, 0.7 mol) in TFA (500 ml) was treated with triphenylmethanol (182 g, 0.7 mol), and stirred at room temperature for one hour. TFA was removed under reduced pressure at a temperature of 45° C. and the resulting dark orange oil was dissolved in EtOAc (700 ml). The EtOAc solution was washed with cold 2N NaOH (3×350 ml), $H_2O$ (2×350 ml), saturated $NaHCO_3$ (350 ml), and saturated NaCl (350 ml). The combined aqueous washings were back extracted with EtOAc (350 ml). The combined organic layers were dried ($MgSO_4$) and concentrated to a yellow solid. Trituration with ether (500 ml) gave product (97.2 g, 43%) as a colorless solid, MP 90°–92° C. (D. Brenner et al., J. Inorg. Chem. 1984, 23, 3793–3797, MP 93°–94° C.). Concentration of the ether triturant to a volume of 100 ml and cooling produced an additional 40.9 g of product, MP 89°–91° C., for a combined yield of 62%.

Part B

N-2-Bromoacetyl-S-triphenylmethyl-2-aminoethanethiol

A solution S-triphenylmethyl-2-aminoethanethiol (48 g, 0.15 mol) and $Et_3N$ (20.9 ml, 0.15 mol) in DCM (180 ml) was slowly added to a stirred solution of bromoacetyl bromide (13.9 ml, 0.15 mol) in DCM (100 ml) at a temperature of −20° C. The reaction was allowed to warm to room temperature over a one hour period. The reaction was washed with 500 ml portions of $H_2O$, 0.2N HCl, saturated $NaHCO_3$, and saturated NaCl. The organic solution was dried ($MgSO_4$) and concentrated to an oil. This oil was crystallized from DCM-hexane to give product (54.9 g, 83%) as a colorless solid, MP 137°–139.5° C. (J. A. Wolff, Ph.D. Thesis, Massachusetts Institute of Technology, February 1992, MP 130°–135° C.

Part C

N,N'-Bis[(2-triphenylmethylthio)ethyl]glycinamide

A solution of N-2-Bromoacetyl-S-triphenylmethyl-2-aminoethanethiol (35.2 g, 0.08 mol), S-triphenylmethyl-2-aminoethanethiol (25.5 g, 0.08 mol), and $Et_3N$ (16.7 ml, 0.12 mol) in DCM (375 ml) was kept at room temperature for 24 hours. The solution was washed with 200 ml portions of $H_2O$ (1×), saturated $NaHCO_3$ (2×), $H_2O$ (1×), and saturated NaCl (1×), dried ($MgSO_4$), and concentrated to give a viscous oil. The oil was dissolved in 70:30 DCM:EtOAc (150 ml) and cooled in an ice bath. The solid which formed was removed by filtration. The filtrate was concentrated to a viscous oil. This oil was purified by flash chromatography over 200–400 mesh, 60 Å silica gel using 70:30 DCM:EtOAc mobile phase to give product (34.4 g, 63%) as a colorless, amorphous foamy solid. $^1H$ NMR ($CDCl_3$) 7.42–7.18 (m, 30H), 3.12–3.01 (m, 4H), 2.48–2.27 (m, 6H).

Part D

Methyl 4-(Methanesulfonylmethyl)benzoate

A solution of methyl 4-(hydroxymethyl)benzoate (10.8 g, 0.065 mol) and proton sponge (19.5 g, 0.091 mol) in DCM (200 ml) was treated with methanesulfonic anhydride (13.94 g, 0.08 mol) and stirred at room temperature for 20 hours. The reaction mixture was washed with 100 ml portions of $H_2O$ (1×), 1N HCl (2×), $H_2O$ (1×), saturated $NaHCO_3$ (1×), and $H_2O$ (1×). The organic phase was dried ($MgSO_4$) and concentrated to give 15.5 g of pale yellow solid. Recrystallization from $CCl_4$ (150 ml) using decolorizing carbon gave product (14.2 g, 90%) as colorless needles, MP 91°–94° C.

Part E

N-[4-(Carbomethoxy)benzyl]-N,N'-bis[(2-triphenylmethylthio)ethyl]glycinamide A solution of N,N'-Bis[(2-triphenylmethylthio)ethyl] glycinamide (16.27 g, 0.024 mol) and methyl 4-(methanesulfonylmethyl)benzoate (4.88 g, 0.02 mol) in ethylene dichloride (200 ml) was heated to reflux for 28 hours. The reaction was washed with 200 ml portions of saturated $NaHCO_3$ and $H_2O$, dried ($MgSO_4$), and concentrated to a light brown oil (30 g). This oil was purified by flash chromatography over 200–400 mesh, 60 Å silica gel using DCM:EtOAc mobile phase to give product (9.9 g, 60%) as a colorless, amorphous foamy solid. $^1$H NMR ($CDCl_3$) 7.90 (d, 2H, J=6.5 Hz), 7.49–7.18 (m, 32H), 3.91 (s, 3H), 3.47 (s, 2H), 3.01 (q, 2H, J=6.2 Hz), 2.88 (s, 2H), 2.43 (t, 2H, J=6.2 Hz), 2.39–2.27 (m, 4H).

Part F

N-[4-(Carboxy)benzyl]-N,N'-bis[(2-triphenylmethylthio)ethyl]glycinamide

A mixture of N-[4-(carbomethoxy)benzyl]-N,N'-bis[(2-triphenylmethylthio)ethyl]glycinamide (6.00 g, 7.26 mmol) in dioxane (65 ml) and 1N NaOH (65 ml) was stirred at room temperature for 24 hours. The mixture was acidified with 2.5M citric acid (100 ml) and the gummy precipitate which formed was extracted into EtOAc (400 ml). The EtOAc solution was washed with $H_2O$ (3×200 ml) and saturated NaCl (100 ml), dried ($MgSO_4$), and concentrated to give product (5.90 g, 100%) as a colorless, amorphous foamy solid. $^1$H NMR ($CDCl_3$) 7.96 (d, 2H, J=8.1 Hz), 7.40–7.16 (m, 32H), 3.71 (s, 3H), 3.49 (s, 2H), 3.00 (q, 2H, J=5.4 Hz), 2.91 (s, 2H), 2.44 (t, 2H, J=5.4 Hz), 2.38–2.30 (m, 4H).

Part G

N-[4-(Carboxy)benzyl]-N,N'-bis[(2-triphenylmethylthio)ethyl]glycinamide N-hydroxysuccinimide ester A solution of N-[4-(carboxy)benzyl]-N,N'-bis[(2-triphenylmethylthio)ethyl]glycinamide (450 mg, 0.55 mmol) and N-hydroxysuccinimide (76 mg, 0.66 mmol) in DCM (10 ml) was treated with a solution of WSCD.HCl (122 mg, 0.66 mmol) in DCM (7 ml) and stirred at room temperature for 22 hours. The reaction mixture was concentrated and the solids redissolved in EtOAc (60 ml). The EtOAc solution was washed with $H_2O$ (2×25 ml), 0.1N NaOH (35 ml), $H_2O$ (2×25 ml), and saturated NaCl (35 ml), dried ($Na_2SO_4$), and concentrated to give product (469 mg, 93%) as a colorless solid.

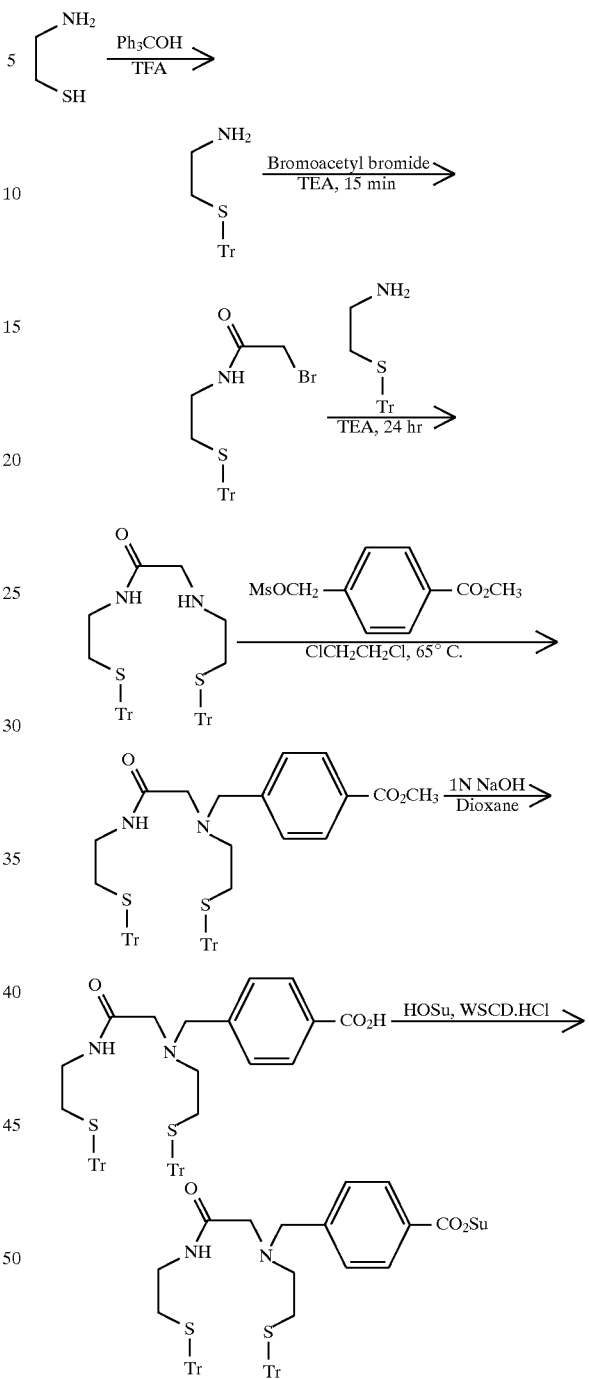

Scheme 22

The title compound was prepared according to Scheme 23 from N-(2-mercaptopropionyl)-glycine (1), which is commercially available from Aldrich. The protection of the thiol group in compound 1 is achieved by reacting with benzoyl chloride under basic conditions to give compound 2. The carboxylic group can be activated by forming its succinimide ester (3), which reacts with glycyl-g-aminobutyric acid in 90% methanol solution to give the benzoyl-protected Me-MAG$_2$-gaba (4). The spectral (IR, $^1$H NMR and FAB-MS) data are completely consistent with the proposed formulation.

Scheme 23.
Synthesis of Benzoyl-Protected Me—MAG₂—gaba

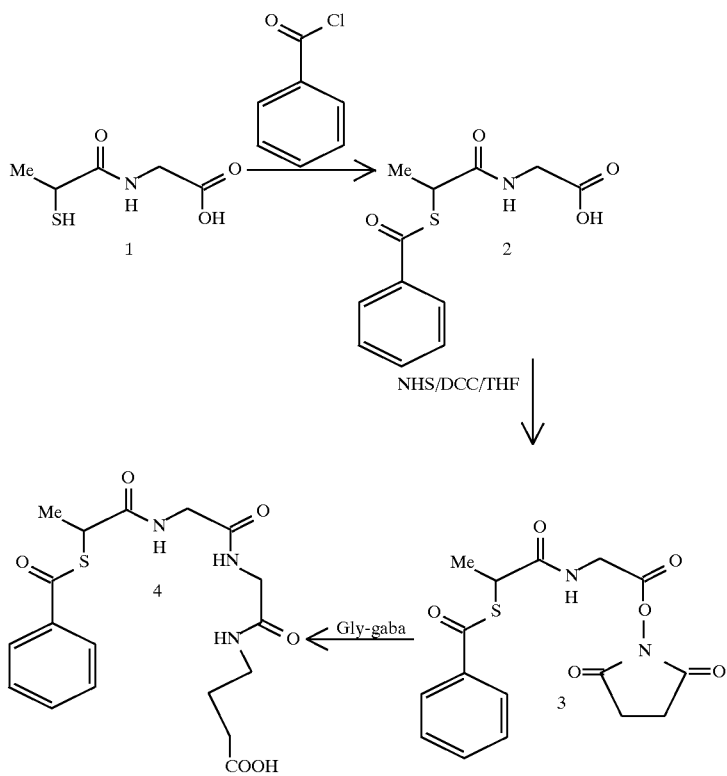

Step 1: N-[2-(benzoylthiol)propionyl]glycine (2).

Sodium hydroxide (4.5 g, 0.109 mol) and N-(2-mercaptopropionyl)glycine (8.20 g, 0.05 mol) were dissolved in a mixture of water (40 mL) and toluene (30 mL). The temperature was lowered to 5°–15° C. using an ice bath. Benzoyl chloride (4.6 mL, 0.051 mol) in toluene (10 mL) was added dropwise with vigorously stirring. After addition, the mixture was stirred at 5°–15° C. for another 30 min., and then at room temperature for 2 hr. The organic layer was separated, washed with H$_2$O (2×20 mL), and discarded. Aqueous fractions were combined and acidified to pH ~1.5 using concentrated HCl while white solid formed. The precipitate was collected by filtration, washed with H$_2$O and small amount of ethanol, and dried under vacuum. The yield was 13.0 g (97%). Anal. Calcd (found) for C$_{12}$H$_{13}$NO$_4$S: C, 53.90 (53.89); H, 4.90 (4.81); N, 5.24 (5.22). IR (KBr disk, in cm$^{-1}$): 3375 (s, n$_{N-H}$) 3200–2500 (br, n$_{O-H}$); 1745 (vs, thioester n$_{C=O}$); 1663, 1625 (vs, amide and carboxylic n$_{C=O}$). $^1$H NMR (DMSO-d$_6$, d in ppm): 1.47 (d, 3H, CH$_3$, J=7.0 Hz); 3.79 (d, 2H, CH$_2$, J=5.9 Hz); 4.40 (q, 1H, CH, J=7.0 Hz); 7.53 (m, 2H, =CH); 7.69 (m, 1H, =CH); 7.90 (dd, 2H, =CH, J=7.0 Hz); 8.59 (t, 1H NH, J=5.8 Hz); 12.6 (bs, 1H, COOH ). DCI-MS: m/z=268 ([M+H]$^+$).

Step 2: N-[2-(Benzoylthio)propionyl]glycine Succinimide Ester (3)

To a suspension of N-hydroxysuccinimide (5.80 g, 0.05 mol) and N-[2-(benzoylthiol)propionyl]glycine (13.35 g, 0.05 mol) in dry THF (400 mL) was added DCC (12.0 g, 0.052 mol) in the same solvent (100 mL THF) at 5°–10° C. The mixture was stirred at 5°–10° C. for 2 hr, and then at room temperature for 2 days. To the reaction mixture was added 2–3 mL of acetic acid and then stirred for another 2 hr. The solid was filtered off, washed with 2×150 mL of THF. The organic fractions were combined and the solvent was removed under reduced pressure to give a white solid, which was collected, washed with diethyl ether, and dried in air. The yield was 14.5 g (80%). Anal. Calcd (found) for C$_{16}$H$_{16}$N$_2$O$_6$S: C, 52.72 (52.70); H 4.43 (4.21); N, 7.69 (7.69). IR (KBr disk, in cm$^{-1}$): 3290 (s, n$_{N-H}$); 1820 (m, succinimide n$_{C=O}$); 1785 (m, ester n$_{C=O}$); 1735 (vs, thioester n$_{C=O}$); 1600 (vs, amide n$_{C=O}$). $^1$H NMR (CDCl$_3$, d in ppm): 1.57 (d, 3H, CH$_3$, J=7.0 Hz); 2.79 (s, 4H, CH$_2$); 4.33 (q, 1H, CH, J=7.0 Hz); 4.39 (m, 2H, CH$_2$); 7.00 (t, 1H, NH, J=5.8 Hz); 7.44 (m, 2H, =CH); 7.59 (m, 1H, =CH); 7.93 (dd, 2H, =CH, J=7.0 Hz). DCI-MS: m/z=365 ([M+H]$^+$).

Step 3: N-[2-(Benzoylthio)propionyl]glycylglycyl-g-Aminobutyric Acid (Bz-Me-MAG$_2$-gaba, 4)

N-[2-(Benzoylthio)-propionyl]glycine succinimide ester (1.82 g, 5 mmol) and glycyl-g-aminobutyric acid (0.80 g, 5 mmol) were suspended in a mixture of methanol (150 mL) and water (30 mL). The mixture was heated to reflux for 5 hr, during which time the cloudy mixture became a clear solution. The solution was then cooled to room temperature and was kept stirring overnight. Evaporation of solvents under reduced pressure give a white solid, which was purified by washing with water, and dried under vacuum. The yield was 1.85 g (93%). Anal. Calcd (found) for C$_{18}$H$_{23}$N$_3$O$_6$S: C, 52.78 (52.69); H, 5.66 (5.70); N, 10.27 (10.17). IR (KBr disk, in cm$^{-1}$): 3380, 3320 (s, n$_{N-H}$); 3100–2500 (br, n$_{O-H}$); 1725 (vs, thioester n$_{C=O}$); 1680, 1640, 1624 (vs, amide n$_{C=O}$). $^1$H NMR (DMSO-d$_6$, d in ppm): 1.49 (d, 3H, CH$_3$, J=7.0 Hz); 1.62 (qin, 2H, CH$_2$, J=7.1 Hz); 2.21 (t, 2H, CH$_2$COOH, J=7.5 Hz); 3.05 (qart, 2H, NH—CH$_2$, J=7.0 Hz); 3.67 (d, 2H, NH—CH$_2$, J=5.7 Hz); 3.75 (d, 2H, NH—CH$_2$, J=7.0 Hz); 4.42 (q, 1H, CH, J=7.0 Hz); 7.57 (m, 2H, =CH); 7.70 (m, 1H, =CH); 7.80 (t, 1H, NH, J=3.0 Hz); 7.90 (dd, 2H, =CH, J=7.0 Hz); 8.14 (t, 1H, NH, J=5.70 Hz); 8.57 (t, 1H, NH, J=5.90 Hz), 12.0 (bs, 1H, COOH). DCI-MS: m/z=410 ([M+H]$^+$).

Synthesis of N-[2-(Benzoylthio)propionyl] glycylglycylglycine (Bz-Me-MAG$_3$)

chloride 2, which reacted with 4-trans-aminomethylcyclohexane carboxylic acid to give compound 3. Deprotection of 3 using hydrazine in ethanol, followed by addition of HCl produces 4. Reaction of 4 with Bz-Me-MAG-Succ in methanol in presence of Et$_3$N afforded Bz-Me-MAG2-ACA 5.

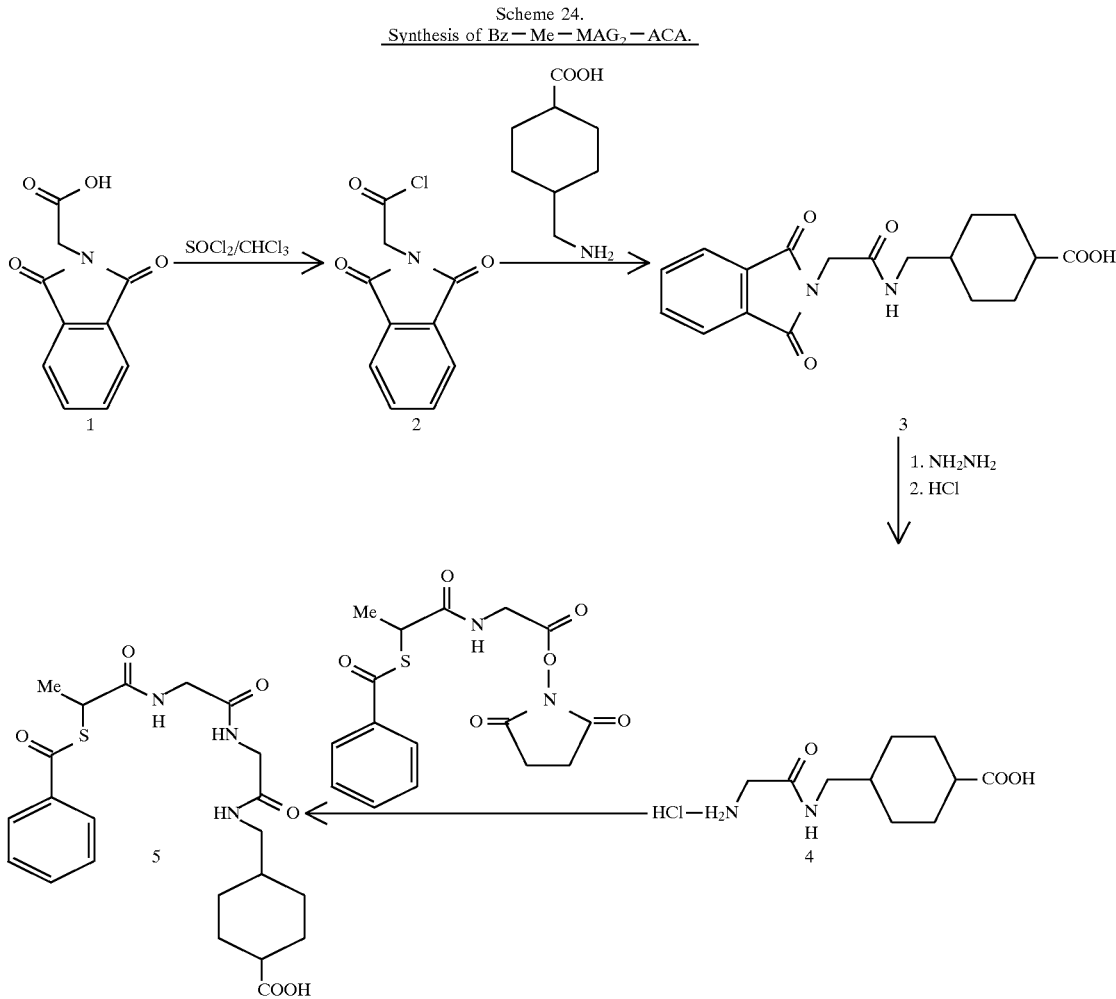

Scheme 24.
Synthesis of Bz—Me—MAG$_2$—ACA.

The title compound was synthesized as described for Bz-Me-MAG$_2$-gaba by substituting glycylglycine for glycyl-g-aminobutyric acid. The yield was 83%. Anal. Calcd (found) for C$_{16}$H$_{19}$N$_3$O$_6$S: C, 50.39 (50.59); H, 5.02 (5.78); N, 11.02 (10.70). IR (KBr disk, in cm$^{-1}$): 3380, 3300 (s, n$_{N-H}$); 3100–2500 (br, n$_{O-H}$); 1738 (vs, thioester n$_{C=O}$); 1680, 1660 (vs, amide n$_{C=O}$). $^1$H NMR (DMSO-d$_6$, d in ppm): 1.48 (d, 3H, CH$_3$, J=7.05 Hz); 3.78(m, 4H, CH$_2$); 3.85 (d, 2H, CH$_2$, J=6.00 Hz); 4.41 (m, 1H, CH); 7.52 (m, 2H, =CH); 7.70 (m, 1H, =CH), 7.90 (m, 2H, =CH); 8.15 (t, 1H, NH, J=3.00 Hz); 8.51 (t, 1H, NH, J=3.00 Hz); 8.80 (t, 1H, NH, J=3.00 Hz). FAB-MS: m/z=382 ([M+H]$^+$). ESI-MS: m/z=381.9 ([M+H]$^+$).

Synthesis of N-[2-(Benzoylthio)-propiony]glycylglycyl-4-Amino-methylcyclohexane Carboxylic Acid (Bz-Me-MAG$_2$-ACA)

Synthesis of Bz-Me-MAG2-ACA involves several steps (Scheme 24). Compound 1 could be easily converted to its Step 1: Phthaloylglycyl Chloride Phthaloylglycine (40 g) was suspended in chloroform (400 mL), followed by addition of thionyl chloride (60 mL). The mixture was heated to reflux for 2 hr, during which time the mixture became a homogeneous clear solution. The solvent and excess of thionyl chloride was removed under reduced pressure to give an off-white solid, which was dried under vacuum and used without further purification. $^1$H NMR was consistent with the proposed structure.

Step 2: 4-trans-[(Phthaloylglycyl)aminomethyl]cyclohexane Carboxylic Acid

Suspended were 4-trans-aminomethylcyclohexane carboxylic acid (7.85 g, 50 mmol) and K$_2$CO$_3$ (5 g, 50 mmol) in DMF (150 mL). To the suspension was added phthaloylglycyl chloride (11.85 g, 50 mmol) in acetonitrile (150 mL). The reaction mixture was refluxed for 3 hr and then filtered while hot. Solvents were removed under reduced pressure to give an oil. Upon addition of diethyl ether (50 mL), a white solid formed. The solid was collected by filtration, washed with diethyl ether, and dried in air. The yield was 10.32 g (60%). $^1$H NMR (in DMSO-$d_6$, d in ppm relative to TMS): 0.87–2.00 (m, 9H, $CH_2$ and CH from cyclohexane ring); 2.10 (m, 1H, CHCOOH); 2.92 (t, 2H, $CH_2$, J=4.6 Hz); 4.19 (s, 2H, $CH_2$); 7.85 (m, 4H, —CH═); 8.21 (t, 1H, NH, J=4.1 Hz).

Step 3: Glycyl-4-trans-(Aminomethyl)cyclohexane Carboxylic Acid Hydrochloride (Gly-ACA.HCl) To a suspension of 4-trans-[(Phthaloylglycyl)aminomethyl]cyclohexane carboxylic acid (10.32 g, 30 mmol) in ethanol (300 mL) was added 85% hydrazine hydrate (100 mL). The mixture was heated to reflux for 12 hr, during which time a white precipitate formed. After solvent was removed, 2N HCl (200 mL) was added to the residue. The mixture was warmed up to 60°–70 ° C. for 20 min and the solid was filtered off and discarded. The filtrate was concentrated to ⅓ of its original volume. The mixture was cooled in an ice bath for 2 hr. The precipitate was collected by filtration, washed with a small amount of water and ethanol, and dried under vacuum. The yield was 3.45 g (45%). $^1$H NMR (in $D_2O$, d in ppm relative to TMS): 1.04 (m, 2H, $CH_2$); 1.45 (m, 2H, $CH_2$); 1.57 (m, 1H CH), 1.81–2.05 (m, 4H, $CH_2$); 2.35 (m, 1H, CHCOOH); 3.15 (d, 2H, $CH_2$, J=4.9 Hz); 3.84 (s, 2H, $CH_2$).

Step 4: N-[2-(Benzoylthio)propiony]glycylglycyl-4-Aminomethylcyclohexane Carboxylic Acid (Bz-Me-$MAG_2$-ACA)

Gly-ACA.HCl (1.25 g, 5 mmol), $Et_3N$ (1.0 g, 10 mmol) and Bz-Me-MAG-Succ (1.82 g, 5 mmol) were suspended in a mixture of methanol (200 mL) and acetonitrile (100 mL). The mixture was refluxed overnight. Solvents were removed under reduced pressure to give a white solid residue, to which was added 6N HCl (10 mL). The solid was separated by filtration, washed with water and small amount of ethanol, and dried under vacuum. The yield was 1.35 g (58%). Anal. Calcd (found) for $C_{22}H_{29}N_3O_6S$: C, 57.00 (58.41); H, 6.31 (6.70); N, 9.06 (9.72). IR (KBr disk, in $cm^{-1}$): 3600–2000 (br, OH—N); 3270 (s, $n_{N-H}$); 1720, 1655, 1625, and 1565 (vs, $n_{C=O}$). FAB-MS: m/z=464 (M+1). $^1$H NMR (in DMSO-$d_6$, d in ppm relative to TMS): 0.81–1.90 (m, 9H, $CH_2$ and CH from cyclohexane ring); 1.48 (d, 3H, $CH_3$, J=5.2 Hz); 2.10 (t, 1H, CHCOOH, J=9.0 Hz); 2.91 (t, 2H, $CH_2$, J=4.6 Hz); 3.68 (d, 2H, $CH_2$, 4.2 Hz); 3.75 (d, 2H, $CH_2$, J=4.1 Hz); 4.42 (q, 1H, CH, J=5.2 Hz); 7.50 (t, 2H, —CH═, J=5.8 Hz); 7.71 (t, 2H, —CH═, J=5.4 Hz); 7.91 (d, 1H, —CH═, J=6.4 Hz); 8.14 (t, 1H, NH, J=4.2 Hz); 8.60 (t, 1H, NH, J=4.1 Hz), 12.00 (bs, 1H, COOH).

Synthesis of 3,4-Bis[3-(Benzoylthioacetyl)amido]benzoic Acid (Bz-MABA)

To a solution of S-benzoylthioacetyl chloride (8.69 g, 40 mmol), freshly prepared from the reaction of S-benzoylthioacetic acid with excess of thionyl chloride in chloroform, in dry THF (300 mL) was added 3,4-diaminobenzoic acid (3.04 g, 20 mmol) while the solution became brown. The solution was refluxed over night, during which time a precipitate formed. The mixture was cooled, and the solid was separated by filtration, washed with THF, ethanol and diethyl ether, and dried under vacuum to give a pale gray solid. The yield was 5.8 g (54%). Anal. Calcd (found) for $C_{25}H_{20}N_2O_6S_2$: C, 59.04 (58.82); H, 3.96 (4.04); N, 5.51 (5.46). IR (KBr disk, in $cm^{-1}$): 3600–2000 (br, OH—N); 3340 (s, $n_{N-H}$); 1690, 1670, 1655, 1610 and 1595 (s or m, $n_{C=O}$). FAB-MS: m/z=509 (M+1). $^1$H NMR (in $CDCl_3$, d in ppm relative to TMS): 4.12 and 4.14 (s, 4H, $CH_2$); 7.50–8.30 (m, 13H, aromatic H's); 9.85 and 9.89 (s, 2H, NH); 12.99 (bs, 1H, COOH).

Scheme 25
Synthesis of 2-(S-Triphenylmethylmercapto) ethylaminoacetyl-S-triphenylmethyl-L-cysteine ethyl ester ($Tr_2$-MA-MAMA).

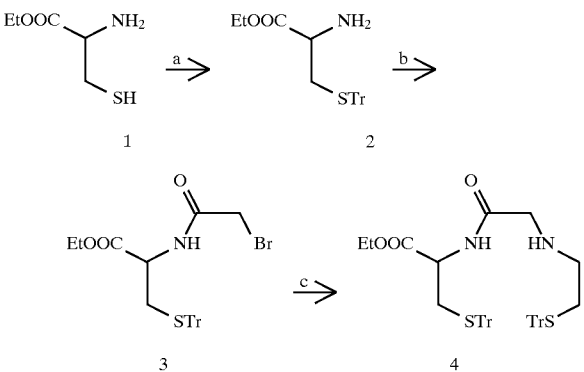

a: Triphenylmethanol, TFA; b: bromoacetyl bromide, TEA, THF; c: S-triphenylmethyl-2-aminoethanethiol, TEA, methylene chloride S-Triphenylmethyl-L-cysteine ethyl ester (2): To a solution of L-cysteine ethyl ester hydrochloride (18.6 g, 0.1 mole) in 200 mL TFA was added triphenylmethanol (52 g, 0.2 mole). The resulting dark brown solution was allowed to stir for 2 h at room temperature under nitrogen. The solvent was removed in vacuo and ethanol (100 mL) added to the residue. A 1M solution of sodium ethoxide (50 mL) was added to the ethanolic solution and stirred for 90 min. during which time the solution turned cloudy. The mixture was filtered, the filtered was concentrated in vacuo to give an oily residue. Flash column chromatography using ethyl acetate: hexane (1:3) and ethyl acetate gave the desired product (containing some ethyl acetate which is difficult to remove) which was stored under vacuum.

N-Bromoacetyl-S-triphenylmethyl-L-cysteine ethyl ester (3): A solution of S-triphenylmethyl-L-cysteine ethyl ester (18 g, 46 mmol.) and triethylamine (6.4 mL, 46 mmol.) in dry THF (250 mL) under nitrogen was cooled to 0° C. A solution of bromoacetyl bromide (9.28 g, 46 mmol.) in dry THF (60 mL) was added dropwise during which time the solution turned cloudy. The reaction mixture was stirred at 0° C. for 1 h and then at room temperature for 1 h. The reaction mixture was filtered and the filtrate was concentrated in vacuo to give an oil. The oil was partitioned between methylene chloride and water (60 mL each), the organic layer washed with 5% HCl, $NaHCO_3$, dried (magnesium sulfate), filtered, and the volatiles removed to give the desired product (69%).

2-(S-Triphenylmethylmercapto)ethylaminoacetyl-S-triphenylmethyl-L-cysteine ethyl ester (4): To a solution of N-bromoacetyl-S-Triphenylmethyl-L-cysteine ethyl ester (1.0 g, 1.98 mmol.) and triethylamine (0.4 mL, 2.9 mmol.) in methylene chloride (10 mL) was added S-triphenylmethyl-2-aminoethanethiol (0.64 g, 2.0 mmol.). The reaction mixture allowed to stir at room temperature for seven days. Water (10 mL) was added. The organic layer was washed with NaHCO3 (2×10 mL), water (2×10 mL), and brine (10 mL), dried (magnesium sulfate), and concentrated in vacuo to give a foamy product. Flash chromatography using ethyl acetate:hexane (3:1) gave the product in 22% yield. MS (M+H)=751, calculated 751.3.

The synthesis of a chelator having a single carboxylic acid group available for attaching the linker is shown in Scheme 26. The synthesis begins with the N-alkylation of Cys(Acm)

OMe with bromoacetaldehyde dimethylacetal. The secondary amine of the alkylation product is now protected from further reaction with the Teoc group. Other protecting groups which are stable to both mild acid and mild base, and can be removed in the presence of sulfur may also be used. The Teoc group is introduced by the use of 2-(trimethylsilyl)ethyl p-nitrophenyl carbonate. The acetal is now hydrolyzed with mild aqueous acid and the aldehyde is reductively aminated with S-triphenylmethyl-2-aminoethanethiol. The one free amine of the chelator is protected with the Teoc group and the methyl ester is hydrolyzed with aqueous base to give the carboxylic acid ready for reaction with the reactive group of a linker modified cyclic compound.

S-protected chelator in a form appropriate for reaction with the reactive group of a linker modified cyclic compound.

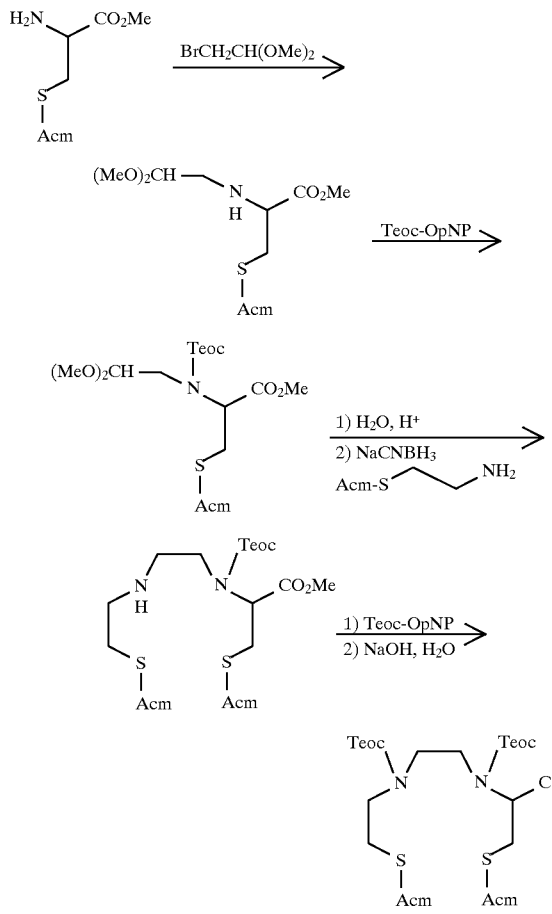

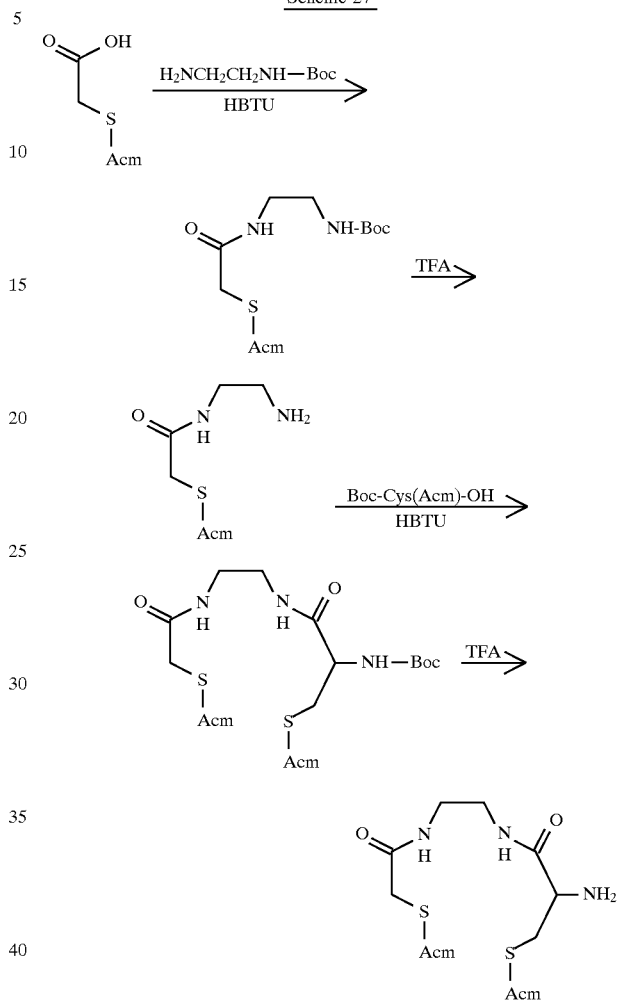

A chelator having one additional amine available for conjugation to the linker modified cyclic compound can be synthesized according to the procedure of Scheme 27. Acm protected thioglycolic acid would be coupled to N-t-butoxycarbonylethylenediamine using any of the standard coupling methods of peptide synthesis. The Boc protecting group would be removed by the use of TFA, and the resulting amine would be coupled to Boc-Cys(Acm)-OH. Removal of the Boc protecting group provides the Also subject to this invention are reagents of the formula $(QL_n)_dC_h$ for radiolabeling which comprise more than one linker modified cyclic compound intermediate attached to a chelator as well as reagents of the formula $(Q)_dL_{n-Ch}$, having two or more cyclic compound intermediates attached to a common linker that also bears a chelator.

An example of a reagent comprising two linker modified cyclic compound intermediates attached to a chelator is shown below (Schemes 28 and 29). Other representative examples are shown in the following schemes. In this scheme, amine groups on two linker intermediate compounds react with the shown two activated ester groups to afford a compound of this invention of formula $(QL_n)_2C_h$.

Scheme 28

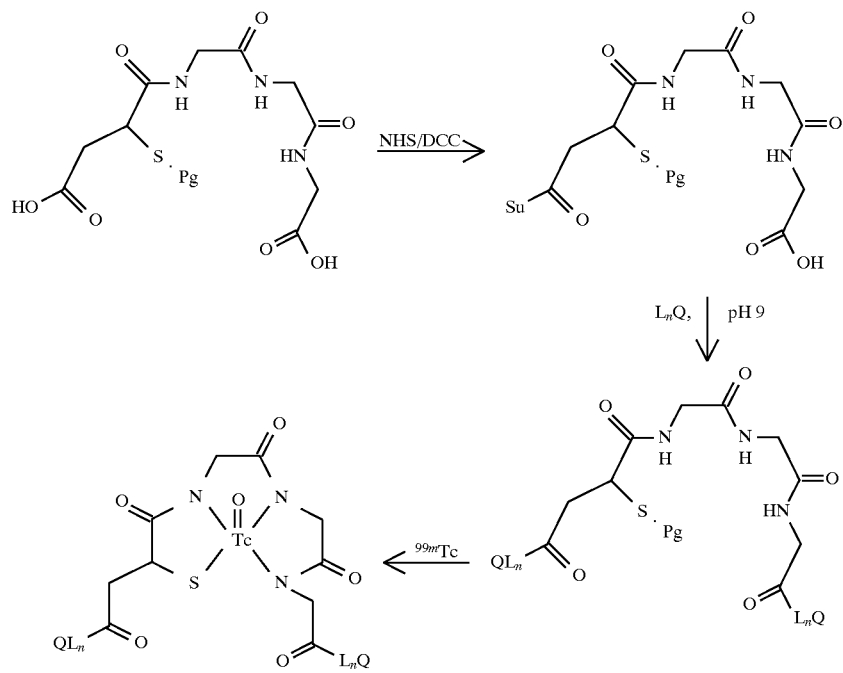

The sulfur protecting group, Pg, shown above, as well as all Pg groups claimed herein, may be any sulfur protecting group capable of being displaced upon reaction with the metal nuclide. Such protecting groups are well known by those skilled in the art. Examples of suitable protecting are taught in U.S. Pat. Nos. 4,897,255, 4,965,392, and 4,980,147, each of which is hereby incorporated herein by reference.

Scheme 29

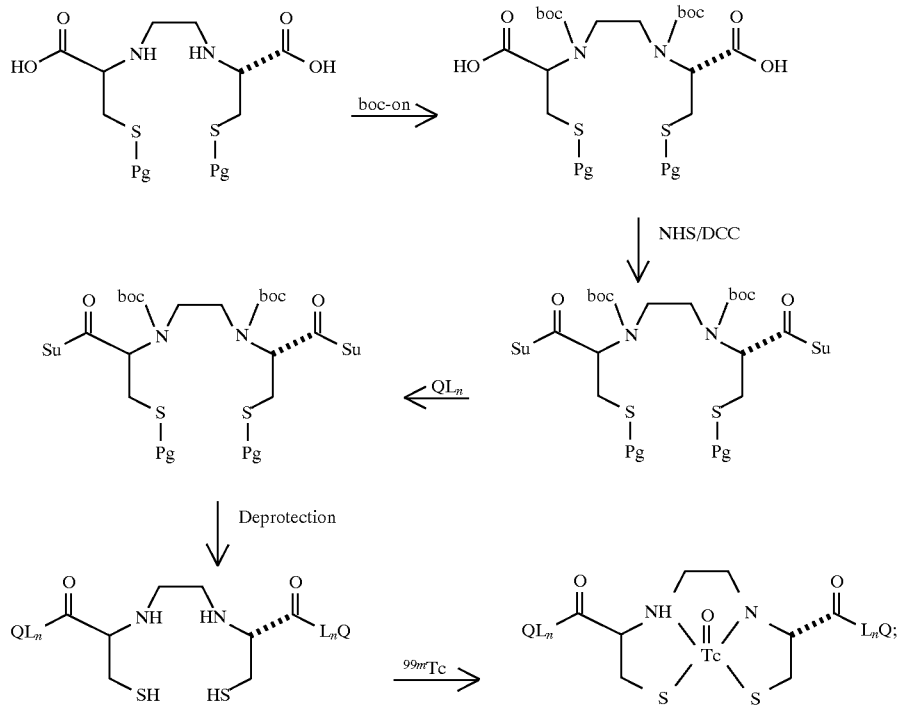

Chelators useful in the synthesis of these reagents are described in Chervu et. al., U.S. Pat. No. 4,883,862 and Bergstein et. al., U.S. Pat. No. 5,279,811. The synthesis of other useful chelators is described in the following schemes.

The following examples illustrate how three such chelators could be prepared. Scheme 30 outlines the synthesis of a $N_2S_2$ ligand having two carboxylic acid group to which the targeting cyclic compound can be conjugated. The synthesis begins with an alkylation reaction on the two amines of DL-2,3-diaminosuccinic acid (Sigma Chemical Co.), using S-triphenylmethyl-2-bromoethanethiol. The secondary amines must now be protected to avoid self-condensation when the carboxylic acids are activated. This can be accomplished with any of the standard amine protecting groups. The Z group would be a good choice because it can be removed under acidic conditions (HBr/HOAc or TFA/trifluoromethanesulfonic acid) at the same time as the trityl protection on sulfur.

Scheme 30

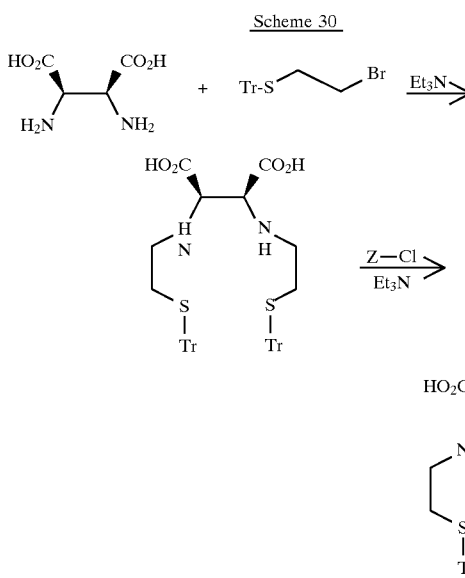

The synthesis of a second $N_2S_2$ having two carboxylic acid groups is shown in Scheme 31. Alkylation of ethylenediamine-N,N'-dipropionic acid (American Tokyo Kasei) with S-triphenylmethyl-2-bromoethanethiol would give the $N_2S_2$ ready for conjugation. The amines are tertiary and no additional protection is required.

Scheme 31

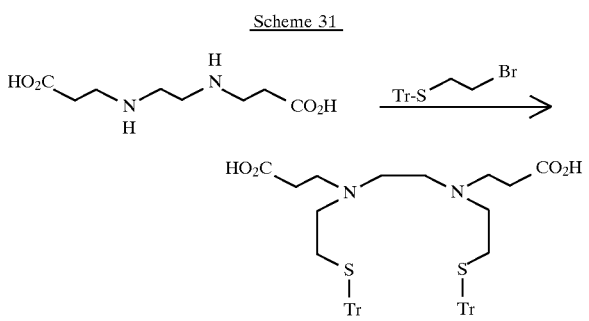

Scheme 32 outlines the synthesis of an $N_2S_2$ ligand having two additional amine groups for conjugation to targeting cyclic compounds bearing reactive electrophilic groups (e.g., active esters). A reductive amination reaction between benzyl amine and glyoxal would give N,N'-dibenzylethylenediamine. Alkylation of the two amines with N-(3-bromopropyl)phthalimide would give the fully protected tetraamine. The benzyl protection on the two secondary amines would be removed by catalytic reduction, and the free amines would then be alkylated with S-triphenylmethyl-2-bromoethanethiol to give the fully protected ligand. Selective deprotection of the primary amines would be accomplished with hydrazine.

Scheme 32

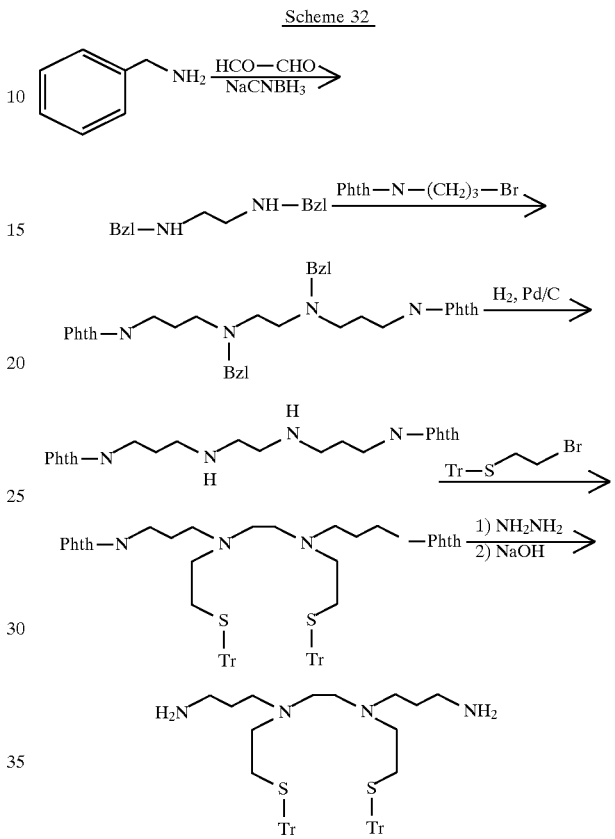

Reagents having two targeting groups and one chelator bound to a common linker can be synthesized according to the route shown in Scheme 33. Reaction of benzylamine with N-(3-bromopropyl)phthalimide will yield N,N-bis(3-phthalimidopropyl)benzylamine (Niitsu and Samejima (1986), *Chem. Pharm. Bul.*, 34, 1032–1038). Treatment with hydrazine will remove the phthalimido protecting groups. N,N-Bis(3-aminopropyl)benzylamine would then be reacted with succinic anhydride to give the diacid, which would be converted to the bis active ester with DCC and N-hydroxysuccinimide. This bis active ester would then be conjugated to a linker modified cyclic compound. Hydrogenation to remove the benzyl protecting group and conjugation with an activated chelator would yield the final product.

Scheme 33

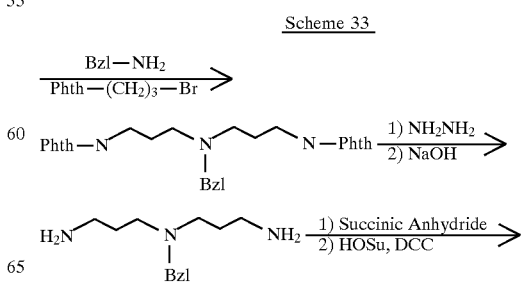

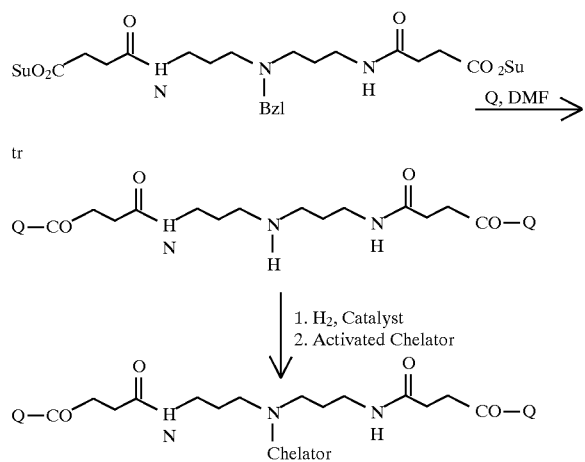

More than two compounds Q and more than one chelator can be joined together by using starburst or cascade dendrimers as linkers. Dendrimers are constructed by adding branched segments onto a functionalized core, producing a product having twice the number of functional groups as the original core. This addition of branched units can be carried through several generations to produce large polyfunctional molecules. One example is the PAMAM (polyamidoamine) dendrimers (Aldrich Chemical Co.), which use ethylenediamine as the initiator core. Scheme 34 shows the generalized preparation of a radiopharmaceutical based on PAMAM dendrimer containing targeting cyclic compounds and chelators in a 2:1 ratio. For this structure a generation=0 (n=1) dendrimer would have two targeting cyclic compounds and one chelator. A generation=1 (n=2) dendrimer would have four targeting cyclic compounds and two dendrimers. The ratio and absolute number of targeting cyclic compounds and chelators would be controlled by the stoichiometry of the conjugation reactions.

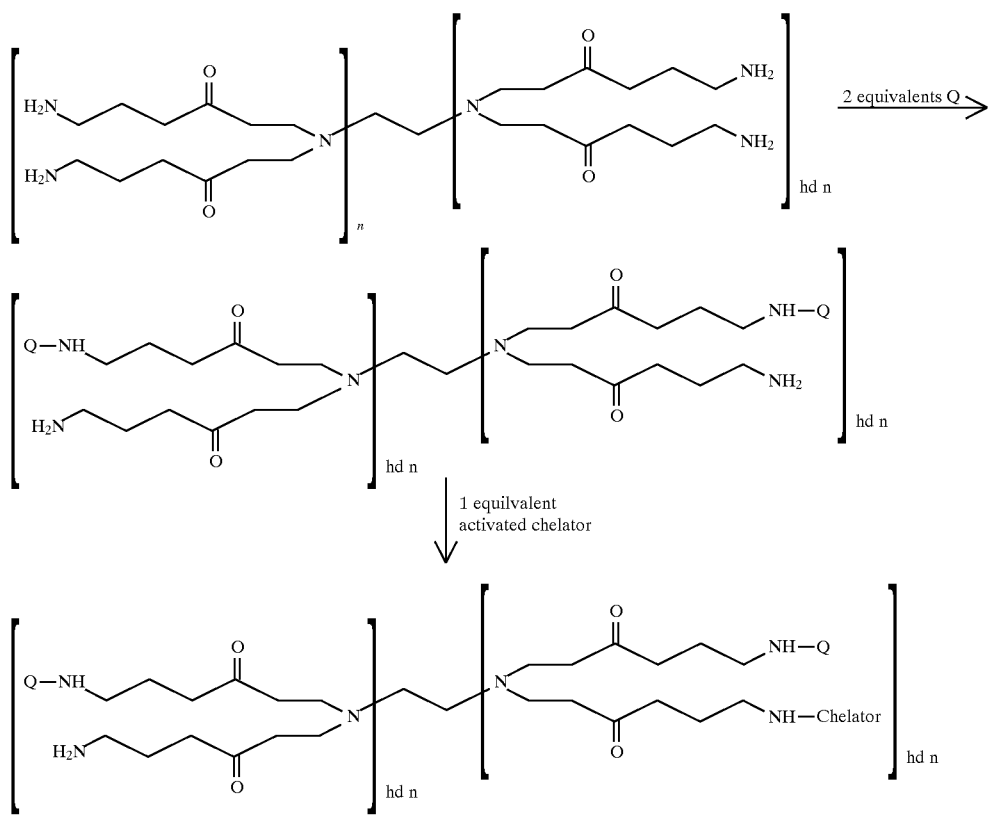

A similar system, called the multiple antigen peptide (MAP) system was developed by Posnett, McGrath, and Tam (J. Biol. Chem., 263, (1988), 1719) to facilitate the generation of antibodies. This system constructs a branching network on a solid support using the two amino groups of lysine. Because the two different amino groups on lysine can be orthogonally protected, this system allows a higher level of control of the conjugation reactions. In Scheme 35 a MAP system terminating in four lysine groups is conjugated first to four targeting cyclic compounds at the alpha amino groups, and them to four chelators at the epsilon amino groups.

Scheme 35
Synthesis of Radiolabeled Compounds

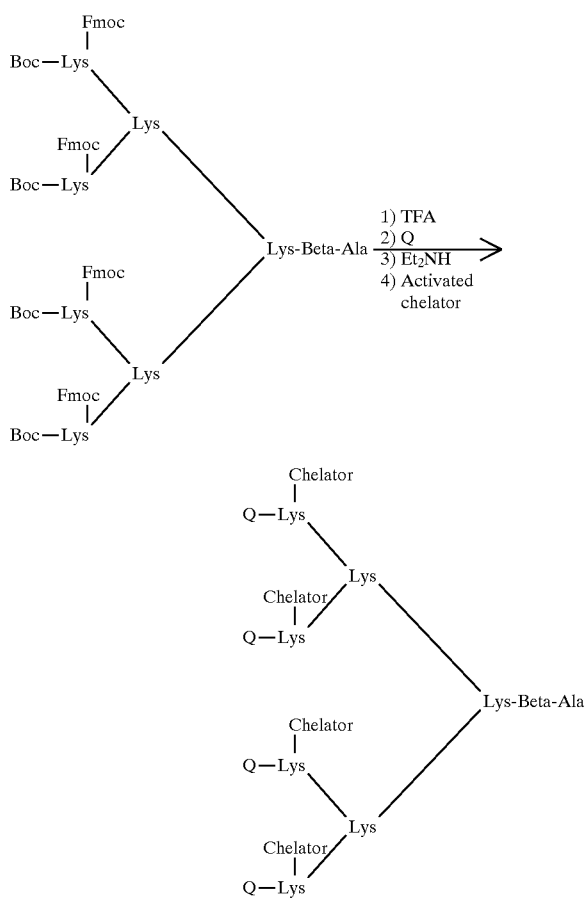

The radiolabeled cyclic platelet glycoprotein IIb/IIIa compounds of the present invention can be synthesized using standard synthetic methods known to those skilled in the art, using radioisotopes of halogens (such as chlorine, fluorine, bromine and iodine), technetium and indium, as well as others. Preferable radioisotopes include $^{123}$I, $^{125}$I, $^{131}$I, $^{99m}$Tc, and $^{111}$In.

The cyclic platelet glycoprotein IIb/IIIa compounds of the invention may be labeled either directly (that is, by incorporating the radiolabel directly into the compounds) or indirectly (that is, by incorporating the radiolabel into the compounds through a chelator which has been incorporated into the compounds. For direct labeling, as those skilled in the art will recognize, the labeling may be isotopic or nonisotopic. With isotopic labeling, one group already present in the cyclic compound is substituted with (exchanged for) the radioisotope. With nonisotopic labeling, the radioisotope is added to the cyclic compounds without substituting with (exchanging for) an already existing group.

Generally, labeled compounds are prepared by procedures which introduce the labeled atom at a late stage of the synthesis. This allows for maximum radiochemical yields, and reduces the handling time of radioactive materials. When dealing with short half-life isotopes, a major consideration is the time required to conduct synthetic procedures, and purification methods. Protocols for the synthesis of radiopharmaceuticals are described in Tubis and Wolf, Eds., "Radiopharmacy", Wiley—Interscience, New York (1976); Wolf, Christman, Fowler, Lambrecht, "Synthesis of Radiopharmaceuticals and Labeled Compounds Using Short-Lived Isotopes", in Radiopharmaceuticals and Labeled Compounds, Vol 1, p. 345–381 (1973), the disclosures of each of which are hereby incorporated herein by reference, in their entirety.

Various procedures may be employed in preparing the radiolabeled compounds of the invention where the radiolabel is a halogen. Some common synthetic methodologies for isotopic halogen labeling of aromatic compounds such as the type present here are iododediazonization, iododeborobation, iododestannylation, iododesilation, iododethallation, and halogen exchange reactions. The most common synthetic methodology for nonisotopic halogen labeling of aromatic compounds such as the type present here is iododeprotonation or electrophilic aromatic substitution reactions. These methods and additional procedures are described in Merkushev, Synthesis, 923 (1988), and Seevers et al, Chem. Rev., 82: 575 (1982), the disclosures of each of which are hereby incorporated herein by reference, in their entirety.

By way of example, isotopically radiolabeled 4, 5 and 6-halo t-butyloxycarbonyl-3-aminomethylbenzoic acid derivatives may be prepared using the general procedures described above for the synthesis of the unlabeled compounds. In carrying out such radiolabeling, it is important that the half-life of the isotope chosen be much longer than the handling time of the reaction sequences. Known starting materials include the 2, 3, and 4-iodo (123I, 125I, and 131I) benzoic acids.

The iodo-radiolabeled Mamb derivatives may also be isotopically prepared from the anilines by the Sandmeyer reaction as described in Ellis et at Aust. J. Chem., 26: 907 (1973).

Alternatively, such compounds may prepared by way of isotopic labeling from the unlabeled bromo or iodo derivatives by various two step reaction sequences, such as through the use of trialkylsilyl synthons as described in Wilson et at J. Org. Chem., 51: 483 (1986) and Wilbur et al J. Label. Compound. Radiopharm., 19: 1171 (1982), the use of trialkylsilyl synthons as described in Chumpradit et al J. Med. Chem., 34: 877 (1991) and Chumpradit et al J. Med. Chem., 32: 1431 (1989), and the use of boronic acid synthons as described in Kabalka et al J. Label. Compound. Radiopharm., 19: 795 (1982) and Koch et al Chem. Ber., 124:2091 (1991). These synthetic transformations are outlined in the Scheme 36 below.

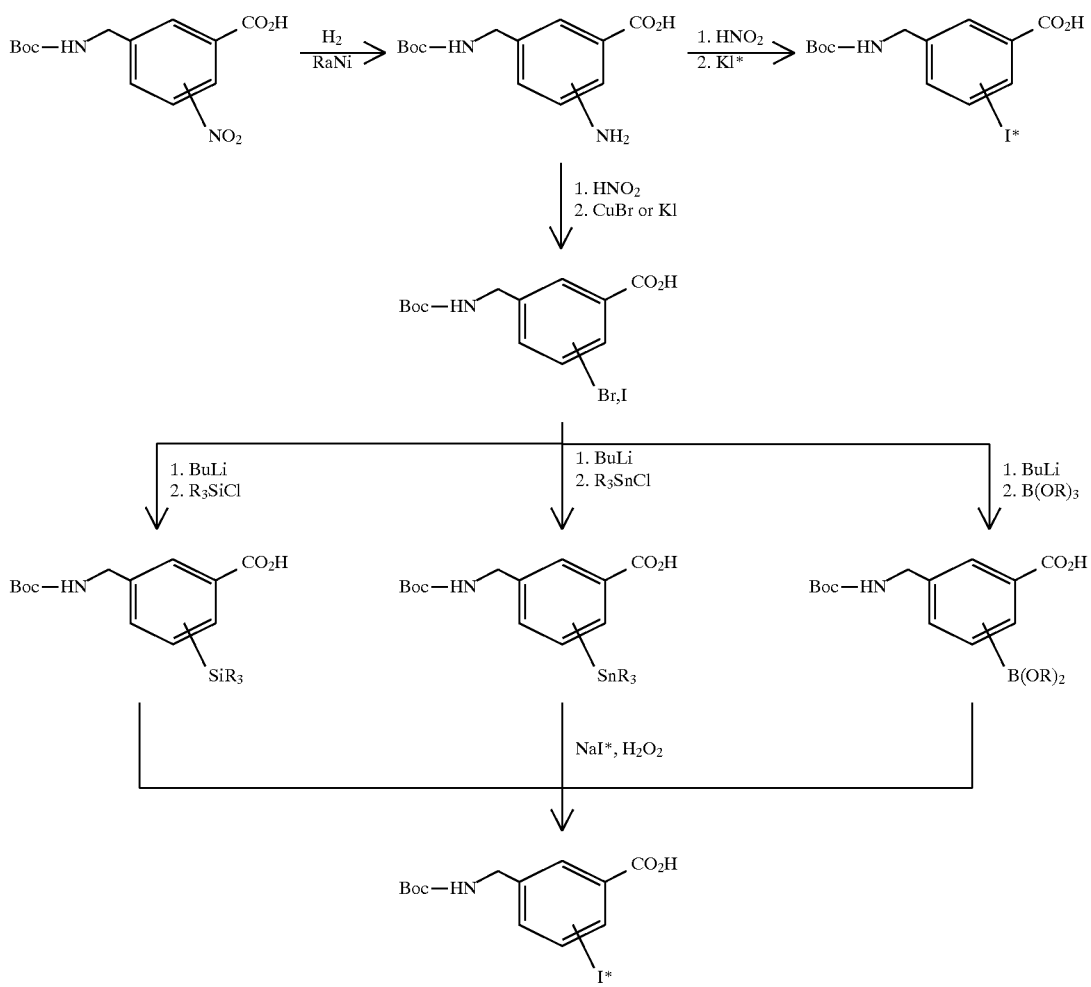

Scheme 36

Although the foregoing protocol may be employed in preparing radiolabeled compounds of the present invention, to maximize radiochemical yields, to reduce the handling time of radioactive materials, and to prepare short half-life halogen labeled compounds, it is preferable to perform the isotopic halogen labeling as one of the final steps in the cyclic compound synthesis. The following provides exemplary procedures for such late stage labeling.

The unlabeled iodo compounds are versatile precursors which can be converted to the labeled derivatives by any of the two step reaction sequences described above. Useful functionality to incorporate into the Mamb portion of the cyclic compound includes the bromo, the nitro, the trialkylsilyl, the trialkyltin, and the boronic acid groups. The synthesis and application of each of these precursors is described above.

The least complex means of radioiodination of the cyclic compounds of the present invention via isotopic labeling during the final stages of their preparation is the substitution of radioactive iodide for a stable iodine atom already present in the molecule. This can often be done by heating the compound with radioactive iodide in an appropriate solvent as described in Ellis et al., Aust. J. Chem., 26: 907 (1973). When applied to aromatic iodides, the extremely small quantities and low concentration of radioactive iodide employed leads to the incorporation of only modest specific activity. This reaction sequence is outlined in the Scheme 37.

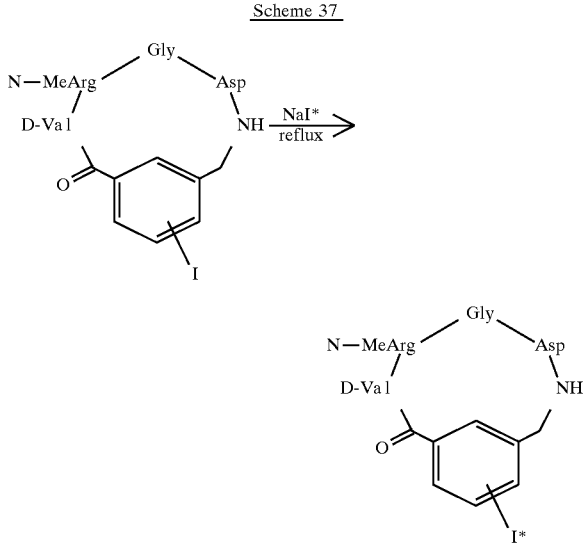

Scheme 37

The cyclic compounds may also be isotopically iodo-labeled during the final stages of their preparation from the anilines by the Sandmeyer reaction as described in Ellis et al., Aust. J. Chem., 26: 907 (1973). This approach leads to a labeled cyclic compound with high specific activity. To avoid complications in the synthesis of the cyclic compound, the nitro group provides an ideal synthon for the aniline.

Alternatively, the cyclic compounds may be isotopically labeled late in the reaction scheme from the unlabeled bromo or iodo derivatives by various two step reaction sequences, as described above, such as through the use of trialkylsilyl synthons as described in Wilson et al., J. Org. Chem., 51: 4833 (1986) and Wilbur et al., J. Label. Compound. Radiopharm., 19: 1171 (1982), through the use of trialkylsilyl synthons as described in Chumpradit et al., J. Med. Chem., 34: 877 (1991) and Chumpradit et al., J. Med. Chem., 32: 1431 (1989), and through the use of boronic acid synthons as described in Kabalka et al., J. Label. Compound. Radiopharm., 19: 795 (1982) and Koch et al., Chem. Ber., 124:2091 (1991).

A related approach where the isotopic halogen radiolabeling may be carried out late in the synthesis scheme involves converting the substituted Mamb derivatives to cyclic compounds that already incorporate the trialkylsilyl, trialkyltin, or boronic acid groups. The synthesis of each Mamb derivative has been described in an earlier section.

The forgoing synthetic transformations on the cyclic compounds are outlined in the Scheme 38.

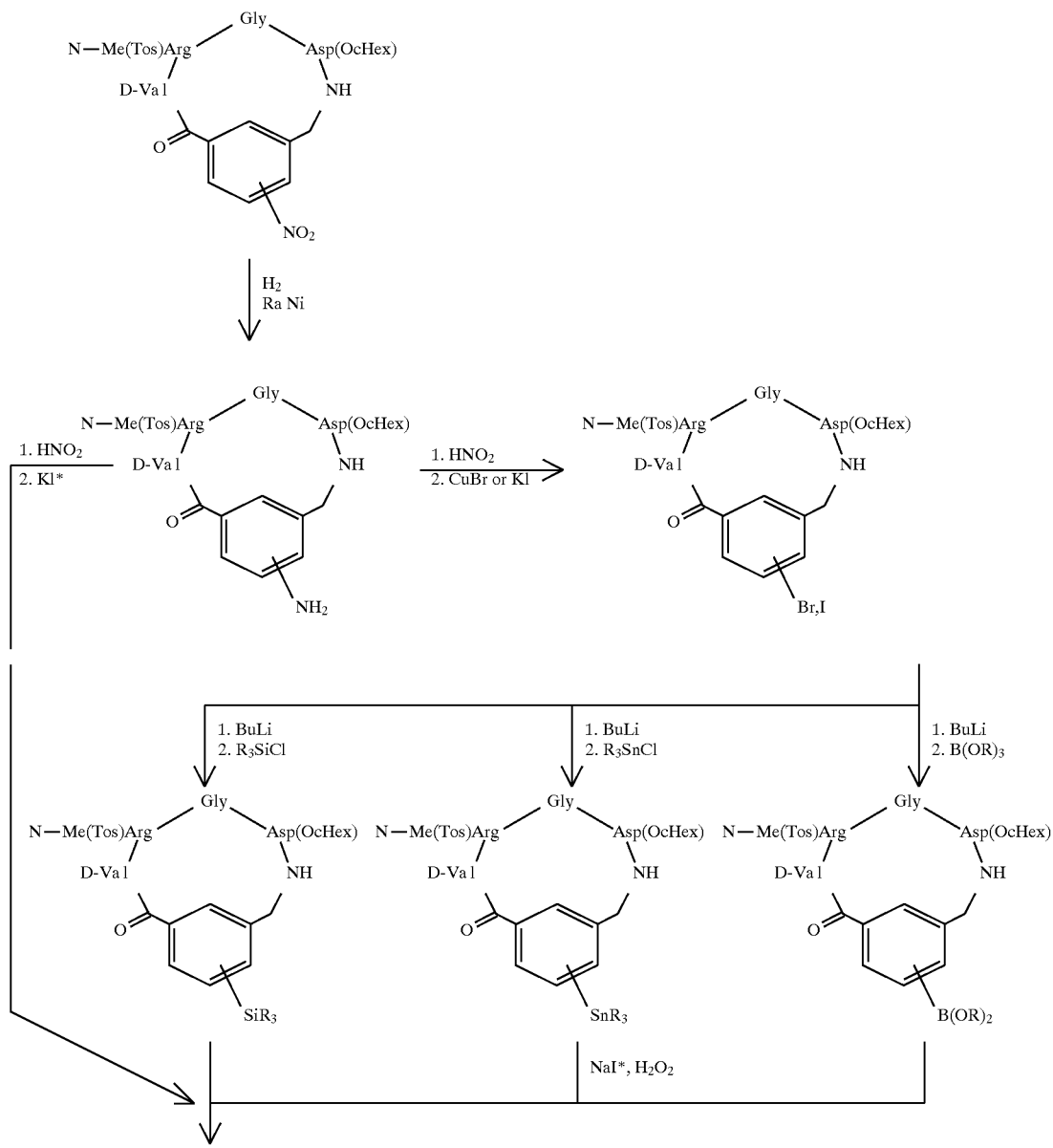

Scheme 38

-continued
Scheme 38

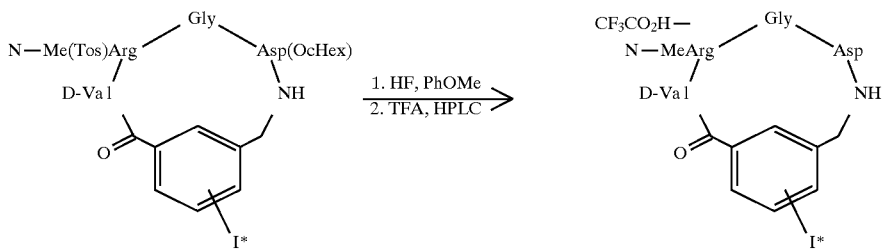

Labeled iodo derivatives may also be readily prepared nonisotopically from the amino, hydroxy, or methoxy substituted cyclic compounds as described in Arora et al J. Med. Chem., 30:918 (1987). Electrophilic aromatic substitution reactions are enhanced by the presence of such electron-donating substituents. This synthetic sequence is outlined in Schemes 39 and 40.

Scheme 39

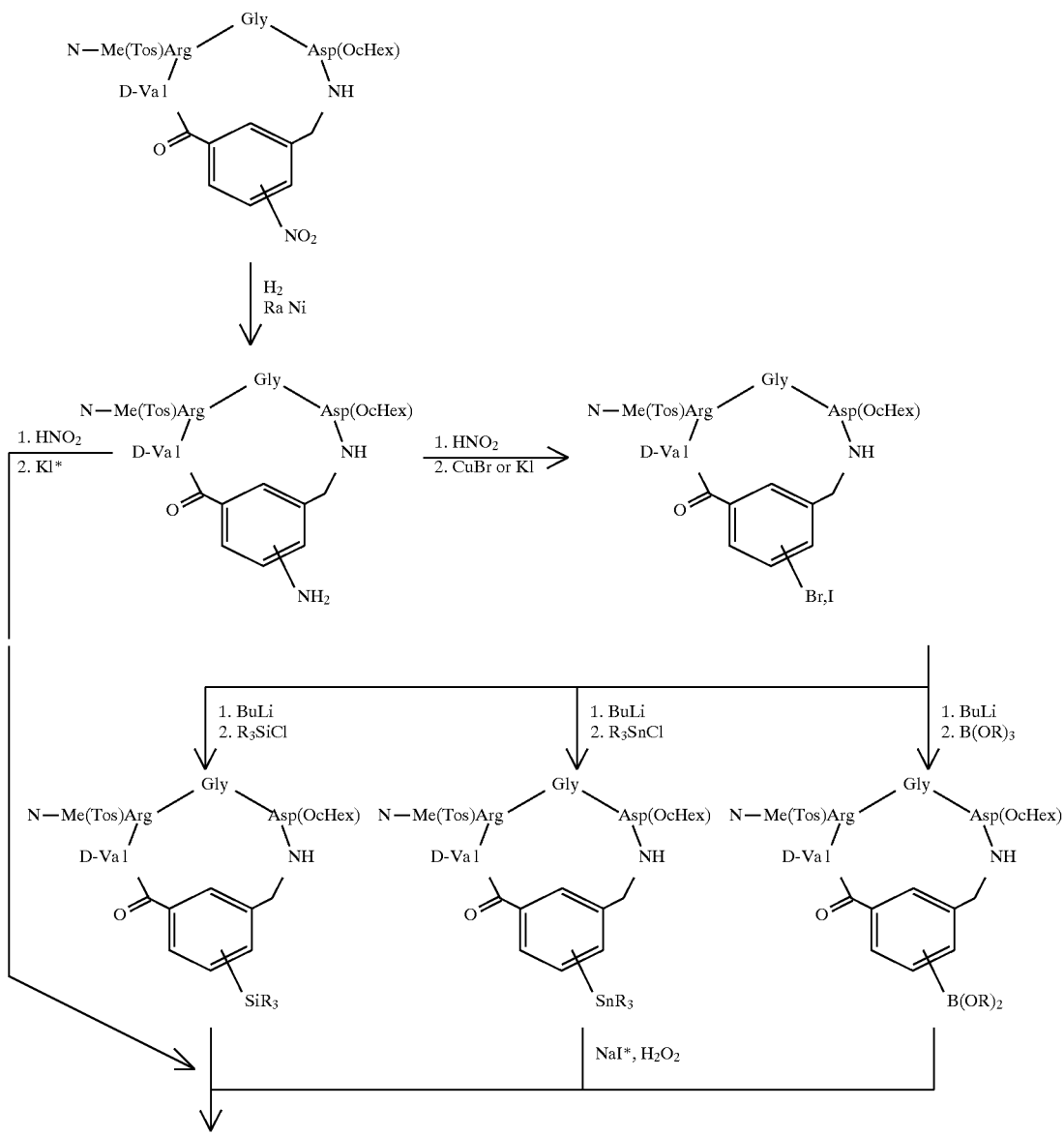

-continued
Scheme 39

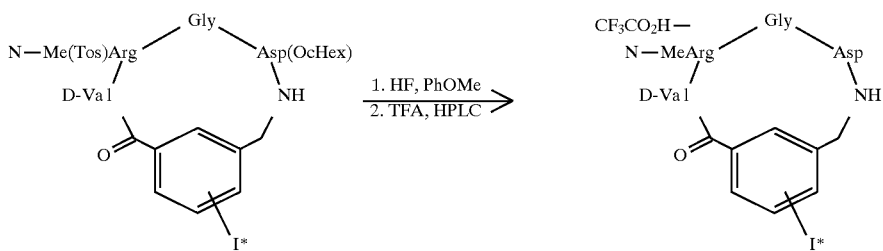

Scheme 40

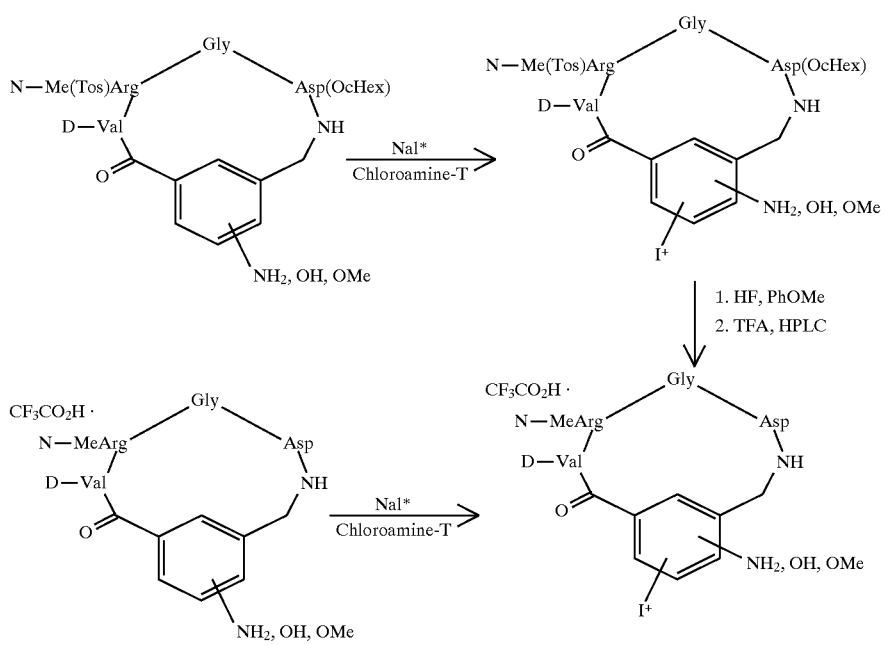

As an alternate approach to the incorporation of a radiolabeled halogen, the methyl substituted cyclic compounds may be converted to the a-halotoluene derivative with NBS or NCS under free-radical halogenation conditions. The benzylic halides may be smoothly replaced by radiolabeled iodide through a nucleophilic substitution reaction. This synthetic sequence is outlined in Scheme 41.

Although primarily illustrated for the radiolabeled iodo compounds, the above described process chemistry can be used to prepare any radioactive halogen isotope.

$^{18}F$ derivatives of these cyclic compounds can be prepared by -conjugation of $^{18}F$ functionalized phenyl intermediates. $^{18}F$-functionalized cyclic compounds can be prepared as shown in Scheme 42 (R. H. Mach et al., J. Med. Chem., Scheme 41

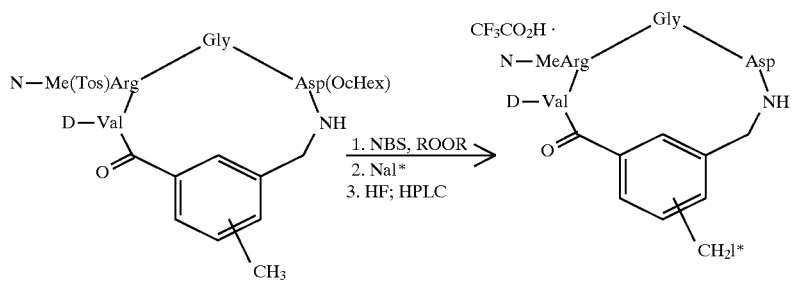

1993, 36,3707–3720). Reaction of p-trimethylammonium-benzaldehyde with [$^{18}$F]CsF/aqueous DMF at 120° C. for 10 min. (aqueous [$^{18}$F]KF/kryptofix/ACN can also be used to generate the $^{18}$F-phenyl compounds from the corresponding trimethylammonium or nitro groups), followed by LAH/THF/pentane and 57% aqueous HI gives the p-$^{18}$F-benzyl iodide.

Scheme 42

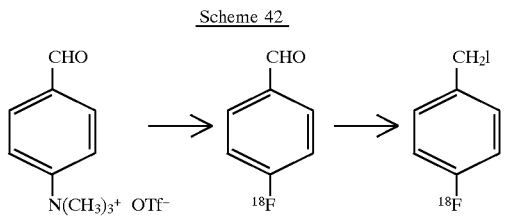

Reaction with the amine functionality of the cyclic compound intermediate cyclo(D-Lys-NMeArg-Gly-Asp-Mamb) or the linker modified cyclic compound Cyclo(D-Val-NMeArg-Gly-Asp-Mamb(5-Aca)) can give the $^{18}$F labeled products suitable for use in positron emission tomography (PET):

indium labeling are disclosed, for example, in Cerqueira et al., Circulation, Vol. 85, No. 1, pp. 298–304 (1992), Pak et al., J. Nucl. Med., Vol. 30, No. 5, p. 793, 36th Ann. Meet. Soc. Nucl. Med. (1989), Epps et al., J. Nucl. Med., Vol. 30, No. 5, p. 794, 36th Ann. Meet. Soc. Nucl. Med. (1989), Pak et al., J. Nucl. Med., Vol. 30, No. 5, p. 794, 36th Ann. Meet. Soc. Nucl. Med. (1989), and Dean et al., J. Nucl. Med., Vol. 30, No. 5, p. 794, 36th Ann. Meet. Soc. Nucl. Med. (1989), the disclosures of each of which are hereby incorporated herein by reference, in their entirety. In addition, specific procedures are provided in the examples below.

Another useful method for labeling the cyclic compounds of the present invention involves preparing a $^{99m}$Tc chelator (at the tracer level) and conjugating it to either a cyclic compound intermediate or a linker modified cyclic compound. This method is termed the prechelate approach. As shown, for example, in the scheme below, 4,5-bis(S-benzoyl)mercaptoacetamidopentanoic acid (1) is complexed with $^{99m}$TcO4 under reducing conditions to form (2). Then (2) is converted to the active ester (3) containing the tetrafluorophenyl group. Complex (3) then may be reacted

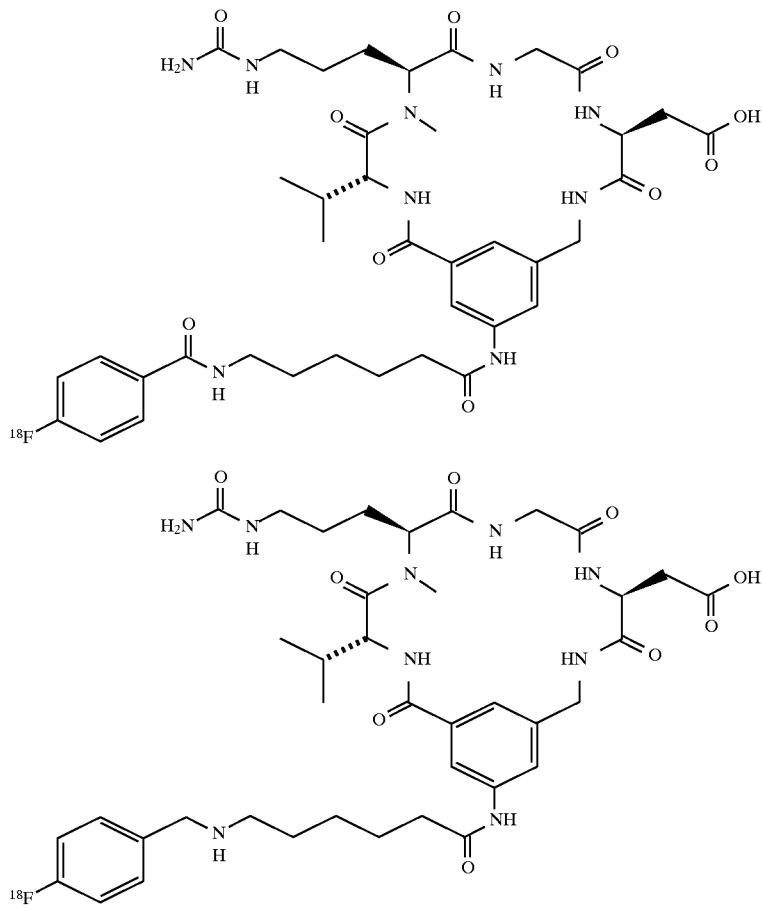

Various procedures may also be employed in preparing the radiolabeled compounds of the invention where the radiolabel is a metal, such as where the radiolabel is technetium or indium. These procedures are utilized for labeling compounds of this invention of formulae: $(QL_n)d^Ch$ and $(Q)d'L_n$—$C_h$. Exemplary procedures for such technetium or with an appropriate cyclic compound intermediate such as (5) or (6), to yield radiolabeled compounds (4). Another appropriate technetium chelator is 2,3-bis(S-benzoyl)mercaptoacetamido-propanoic acid (7). HPLC purification of the $^{99m}$Tc complex may be performed at each step. This approach is depicted in Scheme 43.

Scheme 43
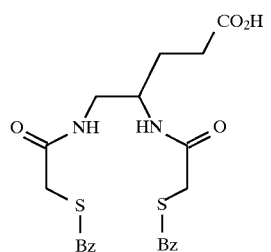
(1)  Bz = Benzoyl
$\xrightarrow{^{99m}TcO_4^-}{Na_2S_2O_4}$
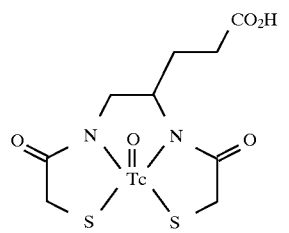
(2)
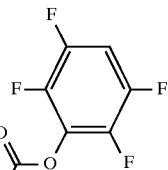
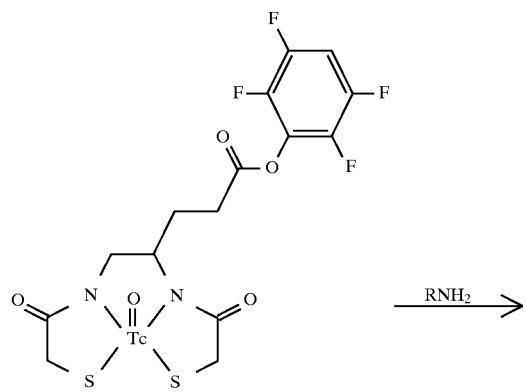
(3)
$\xrightarrow{RNH_2}$
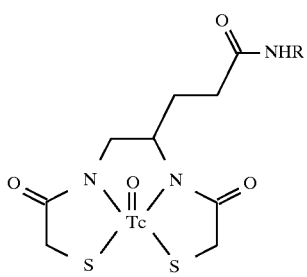
(4)

RNH₂ =

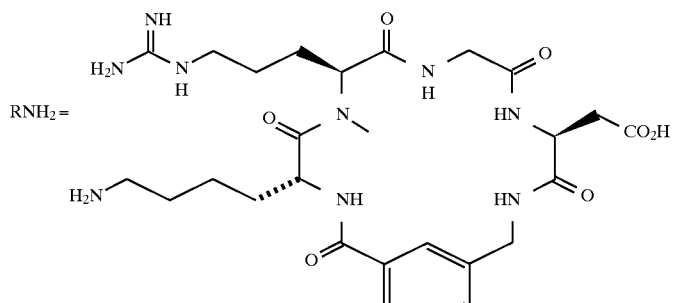

(5)

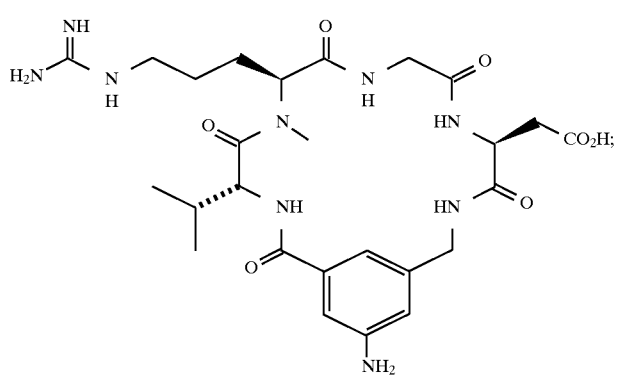

(6)

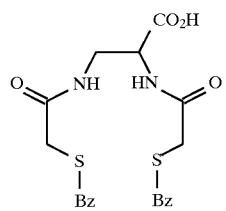

Bz = Benzoyl (7)

EXAMPLES
Section A. Reagents for Radiolabeling

Example 1

Cyclo-(D-Val-NMeArg-Gly-Asp-Mamb(5-Aca))-N-[4-(carboxy)benzyl]-N,N'-bis[(2-triphenylmethylthio)ethyl]-glycinamide Conjugate A solution of N-[4-(carboxy)benzyl]-N,N'-bis[(2-triphenylmethylthio)ethyl]glycinamide N-hydroxysuccinimide ester (0.017 mmol), cyclo-(D-Val-NMeArg-Gly-Asp-Mamb(5-Aca)) (13.9 mg, 0.015 mmol), and Et₃N (6.25 μl, 0.045 mmol) in DMF (350 μl) was allowed to stir at room temperature for 14 hours. The progress of the reaction was monitored by normal phase TLC (90:8:2 CHCl₃:MeOH:HOAc) using the ninhydrin and Sakaguchi tests. The DMF was removed under reduced pressure. The conjugate was purified using reversed-phase HPLC with a preparative Vydac C18 column (2.1 cm) using a 1.0%/min. gradient of 18 to 36% acetonitrile containing 0.1% TFA and then lyophilized to give the TFA salt of the title compound as a fluffy colorless solid (11 mg, 53%); FAB-MS: [M+H]=

Example 2

Cyclo-(D-Lys-NMeArg-Gly-Asp-Mamb)-N-[4-(carboxy)benzyl]-N,N'-bis[(2-triphenylmethylthio)ethyl]glycinamide Conjugate A solution of N-[4-(carboxy)benzyl]-N,N'-bis[(2-triphenylmethylthio)ethyl]glycinamide N-hydroxysuccinimide ester (30 mg, 0.333 mmol), cyclo-(D-Lys-NMeArg-Gly-Asp-Mamb) (23.8 mg, 0.029 mmol), and Et₃N (12 μl, 0.087 mmol) in DMF (0.60 ml) was allowed to stir at room temperature for 63 hours. The progress of the reaction was monitored by normal phase TLC (90:8:2 CHCl₃:MeOH:HOAc) using the ninhydrin and Sakaguchi tests. The DMF was removed under reduced pressure. The conjugate was purified using reversed-phase HPLC with a preparative Vydac C18 column (2.1 cm) using a 0.9%/min. gradient of 18 to 36% acetonitrile containing 0.1% TFA and then lyophilized to give the TFA salt of the title compound as a fluffy colorless solid (24 mg, 60%); ESI-MS: [M]=1397.3.

Example 3

Cyclo(D-Val-NMeArg-Gly-Asp-Mamb(N-hydrazino-nicotinyl-5-Aca)) TFA salt

Part A. Synthesis of Cyclo(D-Val-NMeArg-Gly-Asp-Mamb(N-boc-hydrazino-nicotinyl-5-Aca)) TFA salt To a solution of cyclo(D-Val-NMeArg-Gly-Asp-Mamb (5-Aca) (10 mg, 0.011 mmol), succinimidyl boc-hydrazinonicotinate (4.6 mg, 0.0132 mmol) in DMF (0.3 mL) was added triethylamine (0.0061 mL, 0.044 mmol) and the reaction stirred at room temperature under nitrogen for 24 hours. The solvent was removed in vacuo and the residue dissolved in a solution of acetonitrile-water and lyophilized overnight to give an off-white solid. Purification of part of the product was accomplished by reversed-phase HPLC on a preparative Vydac C-18 column using a 2.0%/min. gradient of 6.3–72% aqueous acetonitrile containing 0.1% TFA and lyophilized to give the TFA salt of the title compound as a fluffy solid. MS (M+H=938.4849, calc. 938.4848).

Part B. Deprotection to Cyclo(D-Val-NMeArg-Gly-Asp-Mamb(N-hydrazino-nicotinyl-5-Aca)) TFA salt Cyclo(D-Abu-Val-NMeArg-Gly-Asp-Mamb(N-boc-hydrazinonicotinyl-5-Aca) TFA salt was dissolved in a mixture of 98:2 TFA:anisole (2 mL) and the reaction mixture stirred for 15 min. The solvent was removed in vacuo and the residue dissolved in a solution of acetonitrile-water and lyophilized to give a white solid. Purification was accomplished by reversed-phase HPLC on a preparative Vydac C-18 column using a 2.0%/min. gradient of 6.3–72% aqueous acetonitrile containing 0.1% TFA and lyophilized to give the TFA salt of the title compound as a fluffy solid. MS (M+H=838.4324, calc. 838.4324).

Example 4

Cyclo(D-Abu-NMeArg-Gly-Asp-Mamb(N-hydrazino-nicotinyl-5-Aca)) TFA salt

Part A. Synthesis of Cyclo(D-Abu-NMeArg-Gly-Asp-Mamb(N-bac-hydrazino-nicotinyl-5-Aca)) TFA salt To a solution of cyclo(D-Abu-NMeArg-Gly-Asp-Mamb (5-Aca) TFA salt (10 mg, 0.0109 mmol), succinimidyl boc-hydrazinonicotinate (4.55 mg, 0.0131 mmol) in DMF (0.4 mL) was added triethylamine (0.0061 mL, 0.044 mmol) and the reaction stirred at room temperature under nitrogen for 24 hours. The solvent was removed in vacuo and the residue dissolved in a solution of acetonitrile-water and lyophilized overnight to give an off-white solid. Purification of part of the product was accomplished by reversed-phase HPLC on a preparative Vydac C-18 column using a 2.0%/min. gradient of 6.3–72% aqueous acetonitrile containing 0.1% TFA and lyophilized to give the TFA salt of the title compound as a fluffy solid. MS (M+H=924.4699, obs. calc.; 924.4692).

Part B. Deprotection to Cyclo(D-Abu-NMeArg-Gly-Asp-Mamb(N-hydrazino-nicotinyl-5-Aca)) TFA salt Cyclo(D-Abu-NMeArg-Gly-Asp-Mamb(N-hydrazinonicotinyl-5-Aca)) TFA salt: Cyclo(D-Abu-NMeArg-Gly-Asp-Mamb(N-boc-hydrazinonicotinyl-5-Aca)) TFA salt was dissolved in a mixture of 98:2 TFA:anisole (2 mL) and the reaction mixture stirred for 15 min. The solvent was removed in vacuo and the residue dissolved in a solution of acetonitrile-water and lyophilized to give a white solid. Purification was accomplished by reversed-phase HPLC on a preparative Vydac C-18 column using a 2.07%/min. gradient of 6.3–85.5% aqueous acetonitrile containing 0.1% TFA and lyophilized to give the TFA salt of the title compound as a fluffy solid. MS (M+H=xx, calc. xx).

Example 5

Cyclo((N-E-hydrazinonicotinyl-D-Lys)-NMeArg-Gly-Asp-Mamb) TFA salt

Part A. Synthesis of Cyclo((N-E-boc-hydrazinonicotinyl-D-Lys)-NMeArg-Gly-Asp-Mamb) TFA salt To a solution of cyclo(D-Lys-NMeArg-Gly-Asp-Mamb) .2TFA (4.2 mg, 0.005 mmol), succinimidyl boc-hydrazinonicotinate (2.1 mg, 0.006 mmol) in DMF (0.15 mL) was added triethylamine (0.003 mL, 0.02 mmol) and the reaction stirred at room temperature under nitrogen for 48 hours. The solvent was removed in vacuo and the residue dissolved in a solution of acetonitrile-water and lyophilized overnight to give an off-white solid. Purification was accomplished by reversed-phase HPLC on a preparative Vydac C-18 column using a 1.7%/min. gradient of 6.3–85.5% aqueous acetonitrile containing 0.1% TFA and lyophilized to give the TFA salt of the title compound as a fluffy solid. MS (M+H=839.4157, calc. 839.4164).

Part B. Deprotection to Cyclo((N-E-hydrazinonicotinyl-D-Lys)-NMeArg-Gly-Asp-Mamb) TFA salt Cyclo((N-E-hydrazinonicotinyl-D-Lys)-NMeArg-Gly-Asp-Mamb) TFA salt: Cyclo((N-E-boc-hydrazinonicotinyl-D-Lys)-NMeArg-Gly-Asp-Mamb) TFA salt (3 mg) was dissolved in a mixture of 98:2 TFA:anisole (2 mL) and the reaction mixture stirred for 15 min. The solvent was removed in vacuo and the residue dissolved in a solution of acetonitrile-water and lyophilized to give a white solid. Purification was accomplished by reversed-phase HPLC on a preparative Vydac C-18 column using a 2.0%/min. gradient of 6.3–72% aqueous acetonitrile containing 0.1% TFA and lyophilized to give the TFA salt of the title compound as a fluffy solid. MS (M+H=739.3629 obs., calc.; 739.3640).

Example 6

Cyclo-([DTPA-D-Lys]-NMeArg-Gly-Asp-Mamb) Conjugate

To a solution of 250 mg (2 mmol.) of cyclo(D-Lys-NMeArg-Gly-Asp-Mamb) in 208 mL of 0.1M Borate (pH 9.88) at room temperature was added DTPA anhydride (743 mg, 10 mmol.) with constant stirring. The reaction was allowed to stir for 2 h. The crude mixture of products obtained after removal of the solvent was purified by preparative HPLC (Vydac $C_{18}$ column, gradient of 0–50% ACN containing 0.1% TFA over 60 min., flow rate 20 mL/min). Two major components were isolated. Component A is Cyclo-([DTPA-D-Lys]-NMeArg-Gly-Asp-Mamb). MS: 979.1 (M+H$^+$)

Example 7

[Cyclo-(D-Lys-NMeArg-Gly-Asp-Mamb)]$_2$—DTPA Conjugate

Component B from the synthesis described in Example 6 is [Cyclo-(D-Lys-NMeArg-Gly-Asp-Mamb)]$_2$—DTPA. MS: 1565.4 (M$^+$)

Section B. Radiolabeled Compounds
Direct Labeling

Example 8

Cyclo-(($^{125}$I)D-Tyr-NMeArg-Gly-Asp-Mamb)

To a 5 mL vial was added 22 mCi (45 μL) aqueous Na$^{125}$I, 100 μL 0.5M phosphate buffer pH 7.5, 4.5 μL 1N HCl, 75 μg of the cyclic compound intermediate Cyclo-(D-Tyr- NMeArg-Gly-Asp-Mamb) dissolved in 75 μL 0.1% aqueous TFA, and 50 μg Chloramine-T dissolved in 50 μL H$_2$O. The reaction was allowed to proceed for 1 minute then 50 μg of sodium metabisulfite dissolved in H$_2$O was added. The product was purified by preparative HPLC. (Zorbax-Rx C$_{18}$ column, flow=1 mL/min, gradient from 100% A to 100% B over 30 minutes; Solvent A=0.1% TFA in H$_2$O, Solvent B=40% ethanol in A. The product had a retention time of 30 min.

Example 9

[($^{125}$I)N-3-(4-hydroxyphenyl)propionyl]-Cyclo-(D-Lys-NMeArg-Gly-Asp-Mamb)

To a 5 mL vial was added 11.4 mCi (25 μL) aqueous Na$^{125}$I, 100 μL 0.5M phosphate buffer pH 7.5, 4.5 μL 1N HCl, 50 μg of the linker modified cyclic compound [N-3-(4-hydroxyphenyl)propionyl]-Cyclo-(D-Tyr-NMeArg-Gly-Asp-Mamb) dissolved in 50 μL 0.1% aqueous TFA, and 50 μg Chloramine-T dissolved in 50 μL H$_2$O. The reaction was allowed to proceed for 1 minute then 50 μg of sodium metabisulfite dissolved in H$_2$O was added. The product was purified by preparative HPLC, using the condition described in Example 8. The product had a retention time of 32 min.
Indirect Labeling Example 10

$^{99m}$TcO(MAMA)-Cyclo-(D-Val-NMeArg-Gly-Asp-Mamb(5-Aca))

Part A. Deprotection

The trityl protecting groups on the reagent described in Example 1 are removed: To a separate, clean 10 cc vial was added the reagent and 0.1 mL trifluoroacetic acid (TFA). The solid dissolved to give a yellow solution.
Part B. Synthesis of $^{99m}$Tc-glucoheptonate A Glucoscan® vial was reconstituted with 1.0 mL Milli-Q H$_2$O. 0.2 mL of the solution was removed and added to a clean 10 cc vial followed by ~200 mCi $^{99m}$TcO$_4^-$. The reaction proceeded at room temperature for 20 minutes.
Part C. Synthesis of $^{99m}$TcO(MAMA)-Cyclo-(D-Val-NMeArg-Gly-Asp-Mamb(5-Aca))

To the deprotected reagent solution from Part A was added 0.2 mL 5N NaOH, and 0.4 mL 0.2M phosphate buffer pH 6. The pH was measured and adjusted as needed to 6. This solution was immediately added to the $^{99m}$Tc-glucoheptonate solution vial, crimped and heated at 100° C. for 15 minutes. After cooling ~2 minutes, 20 μL of the solution was analyzed by HPLC using Method 1. (See Table 1)

Example 11

$^{99m}$TcO(MAMA)-Cyclo-(D-Lys-NMeArg-Gly-Asp-Mamb)

Part A. Deprotection

The trityl protecting groups on the reagent described in Example 2 are removed: To a separate, clean 10 cc vial was added the reagent and 0.1 mL trifluoroacetic acid (TFA). The solid dissolved to give a yellow solution.
Part B. Synthesis of $^{99m}$TcO(MAMA)-Cyclo-(D-Lys-NMeArg-Gly-Asp-Mamb)

To the deprotected reagent solution from Part A was added 0.2 mL 5N NaOH, and 0.4 mL 0.2M phosphate buffer pH 6. The pH was measured and adjusted as needed to 6. This solution was immediately added to the $^{99m}$Tc-glucoheptonate solution vial, generated as described in Example 11, Part B, crimped and heated at 100° C. for 15 minutes. After cooling ~2 minutes, 20 μL of the solution was analyzed by HPLC using Method 1.(See Table 1)

Example 12

$^{99m}$Tc(tricine)$_2$-Cyclo(D-Val-NMeArg-Gly-Asp-Mamb(hydrazino-nicotinyl-5-Aca))

To a solution 6f 70 mg tricine in 1.0 mL of water was added 0.05 mL 1.0N NaOH to raise the pH to 7. 0.1–1.0 mL of $^{99m}$TcO$_4^-$ in saline (10–100 mCi) was added followed by 10 μg of the reagent described in Example 3 dissolved in 100 μL of 0.1N HCl and 100 μg of SnCl$_2$.2H$_2$O dissolved in 0.1N HCl. The reaction proceeded at room temperature for 45 minutes. The product was analyzed by HPLC using the method 1 and by TLC using method 2. (see Table 1)

Example 13

$^{99m}$Tc((EDDA)-Cyclo(D-Val-NMeArg-Gly-Asp-Mamb(hydrazino-nicotinyl-5-Aca))

To a solution of 10 mg ethylenediamine-N,N'-diacetic acid (EDDA) in 1.0 mL of water was added 0.05 mL 1.0N NaOH to raise the pH to 7. 0.1–1.0 mL of $^{99m}$TcO$_4^-$ in saline (10–100 mCi) was added followed by 50 μg of the reagent described in Example 3 dissolved in 100 μL of 0.1N HCl and 100 μg of SnCl$_2$.2H$_2$O dissolved in 0.1N HCl. The reaction proceeded at room temperature for 45 minutes. The product was analyzed by HPLC using the method 1 and by TLC using method 2. (see Table 1)

Example 14

$^{99m}$Tc(tricine)$_2$-Cyclo(D-Abu-NMeArg-Gly-Asp-Mamb(hydrazino-nicotinyl-5-Aca))

To a solution of 70 mg tricine in 1.0 mL of water was added 0.05 mL 1.0N NaOH to raise the pH to 7. 0.1–1.0 mL of $^{99m}$TcO$_4^-$ in saline (10–100 mCi) was added followed by 10 μg of the reagent described in Example 4 dissolved in 100 μL of 0.1N HCl and 100 μg of SnCl$_2$.2H$_2$O dissolved in 0.1N HCl. The reaction proceeded at room temperature for 45 minutes. The product was analyzed by HPLC using the method 1 and by TLC using method 2. (see Table 1)

Example 15

$^{99m}$Tc(tricine)$_2$-Cyclo(D-Lys-NMeArg-Gly-Asp-Mamb(hydrazino-nicotinyl-5-Aca))

To a solution of 70 mg tricine in 1.0 mL of water was added 0.05 mL 1.0N NaOH to raise the pH to 7. 0.1–1.0 mL of $^{99m}$TcO$_4^-$ in saline (10–100 mCi) was added followed by 10 μg of the reagent described in Example 5 dissolved in 100 μL of 0.1N HCl and 100 μg of SnCl$_2$.2H$_2$O dissolved in 0.1N HCl. The reaction proceeded at room temperature for 45 minutes. The product was analyzed by HPLC using the method 1 and by TLC using method 2. (see Table 1)

TABLE 1

Analytical and Yield Data for $^{99m}$Tc Labeled Reagents

| | HPLC Retention Time (min) | % Yield |
|---|---|---|
| Example 10 | 20.4 | 66 |
| Example 11 | 19.6 | 95 |
| Example 12 | 13.4 | 95 |
| Example 13 | 11.5 | 60 |
| Example 14 | 11.5 | 97 |
| Example 15 | 8.8 | 90 |

Example 16

Cyclo-([$^{111}$In-DTPA-D-Lys]-NMeArg-Gly-Asp-Mamb)

50 μL of $^{111}$InCl$_3$ (~100 mCi/mL in 0.05M HCl) obtained from DuPont-NEN Products, Billerica, Ma., was combined with an equal volume of freshly prepared 1.0M ammonium acetate. After about five minutes, 0.1–1 mg of the reagent described in Example 6 dissolved in 0.25 mL water was added. The reaction proceeded at room temperature for 30 minutes. The product was analyzed by HPLC using method 3.

Example 17

$^{111}$In-DTPA-[Cyclo-(D-Lys-NMeArg-Gly-Asp-Mamb)]$_2$

To 0.5 mL of a solution of the reagent described in Example 7 in water (0.9 mg/1 mL) was added $^{111}$InCl$_3$ (~3 mCi) in 0.5 mL of 1N NH$_4$OAc solution. The mixture was allowed to stand at room temperature for 30 minutes then analyzed by HPLC using method 3. (See Table 2)

TABLE 2

Analytical and Yield Data for $^{111}$In-labeked Reagents

| | HPLC Retention Time (min) | % Yield |
|---|---|---|
| Example 16 | 13.3 | 97 |
| Example 17 | 14.5 | 98 |

Section C. $^{99m}$Tc Labeled Reagents Via the Prechelate Approach

The $^{99m}$Tc-labeled reagents described in these examples were synthesized using the prechelate approach. The prechelate approach involves the steps: (1) chelation of $^{99m}$Tc by the chelator; (2) activation of a non-coordinated carboxylic group on the resulting complex by forming its tetrafluorophenyl (TFP) ester; and (3) conjugation of the TFP-ester complex by forming an amide bond with a cyclic compound intermediate or linker modified cyclic compound.

Example 18

Cyclo-([[$^{99m}$TcO(mapt)]$^-$-D-Lys]-NMeArg-Gly-Asp-Mamb)

Part A. Chelation of $^{99m}$Tc

To a clean 10 cc vial was added 0.35 mL Bz-mapt (3.0 mg/mL in 1N NaOH), 0.10 mL SnCl$_2$.2H$_2$O (10 mg/mL in 1N HCl), and 200 mCi $^{99m}$TcO$_4$- in saline. The vial was crimped and placed in a 100° C. water bath for 25 minutes. After cooling ~2 minutes, 10 μL of the solution was analyzed by HPLC using Method 1.

Part B. Activation

To the solution from Part A was added 0.3 mL 0.5M sodium phosphate pH 6, 0.3 mL 2,3,5,6-tetrafluorophenol (100 mg/mL in 90% acetonitrile), 0.3 mL 1-(3-dimethylamino-propyl)-3-ethylcarbodiimide (100 mg/mL in 90% acetonitrile), and ~0.1 mL 1N HCl. The pH was adjusted as needed to pH 6. The vial was crimped and heated at 40° C. for 25 minutes. After cooling ~2 minutes, 20 μL of the solution was analyzed by HPLC using Method 1.

Part C. Conjugation 1.0–2.5 mg of the cyclic compound intermediate Cyclo-(D-Lys-NMeArg-Gly-Asp-Mamb) was dissolved in 0.3 mL 0.5M pH 9 phosphate buffer and added to the solution from Part B. Using 1N NaOH, the pH was adjusted to 9. The reaction was heated at 40° C. for 30 minutes. After cooling ~2 minutes, 25 82 L of the solution was analyzed by HPLC using Method 1. (See Table 3)

Example 19

Cyclo-(D-Val-NMeArg-Gly-Asp-Mamb([$^{99m}$TcO(mapt)]$^-$-5-Aca))

1.0–2.5 mg of the linker modified cyclic compound Cyclo-(D-Val-NMeArg-Gly-Asp-Mamb(5-Aca)) was dissolved in 0.3 mL 0.5M pH 9 phosphate buffer and added to the solution from Example 18, Part B. Using 1N NaOH, the pH was adjusted to 9. The reaction was heated at 40° C. for 30 minutes. After cooling ~2 minutes, 25 μL of the solution was analyzed by HPLC using Method 1. (See Table 3)

Example 20

Cyclo-(D-Abu-NMeArg-Gly-Asp-Mamb([$^{99m}$TcO(mapt)]$^-$-5-Aca))

1.0–2.5 mg of the linker modified cyclic compound Cyclo-(D-Abu-NMeArg-Gly-Asp-Mamb(5-Aca)) was dissolved in 0.3 mL 0.5M pH 9 phosphate buffer and added to the solution from Example 18, Part B. Using 1N NaOH, the pH was adjusted to 9. The reaction was heated at 40° C. for 30 minutes. After cooling ~2 minutes, 25 μL of the solution was analyzed by HPLC using Method 1. (See Table 3)

Example 21

Cyclo-([([$^{99m}$TcO(mapt)]$^-$-5-Aca)D-Lysσ-NMeArg-Gly-Asp-Mamb)

1.0–2.5 mg of the linker modified cyclic compound Cyclo-((5-Aca)D-Lys-NMeArg-Gly-Asp-Mamb) was dissolved in 0.3 mL 0.5M pH 9 phosphate buffer and added to the solution from Example 18, Part B. Using 1N NaOH, the pH was adjusted to 9. The reaction was heated at 40° C. for 30 minutes. After cooling ~2 minutes, 25 μL of the solution was analyzed by HPLC using Method 1. (See Table 3)

Example 22

Cyclo-([[$^{99m}$TcO(MeMAG$_2$gaba)]$^-$-D-Lys]-NMeArg-Gly-Asp-Mamb)

Part A. Chelation

To a 10 mL vial was added 100–250 mCi $^{99m}$TcO$_4$- in 1.0 mL of saline, 1.0 mL of Bz-MeMAG$_2$gaba solution (1 mg/1 mL in 0.5M pH 12 phosphate buffer), followed by of 0.15–0.20 mL of SnCl$_2$.2H$_2$O solution (15 mg/3 mL in 1N HCl). The pH was adjusted to ~11 and the mixture was heated for 30 min at 100° C. The solution was analyzed by HPLC using Method 1.

Part B. Activation

To the solution from Part A was added 0.2 mL of 1N HCl, 0.5 mL of tetrafluorophenol solution (100 mg/mL in 90% $CH_3CN$), and 0.5 mL of (1-[3-(dimehtylamino)propyl]-3-ethylcarbodiimide chloride) solution (100 mg/mL in 90% $CH_3CN$). The pH was adjusted to 6.0 and the mixture was heated at 50° C. for 30 min.

Part C. Conjugation 1.0–2.5 mg of the cyclic compound intermediate Cyclo-(D-Lys-NMeArg-Gly-Asp-Mamb) dissolved in 0.3 mL 0.5M pH 9 phosphate buffer and added to the solution from Part B. Using 1N NaOH, the pH was adjusted to 9. The reaction was heated at 40° C. for 30 minutes. After cooling ~2 minutes, 25 μL of the solution was analyzed by HPLC using Method 1. (See Table 3)

Example 23

Cyclo-(D-Val-NMeArg-Gly-Asp-Mamb([$^{99m}$TcO (MeMAG$_2$gaba)]⁻-5-Aca))

1.0–2.5 mg of the linker modified cyclic compound Cyclo-(D-Val-NMeArg-Gly-Asp-Mamb(5-Aca)) was dissolved in 0.3 mL 0.5M pH 9 phosphate buffer and added to the solution from Example 22, Part B. Using 1N NaOH, the pH was adjusted to 9. The reaction was heated at 40° C. for 30 minutes. After cooling ~2 minutes, 25 μL of the solution was analyzed by HPLC using Method 1. (See Table 3)

Example 24

Cyclo-(D-Abu-NMeArg-Gly-Asp-Mamb([$^{99m}$TcO (MeMAG$_2$gaba)]⁻-5-Aca))

1.0–2.5 mg of the linker modified cyclic compound Cyclo-(D-Abu-NMeArg-Gly-Asp-Mamb(5-Aca)) was dissolved in 0.3 mL 0.5M pH 9 phosphate buffer and added to the solution from Example 22, Part B. Using 1N NaOH, the pH was adjusted to 9. The reaction was heated at 40° C. for 30 minutes. After cooling ~2 minutes, 25 μL of the solution was analyzed by HPLC using Method 1. (See Table 3)

Example 25

Cyclo-([[$^{99m}$TcO(MAG$_3$)]⁻-D-Lys]-NMeArg-Gly-Asp-Mamb)

This example was synthesized following the procedure described in Example 22, substituting Bz-MAG$_3$ as the chelator.(See Table 3)

Example 26

Cyclo-([[$^{99m}$TcO(Me-MAG$_3$)]⁻-D-Lys]-NMeArg-Gly-Asp-Mamb)

This example was synthesized following the procedure described in Example 22, substituting Bz-Me-MAG$_3$ as the chelator. (See Table 3)

Example 27

Cyclo-(D-Val-NMeArg-Gly-Asp-Mamb([$^{99m}$TcO (MeMAG2ACA)]⁻-5-Aca))

The title compound was prepared according to the procedure described in Example 22, substituting Bz-Me-MAG$_2$-ACA as the chelator in Part A and using Cyclo-(D-Val-NMeArg-Gly-Asp-Mamb(5-Aca)) as the linker modified cyclic compound in Part C. (See Table 3)

Example 28

Cyclo-([[$^{99m}$TcO(MABA)]⁻-D-Lys]-NMeArg-Gly-Asp-Mamb)

Part A. Chelation

To a 10 mL vial was added 50–300 mCi $^{99m}$TcO$_4^-$ in 0.5 mL of saline, followed by 0.5 mL of Bz-MABA solution (1 mg/1 mL in 0.5M pH 12 phosphate buffer) and 0.15 mL of Na$_2$S$_2$O$_4$ solution (5 mg/mL in 0.5M in pH 11.5 phosphate buffer) The pH was adjusted to 10–12 using 1N NaOH and the mixture was heated for 30 min. at 100° C. then analyzed by HPLC using method 1.

Part B. Activation

To the solution from Part A was added 0.2 mL of 1N HCl, 0.5 mL of TFP solution (50 mg/0.5 mL in 90% $CH_3CN$), and 0.5 mL of DCI solution (50 mg in 0.5 mL in 90% $CH_3CN$). The pH was adjusted to 6 if necessary and the mixture was heated at 45°–50° C. for 30 min then analyzed by HPLC using method 1.

Part C. Conjugation

To the solution from Part B was added 2–3 mg of the cyclic compound intermediate Cyclo-(D-Lys-NMeArg-Gly-Asp-Mamb) dissolved in 0.5 mL 0.5M phosphate buffer pH 9 and pH was then adjusted to 9.5–10. The solution was heated at 50° C. for 30 min, then analyzed by HPLC using method 1. (See Table 3)

Example 29

Cyclo-(D-Val-NMeArg-Gly-Asp-Mamb([$^{99m}$TcO (MABA)]⁻-5-Aca))

The title compound was synthesized following the procedure described in Example 28, substituting the linker modified cyclic compound Cyclo-(D-Val-NMeArg-Gly-Asp-Mamb(5-Aca)) for the cyclic compound intermediate Cyclo-(D-Lys-NMeArg-Gly-Asp-Mamb) in Part C.

Example 30

Cyclo-(D-Abu-NMeArg-Gly-Asp-Mamb([$^{99m}$TcO (MABA)]⁻-5-Aca))

The title compound was synthesized following the procedure described in Example 28, substituting the linker modified cyclic compound Cyclo-(D-Abu-NMeArg-Gly-Asp-Mamb(5-Aca)) for the cyclic compound intermediate Cyclo-(D-Lys-NMeArg-Gly-Asp-Mamb) in Part C.

Example 31

Cyclo-([[$^{99m}$TcO(MA-MAMA)]-D-Lys]-NMeArg-Gly-Asp-Mamb)

Part A. Deprotection

The trityl groups on the chelator MA-MAMA were removed by dissolving 6 mg in 1 mL of anhydrous trifluoroacetic acid (TFA). The resulting yellow solution was allowed to stand at room temperature for 5 minutes. Triethylsilane (0.5 mL) was added to the yellow solution to give a clear two-layered mixture. Volatiles were removed under reduced pressure to give a white residue.

Part B. Hydrolysis of the Ethyl Ester

To the white residue from Part A was added 0.5 mL of 5N NaOH and 1 mL of THF. The mixture was heated in a water bath (100° C.) for 5 minutes, by which time most of THF was evaporated. To the reaction mixture was added 3 mL of 0.5M phosphate buffer pH 11.5. The pH was adjusted to 10–12 and sodium dithionite (15–30 mg) was added. The mixture was filtered and the total volume was adjusted to 6 mL using 0.5M pH 11.5 phosphate buffer.

Part C. Chelation

To a 10 mL vial was added 50–150 mCi $^{99m}TcO_4^-$ in 0.5 mL of saline, followed by 0.5 mL of ligand solution from Part B. The pH was adjusted to 10–12 using 1N NaOH and the mixture was heated for 30 min at 100° C. then analyzed by HPLC using method 1.

Part D. Activation

To the solution from Part C was added 0.2 mL of 1N HCl, 0.5 mL of TFP solution (50 mg/0.5 mL 90% $CH_3CN$), and 0.5 mL of DCI solution (50 mg in 0.5 mL 90% $CH_3CN$). The pH was adjusted to 6 if necessary and the mixture was heated at 45°–50° C. for 30 min. then analyzed by HPLC using method 1.

Part E. Conjugation

To the solution from Part D was added 2.5 mg of the cyclic compound intermediate Cyclo-(D-Lys-NMeArg-Gly-Asp-Mamb) dissolved in 0.5 mL 0.5M phosphate buffer pH 9 and the pH was then adjusted to 9.5–10. After heating at 50° C. for 30 min, the solution was analyzed by HPLC using method 1.

Example 32

Cyclo-(D-Val-NMeArg-Gly-Asp-Mamb([$^{99m}$TcO (MA-MAMA)]-5-Aca))

The title compound was synthesized following the procedure described in Example 31, substituting the linker modified cyclic compound Cyclo-(D-Val-NMeArg-Gly-Asp-Mamb(5-Aca)) for the cyclic compound intermediate Cyclo-(D-Lys-NMeArg-Gly-Asp-Mamb) in Part E.

TABLE 3

Analytical and Yield Data for $^{99m}$Tc-labeled Reagents

| | HPLC Retention Time (min) | % Yield |
|---|---|---|
| Example 18 | 15.0 | 60 |
| Example 19 | 16.2 | 45 |
| Example 20 | 15.3 | 35 |
| Example 21 | 15.5 | 55 |
| Example 22 | 14.3 | 44 |
| Example 23 | 15.5 | 34 |
| Example 24 | 14.5 | 70 |
| Example 25 | 13.2 | 50 |
| Example 26 | 13.0 | 55 |
| Example 27 | 14.3 | 40 |
| Example 28 | 18.2 | 10 |
| Example 29 | 19.1 | 22 |
| Example 30 | 19.3 | 22 |
| Example 31 | 14.8 | 23 |
| Example 32 | 16.2 | 34 |

Analytical Methods

HPLC Method 1

Column: Vydac $C_{18}$, 250 mm×4.6 mm, 300 Å pore size
Solvent A: 10 mM sodium phosphate, pH 6.0
Solvent B: 100% acetonitrile Gradient:

| 0% B | 30% B | 75% B |
|---|---|---|
| 0' | 15' | 25' |

Flow rate: 1.0 mL/min
Detection by NaI probe

TLC Method 2

ITLC-SG strip, 1 cm×7.5 cm, developed in 1:1 acetone:water.

HPLC Method 3

Column: Vydac $C_{18}$, 250 mm×4.6 mm, 300 Å pore size
Solvent A: 10 mM sodium phosphate, pH 6.0
Solvent B: 75% acetonitrile in Solvent A Gradient:

| 5% B | 5% B | 100% B |
|---|---|---|
| 0' | 5' | 40' |

Flow rate: 1.0 mL/min
Detection by NaI probe

Utility

The radiolabeled compounds of the invention are useful as radiopharmaceuticals for imaging a thrombus such as may be present in a patient with unstable angina, myocardial infarction, transient ischemic attack, stroke, atherosclerosis, diabetes, thrombophlebitis, pulmonary emboli, or prosthetic cardiac devices such as heart valves, and thus may be used to diagnose such present or potential disorders. The patient may be any type of a mammal, but is preferably a human. The radiolabeled compounds may be used alone, or may be employed as a composition with a radiopharmaceutically acceptable carrier, and/or in combination with other diagnostic or therapeutic agents. Suitable radiopharmaceuticals carriers and suitable amounts thereof are well known in the art, and can be found in, for example, Remington's Pharmaceutical Sciences, Gennaro, A. R., ed., Mack Publishing Company, Easton, Pa. (1985), and The United States Pharmacopia—The National Formulary, 22nd Revision, Mack Printing Company, Easton, Pa. (1990), standard reference texts in the pharmaceutical field. Other materials may be added, as convenient, to stabilize the composition, as those skilled in the art will recognize, including antioxidizing agents such as sodium bisulfite, sodium sulfite, ascorbic acid, gentisic acid or citric acid (or their salts) or sodium ethylenediamine tetraacetic acid (sodium EDTA), as is well known in the art. Such other materials, as well as suitable amounts thereof, are also described in Remington's Pharmaceutical Sciences and The United States Pharmacopia—The National Formulary, cited above.

The present invention also includes radiopharmaceutical kits containing the labeled compounds of the invention. Such kits may contain the labeled compounds in sterile lyophilized form, and may include a sterile container of a radiopharmaceutically acceptable reconstitution liquid. Suitable reconstitution liquids are disclosed in Remington's Pharmaceutical Sciences and The United States Pharmacopia—The National Formulary, cited above. Such kits may alternatively contain a sterile container of a composition of the radiolabeled compounds of the invention. Such kits may also include, if desired, other conventional kit components, such as, for example, one or more carriers, one or more additional vials for mixing. Instructions, either as inserts or labels, indicating quantities of the labeled compounds of the invention and carrier, guidelines for mixing these components, and protocols for administration may also be included in the kit. Sterilization of the containers and any materials included in the kit and lyophilization (also referred to as freeze-drying) of the labeled compounds of the invention may be carried out using conventional sterilization and lyophilization methodologies known to those skilled in the art.

To carry out the method of the invention, the radiolabeled compounds are generally administered intravenously, by bolus injection, although they may be administered by any means that produces contact of the compounds with platelets. Suitable amounts for administration will be readily ascertainable to those skilled in the art, once armed with the present disclosure. The dosage administered will, of course, vary depending up such known factors as the particular compound administered, the age, health and weight or the nature and extent of any symptoms experienced by the patient, the amount of radiolabeling, the particular radionuclide used as the label, the rate of clearance of the radiolabeled compounds from the blood. Acceptable ranges for administration of radiolabeled materials are tabulated, for example, in the Physicians Desk Reference (PDR) for Nuclear Medicine, published by Medical Exonomics Company, a well-known reference text. A discussion of some of the aforementioned considerations is provided in Eckelman et al., J. Nucl. Med., Vol. 209, pp. 350–357 (1979). By way of general guidance, a dosage range of the radiolabeled compounds of the invention may be between about 1 and about 40 mCi.

Once the radiolabeled compounds of the invention are administered, the presence of thrombi may be visualized using a standard radioscintographic imaging system, such as, for example, a gamma camera or a computed tomographic device, and thromboembolic disorders detected. Such imaging systems are well known in the art, and are discussed, for example, in Macovski, A., Medical Imaging Systems, Information and Systems Science Series, Kailath, T., ed., Prentice-Hall, Inc., Englewood Cliffs, N.J. (1983). Particularly preferred are single-photon emission computed tomography (SPECT) and positron emission tomography (PET). Specifically, imaging is carried out by scanning the entire patient, or a particular region of the patient suspected of having a thrombus formation, using the radioscintographic system, and detecting the radioisotope signal. The detected signal is then converted into an image of the thrombus by the system. The resultant images should be read by an experienced observer, such as, for example, a nuclear medicine physician. The foregoing process is referred to herein as "imaging" the patient. Generally, imaging is carried out about 1 minute to about 48 hours following administration of the radiolabeled compound of the invention. The precise timing of the imaging will be dependant upon such factors as the half-life of the radioisotope employed, and the clearance rate of the compound administered, as will be readily apparent to those skilled in the art. Preferably, imaging is carried out between about 1 minute and about 4 hours following administration.

The advantage of employing the radiolabeled compounds of the invention, which have the ability to localize specifically and with high affinity in thrombi, to detect the presence of thrombi and/or to diagnose thromboembolic disorders in a patient, will be readily apparent to those skilled in the art, once armed with the present disclosure.

Arteriovenous Shunt Model: Adult mongrel dogs of either sex (9–13 kg) were anesthetized with pentobarbital sodium (35 mg/kg, i.v.) and ventilated with room air via an endotracheal tube (12 strokes/min,25 ml/kg). For arterial pressure determination, the left carotid artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Ma.) triggered from a lead II electrocardiogram generated by limb leads. A jugular vein was cannulated (PE-240) for drug administration. The both femoral arteries and femoral veins were cannulated with silicon treated (Sigmacote, Sigma Chemical Co. St Louis, Mo.), saline filled polyethylene tubing (PE-200) and connected with a 5 cm section of silicon treated tubing (PE-240) to form an extracorporeal arterio-venous shunts (A-V). Shunt patency was monitored using a doppler flow system (model VF-1, Crystal Biotech Inc, Hopkinton, Ma.) and flow probe (2–2.3 mm, Titronics Med. Inst., Iowa City, Iowa) placed proximal to the locus of the shunt. All parameters were monitored continuously on a polygraph recorder (model 7D Grass) at a paper speed of 10 mm/min or 25 mm/sec.

On completion of a 15 min post surgical stabilization period, an occlusive thrombus was formed by the introduction of a thrombogenic surface (4-0 braided silk thread, 5 cm in length, Ethicon Inc., Somerville, N.J.) into the shunt one shunt with the other serving as a control. Two consecutive 1 hr shunt periods were employed with the test agent administered as an infusion over 5 min beginning 5 min before insertion of the thrombogenic surface. At the end of each 1 hr shunt period the silk was carefully removed and weighed and the % incorporation determined via well counting. Thrombus weight was calculated by subtracting the weight of the silk prior to placement from the total weight of the silk on removal from the shunt. The results are shown in Table 4. Arterial blood was withdrawn prior to the first shunt and every 30 min thereafter for determination of blood clearance, whole blood collagen-induced platelet aggregation, thrombin-induced platelet degranulation (platelet ATP release), prothrombin time and platelet count. Template bleeding time was also performed at 30 min intervals.

Figure 1B:
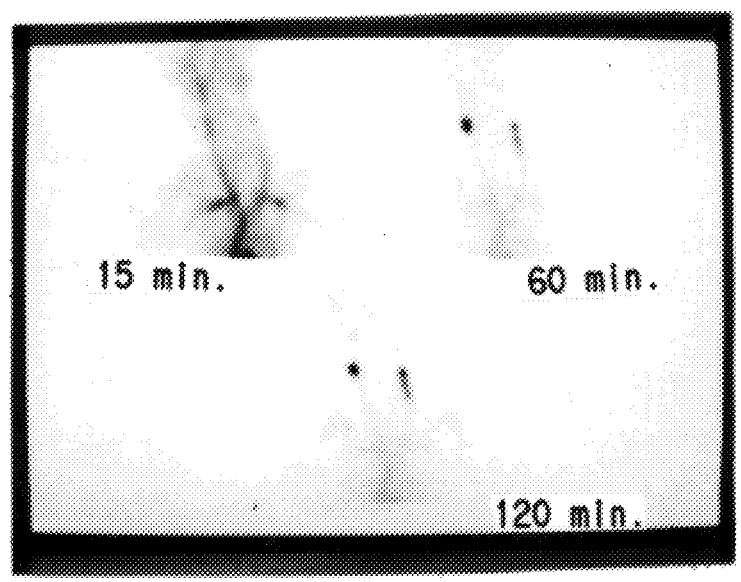
FIG. 1b. Illustrated are typical images of the radiopharmaceutical compound of Example 19 administered at 1 mCi/Kg,i.v. in a canine deep venous thrombosis model. In this model thrombi were formed in the jugular veins during a period of stasis which was followed by reflow. The compounds were administered beginning at reflow. Depicted is the uptake in a rapidly growing venous thrombus at 15, 60 and 120 min post-administration.

Canine Deep Vein Thrombosis Model: This model incorporates the triad of events (hypercoagulatible state, period of stasis, low shear environment) essential for the formation of a venous fibrin-rich actively growing thrombus. The procedure was as follows: Adult mongrel dogs of either sex (9–13 kg) were anesthetized with pentobarbital sodium (35 mg/kg, i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Ma.) triggered from a lead II electrocardiogram generated by limb leads. The right femoral vein was cannulated (PE-240) for drug administration. A 5 cm segment of both jugular veins was isolated, freed from fascia and circumscribed with silk suture. A microthermister probe was placed on the vessel which serves as an indirect measure of venous flow. A balloon embolectomy catheter was utilized to induce the 15 min period of stasis during which time a hypercoagulatible state was then induced using 5 U thrombin (American Diagnosticia, Greenwich Conn.) administered into the occluded segment. Fifteen minutes later, flow was reestablished by deflating the balloon. The agent was infused during the first 5 min of reflow and the rate of incorporation monitored using gamma scintigraphy. The results for Examples 12 and 19 are shown in FIG. 1.

Example 33

TABLE 4

Experimental Data from the Arteriovenous Shunt Model
(mean ± SEM, T/B = thrombus/background)

| Ex. # | Venous Conditions Uptake (% id/g) | T/B ratio | Arterial Conditions Uptake (% id/g) | T/B ratio |
|---|---|---|---|---|
| 8 | 0.25 ± 0.15 | 19 ± 9 | 1.81 ± 0.18 | 173 ± 22 |
| 9 | 0.45 ± 0.11 | 8 ± 3 | 2.60 ± .005 | 44 ± 4 |
| 10 | 0.16 ± 0.02 | 7 ± 0.6 | 5.00 ± 0.51 | 221 ± 16 |
| 12 | 0.46 ± 0.19 | 7.0 ± 2 | 6.15 ± 0.66 | 111 ± 6 |
| 13 | 1.64 ± 1.32 | 33 ± 27 | 8.50 ± 0.20 | 163 ± 14 |
| 16 | 0.08 | 14 | 0.95 ± 0.29 | 128 ± 24 |
| 18 | 0.04 ± .01 | 13 ± 3 | 0.47 ± 0.12 | 147 ± 44 |
| 19 | 0.58 ± 0.22 | 13 ± 4 | 5.75 ± 1.28 | 142 ± 24 |
| 21 | 0.06 ± 0.03 | 4.0 ± 2 | 1.6 ± 0.12 | 113 ± 1 |
| 22 | 0.045 ± 0.02 | 7 ± 4 | 1.28 ± 0.44 | 158 ± 5 |
| 23 | 0.21 ± 0.05 | 7 ± 0.4 | 5.41 ± 0.70 | 195 ± 39 |
| 32 | 0 | 0 | 7.4 | 102 |

Platelet Aggregation Assay: Canine blood was collected into 10 ml citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 µg of was added to each micro test tube, and transmittance set to 0%. 20 µl of various agonists (ADP, collagen, arachidonate, epinephrine, thrombin) were added to each tube, and the aggregation profiles were plotted (% transmittance versus time). The results were expressed as % inhibition of agonist-induced platelet aggregation. For the $IC_{50}$ evaluation, the test compounds were added at various concentrations prior to the activation of the platelets.

Platelet-Fibrinogen Binding Assay: Binding of $^{125}$I-fibrinogen to platelets was performed as described by Bennett et al. (1983) Proc. Natl. Acad. Sci. U.S.A. 80: 2417–2422, with some modifications as described below. Human PRP (h-PRP) was applied to a Sepharose column for the purification of platelet fractions. Aliquots of platelets (5×10$^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated, platelets was separated from the free form by centrifugation and then counted on a gamma counter. For an $IC_{50}$ evaluation, the test compounds were added at various concentrations prior to the activation of the platelets.

The novel cyclic glycoprotein IIb/IIIa compounds of the invention may also possess thrombolytic efficacy, that is, they are capable of lysing (breaking up) already formed platelet-rich fibrin blood clots, and thus may useful in treating a thrombus formation, as evidenced by their activity in the tests described below. Preferred cyclic compounds of the present invention for use in thrombolysis would include those compounds having an $IC_{50}$ value (that is, the molar concentration of the cyclic compound capable of achieving 50% clot lysis) of less than about 1 mM, more preferably an $IC_{50}$ value of less than about 0.1 mM, even ore preferably an $IC_{50}$ value of less than about 0.01M, still more preferably an $IC_{50}$ value of less than bout 0.001 mM, and most preferably an $IC_{50}$ value of bout 0.0005 mM.

$IC_{50}$ determinations may be made using a standard thrombolysis assay, as described below. Another class of preferred thrombolytic compounds of the invention would include those compounds which have a Kd of <100 nM, preferably <10 nM, most preferably 0.1 to 1.0 nM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added 1×10$^{-3}$M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The disclosures of each patent and publication cited in this document are hereby incorporated herein by reference, in their entirety.

Various modifications in the invention, in addition to those shown and described herein will be readily apparent to those skilled in the art from the foregoing description. Such modifications are intended to be within the scope of the appended claims.

What is claimed is:

1. A compound of formulae:

$$(QL_n)_d C_h; (Q)_{d'} L_n—C_h,$$

wherein, d is 1–3, d' is 2–20, $L_n$ is a linking group, $C_h$ is a metal chelator, and Q is a compound of formula (I):

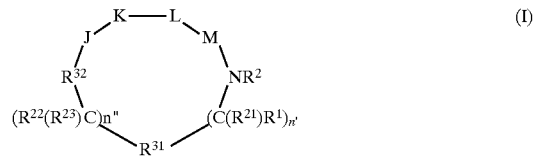

or a pharmaceutically acceptable salt or prodrug form thereof, wherein:

$R^{31}$ is a $C_6$–$C_{14}$ saturated, partially saturated, or aromatic carbocyclic ring system, substituted with 0–4 $R^{10}$ or $R^{10a}$, and optionally bearing a bond to $L_n$; a heterocyclic ring system, optionally substituted with 0–4 $R^{10}$ or $R^{10a}$, and optionally bearing a bond to $L_n$;

$R^{32}$ is selected from:
- —C(=O)—;
- —C(=S)—
- —S(=O)$_2$—;
- —S(=O)—;
- —P(=Z)(ZR$^{13}$)—;

Z is S or O;

n" and n' are independently 0–2;

$R^1$ and $R^{22}$ are independently selected from the following groups:
  hydrogen,
  $C_1$–$C_8$ alkyl substituted with 0–2 $R^{11}$;
  $C_2$–$C_8$ alkenyl substituted with 0–2 $R^{11}$;
  $C_2$–$C_8$ alkynyl substituted with 0–2 $R^{11}$;
  $C_3$–$C_{10}$ cycloalkyl substituted with 0–2 $R^{11}$;
  a bond to $L_n$;
  aryl substituted with 0–2 $R^{12}$;
  a 5–10-membered heterocyclic ring system containing 1–4 heteroatoms independently selected from N, S, and O, said heterocyclic ring being substituted with 0–2 $R^{12}$;
  =O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy;

$R^1$ and $R^{21}$ can alternatively join to form a 3–7 membered carbocyclic ring substituted with 0–2 $R^{12}$;
  when n' is 2, $R^1$ or $R^{21}$ can alternatively be taken together with $R^1$ or $R^{21}$ on an adjacent carbon atom to form a direct bond, thereby to form a double or triple bond between said carbon atoms;

$R^{21}$ and $R^{23}$ are independently selected from:
  hydrogen;
  $C_1$–$C_4$ alkyl, optionally substituted with 1–6 halogen;
  benzyl;
  $R^{22}$ and $R^{23}$ can alternatively join to form a 3–7 membered carbocyclic ring substituted with 0–2 $R^{12}$;
  when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;

$R^1$ and $R^2$, where $R^{21}$ is H, can alternatively join to form a 5–8 membered carbocyclic ring substituted with 0–2 $R^{12}$;

$R^{11}$ is selected from one or more of the following:
  =O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy,
  $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, $C_3$–$C_6$ cycloalkoxy, $C_1$–$C_4$ alkyl (alkyl being substituted with 1–5 groups selected independently from: —NR$^{13}$R$^{14}$, —CF$_3$, NO$_2$, —SO$_2$R$^{13a}$, or —S(=O)R$^{13a}$),
  aryl substituted with 0–2 R$^{12}$,
  a 5–10-membered heterocyclic ring system containing 1–4 heteroatoms independently selected from N, S, and O, said heterocyclic ring being substituted with 0–2 R$^{12}$;

$R^{12}$ is selected from one or more of the following:
  phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S(=O)R$^{13a}$);

$R^{13}$ is selected independently from: H, $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;

$R^{13a}$ is $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;

when two $R^{13}$ groups are bonded to a single N, said $R^{13}$ groups may alternatively be taken together to form —(CH$_2$)$_{2-5}$— or —(CH$_2$)O(CH$_2$)—;

$R^{14}$ is OH, H, $C_1$–$C_4$ alkyl, or benzyl;

$R^2$ is H or $C_1$–$C_8$ alkyl;

$R^{10}$ and $R^{10a}$ are selected independently from one or more of the following:
  phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)N(R$^{13}$)$_2$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl (including —C$_v$F$_w$ where v=1 to 3 and w=1 to (2v+1)), $C_1$–$C_4$ haloalkoxy, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S(=O)R$^{13a}$);

J is β-Ala or an L-isomer or D-isomer amino acid of structure —N(R$^3$)C(R$^4$)(R$^5$)C(=O)—, wherein:

$R^3$ is H or $C_1$–$C_8$ alkyl;

$R^4$ is H or $C_1$–$C_3$ alkyl;

$R^5$ is selected from:
  hydrogen;
  $C_1$–$C_8$ alkyl substituted with 0–2 $R^{11}$;
  $C_2$–$C_8$ alkenyl substituted with 0–2 $R^{11}$;

$C_2$–$C_8$ alkynyl substituted with 0–2 $R^{11}$;
$C_3$–$C_{10}$ cycloalkyl substituted with 0–2 $R^{11}$;
a bond to $L_n$;
aryl substituted with 0–2 $R^{12}$;
a 5–10-membered heterocyclic ring system containing 1–4 heteroatoms independently selected from N, S, or O, said heterocyclic ring being substituted with 0–2 $R^{12}$;
=O, F, Cl, Br, I, —$CF_3$, —CN, —$CO_2R^{13}$, —C(=O)$R^{13}$, —C(=O)N($R^{13}$)$_2$, —CHO, —$CH_2OR^{13}$, —OC(=O)$R^{13}$, —OC(=O)$OR^{13a}$, —$OR^{13}$, —OC(=O)N($R^{13}$)$_2$, —$NR^{13}$C(=O)$R^{13}$, —$NR^{14}$C(=O)$OR^{13a}$, —$NR^{13}$C(=O)N($R^{13}$)$_2$, —$NR^{14}SO_2$N($R^{13}$)$_2$, —$NR^{14}SO_2R^{13a}$, —$SO_3H$, —$SO_2R^{13a}$, —$SR^{13}$, —S(=O)$R^{13a}$, —$SO_2$N($R^{13}$)$_2$, —N($R^{13}$)$_2$, —NHC(=NH)$NHR^{13}$, —C(=NH)$NHR^{13}$, =$NOR^{13}$, $NO_2$, —C(=O)$NHOR^{13}$, —C(=O)$NHNR^{13}R^{13a}$, =$NOR^{13}$, —B($R^{34}$)($R^{35}$), —$OCH_2CO_2H$, 2-(1-morpholino)ethoxy, —SC(=NH)$NHR^{13}$, $N_3$, —Si($CH_3$)$_3$, ($C_1$–$C_5$ alkyl)$NHR^{16}$;
—($C_0$–$C_6$ alkyl)X;

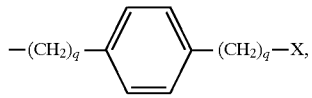

where q is independently 0, 1;

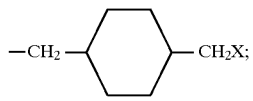

—$(CH_2)_mS(O)_{p'}(CH_2)_2X$, where m=1, 2 and p'=0–2;
wherein X is defined below; and
$R^3$ and $R^4$ may also be taken together to form

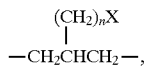

where
n=0, 1 and X is

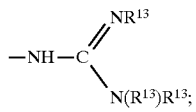

$R^3$ and $R^5$ can alternatively be taken together to form —$(CH_2)_t$— or —$CH_2S(O)_pC(CH_3)_2$—, where t=2–4 and p'=0–2; or
$R^4$ and $R^5$ can alternatively be taken together to form —$(CH_2)_u$—, where u=2–5;
$R^{16}$ is selected from:
an amine protecting group;
1–2 amino acids;
1–2 amino acids substituted with an amine protecting group;
K is a D-isomer or L-isomer amino acid of structure —N($R^6$)CH($R^7$)C(=O)—, wherein:
$R^6$ is H or $C_1$–$C_8$ alkyl;
$R^7$ is selected from:

—($C_1$–$C_7$ alkyl)X;

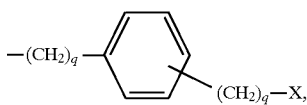

wherein each q is independently 0–2 and substitution on the phenyl is at the 3 or 4 position;

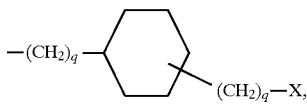

wherein each q is independently 0–2 and substitution on the cyclohexyl is at the 3 or 4 position;

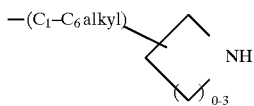

—$(CH_2)_mO$—($C_1$–$C_4$ alkyl)-X, where m=1 or 2;
—$(CH_2)_mS(O)_{p'}$—($C_1$–$C_4$ alkyl)-X, where m=1 or 2 and p'=0–2; and
X is selected from:

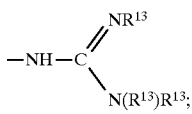

—N($R^{13}$)$R^{13}$; —C(=NH)($NH_2$); —SC(=NH)—$NH_2$;
—NH—C(=NH)(NHCN); —NH—C(=NCN)($NH_2$); —NH—C(=N—$OR^{13}$)($NH_2$);
$R^6$ and $R^7$ can alternatively be taken together to form

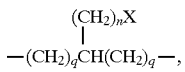

wherein each q is independently 1 or 2 and wherein n=0 or 1 and X is —$NH_2$ or

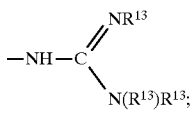

L is —Y($CH_2$)$_vC(=O)$—, wherein:
Y is NH, N($C_1$–$C_3$ alkyl), O, or S; and v=1 or 2;
M is a D-isomer or L-isomer amino acid of structure

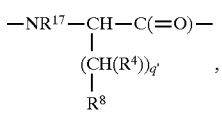

wherein:
q' is 0–2;
$R^{17}$ is H, $C_1$–$C_3$ alkyl;
$R^8$ is selected from:
—$CO_2R^{13}$, —$SO_3R^{13}$, —$SO_2NHR^{14}$, —B($R^{34}$)($R^{35}$), —$NHSO_2CF_3$, —$CONHNHSO_2CF_3$, —PO($OR^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$;

R$^{34}$ and R$^{35}$ are independently selected from:
—OH,
—F,
—N(R$^{13}$)$_2$, or
C$_1$–C$_8$-alkoxy;

R$^{34}$ and R$^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O.

2. A compound of claim 1, wherein:
R$^{31}$ is bonded to (C(R$^{23}$)R$^{22}$)$_{n''}$ and (C(R$^{21}$)R$^1$)$_{n'}$ at 2 different atoms on said carbocyclic ring.

3. A compound of claim 1, wherein:
n'' is 0 and n' is 0;
n'' is 0 and n' is 1;
n'' is 0 and n' is 2;
n'' is 1 and n' is 0;
n'' is 1 and n' is 1;
n'' is 1 and n' is 2;
n'' is 2 and n' is 0;
n'' is 2 and n' is 1; or
n'' is 2 and n' is 2.

4. A compound of claim 1 wherein R$^6$ is methyl, ethyl, or propyl.

5. A compound of claim 1 wherein:
R$^{32}$ is selected from:
—C(=O)—;
—C(=S)—
—S(=O)$_2$;

R$^1$ and R$^{22}$ are independently selected from the following groups:
hydrogen,
C$_1$–C$_8$ alkyl substituted with 0–2 R$^{11}$,
C$_2$–C$_8$ alkenyl substituted with 0–2 R$^{11}$,
C$_2$–C$_8$ alkynyl substituted with 0–2 R$^{11}$,
C$_3$–C$_8$ cycloalkyl substituted with 0–2 R$^{11}$,
C$_6$–C$_{10}$ bicycloalkyl substituted with 0–2 R$^{11}$;
a bond to L$_n$;
aryl substituted with 0–2 R$^{12}$;
a 5–10-membered heterocyclic ring system containing 1–4 heteroatoms independently selected from N, S, or O, said heterocyclic ring being substituted with 0–2 R$^{12}$;
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, NO$_2$;

R$^1$ and R$^{21}$ can alternatively join to form a 5–7 membered carbocyclic ring substituted with 0–2 R$^{12}$;
when n' is 2, R$^1$ or R$^{21}$ can alternatively be taken together with R$^1$ or R$^{21}$ on an adjacent carbon atom to form a direct bond, thereby to form a double or triple bond between said carbon atoms;

R$^{22}$ and R$^{23}$ can alternatively join to form a 3–7 membered carbocyclic ring substituted with 0–2 R$^{12}$;
when n'' is 2, R$^{22}$ or R$^{23}$ can alternatively be taken together with R$^{22}$ or R$^{23}$ on an adjacent carbon atom to form a direct bond, thereby to form a double or triple bond between said carbon atoms;

R$^1$ and R$^2$, where R$^{21}$ is H, can alternatively join to form a 5–8 membered carbocyclic ring substituted with 0–2 R$^{12}$;

R$^{11}$ is selected from one or more of the following:
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$;
C$_1$–C$_5$ alkyl, C$_2$–C$_4$ alkenyl, C$_3$–C$_6$ cycloalkyl, C$_3$–C$_6$ cycloalkylmethyl, C$_2$–C$_6$ alkoxyalkyl, C$_1$–C$_4$ alkyl (substituted with —NR$^{13}$R$^{14}$, —CF$_3$, NO$_2$, —SO$_2$R$^{13}$, or —S(=O)R$^{13a}$)
aryl substituted with 0–2 R$^{12}$,
a 5–10-membered heterocyclic ring system containing 1–4 heteroatoms independently selected from N, S, or O, said heterocyclic ring being substituted with 0–2 R$^{12}$;

R$^3$ is H or CH$_3$;

R$^5$ is H, C$_1$–C$_8$ alkyl, C$_3$–C$_6$ cycloalkyl, C$_3$–C$_6$ cycloalkylmethyl, C$_3$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, (CH$_2$)$_s$NHC(=NH)(NH$_2$), (CH$_2$)$_s$NHR$^{16}$, where s=3–5;
a bond to L$_n$;

R$^3$ and R$^5$ can alternatively be taken together to form —(CH$_2$)$_t$— (t=2–4) or —CH$_2$SC(CH$_3$)$_2$—; or R$^7$ is selected from:
—(C$_1$–C$_7$ alkyl)X;

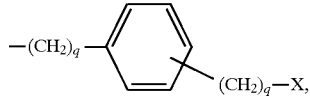

wherein each q is independently 0–2 and substitution on the phenyl is at the 3 or 4 position;

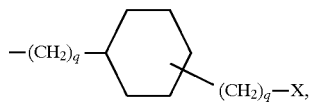

wherein each q is independently 0–2 and substitution on the cyclohexyl is at the 3 or 4 position;

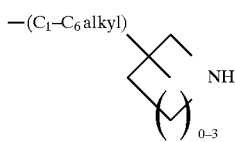

—(CH$_2$)$_m$O—(C$_1$–C$_4$ alkyl)-X, where m=1 or 2;
—(CH$_2$)$_m$S—(C$_1$–C$_4$ alkyl)-X, where m=1 or 2; and
X is selected from:
  —NH—C (=NH)(NH$_2$), —NHR$^{13}$, —C(=NH)(NH$_2$),
  —SC(NH)—NH$_2$;
R$^6$ and R$^7$ can alternatively be taken together to form

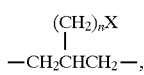

where
n=0 or 1 and X is —NH$_2$ or —NH—C(=NH)(NH$_2$);
L is —Y(CH$_2$)$_v$C(=O)—, wherein:
Y is NH, N(C$_1$–C$_3$ alkyl), O, or S; and v=1 or 2;
M is a D-isomer or L-isomer amino acid of structure

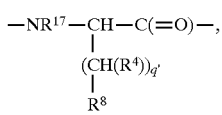

wherein:
q' is 0–2;
R$^{17}$ is H, C$_1$–C$_3$ alkyl;
R$^8$ is selected from:
  —CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$;
R$^{34}$ and R$^{35}$ are independently selected from:
  —OH,
  —F,
  —N(R$^{13}$)$_2$, or
  C$_1$–C$_8$-alkoxy;
R$^{34}$ and R$^{35}$ can alternatively be taken together form:
  a cyclic boron ester where said chain or ring contains from 2 to 20 carbon atoms and, optionally, 1–4 heteroatoms independently selected from N, S, or O;
  a divalent cyclic boron amide where said chain or ring contains from 2 to 20 carbon atoms and, optionally, 1–4 heteroatoms independently selected from N, S, or O;
  a cyclic boron amide-ester where said chain or ring contains from 2 to 20 carbon atoms and, optionally, 1–4 heteroatoms independently selected from N, S, or O.

6. A compound of claim 1, wherein:
R$^{31}$ is selected from the group consisting of:
  (a) a 6 membered saturated, partially saturated or aromatic carbocyclic ring substituted with 0–3 R$^{10}$ or R$^{10a}$, and optionally bearing a bond to L$_{n'}$;
  (b) a 8–11 membered saturated, partially saturated, or aromatic fused bicyclic carbocyclic ring substituted with 0–3 R$^{10}$ or R$^{10a}$, and optionally bearing a bond to L$_{n'}$; or
  (c) a 14 membered saturated, partially saturated, or aromatic fused tricyclic carbocyclic ring substituted with 0–3 R$^{10}$ or R$^{10a}$, and optionally bearing a bond to L$_{n'}$.

7. A compound of claim 1, wherein:
R$^{31}$ is selected from the group consisting of:
  (a) a 6 membered saturated, partially saturated, or aromatic carbocyclic ring of formulae:

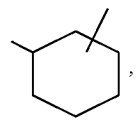

wherein any of the bonds forming the carbocyclic ring may be a single or double bond, and wherein said carbocyclic ring is substituted with 0–3 R$^{10}$, and optionally bears a bond to L$_{n'}$;
  (b) a 10 membered saturated, partially saturated, or aromatic bicyclic carbocyclic ring of formula:

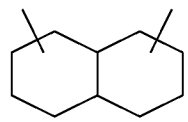

wherein any of the bonds forming the carbocyclic ring may be a single or double bond, wherein said carbocyclic ring is substituted independently with 0–4 R$^{10}$, and optionally bears a bond to L$_{n'}$;
  (c) a 9 membered saturated, partially saturated, or aromatic bicyclic carbocyclic ring of formula:

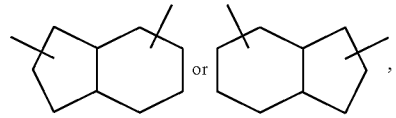

wherein any of the bonds forming the carbocyclic ring may be a single or double bond, wherein said carbocyclic ring is substituted independently with 0–4 R$^{10}$, and optionally bears a bond to L$_{n'}$.

8. A compound of claim 1, wherein:
R$^{31}$ is selected from (the dashed bond may be a single or double bond):

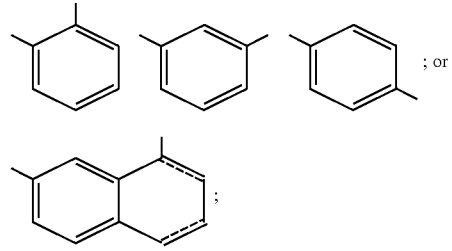

wherein R$^{31}$ may be independently substituted with 0–3 R$^{10}$ or R$^{10a}$, and optionally bears a bond to L$_{n'}$;
n" is 0 or 1; and
n' is 0–2.

9. A compound of claim 1, wherein:

$R^1$ and $R^{22}$ are independently selected from:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —$C(=O)NHOR^{13a}$, —$C(=O)NHN(R^{13})_2$, =$NOR^{13}$, —$B(R^{34})(R^{35})$, $C_3$–$C_6$ cycloalkoxy, —$OC(=O)R^{13}$, —$C(=O)R^{13}$, —$OC(=O)OR^{13a}$, —$OR^{13}$, —$(C_1$–$C_4$ alkyl)-$OR^{13}$, —$N(R^{13})_2$, —$OC(=O)N(R^{13})_2$, —$NR^{13}C(=O)R^{13}$, —$NR^{13}C(=O)OR^{13a}$, —$NR^{13}C(=O)N(R^{13})_2$, —$NR^{13}SO_2N(R^{13})_2$, —$NR^{13}SO_2R^{13a}$, —$SO_3H$, —$SO_2R^{13a}$, —$S(=O)R^{13a}$, —$SR^{13}$, —$SO_2N(R^{13})_2$, $C_2$–$C_6$ alkoxyalkyl, methylenedioxy, ethylenedioxy, $C_1$–$C_4$ haloalkyl, $C_1$–$C_4$ haloalkoxy, —$OCH_2CO_2H$, 2-(1-morpholino)ethoxy, $C_1$–$C_4$ alkyl (alkyl being substituted with —$N(R^{13})_2$, —$CF_3$, $NO_2$, or —$S(=O)R^{13a}$).

10. A compound of claim 1, wherein:

$R^{31}$ is selected from:

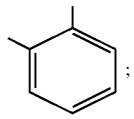;

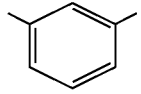;

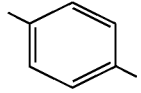;

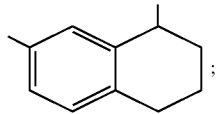;

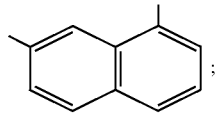;

wherein $R^{31}$ may be independently substituted with 0–3 $R^{10}$ or $R^{10a}$, and may optionally bear a bond to $L_n$;

$R^{32}$ is —$C(=O)$—;

n" is 0 or 1;

n' is 0–2;

$R^1$ and $R^{22}$ are independently selected from H, $C_1$–$C_4$ alkyl, phenyl, benzyl, phenyl—$(C_2$–$C_4)$alkyl, $C_1$–$C_4$ alkoxy; and a bond to $L_n$;

$R^{21}$ and $R^{23}$ are independently H or $C_1$–$C_4$ alkyl;

$R^2$ is H or $C_1$–$C_8$ alkyl;

$R^{13}$ is selected independently from: H, $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;

$R_{13a}$ is $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;

when two $R^{13}$ groups are bonded to a single N, said $R^{13}$ groups may alternatively be taken together to form —$(CH_2)_{2-5}$— or —$(CH_2)O(CH_2)$—;

$R^{14}$ is OH, H, $C_1$–$C_4$ alkyl, or benzyl;

$R^{10}$ and $R^{10a}$ are selected independently from: $C_1$–$C_5$ alkyl, phenyl, halogen, or $C_1$–$C_4$ alkoxy;

J is β-Ala or an L-isomer or D-isomer amino acid of structure —$N(R^3)C(R^4)(R^5)C(=O)$—, wherein:

$R^3$ is H or $CH_3$;

$R^4$ is H or $C_1$–$C_3$ alkyl;

$R^5$ is H, $C_1$–$C_8$ alkyl, $C_3$–$C_6$ cycloalkyl, $C_3$–$C_6$ cycloalkylmethyl, $C_3$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, —$(CH_2)_sNHC(=NH)(NH_2)$, —$(CH_2)_sNHR^{16}$, where s=3–5; and a bond to $L_n$; or $R^3$ and $R^5$ can alternatively be taken together to form —$(CH_2)_t$— (t=2–4) or —$CH_2SC(CH_3)_2$—; or $R^4$ and $R^5$ can alternatively be taken together to form —$(CH_2)_u$—, where u=2–5;

$R^{16}$ is selected from:
an amine protecting group;
1–2 amino acids; or
1–2 amino acids substituted with an amine protecting group;

K is an L-isomer amino acid of structure —$N(R^6)CH(R^7)C(=O)$—, wherein:

$R^6$ is H or $C_1$–$C_8$ alkyl;

$R^7$ is

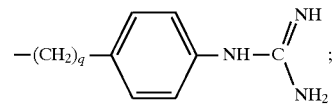

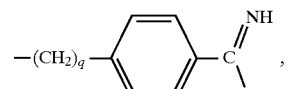, where q=0 or 1;

—$(CH_2)_rX$, where r=3–6;

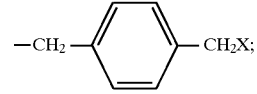

—$(CH_2)_mS(CH_2)_2X$, where m=1 or 2;

—$(C_3$–$C_7$ alkyl)—NH—$(C_1$–$C_6$ alkyl);

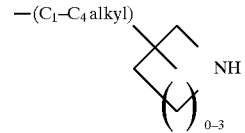

—$(CH_2)_m$—O—$(C_1$–$C_4$ alkyl)—NH—$(C_1$–$C_6$ alkyl), where m=1 or 2;

—$(CH_2)_m$—S—$(C_1$–$C_4$ alkyl)—NH—$(C_1$–$C_6$ alkyl), where m=1 or 2; and

X is —$NH_2$ or —$NHC(=NH)(NH_2)$; or

217

$R^6$ and $R^7$ can alternatively be taken together to form $$-CH_2CHCH_2-,$$
$$|$$
$$(CH_2)_nX$$

where n=0 or 1 and X is —$NH_2$ or —NHC(=NH)($NH_2$);

L is —Y($CH_2$)$_v$C(=O)—, wherein:
  Y is NH, O, or S; and v=1 or 2;

M is a D-isomer or L-isomer amino acid of structure $$-NR^{17}-CH-C(=O)-,$$
$$|$$
$$(CH(R^4))_{q'}$$
$$|$$
$$R^8$$

wherein;
q' is 0–2;
$R^{17}$ is H, $C_1$–$C_3$ alkyl;
$R^8$ is selected from:
  —$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$.

11. The compound of claim 1 that is a 1,3-disubstituted phenyl compound of the formula (II):

(II)

wherein: the shown phenyl ring in formula (II) may be substituted with 0–3 $R^{10}$, and may optionally bear a bond to $L_n$;
  $R^{10}$ is selected independently from: $C_1$–$C_5$ alkyl, phenyl, halogen, or $C_1$–$C_4$ alkoxy;
  $R^1$ is H, $C_1$–$C_4$ alkyl, phenyl, benzyl, phenyl—($C_1$–$C_4$) alkyl, or a bond to $L_n$;
  $R^2$ is H or methyl;
  $R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;
  $R^{13a}$ is $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;
    when two $R^{13}$ groups are bonded to a single N, said $R^{13}$ groups may alternatively be taken together to form —($CH_2$)$_{2-5}$— or —($CH_2$)O($CH_2$)—;
  $R^{14}$ is OH, H, $C_1$–$C_4$ alkyl, or benzyl;
  J is β-Ala or an L-isomer or D-isomer amino acid of structure —N($R^3$)C($R^4$)($R^5$)C(=O)—, wherein:
    $R^3$ is H or $CH_3$;
    $R^4$ is H or $C_1$–$C_3$ alkyl;
    $R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl,

218 phenylmethyl, $CH_2OH$, $CH_2SH$, $CH_2OCH_3$, $CH_2SCH_3$, $CH_2CH_2SCH_3$, ($CH_2$)$_s$$NH_2$, —($CH_2$)$_s$NHC(=NH)($NH_2$), —($CH_2$)$_s$$NHR^{16}$, where s=3–5, or a bond to $L_n$;
  $R^3$ and $R^5$ can alternatively be taken together to form —$CH_2CH_2CH_2$—; or
  $R^4$ and $R^5$ can alternatively be taken together to form —($CH_2$)$_u$—, where u=2–5;
  $R^{16}$ is selected from:
    an amine protecting group;
    1–2 amino acids; or
    1–2 amino acids substituted with an amine protecting group;
  K is an L-isomer amino acid of structure —N($R^6$)CH($R^7$)C(=O)—, wherein:
    $R^6$ is H or $C_1$–$C_8$ alkyl;
    $R^7$ is:

where q=0 or 1;
—($CH_2$)$_r$X, where r=3–6;

—($CH_2$)$_m$S($CH_2$)$_2$X, where m=1 or 2;

—($C_3$–$C_7$ alkyl)—NH—($C_1$–$C_6$ alkyl)

—($CH_2$)$_m$—O—($C_1$–$C_4$ alkyl)—NH—($C_1$–$C_6$ alkyl), where m=1 or 2;

—($CH_2$)$_m$—S—($C_1$–$C_4$ alkyl)—NH—($C_1$–$C_6$ alkyl), where m=1 or 2; and

X is —$NH_2$ or —NHC(=NH)($NH_2$), provided that X is not —$NH_2$ when r=4; or $R^6$ and $R^7$ are alternatively be taken together to form $$-CH_2CHCH_2-,$$
$$|$$
$$(CH_2)_nX$$

where n=0,1 and X is —$NH_2$ or —NHC(=NH)($NH_2$);

L is —Y($CH_2$)$_v$C(=O)—, wherein:
  Y is NH, O, or S; and v=1,2;

M is a D-isomer or L-isomer amino acid of structure $$-NR^{17}-CH-C(=O)-$$
$$\phantom{-NR^{17}-}|$$
$$\phantom{-NR^{17}-}(CH(R^4))_{q'}$$
$$\phantom{-NR^{17}-}|$$
$$\phantom{-NR^{17}-}R^8\quad,$$

wherein:
q' is 0–2;
$R^{17}$ is H, $C_1$–$C_3$ alkyl;
$R^8$ is selected from:
—$CO_2R^{13}$, —$SO_3R^{13}$, —$SO_2NHR^{14}$, —$B(R^{34})(R^{35})$, —$NHSO_2CF_3$, —$CONHNSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$.

12. The compound of claim 1 that is a 1,3-disubstituted phenyl compound of the formula (II):

(II)

wherein:
the phenyl ring in formula (II) may be substituted with 0–3 $R^{10}$ or $R^{10a}$;
$R^{10}$ or $R^{10}$a are selected independently from: H, $C_1$–$C_8$ alkyl, phenyl, halogen, or $C_1$–$C_4$ alkoxy;
$R^1$ is H, $C_1$–$C_4$ alkyl, phenyl, benzyl, or phenyl—$(C_2$–$C_4)$ alkyl;
$R^2$ is H or methyl;
$R^{13}$ is selected independently from: H, $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;
J is β-Ala or an L-isomer or D-isomer amino acid of structure —$N(R^3)C(R^4)(R^5)C(=O)$—, wherein:
$R^3$ is H or $CH_3$;
$R^4$ is H;
$R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, $(CH_2)_sNHR^{16}$, where s=3–5; or a bond to $L_n$;
$R^3$ and $R^5$ can alternatively be taken together to form —$CH_2CH_2CH_2$—;
$R^{16}$ is selected from:
an amine protecting group;
1–2 amino acids;
1–2 amino acids substituted with an amine protecting group;
K is an L-isomer amino acid of structure —$N(R^6)CH(R^7)C(=O)$—, wherein:
$R^6$ is H or $C_3$–$C_8$ alkyl;

$R^7$ is

—$(CH_2)_q$—⌬—$NH$—$C(=NH)NH_2$

—$(CH_2)_q$—⌬—$NH$—$C(=NH)NH_2$, where q=0 or 1;
$(CH_2)_rX$, where r=3–6;

—$CH_2$—⌬—$CH_2X$;  —$CH_2$—⌬—$CH_2X$;

—$(CH_2)_mS(CH_2)_2X$, where m=1 or 2;
—$(C_4$–$C_7$ alkyl)—$NH$—$(C_1$–$C_6$ alkyl)

—$(C_1$–$C_4$ alkyl)⌬$NH$⌬$_{0-3}$

—$(CH_2)_m$—$O$—$(C_1$–$C_4$ alkyl)—$NH$—$(C_1$–$C_6$ alkyl), where m=1 or 2;
—$(CH_2)_m$—$S$—$(C_1$–$C_4$ alkyl)—$NH$—$(C_1$–$C_6$ alkyl), where m=1 or 2; and
X is —$NH_2$ or —$NHC(=NH)(NH_2)$, provided that X is not —$NH$—$NH_2$ when r=4; or
L is —$YCH_2C(=O)$—, wherein:
Y is NH or O;
M is a D-isomer or L-isomer amino acid of structure $$-NR^{17}-CH-C(=O)-$$
$$\phantom{-NR^{17}-}|$$
$$\phantom{-NR^{17}-}(CH(R^4))_{q'}$$
$$\phantom{-NR^{17}-}|$$
$$\phantom{-NR^{17}-}R^8\quad,$$

wherein:
q' is 1;
$R^{17}$ is H, $C_1$–$C_3$ alkyl;
$R^8$ is selected from:
—$CO_2H$ or —$SO_3R^{13}$.
13. The compound of claim 1 that that is a compound of formula (II) above, wherein:
the phenyl ring in formula (II) bears a bond to $L_n$, and may be further substituted with 0–2 $R^{10}$ or $R^{10a}$;
$R^{10}$ or $R^{10a}$ are selected independently from: H, $C_1$–$C_8$ alkyl, phenyl, halogen, or $C_1$–$C_4$ alkoxy;
$R^1$ is H;
$R^2$ is H;
J is β-Ala or an L-isomer or D-isomer amino acid of formula —$N(R^3)CH(R^5)C(=O)$—, wherein:
$R^3$ is H and $R^5$ is H, $CH_3$, $CH_2CH_3$, $CH(CH_3)_2$, $CH(CH_3)CH_2CH_3$, $CH_2CH_2CH_3$, $CH_2CH_2CH_2CH_3$, $CH_2CH_2SCH_3$, $CH_2CH(CH_3)_2$, $(CH_2)_4NH_2$, $(C_3$–$C_5$ alkyl)$NHR^{16}$; or
$R^3$ is $CH_3$ and $R^5$ is H; or
$R^3$ and $R^5$ can alternatively be taken together to form —$CH_2CH_2CH_2$—;

R¹⁶ is selected from:
  an amine protecting group;
  1–2 amino acids;
  1–2 amino acids substituted with an amine protecting group;
K is an L-isomer amino acid of formula —N(CH₃)CH(R⁷)C(=O)—, wherein:
  R⁷ is —(CH₂)₃NHC(=NH)(NH₂);
L is —NHCH₂C(=O)—; and
M is a D-isomer or L-isomer amino acid of structure

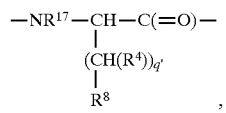

wherein:
  q' is 1;
  R⁴ is H or CH₃;
  R¹⁷ is H;
  R⁸ is
    —CO₂H;
    —SO₃H.

14. The compound of claim 1 that is a compound of formula (II) above, wherein:
  the phenyl ring in formula (II) bears a bond to L_n;
  R¹ and R² are independently selected from H, methyl;
  J is selected from D-Val, D-2-aminobutyric acid, D-Leu, D-Ala, Gly, D-Pro, D-Ser, D-Lys, βAla, Pro, Phe, NMeGly, D-Nle, D-Phg, D-Ile, D-Phe, D-Tyr, Ala, Nᵉ-p-azidobenzoyl-D-Lys, Nᵉ-p-benzoylbenzoyl-D-Lys, Nᵉ-tryptophanyl-D-Lys, Nᵉ-o-benzoylbenzoyl-D-Lys, Nᵉ-p-acetylbenzoyl-D-Lys, Nᵉ-dansyl-D-Lys, Nᵉ-glycyl-D-Lys, Nᵉ-glycyl-p-benzoylbenzoyl-D-Lys, Nᵉ-p-phenylbenzoyl-D-Lys, Nᵉ-m-benzoylbenzoyl-D-Lys, Nᵉ-o-benzoylbenzoyl-D-Lys;
  K is selected from NMeArg, Arg;
  L is selected from Gly, βAla, Ala;
  M is selected from Asp; αMeAsp; βMeAsp; NMeAsp; D-Asp.

15. The compound of claim 1, wherein:
  R³¹ bears a bond to L_n;
  R¹ and R² are independently selected from H, methyl;
  J is selected from: D-Val, D-2-aminobutyric acid, D-Leu, D-Ala, Gly, D-Pro, D-Ser, D-Lys, βAla, Pro, Phe, NMeGly, D-Nle, D-Phg, D-Ile, D-Phe, D-Tyr, Ala;
  K is selected from NMeArg;
  L is Gly;
  M is selected from Asp; αMeAsp; βMeAsp; NMeAsp; D-Asp.

16. A compound as in one of claims 1–15, wherein C_h is selected from the group:

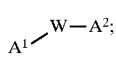

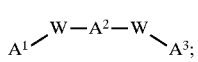

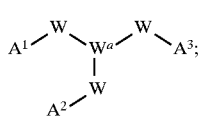

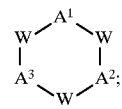

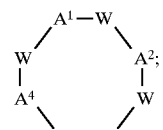

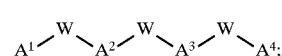

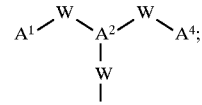

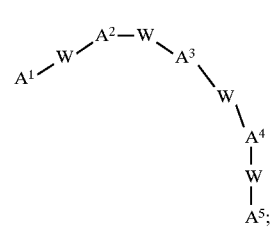

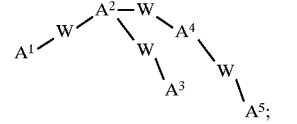

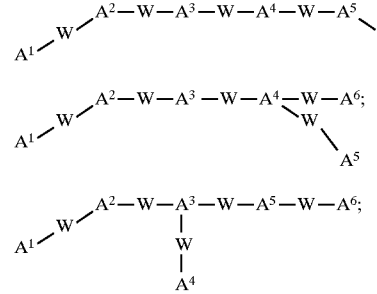

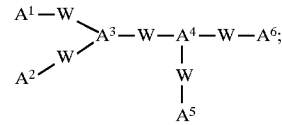

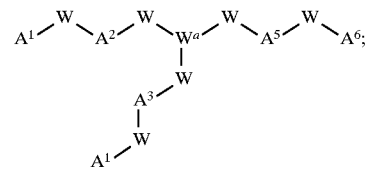

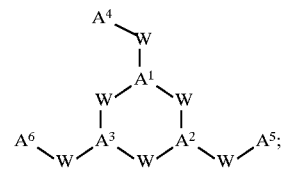

-continued

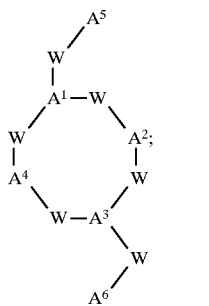

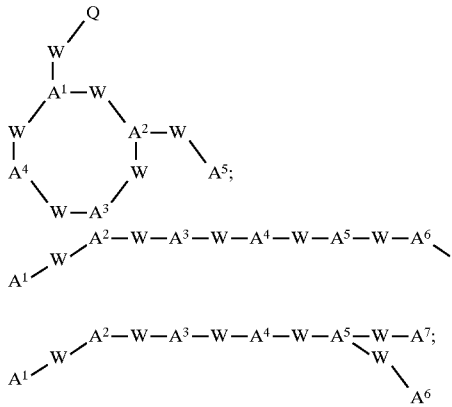

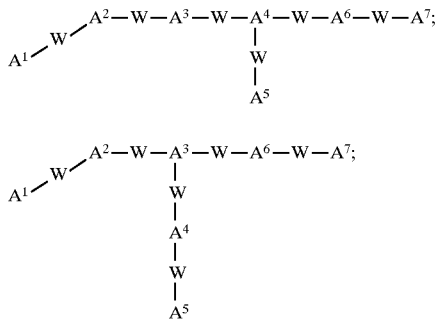

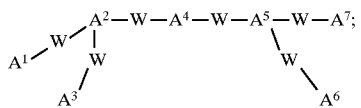

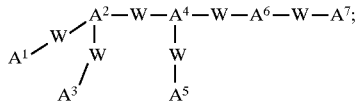

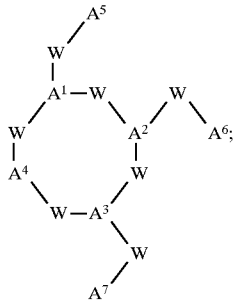

-continued

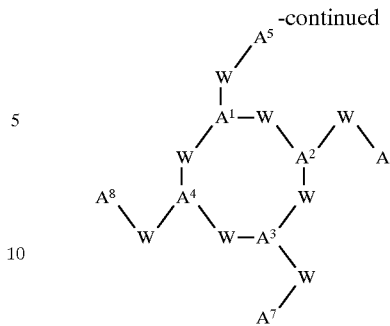

wherein:

$A^1$, $A^2$, $A^3$, $A^4$, $A^5$, $A^6$, $A^7$, and $A^8$ are independently selected at each occurrence from the group: $NR^{40}R^{41}$, S, SH, S(Pg), O, OH, $PR^{42}R^{43}$, $P(O)R^{42}R^{43}$, $P(S)R^{42}R^{43}$, $P(NR^{44})R^{42}R^{43}$;

W is a bond, CH, or a spacer group selected from the group: $C_1$–$C_{10}$ alkyl substituted with 0–3 $R^{52}$, aryl substituted with 0–3 $R^{52}$, cycloalkyl substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$W^a$ is a $C_{1-C10}$ alkyl group or a $C_3$–$C_{14}$ carbocycle;

$R^{40}$, $R^{41}$, $R^{42}$, $R^{43}$, and $R^{44}$ are each independently selected from the group: a bond to $L_n$, hydrogen, $C_1$–$C_{10}$ alkyl substituted with 0–3 $R^{52}$, aryl substituted with 0–3 $R^{52}$, cycloalkyl substituted with 0–3 $R^{52}$, heterocycle substituted with 0–3 $R^{52}$, heterocycloalkyl substituted with 0–3 $R^{52}$, aralkyl substituted with 0–3 $R^{52}$, alkaryl substituted with 0–3 $R^{52}$ and an electron, provided that when one of $R^{40}$ or $R^{41}$ is an electron, then the other is also an electron, and provided that when one of $R^{42}$ or $R^{43}$ is an electron, then the other is also an electron;

additionally, $R^{40}$ and $R^{41}$ may combine to form $=C(C_1$–$C_3$ alkyl)($C_1$–$C_3$ alkyl);

$R^{52}$ is independently selected at each occurrence from the group: a bond to $L_n$, =O, F, Cl, Br, I, —$CF_3$, —CN, —$CO_2R^{53}$, —$C(=O)R^{53}$, —$C(=O)N(R^{53})_2$, —CHO, —$CH_2OR^{53}$, —$OC(=O)R^{53}$, —$OC(=O)OR^{53a}$, —$OR^{53}$, —$OC(=O)N(R^{53})_2$, —$NR^{53}C(=O)R^{53}$, —$NR^{54}C(=O)OR^{53a}$, —$NR^{53}C(=O)N(R^{53})_2$, —$NR^{54}SO_2N(R^{53})_2$, —$NR^{54}SO_2R^{53a}$, —$SO_3H$, —$SO_2R^{53a}$, —$SR^{53}$, —$S(=O)R^{53a}$, —$SO_2N(R^{53})_2$, —$N(R^{53})_2$, —$NHC(=NH)NHR^{53}$, —$C(=NH)NHR^{53}$, =$NOR^{53}$, $NO_2$, —$C(=O)NHOR^{53}$, —$C(=O)NHNR^{53}R^{53a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{53}$, a 5–10-membered heterocyclic ring system containing 1–4 heteroatoms independently selected from N, S, and O;

$R^{53}$, $R^{53a}$, and $R^{54}$ are independently selected at each occurrence from the group: a bond to $L_n$, $C_1$–$C_6$ alkyl, phenyl, benzyl, $C_1$–$C_6$ alkoxy, halide, nitro, cyano, and trifluoromethyl; and Pg is a thiol protecting group capable of being displaced upon reaction with a radionuclide.

17. A compound as in one of claims 1–15, wherein $C_h$ is selected from the group:

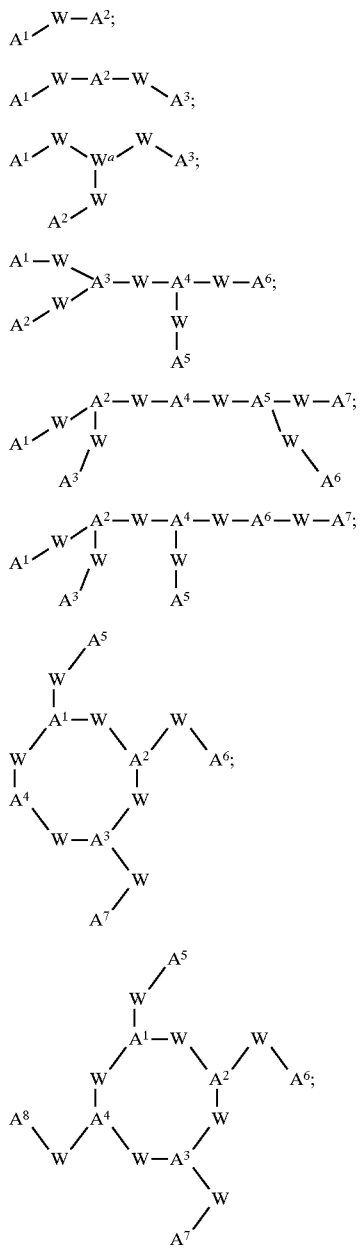

wherein:
A$^1$, A$^2$, A$^3$, A$^4$, A$^5$, A$^6$, A$^7$, and A$^8$ are independently selected at each occurrence from the group: NR$^{40}$R$^{41}$, S, SH, S(Pg), OH;

W is a bond, CH, or a spacer group selected from the group: C$_1$-C$_3$ alkyl substituted with 0-3 R$^{52}$;

W$^a$ is a methylene group or a C$_3$-C$_6$ carbocycle;

R$^{40}$, R$^{41}$, R$^{42}$, R$^{43}$, and R$^{44}$ are each independently selected from the group: a bond to L$_n$, hydrogen, C$_1$-C$_{10}$ alkyl substituted with 0-3 R$^{52}$, heterocycle substituted with 0-3 R$^{52}$, and an electron, provided that when one of R$^{40}$ or R$^{41}$ is an electron, then the other is also an electron, and provided that when one of R$^{42}$ or R$^{43}$ is an electron, then the other is also an electron; additionally, R$^{40}$ and R$^{41}$ may combine to form, =C(C$_1$-C$_3$ alkyl)(C$_1$-C$_3$ alkyl);

R$^{52}$ is independently selected at each occurrence from the group: a bond to L$_n$, =O, F, Cl, Br, I, —CF$_3$, —CN, —CO$_2$R$^{53}$, —C(=O)R$^{53}$, —C(=O)N(R$^{53}$)$_2$, —CHO, —CH$_2$OR$^{53}$, —OC(=O)R$^{53}$, —OC(=O)OR$^{53a}$, —OR$^{53}$, —OC(=O)N(R$^{53}$)$_2$, —NR$^{53}$C(=O)R$^{53}$, —NR$^{54}$C(=O)OR$^{53a}$, —NR$^{53}$C(=O)N(R$^{53}$)$_2$, —NR$^{54}$SO$_2$N(R$^{53}$)$_2$, —NR$^{54}$SO$_2$R$^{53a}$, —SO$_3$H, —SO$_2$R$^{53a}$, —SR$^{53}$, —S(=O)R$^{53a}$, —SO$_2$N(R$^{53}$)$_2$, —N(R$^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}$R$^{53a}$, —OCH$_2$CO$_2$H, 2-(1-morpholino)ethoxy; and R$^{53}$, R$^{53a}$, and R$^{54}$ are independently selected at each occurrence from the group: a bond to L$_n$, C$_1$-C$_6$ alkyl.

18. A compound as in one of claims 1–15, of formula:

(QL$_n$)$_d$C$_h$, wherein d is 1; and

C$_h$ is selected from:

A$^1$—W—A$^2$—W—A$^3$—W—A$^4$, wherein:
A$^1$ and A$^4$ are SH or SPg;
A$^2$ and A$^3$ are NR$^{41}$;
W is independently selected from the group: CHR$^{52}$, CH$_2$CHR$^{52}$, CH$_2$CH$_2$CHR$^{52}$ and CHR$^{52}$C=O; and
R$^{41}$ and R$^{52}$ are independently selected from hydrogen and a bond to L$_n$, and,

A$^1$—W—A$^2$, wherein:
A$^1$ is NH$_2$ or N=C(C$_1$-C$_3$ alkyl)(C$_1$-C$_3$ alkyl);
W is a bond;
A$^2$ is NHR$^{40}$, wherein R$^{40}$ is heterocycle substituted with R$^{52}$, wherein the heterocycle is selected from the group: pyridine, pyrazine, proline, furan, thiofuran, thiazole, and diazine, and R$^{52}$ is a bond to L$_n$.

19. A compound as in one of claims 1–15, of formula:

(QL$_n$)$_d$C$_h$, wherein d is 1; and
wherein C$_h$ is:

A$^1$—W—A$^2$, wherein:
A$^1$ is NH$_2$ or N=C(C$_1$-C$_3$ alkyl)(C$_1$-C$_3$ alkyl);
W is a bond;
A$^2$ is NHR$^{40}$, wherein R$^{40}$ is heterocycle substituted with R$^{52}$, wherein the heterocycle is selected from pyridine and thiazole, and R$^{52}$ is a bond to L$_n$.

20. A compound as in one of claims 1–15, wherein L$_n$ is: a bond between Q and C$_h$; or,
a compound of formula:

M$^1$—[Y$^1$(CR$^{55}$R$^{56}$)$_h$(Z$^1$)$_{h'}$Y$^2$]$_{h''}$—M$^2$ wherein:
M$^1$ is —[(CH$_2$)$_g$Z$^1$]$_{g'}$—(CR$^{55}$R$^{56}$)$_{g''}$—;

$M^2$ is $—(CR^{55}R^{56})_{g''}—[Z^1(CH_2)_g]_{g'}—$;

g is independently 0–10;

g' is independently 0–1;

g" is 0–10;

h is 0–10;

h' is 0–10;

h" is 0–1

$Y^1$ and $Y^2$, at each occurrence, are independently selected from:
a bond, O, $NR^{56}$, C=O, C(=O)O, OC (=O)O, C(=O)NH—, C=$NR^{56}$, S, SO, $SO_2$, $SO_3$, NHC(=O), $(NH)_2C$(=O), $(NH)_2C$=S;

$Z^1$ is independently selected at each occurrence from a $C_6$–$C_{14}$ saturated, partially saturated, or aromatic carbocyclic ring system, substituted with 0–4 $R^{57}$; a heterocyclic ring system, optionally substituted with 0–4 $R^{57}$;

$R^{55}$ and $R^{56}$ are independently selected at each occurrence from:
hydrogen;
$C_1$–$C_{10}$ alkyl substituted with 0–5 $R^{57}$;
($C_1$–$C_{10}$ alkyl)aryl wherein the aryl is substituted with 0–5 $R^{57}$;

$R^{57}$ is independently selected at each occurrence from the group: hydrogen, OH, $NHR^{58}$, C(=O)$R^{58}$, OC(=O)$R^{58}$, OC(=O)O$R^{58}$, C(=O)O$R^{58}$, C(=O)$NR^{58}$—, C≡N, $SR^{58}$, $SOR^{58}$, $SO_2R^{58}$, NHC(=O)$R^{58}$, NHC(=O)$NHR^{58}$, NHC(=S)$NHR^{58}$; or, alternatively, when attached to an additional molecule Q, $R^{57}$ is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C$(=O), $(NH)_2C$=S; and, $R^{58}$ is independently selected at each occurrence from the group: hydrogen; $C_1$–$C_6$ alkyl; benzyl, and phenyl.

21. A compound as in claim 16, wherein $L_n$ is:
a compound of formula:

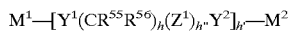

wherein:
$M^1$ is $—[(CH_2)_gZ^1]_{g'}—(CR^{55}R^{56})_{g''}—$;
$M^2$ is $—(C^{55}R^{56})_{g''}—[Z^1(CH_2)_g]_{g'}—$;
g is independently 0–10;
g' is independently 0–1;
g" is 0–10;
h is 0–10;
h' is 0–10;
h" is 0–1

$Y^1$ and $Y^2$, at each occurrence, are independently selected from:
a bond, O, $NR^{56}$, C=O, C(=O)O, OC (=O)O. C(=O)NH—, C=$NR^{56}$, S, SO, $SO_2$, $SO_3$, NHC(=O), $(NH)_2C$(=O), $(NH)_2C$=S;

$Z^1$ is independently selected at each occurrence from a $C_6$–$C_{14}$ saturated, partially saturated, or aromatic carbocyclic ring system, substituted with 0–4 $R^{57}$; a heterocyclic ring system, optionally substituted with 0–4 $R^{57}$;

$R^{55}$ and $R^{56}$ are independently selected at each occurrence from:
hydrogen;

$C_1$–$C_{10}$ alkyl substituted with 0–5 $R^{57}$;
($C_1$–$C_{10}$ alkyl)aryl wherein the aryl is substituted with 0–5 $R^{57}$;

$R^{57}$ is independently selected at each occurrence from the group: hydrogen, OH, $NHR^{58}$, C(=O)$R^{58}$, OC(=O)$R^{58}$, OC(=O)O$R^{58}$, C(=O)O$R^{58}$, C(=O)$NR^{58}$—, C≡N, $SR^{58}$, $SOR^{58}$, $SO_2R^{58}$, NHC(=O)$R^{58}$, NHC(=O)$NHR^{58}$, NHC(=S)$NHR^{58}$; or, alternatively, when attached to an additional molecule Q, R57 is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C$(=O), $(NH)_2C$=S, and $R^{57}$ is attached to an additional molecule Q; and, $R^{58}$ is independently selected at each occurrence from the group:hydrogen; $C_1$–$C_6$ alkyl; benzyl, and phenyl.

22. A compound as in claim 17, wherein $L_n$ is:

wherein:
g" is 0–10;
h is 0–10;
h' is 1–10;

$Y^1$ and $Y^2$, at each occurrence, are independently selected from:
a bond, O, $NR^{56}$, C=O, C(=O)O, OC(=O)O,
C(=O)NH—, C=$NR^{56}$, S, SO, $SO_2$, $SO_3$, NHC(=O), $(NH)_2C$(=O), $(NH)_2C$=S;

$R^{55}$ and $R^{56}$ are independently selected at each occurrence from:
hydrogen;

$C_1$–$C_{10}$ alkyl substituted with 0–5 $R^{57}$;
($C_1$—$C_{10}$ alkyl)aryl wherein the aryl is substituted with 0–5 $R^{57}$;

$R^{57}$ is independently selected at each occurrence from the group: hydrogen, OH, $NHR^{58}$, C(=O)$R^{58}$, OC(=O)$R^{58}$, OC(=O)O$R^{58}$, C(=O)O$R^{58}$, C(=O)$NR^{58}$—, C≡N, $SR^{58}$, $SOR^{58}$, $SO_2R^{58}$, NHC(=O)$R^{58}$, NHC(=O)$NHR^{58}$, NHC(=S)$NHR^{58}$; or, alternatively, when attached to an additional molecule Q, R57 is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C$(=O), $(NH)_2C$=S, and $R^{57}$ is attached to an additional molecule Q; and, $R^{58}$ is independently selected at each occurrence from the group:hydrogen; $C_1$–$C_6$ alkyl; benzyl, and phenyl.

23. A compound as in claim 18, wherein $L_n$ is:

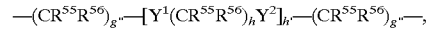

wherein:
g"is 0–5;
h is 0–5;
h' is 1–5;

$Y^1$ and $Y^2$, at each occurrence, are independently selected from:
O, $NR^{56}$, C=O, C(=O)O, OC(=O)O, C(=O)NH—, C=$NR^{56}$, S, SO, $SO_2$, $SO_3$, NHC(=O), $(NH)_2C$(=O), $(NH)_2C$=S;

$R^{55}$ and $R^{56}$ are independently selected at each occurrence from:
hydrogen;

$C_1$–$C_{10}$ alkyl;
($C_1$–$C_{10}$ alkyl)aryl.
24. A compound as in claim 19, wherein $L_n$ is:
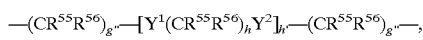
wherein:
g" is 0–5;
h is 0–5;
h' is 1–5;
$Y^1$ and $Y^2$, at each occurrence, are independently selected from:
O, $NR^{56}$, C=O, C(=O)O, OC(=O)O, C(=O)NH—, C=$NR^{56}$, S, NHC(=O), $(NH)_2$C(=O), $(NH)_2$C=S;
$R^{55}$ and $R^{56}$ are independently selected at each occurrence from:
hydrogen.
25. The compound of claim 1, which are:
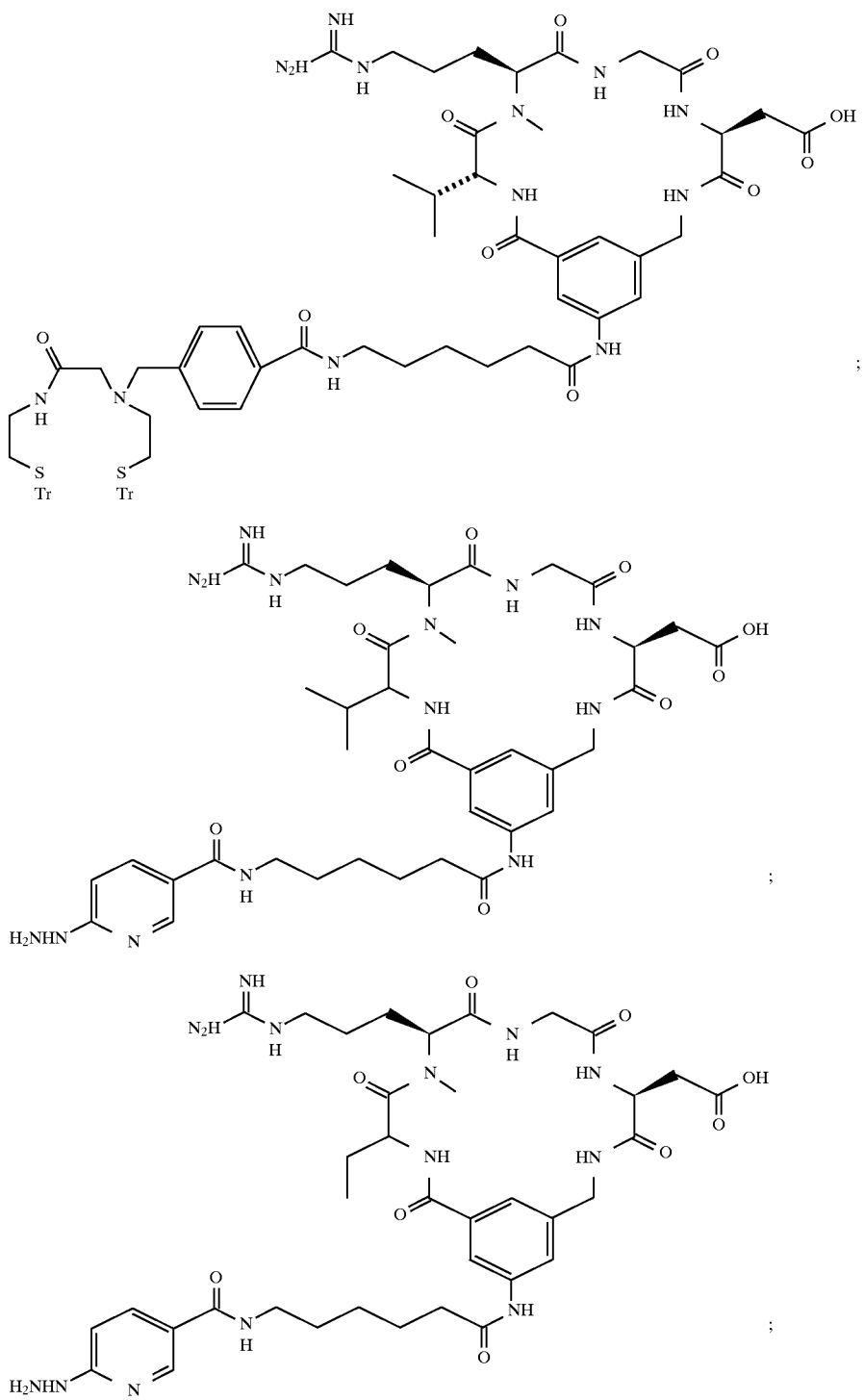

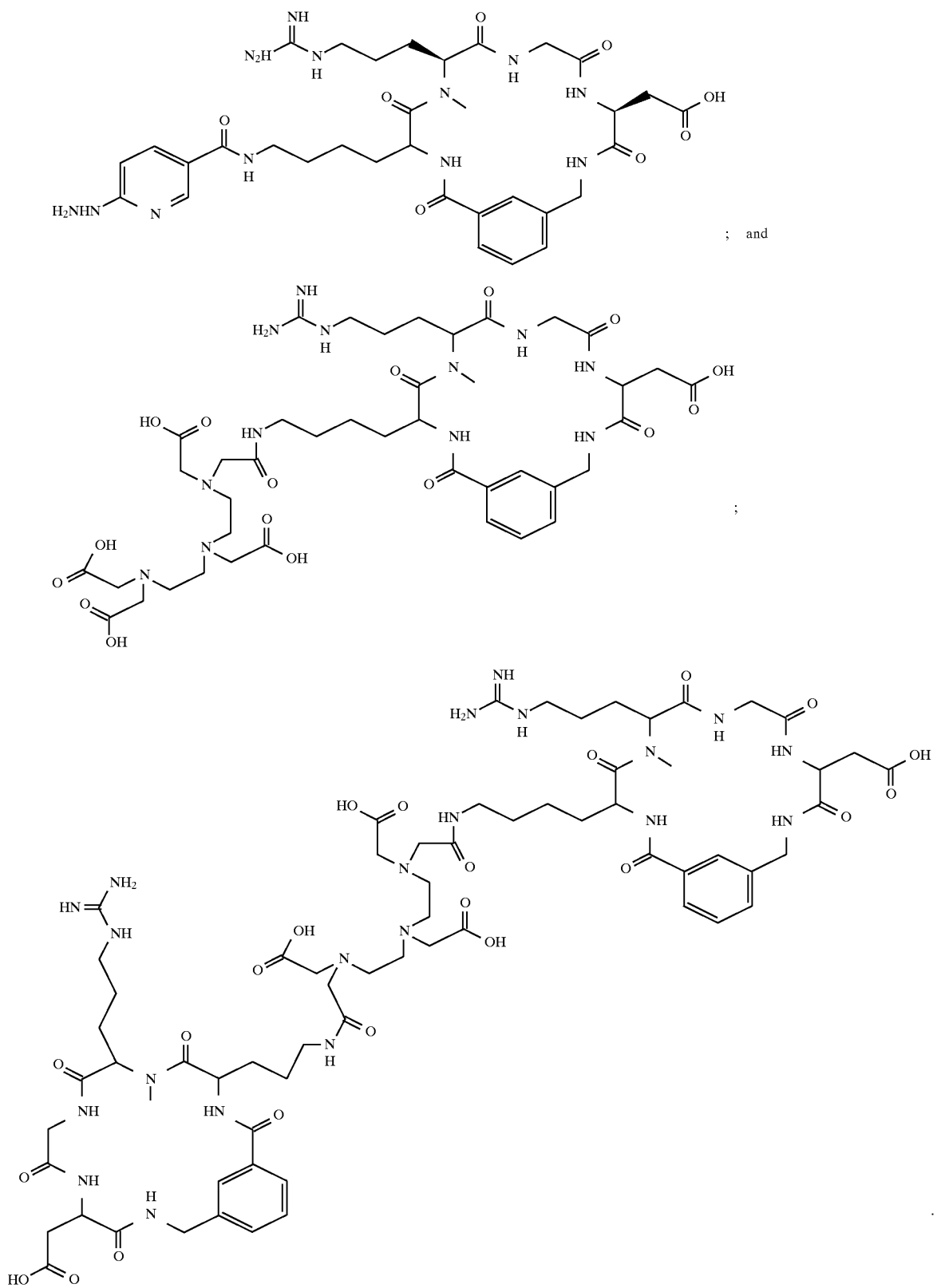

26. A kit for preparing a radiopharmaceutical comprising a predetermined quantity of a sterile, pharmaceutically acceptable reagent of claim 23.

27. A kit for preparing a radiopharmaceutical comprising a predetermined quantity of a sterile, pharmaceutically acceptable reagent of claim 24.

28. A kit for preparing a radiopharmaceutical comprising a predetermined quantity of a sterile, pharmaceutically acceptable reagent of claim 25.

29. A radiopharmaceutical comprising a complex of a reagent of claims 1–15 and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

30. A radiopharmaceutical comprising a complex of a reagent of claim 16 and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

31. A radiopharmaceutical comprising a complex of a reagent of claim 17 and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

32. A radiopharmaceutical comprising a complex of a reagent of claim 18 and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

33. A radiopharmaceutical comprising a complex of a reagent of claim 19 and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

34. A radiopharmaceutical comprising a complex of a reagent of claim 20 and a radionuclide selected from the group $^{99m}$Tc, $^{94m}$Tc, $^{95}$Tc, $^{111}$In, $^{62}$Cu, $^{43}$Sc, $^{45}$Ti, $^{67}$Ga, $^{68}$Ga, $^{97}$Ru, $^{72}$As, $^{82}$Rb, and $^{201}$Tl.

35. A radiopharmaceutical comprising a complex of a reagent of claim 21 and a radionuclide selected from the group $^{99m}$Tc, $^{111}$In, and $^{62}$Cu.

36. A radiopharmaceutical comprising a complex of a reagent of claim 22 and a radionuclide selected from the group $^{99m}$Tc, $^{111}$In, and $^{62}$Cu.

37. A radiopharmaceutical comprising a complex of a reagent of claim 23 and a radionuclide selected from the group $^{99m}$Tc, $^{111}$In, and $^{62}$Cu.

38. A radiopharmaceutical comprising a complex of a reagent of claim 24 and a radionuclide selected from the group $^{99m}$Tc, and $^{111}$In.

39. The radiopharmaceuticals of claim 29, which are:

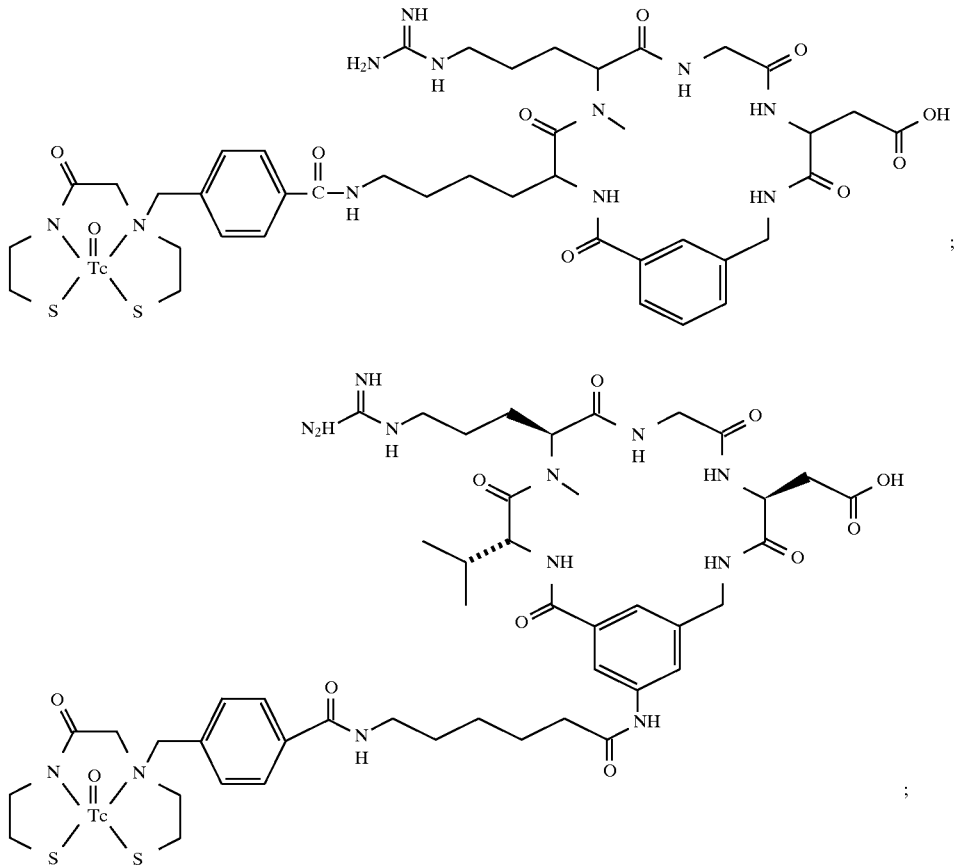

-continued
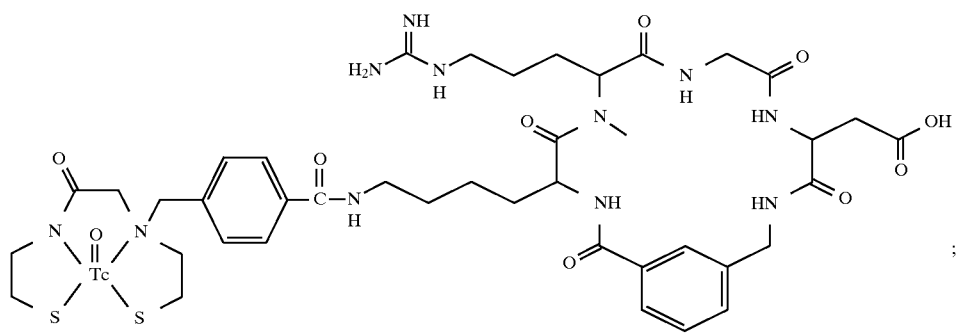
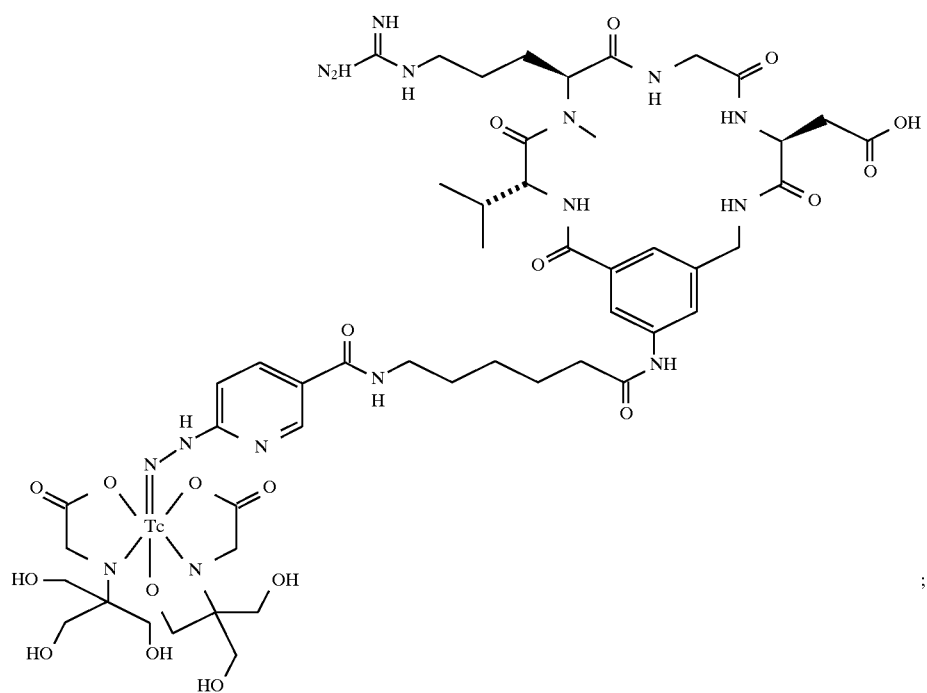
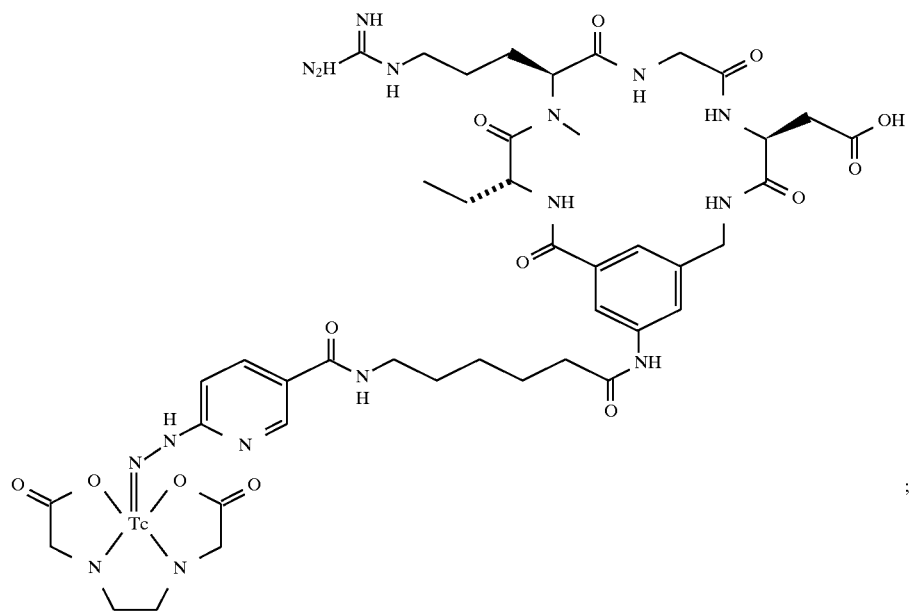

-continued
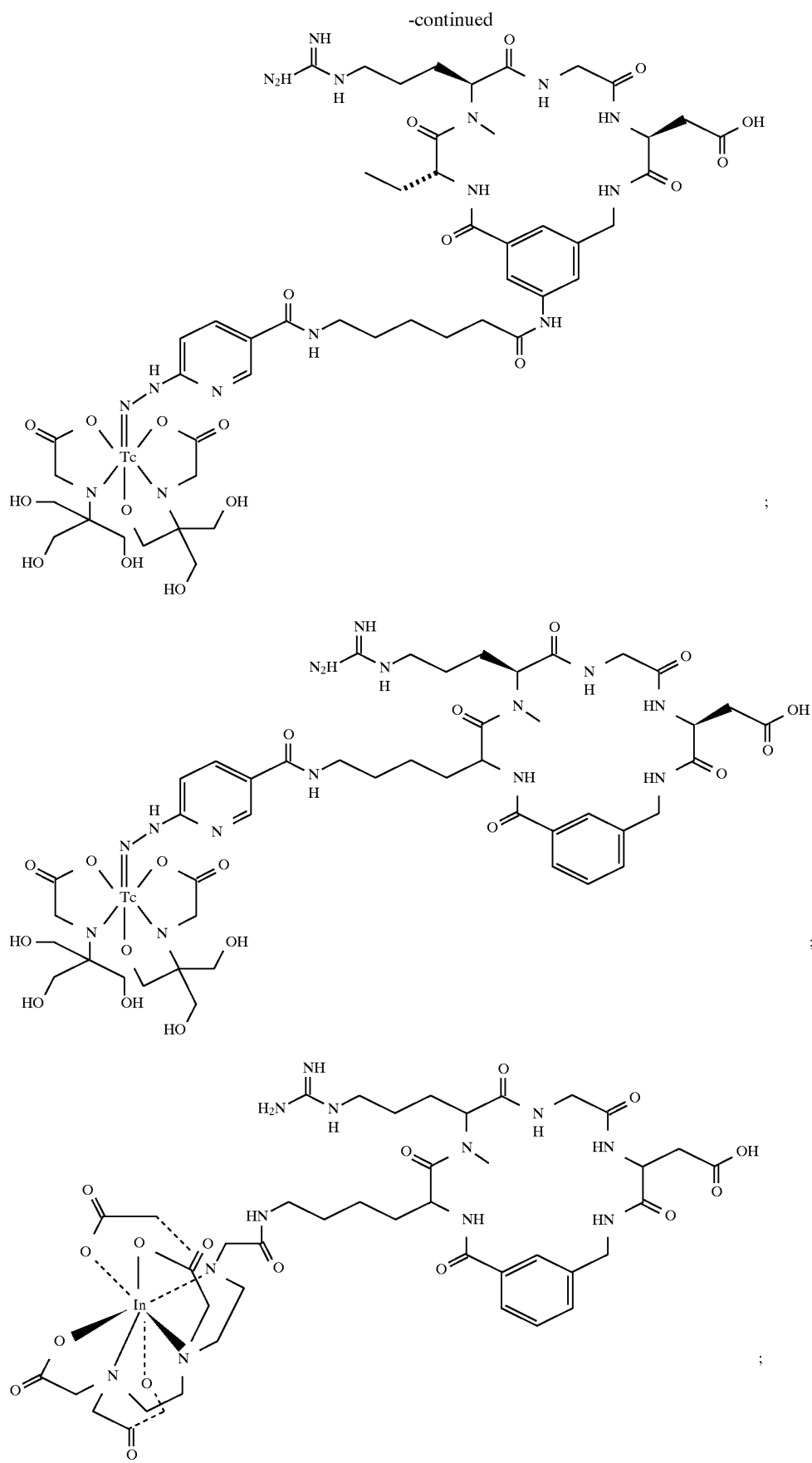

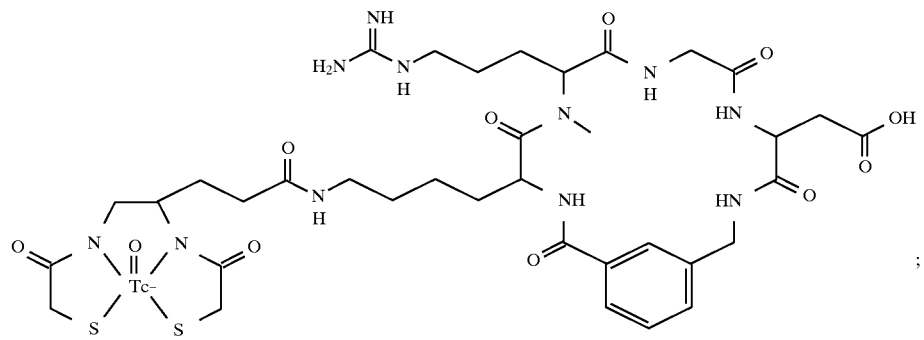
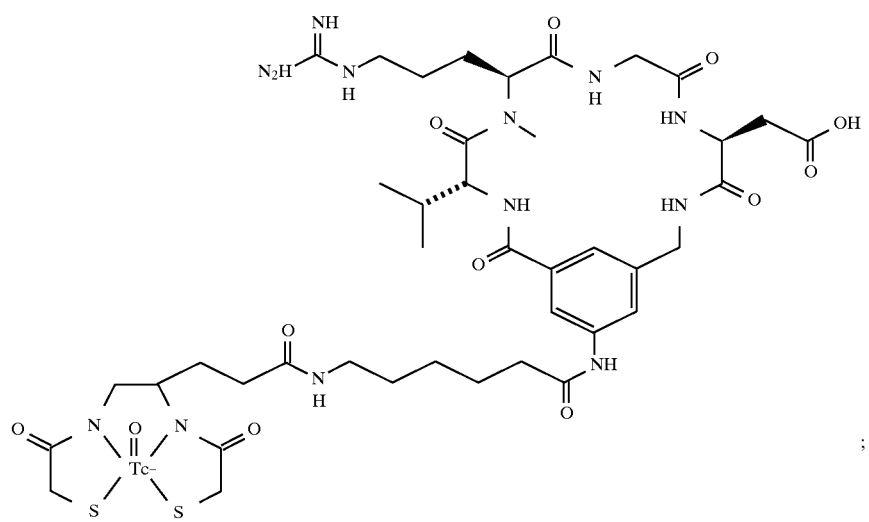
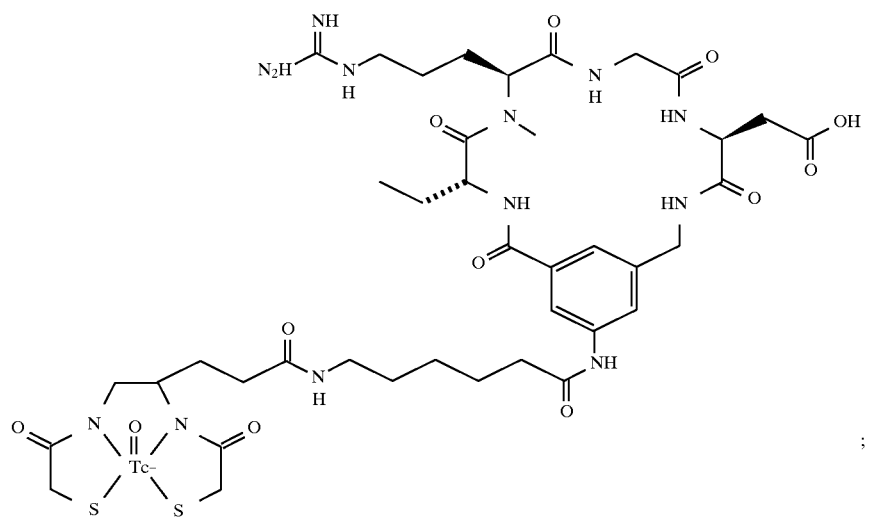

-continued
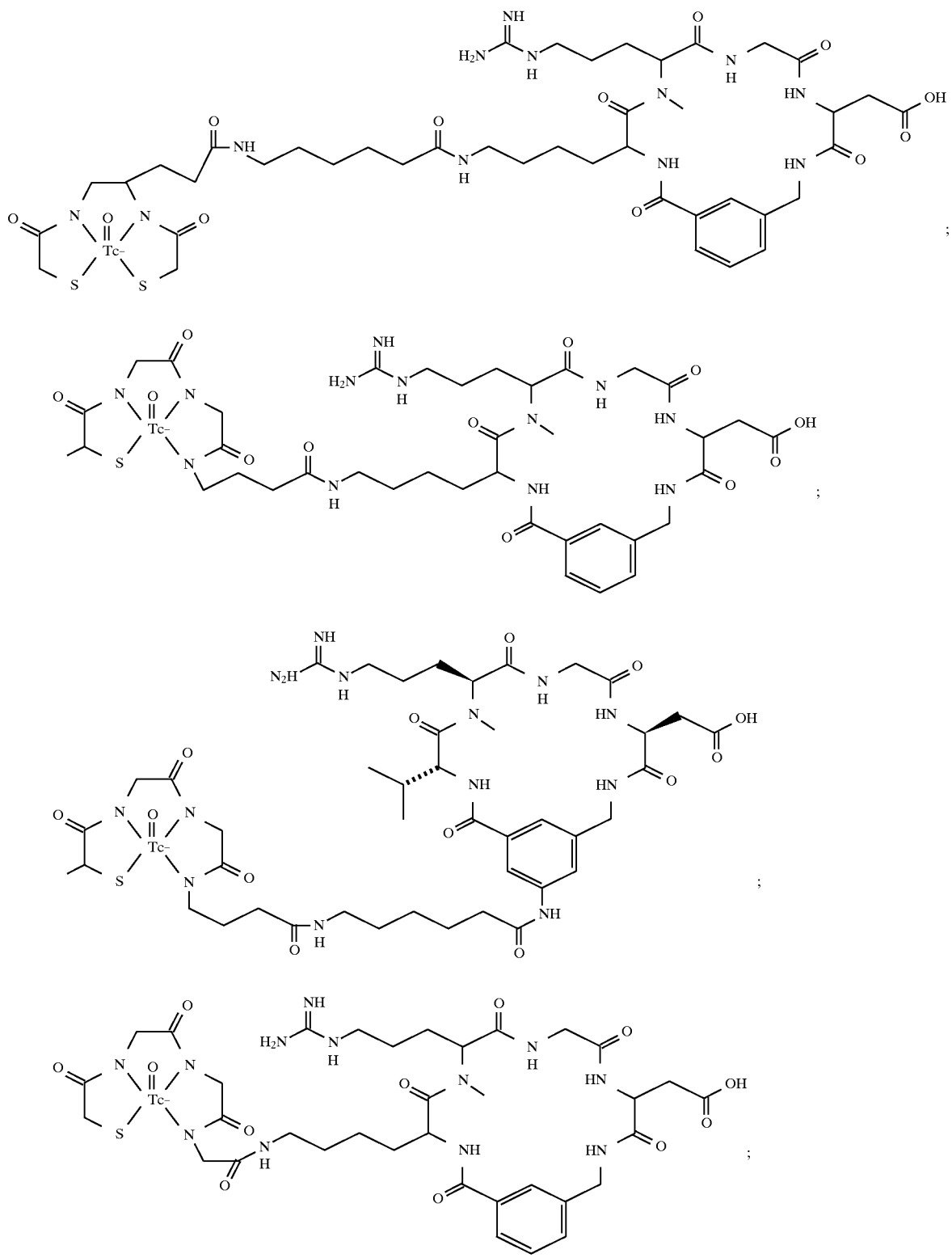

-continued
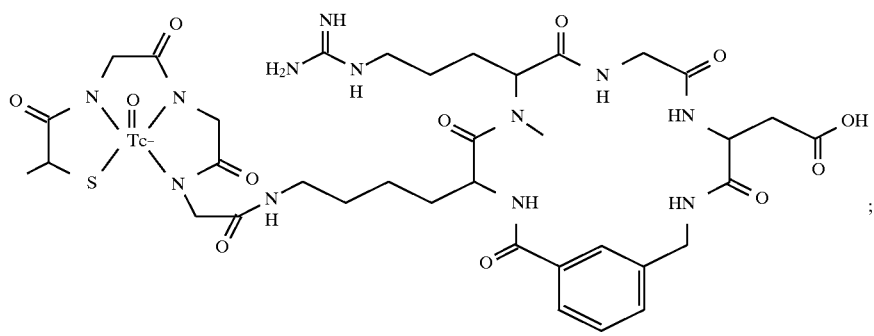
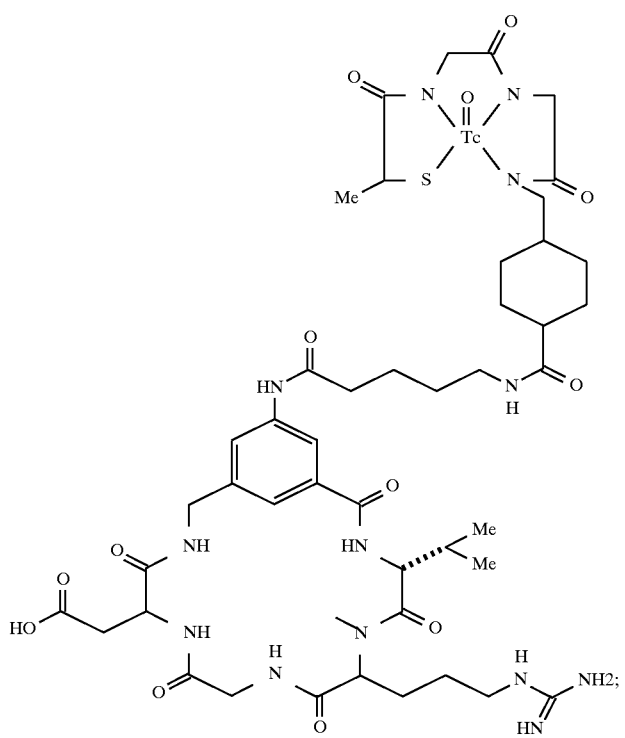
; and
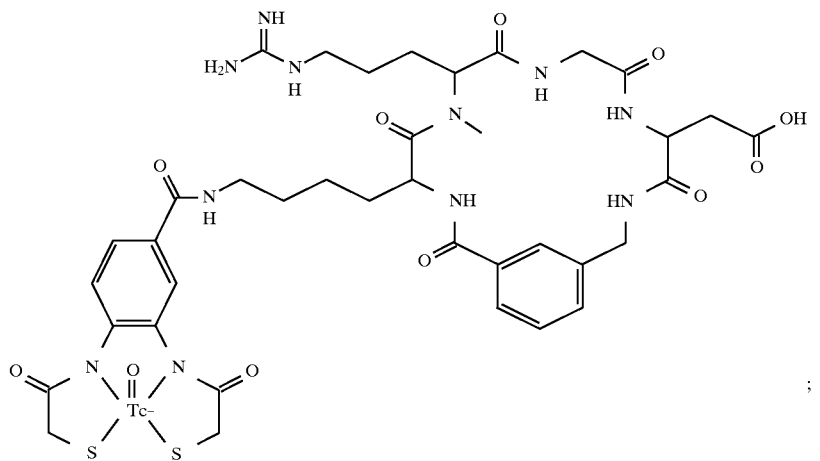
.

-continued

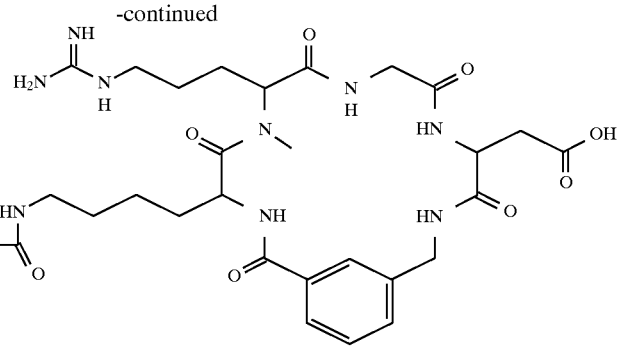
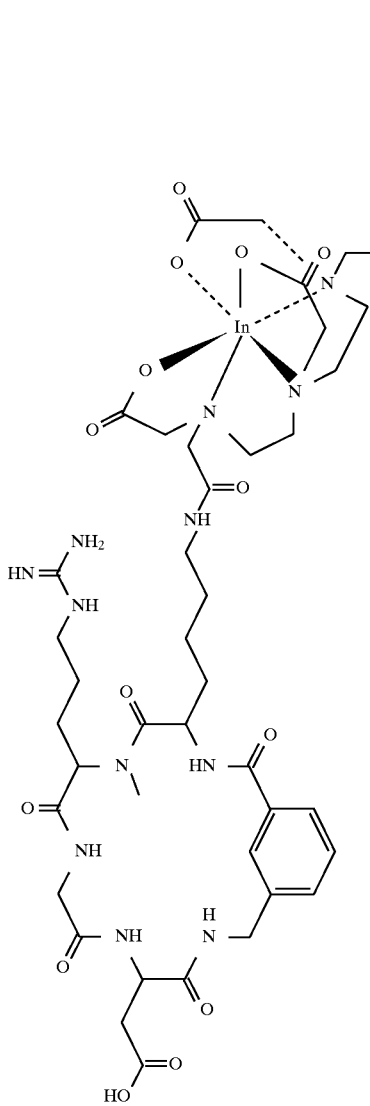

40. A method for visualizing sites of platelet deposition in a mammal by radioimaging, comprising (i) administering to said mammal an effective amount of a radiopharmaceutical of claim 29, and (ii) scanning the mammal using a radioimaging device.

41. A method for visualizing sites of platelet deposition in a mammal by radioimaging, comprising (i) administering to said mammal an effective amount of a radiopharmaceutical of claim 30, and (ii) scanning the mammal using a radioimaging device.

42. A method for visualizing sites of platelet deposition in a mammal by radioimaging, comprising (i) administering to said mammal an effective amount of a radiopharmaceutical of claim 31, and (ii) scanning the mammal using a radioimaging device.

43. A method for visualizing sites of platelet deposition in a mammal by radioimaging, comprising (i) administering to said mammal an effective amount of a radiopharmaceutical of claim 32, and (ii) scanning the mammal using a radioimaging device.

44. A method for visualizing sites of platelet deposition in a mammal by radioimaging, comprising (i) administering to said mammal an effective amount of a radiopharmaceutical of claim 33, and (ii) scanning the mammal using a radioimaging device.

45. A method for visualizing sites of platelet deposition in a mammal by radioimaging, comprising (i) administering to said mammal an effective amount of a radiopharmaceutical of claim 34, and (ii) scanning the mammal using a radioimaging device.

46. A method for visualizing sites of platelet deposition in a mammal by radioimaging, comprising (i) administering to said mammal an effective amount of a radiopharmaceutical of claim 35, and (ii) scanning the mammal using a radioimaging device.

47. A method for visualizing sites of platelet deposition in a mammal by radioimaging, comprising (i) administering to said mammal an effective amount of a radiopharmaceutical of claim 36, and (ii) scanning the mammal using a radioimaging device.

48. A method for visualizing sites of platelet deposition in a mammal by radioimaging, comprising (i) administering to said mammal an effective amount of a radiopharmaceutical of claim 37, and (ii) scanning the mammal using a radioimaging device.

49. A method for visualizing sites of platelet deposition in a mammal by radioimaging, comprising (i) administering to said mammal an effective amount of a radiopharmaceutical of claim 38, and (ii) scanning the mammal using a radioimaging device.

50. A method for visualizing sites of platelet deposition in a mammal by radioimaging, comprising (i) administering to said mammal an effective amount of a radiopharmaceutical of claim 39, and (ii) scanning the mammal using a radioimaging device.

51. A direct radiolabeled compound of formula (I):

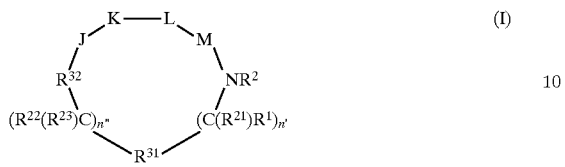

or a pharmaceutically acceptable salt or prodrug form thereof wherein:

$R^{31}$ is a $C_6$–$C_{14}$ saturated, partially saturated, or aromatic carbocyclic ring system substituted with 0–4 $R^{10}$ or $R^{10a}$;

$R^{32}$ is selected from:
—C(=O)—;
—C(=S)—
—S(=O)$_2$—;
—S(=O)—;
—P(=Z)(ZR$^{13}$)—;

Z is S or O;

n" and n' are independently 0–2;

$R^1$ and $R^{22}$ are independently selected from the following groups:
hydrogen,
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$cycloalkyl substituted with 0–2 $R^{11}$;
aryl substituted with 0–2 $R^{12}$;
a 5–10-membered heterocyclic ring system containing 1–4 heteroatoms independently selected from N, S, and O, said heterocyclic ring being substituted with 0–2 $R^{12}$;
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy;

$R^1$ and $R^{21}$ can alternatively join to form a 3–7 membered carbocyclic ring substituted with 0–2 $R^{12}$;

when n' is 2, $R^1$ or $R^{21}$ can alternatively be taken together with $R^1$ or $R^{21}$ on an adjacent carbon atom to form a direct bond, thereby to form a double or triple bond between said carbon atoms;

$R^{22}$ and $R^{23}$ can alternatively join to form a 3–7 membered carbocyclic ring substituted with 0–2 $R^{12}$;

when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;

$R^1$ and $R^2$, where $R^{21}$ is H, can alternatively join to form a 5–8 membered carbocyclic ring substituted with 0–2 $R^{12}$;

$R^{11}$ is selected from one or more of the following:
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, $C_3$–$C_6$ cycloalkoxy, $C_1$–$C_4$ alkyl (alkyl being substituted with 1–5 groups selected independently from: —NR$^{13}$R$^{14}$, —CF$_3$, NO$_2$, —SO$_2$R$^{13a}$, or —S(=O)R$^{13a}$), aryl substituted with 0–2 $R^{12}$,
a 5–10-membered heterocyclic ring system containing 1–4 heteroatoms independently selected from N, S, and O, said heterocyclic ring being substituted with 0–2 $R^{12}$;

$R^{12}$ is selected from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–$C_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S (=O) R$^{13a}$);

$R^{13}$ is selected independently from: H, $C_1$–$C_{10}$ alkyl, $C_3$–$C_{10}$ cycloalkyl, $C_4$–$C_{12}$ alkylcycloalkyl, aryl, —(C$_1$–$C_{10}$ alkyl)aryl, or $C_3$–$C_{10}$ alkoxyalkyl;

$R^{13a}$ is $C_1$–$C_{10}$ alkyl, $C_3$–$C_{10}$ cycloalkyl, $C_4$–$C_{12}$ alkylcycloalkyl, aryl, —(C$_1$–$C_{10}$ alkyl)aryl, or $C_3$–$C_{10}$ alkoxyalkyl;

when two $R^{13}$ groups are bonded to a single N, said $R^{13}$ groups may alternatively be taken together to form —(CH$_2$)$_{2-5}$— or —(CH$_2$)O(CH$_2$)—;

$R^{14}$ is OH, H, $C_1$–$C_4$ alkyl, or benzyl;

$R^{21}$ and $R^{23}$ are independently selected from:
hydrogen;
$C_1$–$C_4$ alkyl, optionally substituted with 1–6 halogen;
benzyl;

$R^2$ is H or $C_1$–$C_8$ alkyl;

$R^{10}$ and $R^{10a}$ are selected independently from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)N(R$^{13}$)$_2$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–$C_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl (including —$C_vF_w$ where v=1 to 3 and w=1 to (2v+1)), $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, $C_1$–$C_4$ alkyl (alkyl being substituted with —$N(R^{13})_2$, —$CF_3$, $NO_2$, or —$S(=O)R^{13a}$);

J is β-Ala or an L-isomer or D-isomer amino acid of structure —$N(R^3)C(R^4)(R^5)C(=O)$—, wherein:

$R^3$ is H or $C_1$–$C_8$ alkyl;

$R^4$ is H or $C_1$–$C_3$ alkyl;

$R^5$ is selected from:
 hydrogen;
 $C_1$–$C_8$ alkyl substituted with 0–2 $R^{11}$;
 $C_2$–$C_8$ alkenyl substituted with 0–2 $R^{11}$;
 $C_2$–$C_8$ alkynyl substituted with 0–2 $R^{11}$;
 $C_3$–$C_{10}$ cycloalkyl substituted with 0–2 $R^{11}$;
 aryl substituted with 0–2 $R^{12}$;
 a 5–10-membered heterocyclic ring system containing 1–4 heteroatoms independently selected from N, S, or O, said heterocyclic ring being substituted with 0–2 $R^{12}$;
 =O, F, Cl, Br, I, —$CF_3$, —CN, —$CO_2R^{13}$, —$C(=O)R^{13}$, —$C(=O)N(R^{13})_2$, —CHO, —$CH_2OR^{13}$, —$OC(=O)R^{13}$, —$OC(=O)OR^{13a}$, —$OR^{13}$, —$OC(=O)N(R^{13})_2$, —$NR^{13}C(=O)R^{13}$, —$NR^{14}C(=O)OR^{13a}$, —$NR^{13}C(=O)N(R^{13})_2$, —$NR^{14}SO_2N(R^{13})_2$, —$NR^{14}SO_2R^{13a}$, —$SO_3H$, —$SO_2R^{13a}$, —$SR^{13}$, —$S(=O)R^{13a}$, —$SO_2N(R^{13})_2$, —$N(R^{13})_2$, —$NHC(=NH)NHR^{13}$, —$C(=NH)NHR^{13}$, =$NOR^{13}$, $NO_2$, —$C(=O)NHOR^{13}$, —$C(=O)NHNR^{13}R^{13a}$, =$NOR^{13}$, —$B(R^{34})(R^{35})$, —$OCH_2CO_2H$, 2-(1-morpholino)ethoxy, —$SC(=NH)NHR^{13}$, $N_3$, —$Si(CH_3)_3$, ($C_1$–$C_5$ alkyl)$NHR^{16}$;
 —($C_0$–$C_6$ alkyl)X;

—(CH₂)$_q$—⟨phenyl⟩—(CH₂)$_q$—X, where q is independently 0, 1;

—CH₂—⟨cyclohexyl⟩—CH₂X;

—$(CH_2)_mS(O)_{p'}(CH_2)_2X$, where m=1,2 and p'=0–2;

wherein X is defined below; and $R^3$ and $R^4$ may also be taken together to form —CH₂CHCH₂—,
      |
    (CH₂)$_n$X where n=0, 1 and X is

—NH—C(=NR^{13})N(R^{13})R^{13};

$R^3$ and $R^5$ can alternatively be taken together to form —$(CH_2)_t$— or —$CH_2S(O)_{p'}C(CH_3)_2$—, where t=2–4 and p=0–2; or $R^4$ and $R^5$ can alternatively be taken together to form —$(CH_2)_u$—, where u=2–5;

$R^{16}$ is selected from:
 an amine protecting group;
 1–2 amino acids;
 1–2 amino acids substituted with an amine protecting group;

K is a D-isomer or L-isomer amino acid of structure —$N(R^6)CH(R^7)C(=O)$—, wherein:

$R^6$ is H or $C_1$–$C_8$ alkyl;

$R^7$ is selected from:
 —($C_1$–$C_7$ alkyl)X;

—(CH₂)$_q$—⟨phenyl⟩—(CH₂)$_q$—X, wherein each q is independently 0–2 and substitution on the phenyl is at the 3 or 4 position;

—(CH₂)$_q$—⟨cyclohexyl⟩—(CH₂)$_q$—X, wherein each q is independently 0–2 and substitution on the cyclohexyl is at the 3 or 4 position;

—($C_1$–$C_6$ alkyl)⟨bicyclic NH⟩$_{0-3}$

—$(CH_2)_mO$—($C_1$–$C_4$ alkyl)-X, where m=1 or 2;
—$(CH_2)_mS(O)_{p'}$—($C_1$–$C_4$ alkyl)-X, where m=1 or 2 and p'=0–2; and X is selected from:

—NH—C(=NR^{13})N(R^{13})R^{13};

—$N(R^{13})R^{13}$; —C(=NH)(NH$_2$); —SC(=NH)—NH$_2$; —NH—C(=NH)(NHCN); —NH—C(=NCN)(NH$_2$); —NH—C(=N—$OR^{13}$)(NH$_2$);

$R^6$ and $R^7$ can alternatively be taken together to form

—(CH₂)$_q$CH(CH₂)$_q$—,
         |
      (CH₂)$_n$X wherein each q is independently 1 or 2 and wherein n=0 or 1 and X is —NH$_2$ or

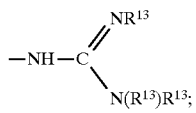

L is —Y(CH$_2$)$_v$C(=O)—, wherein:
Y is NH, N(C$_1$–C$_3$ alkyl), O, or S; and v=1 or 2;
M is a D-isomer or L-isomer amino acid of structure

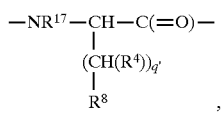

wherein:
q' is 0–2;
R$^{17}$ is H, C$_1$–C$_3$ alkyl;
R$^8$ is selected from:
—CO$_2$R$^{13}$, —SO$_3$R$^{13}$, —SO$_2$NHR$^{14}$, —B(R$^{34}$)(R$^{35}$),
—NHSO$_2$CF$_3$, —CONHNHSO$_2$CF$_3$, —PO(OR$^{13}$)$_2$,
—PO(OR$^{13}$)R$^{13}$, —SO$_2$NH-heteroaryl (said heteroaryl being 5–10-membered and having 1–4 heteroatoms selected independently from N, S, or O),
—SO$_2$NHCOR$^{13}$, —CONHSO$_2$R$^{13a}$,
—CH$_2$CONHSO$_2$R$^{13a}$, —NHSO$_2$NHCOR$^{13a}$,
—NHCONHSO$_2$R$^{13a}$, —SO$_2$NHCONHR$^{13}$;
R$^{34}$ and R$^{35}$ are independently selected from:
—OH,
—F,
—N(R$^{13}$)$_2$, or
C$_1$–C$_8$-alkoxy;
R$^{34}$ and R$^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O; and
wherein the radiolabel is selected from the group: $^{123}$I, $^{125}$I, $^{131}$I, $^{18}$F, $^{11}$C, $^{13}$N, $^{15}$O, $^{75}$Br.

52. A radiolabeled compound of claim 51, wherein:
R$^{31}$ is bonded to (C(R$^{23}$)R$^{22}$)$_{n''}$ and
(C(R$^{21}$)R$^1$)$_{n'}$ at 2 different atoms on said carbocyclic ring.

53. A radiolabeled compound of claim 51, wherein:
n" is 0 and n' is 0;
n" is 0 and n' is 1;
n" is 0 and n' is 2;
n" is 1 and n' is 0;
n" is 1 and n' is 1;
n" is 1 and n' is 2;
n" is 2 and n' is 0;
n" is 2 and n' is 1; or
n" is 2 and n' is 2.

54. A radiolabeled compound of claim 51 wherein R$^6$ is methyl, ethyl, or propyl.

55. A radiolabeled compound of claim 51, wherein:

R$^{31}$ is selected from the group consisting of:
(a) a 6 membered saturated, partially saturated or aromatic carbocyclic ring substituted with 0–3 R$^{10}$ or R$^{10a}$;
(b) a 8–11 membered saturated, partially saturated, or aromatic fused bicyclic carbocyclic ring substituted with 0–4 R$^{10}$ or R$^{10a}$; or
(c) a 14 membered saturated, partially saturated, or aromatic fused tricyclic carbocyclic ring substituted with 0–4 R$^{10}$ or R$^{10a}$.

56. A radiolabeled compound of claim 51, wherein
R$^{31}$ is selected from the group consisting of:
(a) a 6 membered saturated, partially saturated, or aromatic carbocyclic ring of formula:

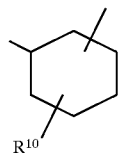

wherein any of the bonds forming the carbocyclic ring may be a single or double bond,
and wherein said carbocyclic ring is substituted independently with 0–4 R$^{10}$;
(b) a 10 membered saturated, partially saturated, or aromatic bicyclic carbocyclic ring of formula:

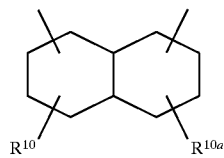

wherein any of the bonds forming the carbocyclic ring may be a single or double bond,
and wherein said carbocyclic ring is substituted independently with 0–4 R$^{10}$ or R$^{10a}$;
(c) a 9 membered saturated, partially saturated, or aromatic bicyclic carbocyclic ring of formula:

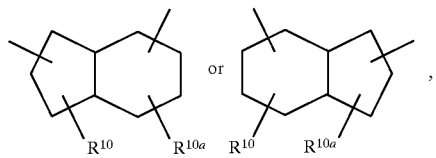

wherein any of the bonds forming the carbocyclic ring may be a single or double bond,
and wherein said carbocyclic ring is substituted independently with 0–4 R$^{10}$ or R$^{10a}$.

57. A radiolabeled compound of claim 51, wherein:
R$^{31}$ is selected from (the dashed bond may be a single or double bond):

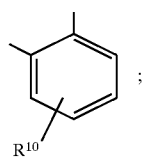

-continued

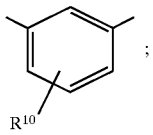

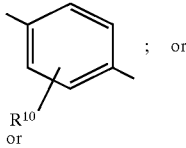; or

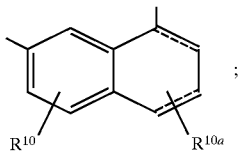;

n" is 0 or 1; and
n' is 0–2.

58. A radiolabeled compound of claim 51, wherein:
$R^1$ and $R^{22}$ are independently selected from: phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —$C(=O)NHOR^{13a}$, —$C(=O)NHN(R^{13})_2$, =$NOR^{13}$, —$B(R^{34})(R^{35})$, $C_3$–$C_6$ cycloalkoxy, —$OC(=O)R^{13}$, —$C(=O)R^{13}$, —$OC(=O)OR^{13a}$, —$OR^{13}$, —$(C_1$–$C_4$ alkyl)-$OR^{13}$, —$N(R^{13})_2$, —$OC(=O)N(R^{13})_2$, —$NR^{13}C(=O)R^{13}$, —$NR^{13}C(=O)OR^{13a}$, —$NR^{13}C(=O)N(R^{13})_2$, —$NR^{13}SO_2N(R^{13})_2$, —$NR^{13}SO_2R^{13a}$, —$SO_3H$, —$SO_2R^{13a}$, —$S(=O)R^{13a}$, —$SR^{13}$, —$SO_2N(R^{13})_2$, $C_2$–$C_6$ alkoxyalkyl, methylenedioxy, ethylenedioxy, $C_1$–$C_4$ haloalkyl, $C_1$–$C_4$ haloalkoxy, —$OCH_2CO_2H$, 2-(1-morpholino)ethoxy, $C_1$–$C_4$ alkyl (alkyl being substituted with —$N(R^{13})_2$, —$CF_3$, $NO_2$, or —$S(=O)R^{13a}$).

59. A radiolabeled compound of claim 51, wherein:
$R^{31}$ is selected from:

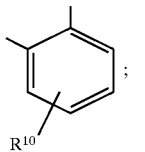; 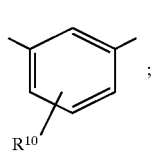; 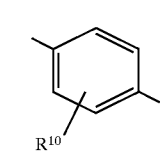;

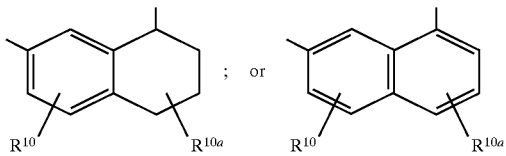

wherein $R^{31}$ may be substituted independently with 0–3 $R^{10}$ or $R^{10a}$;
$R^{32}$ is —$C(=O)$—;
n" is 0 or 1;
n' is 0–2;
$R^1$ and $R^{22}$ are independently selected from H, $C_1$–$C_4$ alkyl, phenyl, benzyl, phenyl—$(C_2$–$C_4)$alkyl, $C_1$–$C_4$ alkoxy;
$R^{21}$ and $R^{23}$ are independently H or $C_1$–$C_4$ alkyl;

$R^2$ is H or $C_1$–$C_8$ alkyl;
$R^{13}$ is selected independently from: H, $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;
$R^{13a}$ is $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;
when two $R^{13}$ groups are bonded to a single N, said $R^{13}$ groups may alternatively be taken together to form —$(CH_2)_{2-5}$— or —$(CH_2)O(CH_2)$—;
$R^{14}$ is OH, H, $C_1$–$C_4$ alkyl, or benzyl;
$R^{10}$ and $R^{10a}$ are selected independently from: $C_1$–$C_5$ alkyl, phenyl, halogen, or $C_1$–$C_4$ alkoxy;
J is β-Ala or an L-isomer or D-isomer amino acid of structure —$N(R^3)C(R^4)(R^5)C(=O)$—, wherein:
$R^3$ is H or $CH_3$;
$R^4$ is H or $C_1$–$C_3$ alkyl;
$R^5$ is H, $C_1$–$C_8$ alkyl, $C_3$–$C_6$ cycloalkyl, $C_3$–$C_6$ cycloalkylmethyl, $C_3$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, —$(CH_2)_sNHC(=NH)(NH_2)$, —$(CH_2)_sNHR^{16}$, where s=3–5;
or
$R^{16}$ is selected from:
an amine protecting group;
1–2 amino acids; or
1–2 amino acids substituted with an amine protecting group;
$R^3$ and $R^5$ can alternatively be taken together to form —$(CH_2)_t$— (t=2–4) or —$CH_2SC(CH_3)_2$—; or
$R^4$ and $R^5$ can alternatively be taken together to form —$(CH_2)_u$—, where u=2–5;
K is an L-isomer amino acid of structure —$N(R^6)CH(R^7)C(=O)$—, wherein:
$R^6$ is H or $C_1$–$C_8$ alkyl;
$R^7$ is

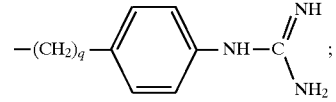;

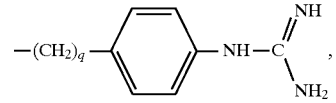, where q=0 or 1;
—$(CH_2)_rX$, where r=3–6;

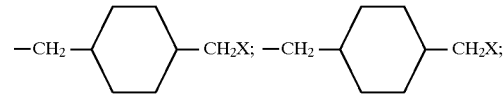

—$(CH_2)_mS(CH_2)_2X$, where m=1 or 2;
—$(C_3$–$C_7$ alkyl)—NH—$(C_1$–$C_6$ alkyl)

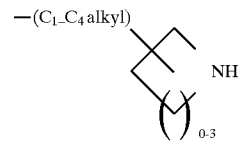

—$(CH_2)_m$—O—$(C_1$–$C_4$ alkyl)—NH—$(C_1$–$C_6$ alkyl), where m=1 or 2;

—(CH$_2$)$_m$—S—(C$_1$–C$_4$ alkyl)—NH—(C$_1$–C$_6$ alkyl), where m=1 or 2; and

X is —NH$_2$ or —NHC(=NH)(NH$_2$); or R$^6$ and R$^7$ can alternatively be taken together to form

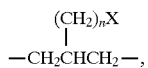

where n=0 or 1 and X is —NH$_2$ or —NHC(=NH)(NH$_2$);

L is —Y(CH$_2$)$_v$C(=O)—, wherein:
Y is NH, O, or S; and v 1 or 2;

M is a D-isomer or L-isomer amino acid of structure

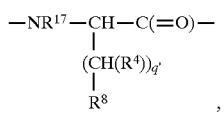

wherein:
q' is 0–2;
R$^{17}$ is H, C$_1$–C$_3$ alkyl;
R$^8$ is selected from:
—CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$.

60. A radiolabeled compound of claim 51 that is a radiolabeled 1,3-disubstituted phenyl the formula (II):

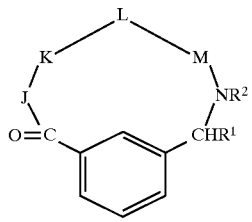

(II)

wherein:
the shown phenyl ring in formula (II) may be further substituted with 0–3 R$^{10}$;
R$^{10}$ is selected independently from: C$_1$–C$_5$ alkyl, phenyl, halogen, or C$_1$–C$_4$ alkoxy;
R$^1$ is H, C$_1$–C$_4$ alkyl, phenyl, or phenyl—(C$_1$–C$_4$)alkyl;
R$^2$ is H or methyl;
R$^{13}$ is selected independently from: H, C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;
R$^{13a}$ is C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;
when two R$^{13}$ groups are bonded to a single N, said R$^{13}$ groups may alternatively be taken together to form —(CH$_2$)$_{2-5}$— or —(CH$_2$)O(CH$_2$)—;
R$^{14}$ is OH, H, C$_1$–C$_4$ alkyl, or benzyl;
J is β-Ala or an L-isomer or D-isomer amino acid of structure —N(R$^3$)C(R$^4$)(R$^5$)C(=O)—, wherein:
R$^3$ is H or CH$_3$;
R$^4$ is H or C$_1$–C$_3$ alkyl;

R$^5$ is H, C$_1$–C$_8$ alkyl, C$_3$–C$_6$ cycloalkyl, C$_3$–C$_6$ cycloalkylmethyl, C$_1$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, —(CH$_2$)$_s$NHC(=NH)(NH$_2$), —(CH$_2$)$_s$NHR$^{16}$, where s=3–5; or R$^{16}$ is selected from:
an amine protecting group;
1–2 amino acids; or
1–2 amino acids substituted with an amine protecting group;

R$^3$ and R$^5$ can alternatively be taken together to form —CH$_2$CH$_2$CH$_2$—; or R$^4$ and R$^5$ can alternatively be taken together to form —(CH$_2$)$_u$—, where u=2–5;

K is an L-isomer amino acid of structure —N(R$^6$)CH(R$^7$)C(=O)—, wherein:
R$^6$ is H or C$_1$–C$_8$ alkyl;
R$^7$ is:

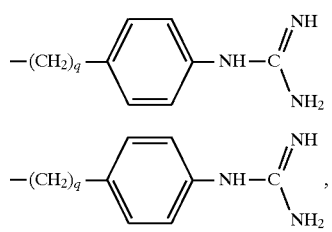

where q=0 or 1;
—(CH$_2$)$_r$X, where r=3–6;

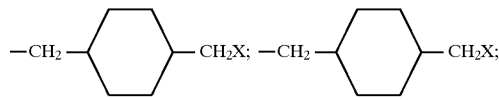

—(CH$_2$)$_m$S(CH$_2$)$_2$X, where m=1 or 2;
—(C$_3$–C$_7$ alkyl)—NH—(C$_1$–C$_6$ alkyl)

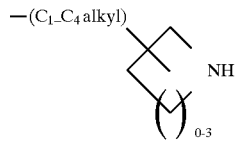

—(CH$_2$)$_m$—O—(C$_1$–C$_4$ alkyl)—NH—(C$_1$–C$_6$ alkyl), where m=1 or 2;
—(CH$_2$)$_m$—S—(C$_1$–C$_4$ alkyl)—NH—(C$_1$–C$_6$ alkyl), where m=1 or 2; and X is —NH$_2$ or —NHC(=NH)(NH$_2$), provided that X is not —NH$_2$ when r=4; or R$^6$ and R$^7$ are alternatively be taken together to form

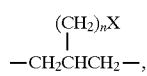

where n=0,1 and X is —NH$_2$ or —NHC(=NH)(NH$_2$);
L is —Y(CH$_2$)$_v$C(=O)—, wherein:
Y is NH, O, or S; and v=1,2;

M is a D-isomer or L-isomer amino acid of structure

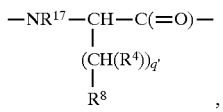

wherein:
q' is 0–2;
$R^{17}$ is H, $C_1$–$C_3$ alkyl;
$R^8$ is selected from:
—$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$.

61. A radiolabeled compound of claim 51 that is a radiolabeled 1,3-disubstituted phenyl of the formula (II):

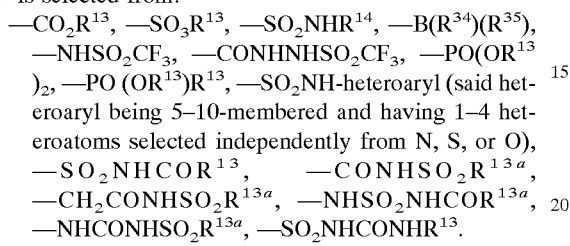

wherein:
the phenyl ring in formula (II) may be further substituted with 0–3 $R^{10}$ or $R^{10a}$;
$R^{10}$ or $R^{10a}$ are selected independently from: H, $C_1$–$C_8$ alkyl, phenyl, halogen, or $C_1$–$C_4$ alkoxy;
$R^1$ is H, $C_1$–$C_4$ alkyl, phenyl, benzyl, or phenyl—$(C_2$–$C_4)$ alkyl;
$R^2$ is H or methyl;
$R^{13}$ is selected independently from: H, $C_1$–$C_{10}$ alkyl, $C_3$–$C_{10}$ cycloalkyl, $C_4$–$C_{12}$ alkylcycloalkyl, aryl, —$(C_1$–$C_{10}$ alkyl)aryl, or $C_3$–$C_{10}$ alkoxyalkyl;
J is β-Ala or an L-isomer or D-isomer amino acid of structure —$N(R^3)C(R^4)(R^5)C(=O)$—, wherein:
$R^3$ is H or $CH_3$;
$R^4$ is H;
$R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, $(CH_2)_sNHR^{16}$, where s=3–5;
$R^3$ and $R^5$ can alternatively be taken together to form —$CH_2CH_2CH_2$—;
$R^{16}$ is selected from:
an amine protecting group;
1–2 amino acids;
1–2 amino acids substituted with an amine protecting group;
K is an L-isomer amino acid of structure —$N(R^6)CH(R^7)C(=O)$—, wherein:
$R^6$ is H or $C_3$–$C_8$ alkyl;

$R^7$ is

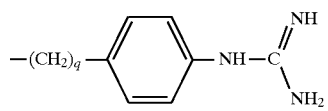

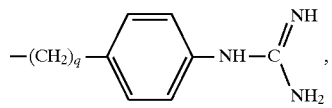

where q=0 or 1;
—$(CH_2)_rX$, where r=3–6;

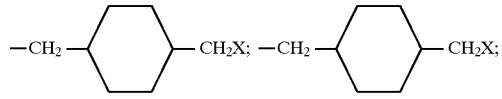

—$(CH_2)_mS(CH_2)_2X$, where m=1 or 2;
—$(C_4$–$C_7$ alkyl)—NH—$(C_1$–$C_6$ alkyl)

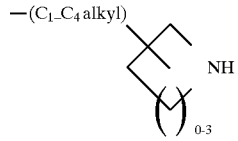

—$(CH_2)_m$—O—$(C_1$–$C_4$ alkyl)—NH—$(C_1$–$C_6$ alkyl), where m=1 or 2;
—$(CH_2)_m$—S—$(C_1$–$C_4$ alkyl)—NH—$(C_1$–$C_6$ alkyl), where m=1 or 2; and
X is —$NH_2$ or —$NHC(=NH)(NH_2)$, provided that X is not —$NH_2$ when r=4; or
L is —$YCH_2C(=O)$—, wherein:
Y is NH or O;
M is a D-isomer or L-isomer amino acid of structure

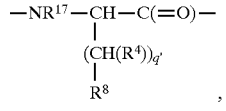

wherein:
q' is 1;
$R^{17}$ is H, $C_1$–$C_3$ alkyl;
$R^8$ is selected from:
—$CO_2H$ or —$SO_3R^{13}$.

62. A radiolabeled compound of claim 51 that is a radiolabeled compound of formula (II) above, wherein:
the phenyl ring in formula (II) may be further substituted with 0–2 $R^{10}$ or $R^{10a}$;
$R^{10}$ or $R^{10a}$ are selected independently from: H, $C_1$–$C_8$ alkyl, phenyl, halogen, or $C_1$–$C_4$ alkoxy;
$R^1$ is H;
$R^2$ is H;
J is β-Ala or an L-isomer or D-isomer amino acid of formula —$N(R^3)CH(R^5)C(=O)$—, wherein:
$R^3$ is H and $R^5$ is H, $CH_3$, $CH_2CH_3$, $CH(CH_3)_2$, $CH(CH_3)CH_2CH_3$, $CH_2CH_2CH_3$, $CH_2CH_2CH_2CH_3$, $CH_2CH_2SCH_3$, $CH_2CH(CH_3)_2$, $(CH_2)_4NH_2$, $(C_3$–$C_5$ alkyl)$NHR^{16}$; or
$R^3$ is $CH_3$ and $R^5$ is H; or
$R^3$ and $R^5$ can alternatively be taken together to form —$CH_2CH_2CH_2$—;

R¹⁶ is selected from:
  an amine protecting group;
  1–2 amino acids;
  1–2 amino acids substituted with an amine protecting group;
K is an L-isomer amino acid of formula —N(CH₃)CH(R⁷)C(=O)—, wherein:
  R⁷ is —(CH₂)₃NHC(=NH)(NH₂);
L is —NHCH₂C(=O)—; and
M is a D-isomer or L-isomer amino acid of structure

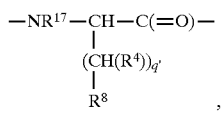

wherein:
  q' is 1;
  R⁴ is H or CH₃;
  R¹⁷ is H;
  R⁸ is
    —CO₂H;
    —SO₃H.

63. A radiolabeled compound of claim 51 that is a radiolabeled compound of formula (II), or a pharmaceutically acceptable salt thereof, wherein:
  R¹ and R² are independently selected from H, methyl;
  J is selected from D-Val, D-2-aminobutyric acid, D-Leu, D-Ala, Gly, D-Pro, D-Ser, D-Lys, βAla, Pro, Phe, NMeGly, D-Nle, D-Phg, D-Ile, D-Phe, D-Tyr, Ala, Nᵉ-p-azidobenzoyl-D-Lys, Nᵉ-p-benzoylbenzoyl-D-Lys, Nᵉ-tryptophanyl-D-Lys, Nᵉ-o-benzoylbenzoyl-D-Lys, Nᵉ-p-acetylbenzoyl-D-Lys, Nᵉ-dansyl-D-Lys, Nᵉ-glycyl-D-Lys, Nᵉ-glycyl-p-benzoylbenzoyl-D-Lys, Nᵉ-p-phenylbenzoyl-D-Lys, Nᵉ-m-benzoylbenzoyl-D-Lys, Nᵉ-o-benzoylbenzoyl-D-Lys;
  K is selected from NMeArg, Arg;
  L is selected from Gly, β-Ala, Ala;
  M is selected from Asp; αMeAsp; βMeAsp; NMeAsp; D-Asp.

64. A radiolabeled compound of claim 51 that is a radiolabeled compound of formula (II), or a pharmaceutically acceptable salt thereof, wherein:
  R¹ and R² are independently selected from H, methyl;
  J is selected from D-Val, D-2-aminobutyric acid, D-Leu, D-Ala, Gly, D-Pro, D-Ser, D-Lys, βAla, Pro, Phe, NMeGly, D-Nle, D-Phg, D-Ile, D-Phe, D-Tyr, Ala,
  K is selected from NMeArg;
  L is Gly;
  M is selected from Asp; αMeAsp; βMeAsp; NMeAsp; D-Asp.

65. The radiolabeled compounds of claim 51 that are:
  the radiolabeled compound of formula (II) wherein R¹ and R² are H; J is D-Val; K is NMeArg; L is Gly; and M is Asp;
  the radiolabeled compound of formula (II) wherein R¹ and R² are H; J is D-2-aminobutyric acid; K is NMeArg; L is Gly; and M is Asp;
  the radiolabeled compound of formula (II) wherein R¹ and R² are H; J is D-Leu; K is NMeArg; L is Gly; and M is Asp;
  the radiolabeled compound of formula (II) wherein R¹ and R² are H; J is D-Ala; K is NMeArg; L is Gly; and M is Asp;
  the radiolabeled compound of formula (II) wherein R¹ and R² are H; J is Gly; K is NMeArg; L is Gly; and M is Asp;
  the radiolabeled compound of formula (II) wherein R¹ and R² are H; J is D-Pro; K is NMeArg; L is Gly; and M is Asp;
  the radiolabeled compound of formula (II) wherein R¹ and R² are H; J is D-Lys; K is NMeArg; L is Gly; and M is Asp;
  the radiolabeled compound of formula (II) wherein R¹ and R² are H; J is β-Ala; K is NMeArg; L is Gly; and M is Asp;
  the radiolabeled compound of formula (II) wherein R¹ and R² are H; J is NMeGly; K is NMeArg; L is Gly; and M is Asp;
  the radiolabeled compound of formula (II) wherein R¹ is methyl (isomer 1); R² are H; J is D-Val; K is NMeArg; L is Gly; and M is Asp;
  the radiolabeled compound of formula (II) wherein R¹ is methyl (isomer 2); R² are H; J is D-Val; K is NMeArg; L is Gly; and M is Asp;
  the radiolabeled compound of formula (II) wherein R¹ is phenyl (isomer 1); R² are H; J is D-Val; K is NMeArg; L is Gly; and M is Asp;
  the radiolabeled compound of formula (II) wherein J=D-Met, K=NMeArg, L=Gly, M=Asp, R¹=H, R²=H;
  the radiolabeled compound of formula (II) wherein J=D-Abu, K=diNMe-guanidinyl-Orn, L=Gly, M=Asp, R¹=H, R²=H;
  the radiolabeled compound of formula (II) wherein J=D-Abu, K=diNMe-Lys, L=Gly, M=Asp, R¹=H, R²=H;
  the radiolabeled compound of formula (II) wherein R¹ and R² are H; J is Nᵉ-p-azidobenzoyl-D-Lysine; K is NMeArg; L is Gly; and M is Asp;
  the radiolabeled compound of formula (II) wherein R¹ and R² are H; J is Nᵉ-p-benzoylbenzoyl-D-Lysine; K is NMeArg; L is Gly; and M is Asp;
  the radiolabeled compound of formula (II) wherein R¹ and R² are H; J is Nᵉ-tryptophanyl-D-Lysine; K is NMeArg; L is Gly; and M is Asp;
  the radiolabeled compound of formula (II) wherein R¹ and R² are H; J is Nᵉ-o-benzoylbenzoyl-D-Lysine; K is NMeArg; L is Gly; and M is Asp.
  the radiolabeled compound of formula (II) wherein R¹ and R² are H; J is Nᵉ-p-acetylbenzoyl-D-Lysine; K is NMeArg; L is Gly; and M is Asp;
  the radiolabeled compound of formula (II) wherein R¹ and R² are H; J is Nᵉ-dansyl-D-Lysine; K is NMeArg; L is Gly; and M is Asp;
  the radiolabeled compound of formula (II) wherein R¹ and R² are H; J is Nᵉ-glycyl-D-Lysine; K is NMeArg; L is Gly; and M is Asp;
  the radiolabeled compound of formula (II) wherein R¹ and R² are H; J is Nᵉ-glycyl-p-benzoylbenzoyl-D-Lysine; K is NMeArg; L is Gly; and M is Asp;
  the radiolabeled compound of formula (II) wherein R¹ and R² are H; J is Nᵉ-p-phenylbenzoyl-D-Lysine; K is NMeArg; L is Gly; and M is Asp;
  the radiolabeled compound of formula (II) wherein R¹ and R² are H; J is Nᵉ-m-benzoylbenzoyl-D-Lysine; K is NMeArg; L is Gly; and M is Asp;
  the radiolabeled compound of formula (II) wherein R¹ and R² are H; J is Nᵉ-o-benzoylbenzoyl-D-Lysine; K is NMeArg; L is Gly; and M is Asp;

the radiolabeled compound of formula (III) wherein $R^1$ and $R^2$ are H; J is D-Val; K is NMeArg; L is Gly; and M is Asp;

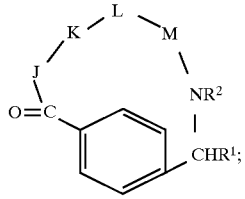

(III)

the radiolabeled compound of formula (II) wherein $R^1$ and $R^2$ are H; J is D-Val; K is D-NMeArg; L is Gly; and M is Asp;

the radiolabeled compound of formula (II) wherein $R^1$ and $R^2$ are H; J is D-Nle; K is NMeArg; L is Gly; and M is Asp;

the radiolabeled compound of formula (II) wherein $R^1$ and $R^2$ are H; J is D-Phg; K is NMeArg; L is Gly; and M is Asp;

the radiolabeled compound of formula (II) wherein $R^1$ and $R^2$ are H; J is D-Phe; K is NMeArg; L is Gly; and M is Asp;

the radiolabeled compound of formula (V) wherein $R^1$ and $R^2$ are H; J is D-Ile; K is NMeArg; L is Gly; and M is Asp;

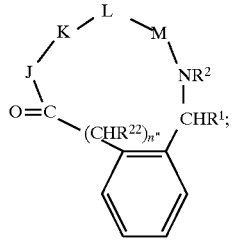

(V)

the radiolabeled compound of formula (V) wherein n"=1; $R^1$, $R^2$, and $R^{22}$ are H; J is D-Val; K is NMeArg; L is Gly; and M is Asp;

the radiolabeled compound of formula (V) wherein n"=0; $R^1$ and $R^2$ are H; J is D-Val; K is NMeArg; L is Gly; and M is Asp;

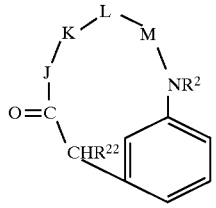

(VI)

the radiolabeled compound of formula (VI) wherein $R^2$ and $R^{22}$ are H; J is D-Val; K is NMeArg; L is Gly; and M is Asp;

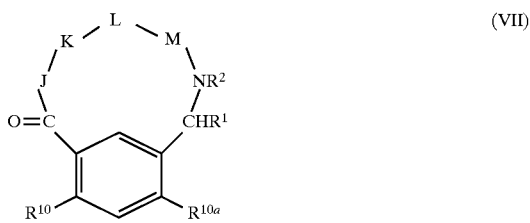

(VII)

the radiolabeled compound of formula (VII) wherein $R^1$,$R^2$, and $R^{10}$ are H; $R^{10a}$ is Cl; J is D-Val; K is NMeArg; L is Gly; and M is Asp;

the radiolabeled compound of formula (VII) wherein $R^1$,$R^2$, and $R^{10}$ are H; $R^{10a}$ is I; J is D-Val; K is NMeArg; L is Gly; and M is Asp;

the radiolabeled compound of formula (VII) wherein $R^1$,$R^2$, and $R^{10}$ are H; $R^{10a}$ is I; J is D-Abu; K is NMeArg; L is Gly; and M is Asp;

the radiolabeled compound of formula (VII) wherein $R^1$,$R^2$, and $R^{10}$ are H; $R^{10a}$ is Me; J is D-Val; K is NMeArg; L is Gly; and M is Asp;

the radiolabeled compound of formula (VII) wherein $R^1$,$R^2$, and $R^{10a}$ are H; $R^{10}$ is Cl; J is D-Val; K is NMeArg; L is Gly; and M is Asp;

the radiolabeled compound of formula (VII) wherein $R^1$,$R^2$, and $R^{10a}$ are H; $R^{10}$ is MeO; J is D-Val; K is NMeArg; L is Gly; and M is Asp;

the radiolabeled compound of formula (VII) wherein $R^1$,$R^2$, and $R^{10}$ are H; $R^{10}$ is Me; J is D-Val; K is NMeArg; L is Gly; and M is Asp;

the radiolabeled compound of formula (VII) wherein $R^1$,$R^2$, and $R^{10}$ are H; $R^{10a}$ is Cl; J is D-Abu; K is NMeArg; L is Gly; and M is Asp;

the radiolabeled compound of formula (VII) wherein $R^1$, $R^2$, and $R^{10}$ are H; $R^{10a}$ is Me; J is D-Abu; K is NMeArg; L is Gly; and M is Asp;

the radiolabeled compound of formula (II) wherein $R^1$ and $R^2$ are H; J is D-Tyr; K is NMeArg; L is Gly; and M is Asp;

the radiolabeled compound of formula (II) wherein $R^1$ and $R^2$ are H; J is D-Val; K is NMeAmf; L is Gly; and M is Asp;

the radiolabeled compound of formula (II) wherein $R^1$ and $R^2$ are H; J is D-Val; K is NMeArg; L is Gly; and M is βMeAsp;

the radiolabeled compound of formula (II) wherein $R^1$ is H; $R^2$ is $CH_3$; J is D-Val; K is NMeArg; L is Gly; and M is Asp;

the radiolabeled compound of formula (III) wherein $R^1$ and $R^2$ are H; J is D-Val; K is NMeArg; L is Gly; and M is Asp;

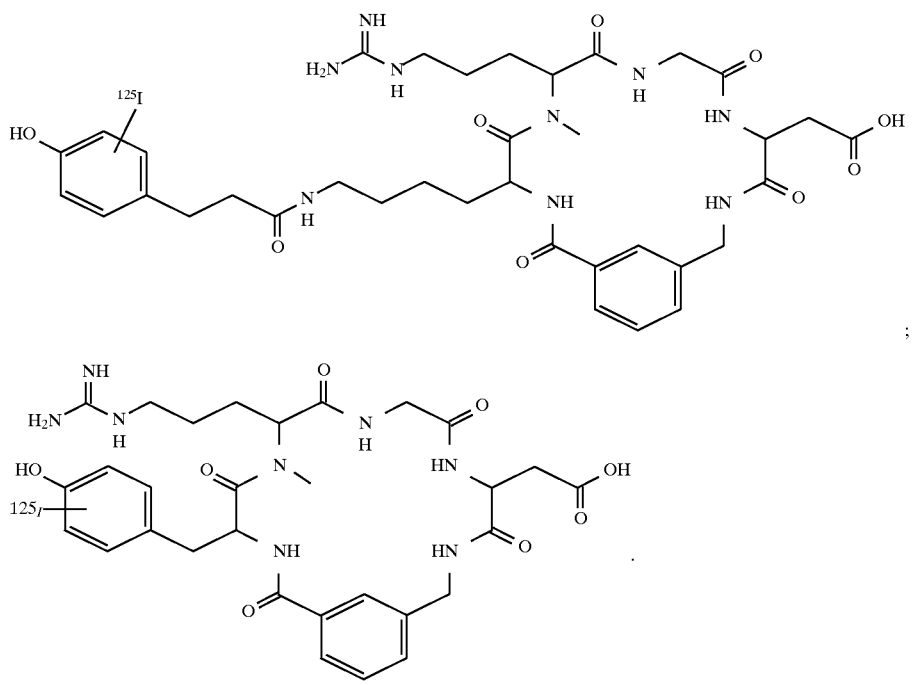

;

66. A radiolabeled compound as in one of claims 51–65 wherein the radiolabel is selected from the group: $^{18}F$, $^{11}C$, $^{123}I$, and $^{125}I$.

67. A radiolabeled compound of claim 66 wherein the radiolabel is $^{123}I$.

68. A radiopharmaceutical composition comprising a radiopharmaceutically acceptable carrier and a radiolabeled compound of any of claims 51–67.

69. A method of determining platelet deposition in a mammal comprising administering to said mammal a radiopharmaceutical composition comprising a compound of any of claims 51–67, and imaging said mammal.

70. A method of diagnosing a disorder associated with platelet deposition in a mammal comprising administering to said mammal a radiopharmaceutical composition comprising a compound of any of claims 51–67, and imaging said mammal.